United States Patent [19]
Furuya et al.

[11] Patent Number: 6,048,863
[45] Date of Patent: *Apr. 11, 2000

[54] CONDENSED-RING THIOPHENE DERIVATIVES AND THIENOPYRIMIDINE DERIVATIVES, THEIR PRODUCTION AND USE

[75] Inventors: Shuichi Furuya; Nobuo Choh, both of Tsukuba; Koichi Kato, Kawanishi; Shuji Hinuma, Tsukuba, all of Japan

[73] Assignee: Takeda Chemical Industries, Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/682,442

[22] Filed: Jul. 17, 1996

Related U.S. Application Data

[62] Continuation of application No. PCT/JP96/00263, Feb. 7, 1996, which is a continuation-in-part of application No. 08/454,304, filed as application No. PCT/JP95/00728, Apr. 14, 1995, Pat. No. 5,817,819.

[30] Foreign Application Priority Data

| | | | |
|---|---|---|---|
| Apr. 19, 1994 | [JP] | Japan | 6-080732 |
| Aug. 19, 1994 | [JP] | Japan | 6-195541 |
| Nov. 4, 1994 | [JP] | Japan | 6-271010 |
| Feb. 8, 1995 | [JP] | Japan | 7-020717 |
| Feb. 28, 1995 | [JP] | Japan | 7-040151 |
| Oct. 19, 1995 | [JP] | Japan | 7-271638 |

[51] Int. Cl.$^7$ ............ A61K 31/505; C07D 495/04
[52] U.S. Cl. ............ 514/258; 544/127; 544/278; 544/238; 546/114; 514/234.2; 514/253; 514/254; 514/301
[58] Field of Search ............ 544/278; 514/258

[56] References Cited

U.S. PATENT DOCUMENTS

| | | | |
|---|---|---|---|
| 4,661,472 | 4/1987 | Rivier et al. | 514/15 |
| 5,140,009 | 8/1992 | Haviv et al. | 514/16 |
| 5,171,835 | 12/1992 | Janaky et al. | 530/313 |

FOREIGN PATENT DOCUMENTS

| | | | |
|---|---|---|---|
| 640606 | 3/1995 | European Pat. Off. | 544/278 |
| 61-191698 | 8/1986 | Japan . | |

OTHER PUBLICATIONS

Fujino et al., "Synthetic Analogs of Luteinizing Hormone Releasing Hormone (LH–RH) Substituted in Position 6 and 10", Biochemical and Biophysical Research Communications, vol. 60, No. 1, 1974 pp. 406–413.

Seirikagaku 2, Bunkodo, pp. 610–618, 1986. (Abstract).

Receptor Kiso To Rinsho, Asakurashoten, pp. 297–304, 1993. (Abstract).

R. C. Coombes, British Journal of Cancer, vol. 59, 1989, pp. 815–832.

Toguchi et al. "Clinical Progress with LHRH Analogues in Prostatic Cancer", The Journal of International Medical Research, vol. 18 (suppl 1) (1990) pp. 35–41.

Schally et al., "Isolation of the Luteinizing Hormone and Follicle–Stimulating Hormone–Releasing Hormone from Porcine Hypothalami", The Journal of Biological Chemistry, vol. 246, No. 23, (1971), pp. 7230–7236.

Burgus et al., "Primary Structure of the Ovine Hypothalamic Luteinizing Hormone–Releasing Factor (LRF)", Proceedings of the National Academy of Sciences, vol. 69, No. 1 (1972) pp. 278–282.

Bienstock et al., "Conformational Analysis of a Highly Potent Dicyclic Gonadotropin–Releasing Hormone Antagonist by Nuclear Magnetic Resonance and Molecular Dynamics", Journal of Medicinal Chemistry, vol. 36, (1993), pp. 3265–3273.

Reissmann et al., Human Reproduction, vol. 10, pp. 1974–1981, 1995.

*Primary Examiner*—Emily Bernhardt
*Attorney, Agent, or Firm*—Foley & Lardner

[57] ABSTRACT

Thienopyrimidine derivatives of formula:

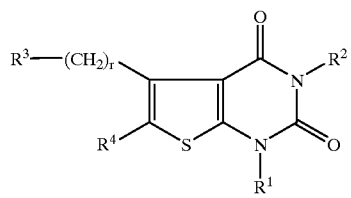

The present thienopyrimidine derivatives are useful for treating mammals suffering from disorders related to gonadotropin realeasing hormone (GnRH).

8 Claims, No Drawings

CONDENSED-RING THIOPHENE DERIVATIVES AND THIENOPYRIMIDINE DERIVATIVES, THEIR PRODUCTION AND USE

This application is a continuation application of PCT Application No. PCT/JP96/00263 filed on Feb. 7, 1996, which is a continuation-in-part application of U.S. Ser. No. 08/454,304 filed on Jun. 16, 1995, which is a § 371 application, of PCT application No. PCT/JP95/00728 filed on Apr. 14, 1995, now U.S. Pat. No. 5,817,319.

The substituent designations of the formulae according to the first embodiment are specific to the first embodiment and may be the same or different than the substituent designations of formulae of the second embodiment.

TECHNICAL FIELD OF THE FIRST EMBODIMENT

A first embodiment of the present invention relates to a pharmaceutical composition for antagonizing a gonadotropin-releasing hormone (GnRH) containing a condensed-bicyclic compound comprising a homo or hetero 5 to 7-membered ring group and a homo or hetero 5 to 7-membered ring group. The first embodiment of the present invention also relates to novel condensed-ring thiophene derivatives and salts thereof. The first embodiment further relates to methods for manufacturing the novel condensed-ring thiophene derivatives and the salts thereof.

BACKGROUND ART OF THE FIRST EMBODIMENT

Secretion of anterior pituitary hormone undergoes the control of peripheral hormone secreted from target organs for the respective hormones and by secretion-accelerating or -inhibiting hormone from hypothalamus, which is the upper central organ of anterior lobe of pituitary (in this specification, these hormones are collectively called "hypothalamic hormone"). At the present stage, as hypothalamic hormones, nine kinds of hormones including, for example, thyrotropin releasing hormone (TRH) or gonadotropin releasing hormone {GnRH: sometimes called as LH-RH (luteinizing hormone releasing hormone)} are confirmed their existence (cf. Seirigaku 2, compiled by M. Iriku and K. Toyama, published by Bunkohdo, p610–618, 1986). These hypothalamic hormones are assumed to show their actions via the receptor which is considered to exist in the anterior lobe of pituitary (cf. ibid), and observational studies of receptor genes specific to those hormones, including cases of human, have been developed (Receptor Kiso To Rinsho, compiled by H. Imura, et al., published by Asakura Shoten, p297–304, 1993). Accordingly, antagonists or agonists specifically and selectively acting on these receptors control the action of hypothalamic hormone and controlling the secretion of anterior pituitary hormone. As the results,they are expected to be useful for prophylactic and therapeutic agents of anterior pituitary hormone dependent diseases.

Leuprorelin acetate [Fujino et al., Biological and Biophysical Research Communications, Vol.60, 00.406–413, 1974); Oliver, R. T. D. et al., British Journal of Cancers, Vol.59, p.823, 1989; and Toguchi et al., Journal of International Medical Research, Vol.18, pp. 35–41], which is a highly potent derivative of gonadotropic hormone-releasing hormone, one of the hypothalamic hormones, (hereinafter sometimes abbreviated as GnRH) [Schally A. V. et at., Journal of Biological Chemistry, Vol. 246, pp.7230–7236, 1971; and Burgus, R. et al., Proceeding of Natural Academic Science, USA, Vol.69, pp278–282, 1972], by administration of multiple doses, lowers release.production of gonadotropic hormone in pituitary, causing lowering of reactivity on gonadotropic hormone is spermary and ovary to suppress secretion of testosterone and estrogen. Leuprorelin acetate has, therefore, been known to show antitumor activity on such hormone-dependent cancers as exemplified by prostate cancer, and has been widely used in the clinical field. Leuprorelin acetate has been widely used clinically also as a therapeutic agent of e.g. endometriosis and precocious puberty. The high antitumor activity of leuprorelin acetate is assumed to be due to its high resistance, as compared with natural GnRH, against protease,and to high affinity to GnRH receptor causing desensitization of GnRH due to decrease in number of receptors. However, as leuprorelin acetate is an ultra-agonist on GnRH receptor, it has been known that, immediately after the first administration, a transient aggravation accompanied with the rise of serum testosterone concentration due to pituitary-gonadotropic action (acute action) is observed. Circumstances being such as above, GnRH antagonistic drugs which are expected to have substantially the same therapeutic effects as described above but not to cause the above-mentioned transient pituitary-gonadotropic action (acute action) have been desired. As compounds having such GnRH antagonistic activity, a number of compounds including, for example, derivatives of GnRH such as straight-chain peptides, (U.S. Pat. Nos. 5,140,009, 5,171,835), cyclic hexapeptide derivatives [JPA S61(1986)-191698] or bicyclic peptide derivatives [Journal of medicinal chemistry, Vol.36, pp.3265–3273, 1993]. These compounds are, however, all peptides, which leave many problems including, for example, dosage forms, stability of drugs, durability of actions and stability on metabolism. For solving these problems, orally administrable GnRH antagonistic drugs, especially non-peptide ones, are strongly desired. At the present stage, however, no report on non-peptide GnRH antagonistic drugs has been made.

An object of the first embodiment of the invention lies in providing novel compounds having excellent gonadotropic hormone releasing hormone antagonistic activity as well as excellent gonadotropic hormone releasing hormone antagonistic agents.

DISCLOSURE OF THE FIRST EMBODIMENT

Thus, the first embodiment of the present invention provides a pharmaceutical composition for antagonizing a gonadotropin-releasing hormone (GnRH) containing a condensed-bicyclic compound consisting of a homo or hetero 5 to 7 membered ring and a homo or hetero 5 to 7 membered ring. The first embodiment also provides novel condensed-ring thiophene derivatives and salts thereof. The first embodiment further provides methods for manufacturing the novel condensed-ring thiophene derivatives and the salts thereof.

More specifically, the first embodiment provides:

(1) A compound of the formula (I):

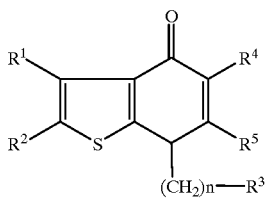

(I)

wherein $R^1$ and $R^2$ are each independently hydrogen or a group bonded through a carbon atom, a nitrogen atom or a sulfur atom;
$R^3$ is an optionally substituted homo- or hetero-cyclic group;
$R^4$ is hydrogen, formyl, cyano a lower alkyl group substituted by a group bonded through a sulfur atom or an optionally substituted hydroxyl group, a carbonyl group which may be substituted with an optionally substituted hydrocarbon residue, an esterified or amidated carboxyl group;
$R^5$ is hydrogen or a group bonded through a carbon atom;
n is 0 to 3;
with the proviso that the homo- or hetero-cyclic group shown by $R^3$ is not substituted by a group, which is described in EP-A-443568 and EP-A-520423, of the formula:

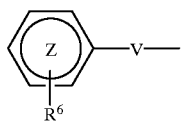

in which $R^6$ is an optionally substituted 5 to 7 membered heterocyclic group having as a group capable of constituting the ring, carbonyl, thiocarbonyl, an optionally oxidized sulfur atom or a group convertible them, a group capable of forming an anion or a group convertible into an anion;
Z is an optionally substituted aromatic hydrocarbon residue optionally containing a hetero atom or an optionally substituted heterocyclic group;
V is a chemical bond or a spacer group,
or a salt thereof,
(2) a compound according to (1), wherein $R^3$ is a group of the formula:

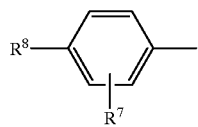

in which $R^7$ is hydrogen, halogen or a group bonded through a carbon atom, a nitrogen atom, an oxygen atom or a sulfur atom;
$R^8$ is hydrogen, halogen, nitro, cyano or a hydrocarbon residue which may be substituted by a group bonded through an oxygen atom, a nitrogen atom or a sulfur atom,
(3) a compound according to (1), wherein either one of $R^1$ or $R^2$ is a group of the formula:

$R^9$—$(CH_2)_m$— in which $R^9$ is a group bonded through a nitrogen atom;
m is 0 to 3, and the other one is a group of the formula:

$R^{10}$—A— in which $R^{10}$ is an optionally substituted phenyl; A is a chemical bond or a spacer group,
(4) a compound of the formula (II):

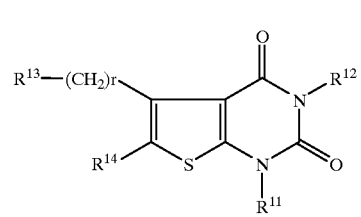

(II)

wherein $R^{11}$ is hydrogen, lower alkyl, a group of the formula:

Q—$(CH_2)_p$— in which Q is aryl which may be substituted by a) halogen, b) nitro, c) cyano, d) amino, e) an optionally substituted f) carboxyl, lower alkylenedioxy or g) a group of the formula: —A—$R^{15}$ in which A is a chemical bond or a spacer group, $R^{15}$ is alkyl, an optionally substituted cycloalkyl or an optionally substituted heterocyclic group;
$R^{12}$ is hydrogen, alkyl, an optionally substituted aryl, an optionally substituted aralkyl, an optionally substituted cycloalkyl; $R^{13}$ is an optionally substituted amino,;
$R^{14}$ is an optionally substituted aryl;
r is 0 to 3,
or a salt thereof,
(5) a compound according to (4), wherein $R^{11}$ is a group of the formula:

Q—$(CH_2)$—p— in which Q is aryl which may be substituted by a) halogen, b) nitro, c) cyano, d) amino, e) an optionally substituted f) carboxyl, lower alkylenedioxy or g) a group of the formula —A—$R^{15}$ in which A is a chemical bond or a spacer group, $R^{15}$ is alkyl,
(6) a compound according to (4), wherein Q is aryl which may be substituted by halogen,
(7) a compound according to (4), wherein $R^{13}$ is optionally substituted mono-aralkylamino,
(8) a compound according to (4), wherein $R^{13}$ is optionally substituted benzylamino,
(9) a compound according to (4), wherein $R^1$ is optionally substituted phenyl,
(10) a compound which is 3-(N-benzyl-N-methylaminomethyl)-4,7-dihydro-7-(2-methoxybenzyl)-2-(4-methoxyphenyl)-4-oxothieno]2,3-b]pyridine-5-carboxylic acid ethyl ester of its salt,
(11) a compound which is 3-(N-benzyl-N-methylaminomethyl)-4,7-dihydro-7-(2-fluorobenzyl)-2-(4-methoxyphenyl)-4-oxothieno[2,3-b]pyridine-5-carboxylic acid ethyl ester or its salt,

(12) a compound which is 2-(4-acetylaminophenyl)-3-(N-benzyl-N-methylaminomethyl)-4,7-dihydro-7-(2-fluorobenzyl)-4-oxothieno[2,3-b]pyridine-5-carboxylicacid ethyl ester or its salt,

(13) a compound which is 5-benzylaminomethyl-1-(2-chloro-6-fluorobenzyl)-2,4(1H,3H)-dioxo-6-(4-methoxyphenyl)-3-phenylthieno[32,3-d]pyrimidine or its salt,

(14) a compound which is 5-benzoyl-3-(N-benzyl-N-methylaminomethyl)-7-(2,6-difluorobenzyl)-4,7-dihydro-4-oxo-2-(4-propionylaminophenyl)thieno[2,3-b]pyridine or its salt,

(15) a compound which is 5-benzoyl-3-(N-benzyl-N-methylaminomethyl)-7-(2,6-difluorobenzyl)-4,7-dihydro-2-(4-N'-methylureidophenyl)-4-oxothieno[2,3-b]pyridine or its salt,

(16) a compound which is 3-(N-benzyl-N-methylaminomethyl)-7-(2,6-difluorobenzyl)-4,7-dihydro-5-isobutyryl-4-oxo-2-(4-propionylaminophenyl)-thieno[2,3-b]pyridine or its salt,

(17) a compound which is 3-(N-benzyl-N-methylaminomethyl)-7-(2,6-difluorobenzyl)-4,7-dihydro-5-isobutyryl-2-(4-N'-methylureidophenyl)-4-oxothieno[2,3-b]pyridine or its salt,

(18) a compound which is 3-(N-benzyl-N-methylaminomethyl)-7-(2,6-difluorobenzyl)-4,7-dihydro-2-(4-N'-methylureidophenyl)-4-oxothieno[2,3-b]pyridine-5-(N-isopropyl)carboxamide or its salt,

(19) a compound which is 3-(N-benzyl-N-methylaminomethyl)-7-(2,6-difluorobenzyl)-4,7-dihydro-2-(4-N'-methylureidophenyl)-4-oxothieno[2,3-b]pyridine-5-(N-isopropyl-N-methyl)carboxamide or its salt,

(20) a compound which is 3-(N-benzyl-N-methylaminomethyl)-7-(2,6-difluorobenzyl)-4,7-dihydro-2-(4-N'-methylureidophenyl)-4-oxothieno[2,3-b]pyridine-5-(N-benzyl-N-methyl)carboxamide or its salt,

(21) a method for producing a compound of (3), which comprises reacting a compound of the formula (III):

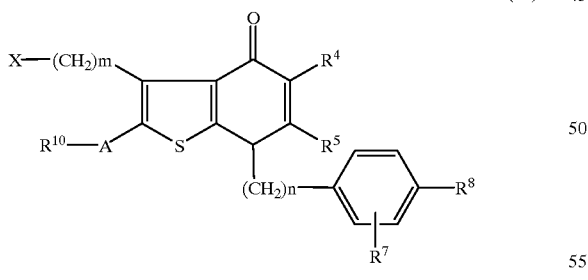

(III)

wherein $R^4$, $R^5$ and n are the same meaning as defined in (1);
$R^7$ and $R^8$ are the same meaning as defined in (2);
$R^{10}$ and m are the same meaning as defined in (3);
X is a leaving group; or a salt thereof, with a compound of the formula:

$R^9H$ wherein $R^9$ is the same meaning as defined in (3), or a salt thereof,

(22) a method for producing a compound of (5), which comprises reacting a compound of the formula (IV):

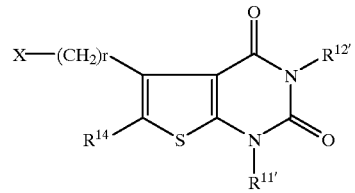

(IV)

wherein $R^{11'}$ is a group of the formula:

$Q—(CH_2)p—$ in which Q is aryl which may be substituted by a) halogen, b) nitro, c) cyamo, d) amino, e) an optionally substituted f) carboxyl, lower alkylenedioxy or g) a group of the formula: $—A—R^{15}$ in which A is a chemical bond or a spacer group, $R^{15}$ is alkyl;

$R^{12'}$ is alkyl, optionally substituted aryl, optionally substituted ararkyl or optionally substituted cycloalkyl;

$R^{14'}$ and r are the same meaning as defined in claim 4;

X is a leaving group; or a salt thereof, with a compound of the formula:

$R^{13}H$ wherein $R^{13}$ is the same meaning as defined in (4), or a salt thereof,

(23) a gonadotropin-releasing hormone antagonistic composition, which comprises an optionally substituted condensed-bycyclic compound consisting of a homo or hetero 5 to 7 membered and a homo or hetero 5 to 7 membered ring; carrier; excipient or diluent,

(24) a composition according to (23), wherein the optionally substituted condensed-bicyclic compound is a compound of the formula (IV):

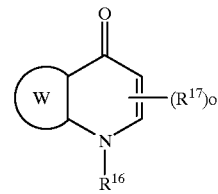

(V)

in which a ring W is an optionally substituted homo or hetero 5 to 7 membered ring;
$R^{16}$ is an optionally substituted hydrocarbone residue;
$R^{17}$ is hydrogen, or a group bonded through a carbon atom, a nitrogen atom, oxygen atom or sulfur atom;
o is 1 or 2,

(25) a composition according to (24), wherein the ring W is a ring the formula (VI):

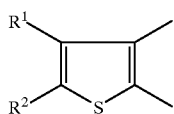

(VI)

in which R¹ and R² are each independently hydrogen, or a group bonded through a carbon atom, a nitrogen atom, oxygen atom or a sulfur atom,

(26) a composition according to (23), wherein the optionally substituted condensed-bicyclic compound is a compound of the formula (VII):

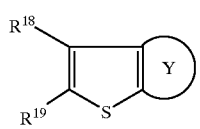

(VII)

in which a ring Y is an optionally substituted hetero 5 to 7 membered ring;
R¹⁸ and R¹⁹ are each independently an optionally substituted hydrocarbon residue,

(27) a composition according to (26), wherein the ring Y is a ring of the formula (VIII):

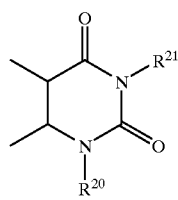

(VIII)

in which R²⁰ and R²¹ are each independently hydrogen, an optionally substituted hydrocarbon residue,

(28) a composition according to (23), which is a composition for preventing or treating a sex hormone dependent disease,

(29) a composition according to (23), which is a composition for preventing or treating a sex hormone dependent cancer, benign prostatic hypertrophy or myoma of the uterus,

(30) a composition according to (29), wherein the sex hormone dependent cancer is selected from the group consisting of prostatic cancer, uterus cancer, breast cancer and pitutiary adenoma,

(31) a composition according to (28), wherein the sex hormone depending disease is selected from the group consistion of prostatauxe, endometriosis, myoma uteri and precocious puberty,

(32) a pregnancy controlling composition, which comprises a compound or a salt thereof claimed in (23), carrier, excipient or diluent,

(33) a menstrual cycle controlling composition, which comprises a compound or a salt thereof claimed in (23), carrier, excipient or diluent, and

(34) a composition according to (32), which is a composition for contraception,

(35) a method for antagonizing gonadotropin-releasing hormone in a mammal in need thereof comprising administering an effective amount of a composition according to (23) to a mammal suffering from a gonadotropin-releasing hormone derived disorder,

(36) a method according to (35), wherein the gonadotropin-releasing hormone derived disorder is a sex hormone dependent disease,

(37) a method according to (35), wherein the gonadotropin-releasing hormone derived disorder is a sex hormone dependent cancer, benign prostatic hypertropy or myoma of the uterus,

(38) a method according to (37), wherein the sex hormone dependent cancer is selected from the group consisting of prostatic cancer, uterus cancer, breast cancer and pitutiary adenoma,

(39) a method according to (36), wherein the sex hormone depending disease is selected from the group consisting of prostatauxe, endometriosis, myoma uteri and precocious puberty,

(40) a method for controlling pregnancy in a mammal in need thereof comprising administering an effective amount of a composition according to (23),

(41) a method for controlling menstrual cycle in a mammal in need thereof comprising administering an effective amount of a composition according to (23),

(42) a method for contraception in a mammal in need thereof comprising administering an effective amount of a composition according to (23),

(43) a use of an optionally substituted condensed-bicyclic compound consisting of a homo or hetero 5 to 7 membered ring and a homo or hetero 5 to 7 membered ring for producing a gonadotropin-releasing hormone antagonistic composition for antagonizing gonadotropin releasing hormone in a mammal suffering from a gonadotropin-releasing hormone derived disorder,

(44) a use according to (43), wherein the gonadotropin-releasing hormone derived disorder is a sex hormone dependent disease,

(45) a use according to (43), wherein the gonadotropin-releasing hormone derived disorder is a sex hormone dependent cancer, benign prostatic hypertropy or myoma of the uterus,

(46) a use according to (45), wherein the sex hormone dependent cancer is selected from the group consisting of prostatic cancer, uterus cancer, breast cancer and pututiary adenoma,

(47) a use according to (45), wherein the sex hormone depending disease is selected from the group consisting of prostatauxe, endometriosis, myoma uteri and precocious puberty,

(48) a use of an optionally substituted condensed-bicyclic compound consisting of a homo or hetero 5 to 7 membered ring and a homo or hetero 5 to 7 membered ring for producing a gonadotropin-releasing hormone antagonistic composition for controlling pregnancy in a mammal in need thereof,

(49) a use of an optionally substituted condensed-bicyclic compound consisting of a homo or hetero 5 to 7 membered ring and a homo or hetero 5 to 7 membered ring for producing a gonadotropin-releasing hormone antagonistic composition for controlling menstrual cycle in a mammal in need thereof, and

(50) a use of an optionally substituted condensed-bicyclic compound consisting of a homo or hetero 5 to 7 membered ring and a homo or hetero 5 to 7 membered ring for producing a gonadotropin-releasing hormone antagonistic composition for contraception in a mammal in need thereof.

Examples of the groups bonded through the carbon atom shown by $R^1$, $R^2$, $R^5$ and $R^7$, include, each optionally substituted, alkyl (e.g. $C_{1-6}$ alkyl such as methyl, ethyl, propyl, isopropyl, butyl, t-butyl, pentyl and hexyl), cycloalkyl (e.g. $C_{3-6}$ cycloalkyl such as cyclopropyl, cyclopentyl and cyclohexyl), alkoxyalkyl (e.g. $C_{1-3}$ alkoxy-$C_{1-6}$ alkyl such as methoxymethyl, ethoxymethyl, ethoxybutyl and propoxyhexyl), hydroxyalkyl (e.g. $C_{1-6}$ alkyl such as hydroxymethyl, hydroxyethyl, hydroxybutyl and hydroxypropyl), alkenyl (e.g. $C_{2-6}$ alkenyl such as vinyl, butadienyl and hexatrienyl), formyl, carboxyl, alkoxycarbonyl (e.g. $C_{1-6}$ alkoxycarbonyl such as methoxycarbonyl, ethoxycarbonyl and t-butoxycarbonyl), cyano, amido, mono-, di-alkylcarbamoyl (e.g. mono-, di-$C_{1-6}$ alkylcarbamoyl such as methyl carbamoyl, ethylcarbamoyl, hexylcarbamoyl, dimethylcarbamoyl and methylethylcarbamoyl), amidino, aryl (e.g. $C_{6-14}$ aryl such as phenyl,naphthyl and anthracenyl), aralkyl (e.g. $C_{7-20}$ aralkyl such as benzyl, benzhydryl and trityl) and heterocyclic groups having a bond at the carbon atom (e.g. 5-membered cyclic groups containing, besides the carbon atom, 1 to 4 hetero-atoms selected from oxygen atom, sulfur atom and nitrogen atom, such as 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl and 1H- or 2H-tetrazolyl; 6-membered cyclic groups containing, besides the carbon atom, 1 to 4 hetero-atoms selected from oxygen atom, sulfur atom and nitrogen atom, such as N-oxido-2-, 3- or 4-pyridyl, 2-, 4- or 5-pyrimidinyl, N-oxido-2-, 4- or 5-pyrimidinyl, 2- or 3-thiomorpholinyl, 2- or 3-morpholinyl, oxoimidazinyl, dioxotriazinyl, pyrrolidinyl, piperidinyl, pyranyl, thiopyranyl, 1,4-oxadinyl, 1,4-thiazinyl, 1,3-thiazinyl, 2- or 3-piperazinyl, triazinyl, oxotriazinyl, 3- or 4-pyridazinyl, pyrazinyl and N-oxido-3- or 4-pyridazinyl; and 5- to 8-membered cyclic groups or condensed ring thereof containing, besides the carbon atom, 1 to 4 hetero-atoms e.g. oxygen atom, sulfur atom or nitrogen atom, for example, bicyclic or tricyclic condensed cyclic groups containing, besides the carbon atom, 1 to 4 hetero-atoms selected from oxygen atom, sulfur atom and nitrogen atom, such as benzofuryl, benzothiazolyl, benzoxazolyl, tetrazolo[1,5-b] pyridazinyl, triazolo[4,5-b]pyridazinyl, benzoimidazolyl, quinolyl, isoquinolinyl, cinnolinyl, phthalazinyl, quinazolinyl, quinoxalinyl, indolizinyl, quinolizinyl, 1,8-naphthylizinyl, purinyl, pteridinyl, dibenzofuranyl, carbazolyl, acrydinyl, phenanthridinyl, chromanyl, benzoxazinyl, phenazinyl, phenothiazinyl and phenoxazinyl).

Examples of the substituents, which the above-mentioned groups bonded through the carbon atom may have, include $C_{6-14}$ aryl (e.g. phenyl and naphthyl) optionally substituted with 1 to 4 substituents selected from, for example, (a) hydroxyl, (b) amino, (c) mono- or di-$C_{1-6}$ alkyl amino (e.g. methylamino, ethylamino, propylamino, propylamino, dimethylamino and diethylamino) and (d) $C_{1-6}$ alkoxy (e.g. methoxy, ethoxy, propoxy and hexyloxy) and (e) halogen (fluorine, chlorine, bromine, iodine); mono- or di-$C_{1-6}$ alkylamino (e.g. methylamino, ethylamino, propylamino, dimethylamino and diethylamino); $C_{1-4}$ acylamino (e.g. formylamino and acetylamino); hydroxyl; carboxyl; nitro; $C_{1-6}$ alkoxy (e.g. methoxy, ethoxy, propoxy, isopropoxy and butoxy); $C_{1-6}$ alkyl-carbonyloxy (e.g. acetoxy and ethyl carbonyloxy)), halogen (e.g. fluorine, chlorine, bromine and iodine), and such optionally substituted groups bonded through nitrogen atom as described below. Number of the substituents ranges from 1 to 6, preferably 1 to 3.

Examples of the groups bonded through nitrogen atom shown by $R^1$, $R^2$, $R^7$, $R^9$ and $R^{17}$, include, each optionally substituted, groups shown by

—$NR^{22}R^{23}$ wherein $R^{22}$ is hydrogen, alkyl, cycloalkyl, aryl, heterocyclic groups and —SOp— (p is 1 to 2) and $R^{14}$ is hydrogen or alkyl, and heterocyclic groups bonded through a nitrogen atom (e.g. 1H-1-pyrrolyl, 1-imidazolyl, pyrazolyl, indolyl, 1H-1-indazolyl, 7-purinyl, 1-pyrrolidinyl, 1-pyrrolinyl, 1-imidazolidinyl, pyrazolidinyl, piperazinyl, pyrazolidinyl, 4-morpholinyl and 4-thiomorpholinyl). Said alkyl, cycloalkyl, aryl and a heterocyclic group are the same meaning as described in the above.

Examples of the substituents, which the group bonded through nitrogen atom may have, include $C_{1-6}$ alkyl (e.g. methyl, ethyl, propyl, isopropyl, butyl, isobutyl, sec-butyl and tert-butyl), $C_{2-6}$ alkenyl (e.g. vinyl, 1-methylvinyl, 1-propenyl and allyl), $C_{2-6}$ alkynyl (e.g. ethynyl, 1-propynyl and propargyl), $C_{3-6}$ cycloalkyl (e.g. cyclopropyl, cyclobutyl, cyclopentyl and cyclohexyl), $C_{5-7}$ cycloalkenyl (e.g. cyclopentenyl and cyclohexenyl), $C_{7-11}$ aralkyl (e.g. benzyl, α-methylbenzyl and phenethyl), $C_{6-14}$ aryl (e.g. phenyl and naphthyl), $C_{1-6}$ alkoxy (e.g. methoxy, ethoxy, propoxy, isopropoxy, n-butoxy, isobutoxy, sec-butoxy and tert-butoxy), $C_{6-14}$ aryloxy (e.g. phenoxy), $C_{1-6}$ alkanoyl (e.g. formyl, acetyl, propionyl, n-butyryl and isobutyryl), $C_{6-14}$ aryl-carbonyl (e.g. benzoyl), $C_{1-6}$ alaknoyloxy (e.g. formyloxy, acetyloxy, propionyloxy and iso-butyryloxy), $C_{6-14}$ aryl-carbonyloxy (e.g. benzoyloxy), carboxyl, $C_{1-6}$ alkoxy-carbonyl (e.g. methoxycarbonyl, ethoxycarbonyl, n-propoxycarbonyl, iso-propoxycarbonyl, n-butoxycarbonyl, isobutoxycarbonyl and tert-butoxycarbonyl), carbamoyl group, N-mono-$C_{1-4}$ alkylcarbamoyl (e.g. N-methylcarbamoyl, N-ethylcarbamoyl, N-propylcarbamoyl, N-isopropylcarbamoyl and N-butylcarbamoyl), N,N-di-$C_{1-4}$ alkylcarbamoyl (e.g. N,N-di methylcarbamoyl, N,N-diethylcarbamoyl, N,N-dipropylcarbamoyl and N,N-dibutylcarbamoyl), cyclic aminocarbonyl (e.g. 1-aziridinylcarbonyl, 1-azetidinylcarbonyl, 1-pyrrolidinylcarbonyl, 1-piperidinylcarbonyl, N-methylpiperazinylcarbonyl and morpholinocarbonyl), halogen (fluorine, chlorine, bromine and iodine), mono- or tri-halogeno-$C_{1-4}$ alkyl (e.g. chloromethyl, dichloromethyl, trifluoromethyl and trifluoroethyl), oxo group, amidino, imino group, amino, mono- or di $C_{1-4}$ alkylamino (e.g. methylamino, ethylamino, propylamino, isopropylamino, butylamino, dimethylamino, diethylamino, dipropylamino, diisopropylamino and dibutylamino), 3- to 6-membered cyclic amino group containing, besides the carbon atom and one nitrogen atom, 1 to 3 hetero-atoms selected from oxygen atom, sulfur atom and nitrogen atom (e.g. aziridinyl, azetidinyl, pyrrolidinyl, pyrrolinyl, pyrrolyl, imidazolyl, pyrazolyl, imidazolidinyl, piperidino, morpholino, dihydropyridyl, N-methylpiperazinyl and N-ethylpiperazinyl), $C_{1-6}$ alkanoylamino (e.g. formamide, acetamide, trifluoroacetamide, propionylamindo, butyrylamido and isobutyrylamido), benzamido, carbamoylamino, N-$C_{1-4}$ alkylcarbamoylamino (e.g.

N-methylcarbamoylamino), N-ethylcarbamoylamino, N-propylcarbamoylamino, N-isopropylcarbamoylamino and N-butylcarbamoylamino), N,N-di-$C_{1-4}$ alkylcarbamoylamino (e.g. N,N-dimethylcarbamoylamino, N,N-diethylcarbamoylamino, N,N-dipropylcarbamoylamino and N,N-dibutylcarbamoylamino), $C_{1-3}$ alkylenedioxy (e.g. methylenedioxy and ethylenedioxy), —B(OH)$_2$, hydroxyl, epoxy (—O—), nitro, cyano, mercapto, sulfo, sulfino, phosphono, dihydroxyboryl, sulfamoyl, $C_{1-6}$ alkylsulfamoyl, (e.g. N-methylsulfamoyl, N-ethylsulfamoyl, N-propylsulfamoyl, N-isopropylsulfamoyl and N-butyl sulfamoyl), di-$C_{1-6}$ alkylsulfamoyl (e.g. N,N-dimethylsulfamoyl, N,N-diethylsulfamoyl, N,N-dipropylsulfamoyl and N,N-dibutylsulfamoyl), $C_{1-6}$ alkylthio (e.g. methylthio, ethylthio, propylthio, isopropylthio, n-butylthio, sec-butylthio and tert-butylthio), phenylthio, $C_{1-6}$ alkylsulfinyl (e.g. methylsulfinyl, ethylsulfinyl, propylsulfinyl and butylsulfinyl), phenylsulfinyl, $C_{1-6}$ alkylsulfonyl (e.g. methylsulfonyl, ethylsulfonyl, propylsulfonyl and butylsulfonyl), and phenylsulfonyl. The number of the substituents ranges from 1 to 6, preferably 1 to 3.

Examples of the groups bonded through oxygen atom shown by $R^1$, $R^2$ and $R^7$, include hydroxyl, each optionally substituted, alkoxyl, cycloalkoxy, aryloxy, aralkyloxy and heterocyclic hydroxyl groups. The alkyl, cyloalkyl, aryl, aralkyl and heterocyclic groups, in the said alkoxy, cycloalkoxy, aryloxy, aralkyloxy and heterocyclic hydroxyl groups, are of the same meaning as above.

The substituents, which the said oxygen atom may have, are of the same meaning as that of the above-mentioned groups bonded through nitrogen atom.

Examples of the groups bonded through sulfur atom, shown by $R^1$, $R^2$, $R^7$ and $R^{12}$, include mercapto, alkylthio, cycloalkylthio, arylthio, aralkylthio and heterocyclic thio groups. The alkyl, cycloalkyl, aryl, aralkyl and heterocyclic groups, in the said alkylthio, cycloalkylthio, arylthio, aralkylthio and heterocyclic thio groups, are of the same meaning as defined above.

The substituents, which the said sulfur atom may have, are of the same meaning as that of the substituents which the above-mentioned optionally substituted groups bonded through nitrogen atom may have.

Examples homocyclic groups in the optionally substituted homocyclic groups shown by $R^3$ include 3- to 7-membered cyclic hydrocarbon groups consisting of only carbon atoms, for example, $C_{3-7}$ cycloalkane (e.g. cyclopropane, cyclobutane, cyclopentane, cyclohexane and cycloheptane) and $C_{3-7}$ cycloalkene (e.g. cyclopropene, cyclobutene, cyclopentene, cyclohexene and cycloheptene).

Examples of the substituents which the said homocyclic groups may have, include $C_{1-15}$ alkyl (e.g. methyl, ethyl, propyl, isopropyl, butyl, isobutyl, s-butyl, t-butyl, pentyl, hexyl, heptyl, octyl, nonyl, decyl, undecyl, dodecyl, tridecyl, tetradecyl and pentadecyl), $C_{3-10}$ cycloalkyl (e.g. cyclopropyl, cyclobutyl, cyclopentyl and cyclohexyl), $C_{2-10}$ alkenyl (e.g. vinyl, allyl, 2-methylallyl, 2-butenyl, 3-butenyl and 3-octenyl), $C_{2-10}$ alkynyl (e.g. ethynyl, 2-propynyl and 3-hexynyl), $C_{3-10}$ cycloalkyl (e.g. cyclopropenyl, cyclopentenyl and cyclohexenyl), $C_{6-10}$ aryl (e.g. phenyl and naphthyl), $C_{1-19}$ aralkyl, (e.g. benzyl, phenylethyl and trityl), nitro, hydroxyl, mercapto, oxo, thioxo, cyano, carbamoyl, carboxyl, $C_{1-5}$ alkoxy-carbonyl (e.g. methoxycarbonyl and ethoxycarbonyl), sulfo, halogen (e.g. fluorine, chlorine, bromine and iodine), $C_{1-6}$ alkoxy (e.g. methoxy, ethoxy, propoxy, isopropoxy, butoxy, isobutoxy, s-butoxy and t-butoxy), $C_{6-10}$ aryloxy (e.g. phenoxy), $C_{1-6}$ alkylthio (e.g. methylthio, ethylthio, n-propylthio, isopropylthio, n-butylthio and t-butylthio), $C_{6-10}$ arylthio (e.g. phenylthio), $C_{1-6}$ alkylsulfinyl (e.g. methylsulfinyl and ethylsulfinyl), $C_{6-10}$ arylsulfinyl (e.g.phenylsulfinyl), $C_{1-6}$ alkylsulfonyl (e.g. methylsulfonyl and ethylsulfonyl), $C_{6-10}$ arylsulfonyl (e.g. phenylsulfonyl), amino, $C_{1-6}$ acylamino (e.g. acetylamino and propylamino), mono- or di-$C_{1-4}$ alkylamino (e.g. methylamino, ethylamino, n-propylamino, isopropylamino, n-butylamino, dimethylamino and diethylamino), $C_{3-8}$ cycloalkylamino (e.g. cyclopropylamino, cyclobutylamino, cyclopentylamino and cyclohexylamino), $C_{6-10}$ arylamino (e.g. anilino), $C_{1-6}$ aralkyl (e.g. formyl, acetyl and hexanoyl), $C_{6-10}$ aryl-carbonyl (e.g. benzoyl), and 5- to 6-membered heterocyclic group containing, besides carbon atom, 1 to 4 hetero-atoms selected from oxygen, sulfur and nitrogen (e.g. 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, quinolyl, isoquinolyl and indolyl). Number the substituents ranges from 1 to 6, preferably from 1 to 3.

Examples of the above-mentioned optionally substituted heterocyclic groups shown by $R^3$ include 5-to 8-membered cyclic groups or condensed ring thereof containing, besides carbon atom, 1 to 4 hetero-atoms such as oxygen atom, sulfur atom and nitrogen atom, for example, 5-membered cyclic groups containing, besides carbon atom, 1 to 4 hetero-atoms selected from oxygen atom, sulfur atom and nitrogen atom, as exemplified by 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3, 4- or 5-isoxazolyl, 3-, 4- or 5-isothiazolyl, 3- or 5-(1,2,4-oxadiazolyl), 1,3,4-oxazolyl, 3- or 5-(1,2,4-thiadiazolyl), 1,3,4-thiadiazolyl, 4- or 5-(1,2,3-thiadiazolyl), 1,2,5-thiadiazolyl, 1,2,5-thiadiazolyl, 1,2,3-triazolyl, 1,2,4-triazolyl, and 1H- or 2H-tetrazolyl; 6-membered cyclic groups containing, besides, carbon atom, 1 to 4 hetero-atoms selected from oxygen atom, sulfur atom and nitrogen atom, as exemplified by N-oxido-2-, 3- or 4-pyridyl, 2-, 4- or 5-pyrimidinyl, N-oxido-2-, 4-or 5-pyrimidinyl, thiomorpholinyl, morpholinyl, oxoimidazinyl, dioxotriazinyl, pyrrolidinyl, piperazinyl, pyranyl, thiopyranyl, 1,4-oxadinyl, 1,4-thiazinyl, 1,3-thiazinyl, piperazinyl, triazinyl, oxotriazinyl, 3- or 4-pyridazinyl, pyrazinyl and N-oxido-3- or 4-pyridazinyl; bicyclic or tricyclic condensed ring groups containing, besides carbon atom, 1 to 4 hetero-atoms selected from oxygen atom, sulfur atom and nitrogen atom, as exemplified by benzofuryl, benzothiazolyl, benzoxazolyl, tetrazolo[1,4-b]pyridazinyl, triazolo[4,5-b]pyridazinyl, benzoimidazolyl, quinolyl, isoquinolyl, cinnolinyl, phthaladinyl, quinazolinyl, quinoxalinyl, indolidinyl, quinolidinyl, 1,8-napthylidinyl, purinyl, pteridinyl, dibenzofuranyl, carbazolyl, acridinyl, phenathridinyl, chromanyl, benzoxadinyl, phenazinyl, phenothiazinyl and phenoxazinyl.

Examples of substituents, which said heterocyclic groups may have, $C_{1-6}$ alkyl (e.g. methyl,ethyl, propyl, isopropyl, butyl, isobutyl, sec-butyl and tert-butyl), $C_{2-6}$ alkenyl (e.g. vinyl,1-methylvinyl, 1-propenyl and allyl), $C_{2-6}$ alkynyl (e.g. ethynyl, 1-propinyl and propargyl), $C_{3-6}$ cycloalkyl (e.g. cyclopropyl, cyclobutyl, cyclopentyl) and cyclohexyl), $C_{5-7}$ cycloalkenyl (e.g. cyclopentenyl and cyclohexenyl), $C_{7-11}$ aralkyl (e.g. benzyl, a-methylbenzyl and phenethyl), $C_{6-14}$ aryl (e.g. phenyl and naphthyl), $C_{1-6}$ alkoxy (e.g.methoxy, ethoxy, propoxy, iso-propoxy, n-butoxy, iso-butoxy, sec-butoxy and tert-butoxy), $C_{6-14}$ aryloxy (e.g.

phenoxy), $C_{1-6}$ alkanoyl (e.g. formyl, acetyl, propionyl, n-butyryl and iso-butyryl), $C_{6-14}$ aryl-carbonyl (e.g. benzoyl), $C_{1-6}$ alkanoyloxy (e.g. formyloxy, acetyloxy, propionyloxy, n-butyryloxy and isobutyryloxy), $C_{6-14}$ aryl-carbonyloxy (e.g. benzoyloxy), carboxyl, $C_{1-6}$ alkoxy-carbonyl (e.g. methoxycarbonyl, ethoxycarbonyl, n-propoxycarbonyl, iso-propoxycarbonyl, n-butoxycarbonyl, isobutoxycarbonyl and tert-butoxycarbonyl), carbamoyl group, N-mono-$C_{1-4}$ alkylcarbamoyl (e.g. N-methylcarbamoyl, N-ethylcarbamoyl, N-propylcarbamoyl, N-isopropylcarbamoyl and N-butylcarbamoyl), N,N-di-$C_{1-4}$ alkylcarbamoyl (e.g. N,N-dimethylcarbamoyl, N,N-diethylcarbamoyl, N,N-dipropylcarbamoyl and N,N-dibutylcarbamoyl), cyclic aminocarbonyl (e.g. 1-aziridinylcarbonyl, 1-azetidinylcarbonyl, 1-pyrrolidinylcarbonyl, 1-piperidinylcarbonyl, N-methylpiperazinylcarbonyl and morpholinocrbonyl), halogen (fluorine, chlorine, bromine, iodine), mono-, di or tri-halogeno $C_{1-4}$ alkyl (e.g. chloromethyl, dichloromethyl, trifluoromethyl and trifluoroethyl), oxo group, amidino, imino group, amino, mono- or di-$C_{1-4}$ alkylamino (e.g. methylamino, ethylamino, propylamino, isopropylamino, butylamino, dimethylamino, diethylamino, dipropylamino, diisopropylamino and dibutylamino), 3- to 6-membered cyclic amino group optionally containing, besides carbon atoms and one nitrogen atom, 1 to 3 hetero-atoms selected from oxygen atom, sulfur atom and nitrogen atom (e.g. aziridinyl, azetidinyl, pyrrolidinyl, pyrrolinyl, pyrrolyl, imidazolyl, pyrazolyl, imidazolidinyl, piperidino, morpholino, dihydropyridyl, pyridyl, N-methylpiperazinyl and N-ethylpiperazinyl), $C_{1-6}$ alkanoylamino (e.g. formamido, acetamido, trifluoroacetamido, propionylamido, butylamido and isobutyrylamido), benzamide, carbamoylamino, N-$C_{1-4}$ alkylcarbamoylamino (e.g. N-methylcarbamoylamino, N-ethylcarbamoylamino, N-propylcarbamoylamino, N-isopropylcarbamoylamino and N-butylcarbamoylamino), N,N-di-$C_{1-4}$ alkylcarbamoylamino (e.g. N,N-dimethylcarbamoylamino, N,N-diethylcarbamoylamino, N, N-dipropylcarbamoylamino and N,N-dibutylcarbamoylamino), $C_{1-3}$ alkylenedioxy (e.g. methylenedioxy and ethylenedioxy), —B(OH)$_2$, hydroxyl, epoxy (—O—), nitro, cyano, mercapto, sulfo, sulfino, phosphono, dihydroxyboryl, sulfamoyl, $C_{1-6}$ alkylsulfamoyl (e.g. N-methylsulfamoyl, N-ethylsulfamoyl, N-propylsulfamoyl, N-isopropylsulfamoyl and N-butylsulfamoyl), di-$C_{1-6}$ alkylsulfamoyl (e.g. N,N-dimethylsulfamoyl, N,N-diethylsulfamoyl, N,N-dipropylsulfamoyl and N,N-dibutylsulfamoyl), $C_{1-6}$ alkylthio (e.g. methylthio, ethylthio, propylthio, isopropylthio, n-butylthio, sec-butylthio and tert-butylthio), phenylthio, $C_{1-6}$ alkylsulfinyl (e.g. methylsulfinyl, ethylsulfinyl, propylsulfinyl and butylsulfinyl), phenylsulfinyl, $C_{1-6}$ alkylsulfonyl (e.g. methylsulfonyl, ethylsulfonyl, propylsulfonyl and butylsulfonyl) and phenylsulfonyl. Number of the substituents ranges from 1 to 6, preferably 1 to 3.

As the ester group in the optionally esterified carboxyl group shown by $R^4$, mention is made of, for example, alkyl, cycloalkyl, aryl and heterocyclic groups, and these are of the same meaning as defined above.

Examples of the amidated carboxyl groups shown by $R^4$ include groups shown by —CONR$^{22}$R$^{23}$ (wherein R$^{22}$ and R$^{23}$ are of the same meaning as defined above).

As the lower alkyl in the lower alkyl substituted by a group bonded through a sulfur atom shown by $R^4$, mentioned is made of, for example, $C_{1-6}$ alkyl such as methyl, ethyl, propyl, i-propyl, butyl, i-butyl, s-butyl, pentyl, hexyl and the like. The group bonded through a sulfur atom is as the same meaning as defined above.

The lower alkyl in the lower alkyl substituted by an optionally substituted hydroxyl shown by $R^4$ is the same meaning as defined above.

As substituents on the lower alkyl group, having optionally substituted hydroxyl, shown by the above-mentioned $R^4$, use is made of, for example, $C_{1-6}$ alkyl (e.g. methyl, ethyl, n-propyl, i-propyl, n-butyl and tert-butyl) optionally having 1 to 4 substituents selected from halogen (e.g. chlorine, bromine and fluorine), $C_{6-10}$ aryl (e.g. phenyl and naphthyl), $C_{7-12}$ aralkyl (e.g. benzyl and phenylethyl) and nitro; $C_{6-10}$ aryl (e.g. phenyl and naphthyl) optionally having 1 to 4 substituents selected from halogen (e.g. chlorine, bromine and fluorine), $C_{1-6}$ alkyl (e.g. methyl, ethyl and n-propyl), $C_{1-10}$ aryl (e.g. phenyl and naphthyl); $C_{7-12}$ aralkyl (e.g. benzyl, phenylethyl and naphtylmethyl) optionally having 1 to 4 substituents selected from halogen, (e.g. chlorine, bromine and fluorine), $C_{1-6}$ alkyl (e.g. methyl, ethyl and and n-propyl), $C_{6-10}$ aryl (e.g. phenyl and naphthyl), $C_{7-12}$ aralkyl (e.g. benzyl and phenethyl) and nitro; $C_{1-6}$ alkyl-carbonyl (e.g. acetyl and propionyl) optionally having 1 to 3 substituents selected from formyl, halogen (e.g. chlorine, bromine and fluorine), $C_{1-6}$ alkyl (e.g. methyl, ethyl and n-propyl), $C_{6-10}$ aryl(e.g. phenyl and naphthyl), $C_{7-12}$ aralkyl (e.g. benzyl and phenylethyl) and nitro; $C_{6-10}$ aryloxy-carbonyl (e.g. phenyloxycarbonyl and naphthyloxycarbonyl) optionally having 1 to 4 substituents selected from halogen (e.g. chlorine, bromine and fluorine), $C_{1-6}$ alkyl (e.g. methyl, ethyl and n-propyl), $C_{6-10}$ aryl(e.g. phenyl and naphthyl), $C_{7-12}$ aralkyl (e.g. benzyl and phenylethyl)and nitro; $C_{6-10}$ aryl-carbonyl (e.g. benzoyl and naphthylcarbonyl) optionally having 1 to 4 substituents selected from halogen (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. benzyl and phenylethyl) and nitro; $C_{7-12}$ aralkyl-carbonyl (e.g.benzylcarbonyl and phenethylcarbonyl) optionally having 1 to 4 substituents selected from halogen (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. benzyl and phenethyl) and nitro; and pyranyl or furanyl, tri ($C_{1-4}$ alkyl) silyl (e.g. trimethylsilyl and triethylsilyl) optionally having 1 to 4 substituents selected from halogen (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. benzyl and phenethyl) and nitro.

As the hydrocarbon residue in the carbonyl group optionally substituted by the hydrocarbon residue, shown by $R^4$, mention is made of, for example, saturated or unsaturated hydrocarbon residues having up to 25 carbon atoms. Examples of them include alkyl (e.g. $C_{1-8}$ alkyl such as methyl, ethyl, propyl, isopropyl, butyl, t-butyl, pentyl and hexyl), cycloalkyl (e.g. $C_{3-6}$ cycloalkyl such as cyclopropyl, cyclobutyl and cyclohexyl), alkoxyalkyl (e.g. $C_{1-3}$ alkoxy-$C_{1-6}$ alkyl such as methoxymethyl, ethoxymethyl, ethoxybutyl and propoxyhexyl), alkenyl (e.g. $C_{2-6}$ alkenyl such as vinyl, butenyl, butadienyl and hexatrienyl), aryl (e.g. $C_{6-14}$ aryl such as phenyl, naphthyl and antracenyl) and aralkyl (e.g. $C_{7-20}$ aralkyl such as benzyl, benzhydrile and trityl).

The optionally substituted 5 to 7 membered heterocyclic group having as a group capable of constituting the ring, carbonyl, thiocarbonyl, an optionally oxidized sulfur atom or a group convertible them, shown by $R^6$, in the same meaning as defined on page 5, line 45 to page 9, line 35 of EP-A-0520423.

Examples of the anion-forming groups or groups convertible to amino, shown by the above-mentioned $R^6$, include carboxyl, $C_{1-4}$ alkoxycarbonyl, cyano, tetrazolyl, trifluoromethanesulfonic acid amido, phosphoric acid group and sulfonic acid group. As the spacer group shown by V, mention is made of, for example, —(C=O)—, —O—, —S—, —NH—, —(C=O)—NH—, —O—CH$_2$—, —S—CH$_2$— and —CH=CH—.

The optionally substituted aromatic hydrocarbon residue optionally containing a hetero atom and the optionally substituted heterocyclic group, shown by the ring Z, is the same meaning as defined on page 5, lines 38 to 44 of EP-A-0520423.

As the aryl shown by $R^{11}$ or in the optionally substituted aryl shown by $R^{12}$ and $R^{14}$, mention is made of, for example, mono cyclic- or condensed polycyclic-aromatic hydrocarbon residues. Preferable example of them includes $C_{6-14}$ aryl such as phenyl, naphthyl, anthryl, phenanthryl, acenaphthylenyl and the like. Among these, phenyl, 1-naphthyl and 2-naphthyl are more preferable.

The number of substituent is one or more, preferably one to three. Examples of the substituents include, $C_{1-3}$ alkyl (e.g. methyl, ethyl, propyl), $C_{2-4}$ alkenyl (e.g. vinyl, allyl, 2-buetnyl), $C_{3-4}$ alkynyl (e.g. propargyl, 2-butynyl), $C_{3-7}$ cycloalkyl (e.g. cyclopropyl, cyclobutyl, cyclopentyl, cyclohexyl), aryl (e.g. phenyl, naphthyl), 5- to 9-membered aromatic heterocyclic group having 1 to 4 hetero atoms selected from a nitrogen atom, an oxygen atom and a sulfur atom (e.g. furyl, thienyl, pyrrolyl, thiazolyl, imidazolyl, pyrazolyl, pyridyl), 5- to 9-membered nonaromatic heterocyclic group having 1 to 4 hetero atoms selected from a nitrogen atom, an oxygen atom and a sulfur atom (e.g. oxiranyl, azetidinyl, oxethanyl, thietanyl, pyrrolidinyl, tetrahydrofuryl, thioranyl, piperidinyl, tetrahydropyranyl, morpholinyl, thiomorpholinyl, piperazynyl), $C_{7-10}$ aralkyl (e.g. benzyl, phenethyl), amino, N-monosubstituted amino (e.g. N—$C_{1-6}$ alkyl amino such as methylamino, ethylamino, propylamino), N,N-disubstituted amino [e.g. N,N-di($C_{1-6}$ alkyl) amino such as dimethylamino, diethylamino], amidino, acyl (e.g. $C_{1-8}$ alkyl-carbonyl such as acetyl, propionyl, butyryl; $C_{6-14}$ aryl-carbonyl such as benzoyl; $C_{7-12}$ aralkyloxy-carbonyl such as benzyloxycarbonyl), carbamoyl, N-monosubstituted carbamoyl [e.g. N-($C_{1-6}$) alkyl)carbamoyl such as methylcarbamoyl, ethylcarbamoyl, ethylcarbamoyl, propylcarbamoyl], N,N-disubstituted carbamoyl [e.g. N,N-di($C_{1-6}$ alkyl)carbamoyl such as dimethylcarbamoyl, diethylcarbamoyl], sulfamoyl, N-monosubstituted sulfamoyl [e.g. N-($C_{1-6}$ alkyl)sulfamoyl such as methylsulfamoyl, ethylsulfamoyl, substituent (e.g. $C_{1-3}$ alkyl, halogen, $C_{1-3}$ alkylthio, hydroxyl), $C_{2-4}$ alkenyloxy (e.g. vinyloxy, allyloxy), cycloalkyloxy (e.g. $C_{3-7}$ cycloalkyloxy such as cyclopropyloxy, cyclobutyloxy), aralkyloxy (e.g. $C_{7-10}$ aralkyloxy such as benzyloxy), aryloxy (e.g. phenyloxy, naphthyloxy), mercapto, $C_{1-3}$ alkylthio (e.g. methylthio, ethylthio, propylthio), aralkylthio (e.g. $C_{7-10}$ aralkylthio such as benzylthio), arylthio (e.g. phenylthio, naphthylthio), $C_{1-3}$ alkylenedioxy (e.g. methylenedioxy, ethylenedioxy, propylenedioxy), sulfo, cyano, azide, nitro, nitroso, halogen *fulorine, chlorine, bromine iodine), and the like.

As the aralkyl in the optionally substituted aralkyl shown by $R^{12}$, mention is made of, for example, aryl-alkyl. The aryl is of the same meaning as defined above. Examples of the alkyl include $C_{1-6}$ alkyl such as methyl, ethyl, propyl, butyl, pentyl, hexyl. The substituents are of the same meaning as defined in the substituents which the above aryl, shown by $R^{12}$, may have.

As the cycloalkyl in the optionally substituted cycloalkyl shown by $R^{11}$ and $R^{12}$, mention is made of, for example, $C_{3-10}$ cycloalkyl and $C_{3-10}$ bicycloalkyl. The preferable examples of them include cyclolprolyl, cyclobutyl, cyclopentyl, cyclohexyl, cycloheptyl, cyclooctyl, bicyclo[2,2,1]heptyl, bicyclo[2,2,2]octyl, bicyclo[3,2,1]octyl, bicyclo[3,2,1]nonyl, bicyclo[4,2,1]nonyl, bicyclo[4,3,1]decyl. Among these, cyclopentyl and cyclohexyl are more preferable. The substituents are of the same meaning as definede in the substituents which aryl, shown by $R^{12}$, may have.

As the heterocyclic group in the optionally substituted heterocyclic group shown by $R^{11}$, mention is made of, for example, 5- to 13-membered aromatic heterocyclic group having one to four hetero atom(s) sedected from an oxygen atom, a sulfur atom and a nitrogen atom; or saturated or unsaturated non-aromatic heterocyclic group.

Examples of the aromatic heterocyclic group include an aromatic monocyclic heterocyclic group (e.g. furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl), an aromatic condensed-ring heterocyclic group {e.g. benzofuranyl, isobenzofuranyl, benzo[b]thienyl, indoryl, isoindoryl, 1H-indazolyl, benzoimidazolyl, benzoxazolyl, 1,2-benzoisoxazolyl, benzothiazolyl, 1,2-binzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyridazinyl, 1,2–4-tiazolo[4,3-a]pyridyl, 1,2,4-triazolo[4,3-b]pyridazinyl}.

Examples of the non-aromatic heterocyclic group include oxylanyl, azetizinyl, oxethanyl, thiethanyl, pyrrolidinyl, tetrahydrofuranyl, thiolanyl, piperidyl, tetrahydropyranyl, morpholinyl, thiomorpholinyl, piperazinyl.

The heterocyclic group may have one or more substituents, preferably one to three substituents. The substituents are of the same meaning as defined in the optionally substituted aryl shown by $R^{12}$.

As the substituents in the optionally substituted carboxyl group shown by Q, mention is made of, for example, alkyl, cycloalkyl, aryl, aralkyl, a heterocyclic group. These are of the same meaning as defined above.

As the lower alkylenedioxy shown by Q, mention is made of, for example, $C_{1-6}$ alkylenedioxy (e.g. methylenedioxy, ethylenedioxy, propylenedioxy, 2,2-dimethylmetylenedioxy).

As the lower alkyl shown by $R^{11}$, mention is made of, for example, $C_{1-6}$ alkyl (e.g. methyl, ethyl, propyl, isopropyl, butyl, t-butyl, pentyl, hexyl).

As the optionally substituted amino group shown by $R^{13}$, mention is made of, for example, a group of the formula: —NR$^{22'}$R$^{23'}$ wherein R$^{22'}$ is an optionally substituted aryl, an optionally substituted heterocyclic group;

R$^{23'}$ is hydrogen, an optionally substituted alkyl). The optionally substituted alkyl, optionally substituted cycloalkyl, optionally substituted aryl and optionally substituted heterocyclic group are of the same meaning as defined above.

As the spacer group shown by the symbol "A", mention is made of, fro example, $C_{1-4}$ alkylene (e.g. methylene, ethylene), $C_{2-6}$ (e.g. vinylene, butadienylene); a group of the formula: —(CH$_2$)cNR$^{24}$— in which c is 0 to 3, R$^{24}$ is hydrogen, $C_{1-6}$ alkyl (e.g. methyl, ethyl, butyl); a group of the formula: —CO—; a group of the formula: —CONR$^{22}$— in which R$^{22}$ is of the same meaning as defined above; —O—; —S—; a group of the formula: —NR$^{22}$S(O)e— in which e is 0 to 2, R$^{22}$ is of the same meaning as defined above.

Preferable example of the homo or hetero 5- to 7-membered ring group (ring W') in the optionally substituted condensed-bicyclic compound consisting of a homo or hetero 5- to 7-membered ring group (ring W') and a homo or hetero 5- to 7-membered ring group (ring Y') includes a homo or hetero 5- or 6-membered ring group, more preferably a hetero 5- or 6-membered cyclic group. The concrete examples of the ring W' include ring groups of the formulae:

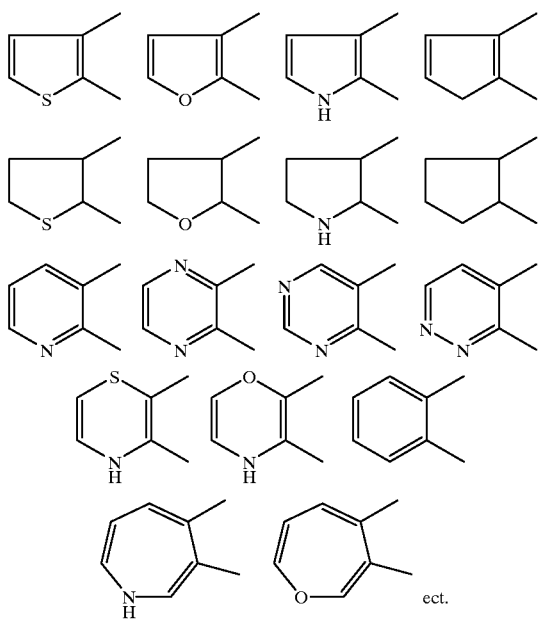

Among these cyclic groups, those of the formulae

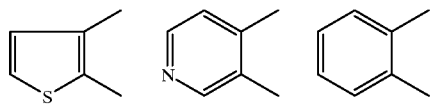

are preferable. Further, the cyclic group of the formula

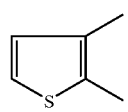

is especially preferable.

Most preferable example of the said W ring is that of the formula

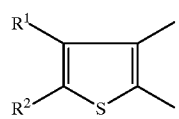

wherein R$^1$ and R$^2$ are of the same meaning as defined above.

Preferable example of the homo or hetero 5- to 7-membered ring group (ring Y') in the optionally substituted condensed-bicyclic compound consisting of a homo or hetero 5- to 7-membered ring group (ring W') and a homo or hetero 5- to 7-membered ring group (ring Y') includes a homo or hetero 6-membered ring group, more preferably a hetero 6-membered cyclic group. The concrete examples of the ring W' include ring groups of the formulae:

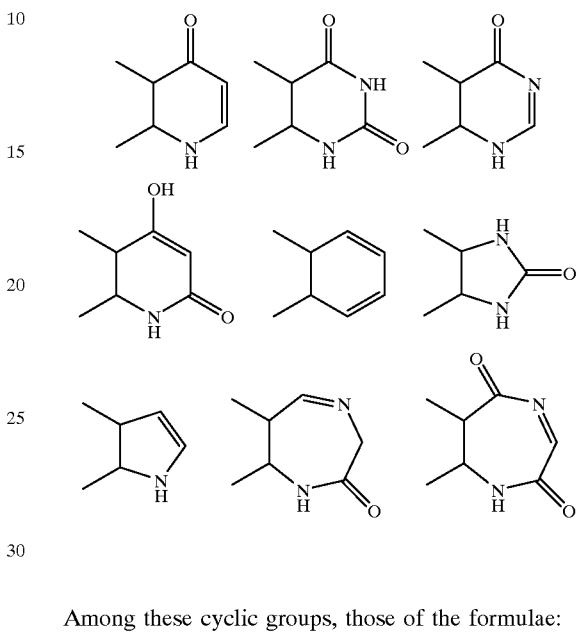

Among these cyclic groups, those of the formulae:

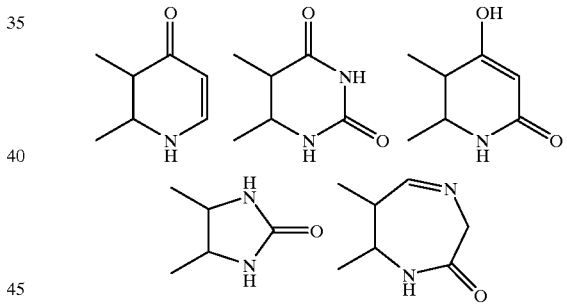

are preferable.

Further, the cyclic groups of the formulae:

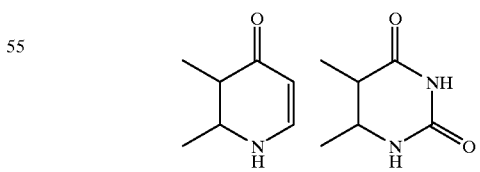

are more preferable.

More preferable examples of the said Y' ring is a ring group of the formula:

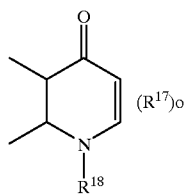

wherein $R^{16}$ is an optionally substituted hydrocarbons residue, $R^{17}$ is hydrogen, or a group bonded through a carbon atom, a nitrogen atom, oxygen atom or sulfur atom, o is 1 or 2;

or a ring group of the formula:

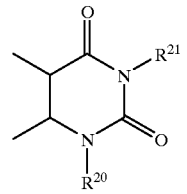

wherein $R^{20}$ and $R^{21}$ are each independently hydrogen, an optionally substituted hydrocarbon residure.

Examples of the hydrocarbon residues in the optionally substituted hydrocarbon residues shown by $R^{16}$, $R^{20}$ and $R^{21}$ include the alkyl, cycloalkyl, aryl and aralkyl described in the foregoing.

Examples of the substituents, which the said hydrocarbon residues may optionally have, include those optionally having 1 to 5 substituents selected from, for example, nitro, hydroxyl, oxo, thioxo, cyano, carbamoyl, carboxyl, $C_{1-4}$ alkoxy-carbonyl (e.g. methoxycarbonyl and ethoxycarbonyl), sulfo, halogen (fluorine, chlorine, bromine and iodine), $C_{1-6}$ alkoxy (e.g. methoxy, ethoxy, propoxy, isopropoxy, butoxy, isobutoxy, 2-butoxy and t-butoxy), $C_{6-12}$ aryloxy (e. g. phenoxy), halogeno $C_{6-16}$ aryl (e. g. o-, m- or p-chlorophenoxy, and o-, m- or p-bromophenoxy), $C_{1-6}$ alkylthio (e.g. methylthio, ethylthio, n-propiothio, isopropylthio, n-butylthio and t-butylthio), $C_{6-12}$ arylthio (e.g. phenylthio), $C_{1-6}$ (alkylsulfinyl (e.g. methylsulfinyl and ethylsulfinyl), $C_{1-6}$ alkylsulfonyl (e.g. methylsulfonyl and ethylsulfonyl), amino, $C_{1-6}$ acylamino (e.g. formylamino, acetylamino and propylamino), mono- or di-$C_{1-4}$ alkylamino (e.g. methylamino, ethyl amino, n-propyl amino, isopropylamino, n-butylamino, dimethylamino and diethylamino), $C_{1-6}$ (acyl (e. g. formyl, acetyl and hexanoyl), $C_{6-12}$ arylcarbonyl (e.g. benzoyl), 5- or 6-membered heterocyclic groups containing, besides carbon atoms, 1 to 4 hetero-atoms selected from oxygen, sulfur and nitrogen, as exemplified by 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1 H or 2H-tetrazolyl, 2-, 3- or 4-pyridyl, 2-, 4- or 5-pyrimidyl, 3- or 4-pyridazininyl, quinolyl, isoquinolyl and indolyl, and $C_{1-10}$ haloalkyl (e.g. difluoromethyl, trifluoromethyl, trifluoroethyl and trichloroethyl), and, in the case of the hydrocarbon group is cycloalkyl, cycloalkenyl, aryl or aralkyl group, $C_{1-6}$ alkyl (e.g. methyl, ethyl, propyl, isopropyl and butyl). The number of substituents ranges from 1 to 6, preferably 1 to 3.

The group bonded through a carbon atom, a nitrogen atom, an oxygen atom or a sulfur atom shown by $R^{17}$ is of the same meaning as defined above.

$R^1$ and $R^2$ are preferably such ones as either one of them being a group of the formula:

$$R^9\text{—}(CH_2)m\text{—}$$

wherein $R^9$ is a group bonded through nitrogen atom, and m is an integer of 0 to 3 and the other one being a group represented by the general formula:

$$R^{10}\text{—}A\text{—}$$

wherein $R^{10}$ is an optionally substituted phenyl group and A is spacer group.

The optionally substituted group, bonded through nitrogen atom, shown by the above-mentioned $R^9$ is of the same meaning as described above.

Examples of the substituents in optionally substituted phenyl group shown by the above-mentioned $R^{10}$ include halogen (fluorine, chlorine, bromine and iodine), $C_{1-8}$ alkyl (e.g. methyl, ethyl, propyl, isopropyl, butyl, isobutyl, sec-butyl, tert-butyl, pentyl, isopentyl and neopentyl) optionally substituted with 1 to 3 halogen atoms (fluorine, chlorine, bromine and iodine), $C_{1-8}$ alkoxy (e.g. methoxy, ethoxy, propoxy, isopropoxy, butoxy and isobutoxy) optionally substituted with 1 to 3 halogen atoms (e.g. fluorine, chlorine, bromine and iodine), $C_{1-8}$ alkylthio (e.g. methylthio, ethylthio, propylthio, isopropylthio, butylthio, sec-butylthio, tert-butylthio, pentylthio, isopentylthio and neopentylthio) optionally substituted with 1 to 3 halogen atoms (fluorine, chlorine, bromine and iodine), $C_{1-6}$ aralkyloxy (e.g. formyloxy, acetoxy and propionyloxy), hydroxyl, carboxyl, $C_{1-6}$ alkoxy-carbonyl (e.g.methoxycarbonyl, ethoxycarbonyl and t-butoxycarbonyl), cyano, nitro, amido, and mono- or di-$C_{1-6}$ alkylcarbamoyl (e.g. methylcarbamoyl, ethylcarbamoyl and dimethylcarbamoyl). The number of substituents ranges from 1 to 5, preferably 1 to 3.

The spacer groups shown by A is of the same meaning as defined above.

$R^3$ is preferably a group of the formula:

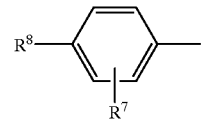

wherein $R^7$ is hydrogen or a group bonded through a carbon, nitrogen, oxygen or sulfur atom, and $R^8$, halogen, nitro, cyano or an optionally substituted aliphatic hydrocarbon residue bonded through oxygen, nitrogen or sulfur atom.

The above-mentioned optionally substituted groups bonded through carbon, nitrogen oxygen or sulfur atom, shown by $R^7$ are of the same meaning as defined above.

Examples of the optionally substituted aliphatic hydrocarbon residue, in the optionally substituted aliphatic hydrocarbon residue bonded through oxygen, nitrogen or sulfur atom shown by the above-mentioned $R^8$, include $C_{1-15}$ alkyl (e.g. methyl, ethyl, propyl, isopropyl, butyl, isobutyl, s-butyl, pentyl, hexyl, heptyl, octyl, nonyl, decyl, undecyl, dodecyl, tridecyl, tetradecyl and pentadecyl), $C_{3-8}$ cycloalkyl (e.g. cyclopropyl, cyclobutyl, cyclopentyl and cyclohexyl), $C_{2-10}$ alkenyl (e.g. vinyl, allyl, 2-methylallyl, 2-butenyl, 3-butenyl and 3-octenyl), $C_{2-10}$ alkynyl (e.g. ethynyl, 2-propynyl and 3-hexynyl)and $C_{1-6}$ alkoxy (e.g. methoxy, ethoxy, propoxy and butoxy). Examples of the substituents, which the said hydrocarbon group may have, include nitro, hydroxyl, oxo, thioxo, cyano, carbamoyl, carboxyl, $C_{1-4}$ alkoxy-carbonyl (e.g. methoxycarbonyl and ethoxycarbonyl), sulfo, halogen (fluorine, chlorine, bromine and iodine), $C_{1-4}$ alkoxy (e.g. methoxy, ethoxy, propoxy, isopropoxy, butoxy, isobutoxy, s-butoxy and t-butoxy), $C_{1-4}$ alkylthio (e.g. methylthio, ethylthio, n-propylthio, isopropylthio, n-butylthio and t-butylthio), amino, $C_{1-6}$ alkanoylamino (e.g. acetylamino and propionylamino), mono- or di-$C_{1-4}$ alkylamino (e.g. methylamino, ethylamino, n-propylamino, isopropylamino, n-butylamino, dimetylamino and diethylamino), $C_{1-4}$ alkanoyl (e.g. formyl, acetyl and propionyl), 5- or 6-membered heterocyclic groups containing, besides carbon atoms, 1 to 4 heteroatoms selected from oxygen, sulfur and nitrogen, which may optionally have 1 to 4 substituents selected from (a) halogen (e.g. fluorine, chlorine, bromine and iodine); and (b) $C_{1-4}$ alkyl (e.g. methyl, ethyl, propyl and isopropyl), as exemplified by 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, quinolyl, isoquinolyl and indolyl, and $C_{1-6}$ haloalkyl (e.g. difluoromethyl, trifluoromethyl, trifluoroethyl and trichloroethyl). Number of the substituents ranges from 1 to 4, preferably 1 to 3.

$R^{11}$ is preferably a group of the formula:

—(CH$_2$)pQ' wherein p is an integer of 1 to 3;

Q' is aryl which may be substituted by halogen, nitro, cyano, amino, an optionally substituted carboxyl group, lower alkylenedioxy or a group of the formula: —A—$R^{16}$ in which $R^{15}$ is a lower alkyl group, A is of the same meaning as defined above.

The aryl which may be substituted by halogen, nitro, cyano, amino, the optionally substituted carboxyl group, lower alkylenedioxy or the group of the formula: —A—$R^{16}$, shown by Q', are the of the same meaning as defined above. The lower alkyl group is of the same meaning as defined above.

Q' is preferably an aryl which may be substituted by halogen (fluorine, chlorine, bromine, nitrogen).

$R^{13}$ is preferably an optionally substituted monoaralkylamino. The optionally substituted aralkyl in the optionally substituted monoaralkylamino is of the same meaning as defined above. The aralkyl is preferably benzyl.

$R^{14}$ is preferably optionally substituted phenyl which is of the same meaning as defined above.

The optionally substituted condensed-bicyclic compound consisting of a homo or hetero 5- to 7-membered ring group and a homo or hetero 5- to 7-membered ring group is preferably a compound of the formula (V):

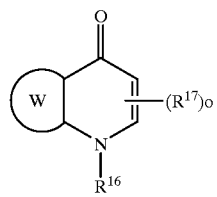

(V)

wherein ring W, $R^{16}$, $R^{17}$ and o are the same meaning as defined above; or a compound of the formula (VII):

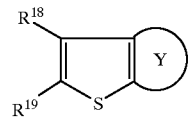

(VII)

wherein $R^{18}$ and $R^{19}$ are each independently an optionally substituted hydrocarbon residue and ring Y is of the same meaning as defined above.

The optionally substituted hydrocarbon residue shown by $R^{18}$ or $R^{19}$ is the same meaning as defined above.

The ring Y is preferably an optionally substituted hetero 5- to 7-membered ring group except for 4-pyridone. More preferably, the ring Y is a ring group of the formula (VIII):

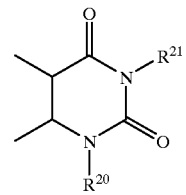

(VIII)

wherein $R^{20}$ and $R^{21}$ are of the same meaning as defined above.

The ring W is preferably a ring group of the formula (VI):

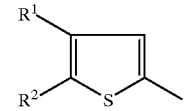

(VI)

wherein $R^1$ and $R^2$ are of the same meaning as defined above.

The compounds (I), (II), (VII) and their salts can be produced easily by per se known methods, as exemplified by the following production methods 1 to 16.

The above-mentioned optionally substituted condensed-bicyclic compound consisting of a homo or hetero 5- to 7-membered ring group and a homo or hetero 5- to 7-membered ring group can be produced by the production methods 1 to 16 or the same production methods thereof.

[Production Method 1]

In accordance with the method disclosed by K. Gewald, E. Schinke and H. BØttcher, Chem. Ber., 99, 94–100 (1966), an adequate ketone or aldehyde having an active methylene (i) was allowed to react with a cyanoacetic acid ester derivative and sulfur to convert into a 2-aminothiophene derivative (ii). More specifically, in the case of using ketone ($R^{1'}\neq H$), it is subjected to heating under reflux together with a cyanoacetic acid ester derivative, in the presence of acetic acid and ammonium acetate, in a proper solvent such as toluene to give an alkylidene cyanoacetic acid ester derivative, which is then heated in an adequate solvent, for example, ethanol in the presence of sulfur and a base to afford a 2-aminothiophene derivative (ii). And, in the case of using aldehyde ($R^{1'}=H$), it is heated in a proper solvent, for example, dimethylformamide, in the presence of a cyanoacetic acid ester derivative, sulfur and a base to give a 2-aminothiophene derivative (ii). The compound (ii) thus obtained is heated, in accordance with the method disclosed by Kuwata et al. [cf. German Patent 2,435,025], with diethyl ethoxymethylenemalonate to give an adduct (iii). The adduct is stirred in a solvent, which does not give undesirable effect on the reaction, (e.g. alcohols such as ethanol and methanol), in the presence of a base (e.g. alkali metal hydroxide such as potassium hydroxide and sodium hydroxide) at temperatures ranging from about 10 to 7° C. to give carboxylic acid (iv). Then, the carboxylic acid (iv) thus obtained was subjected to ring-closure by heating in polyphosphoric acid ester (PPE) to give a thieno[2,3-b]pyridine derivative (v). The compound (v) is stirred in a solvent, which does not give undesirable effect on the reaction, (e.g. amides such as dimethylformamide and hydrocarbons such as carbon tetrachloride and chloroform) in the presence of α, α'-azobisisobutyronitrile, at temperatures ranging from about 30 to 100° C. to give a compound (Ib). The compound (Ib) is stirred together with various amines in a solvent, which does not give undesirable effect on the reaction, (e.g. amides such as dimethylformamide and dimethylacetamide, nitrile such as acetonitrile and alcohols such as ethanol) in the presence of a base at temperatures ranging from about 10 to 100° C. to produce the compound (I). The production method 1 described above is shown in Scheme 1:

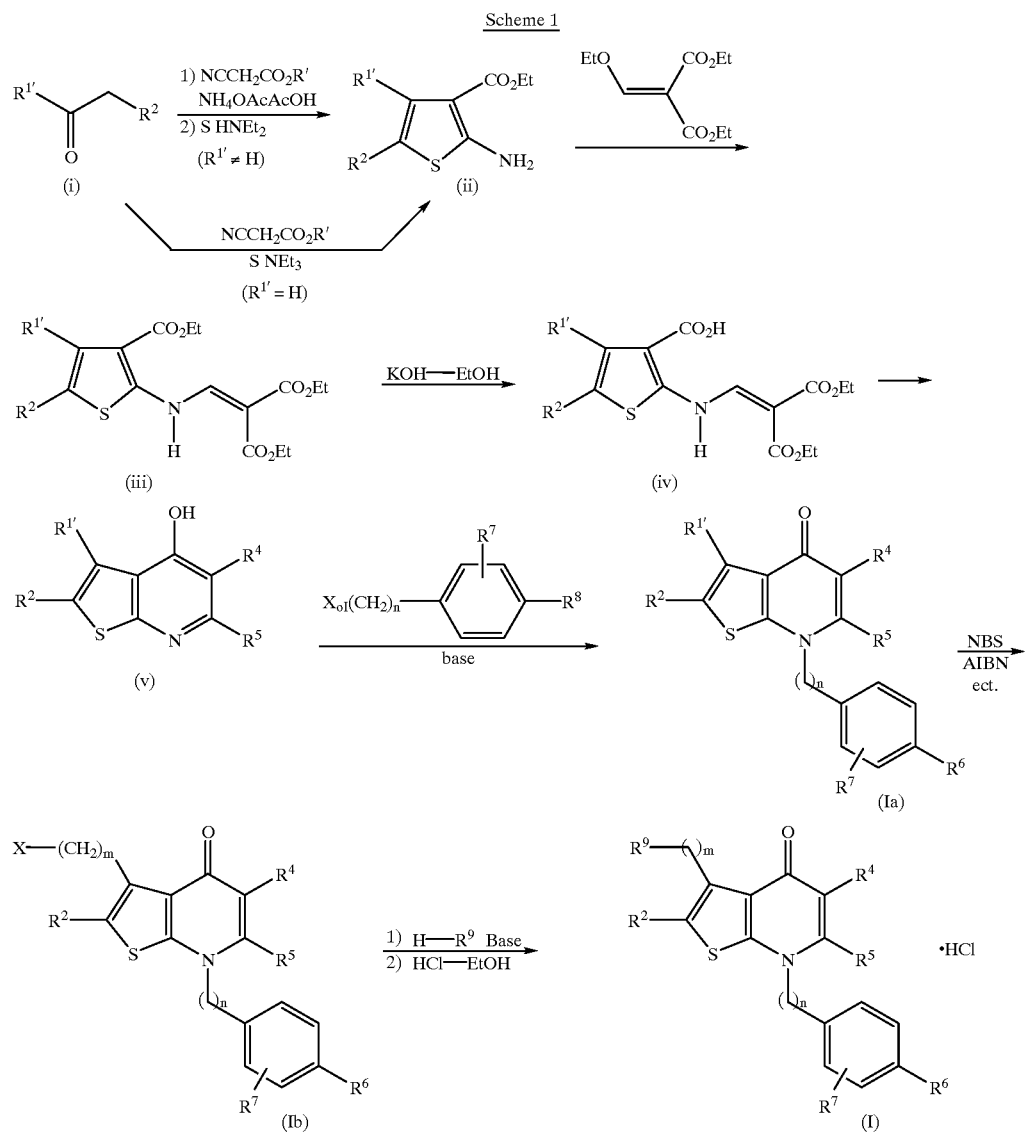

Scheme 1 dimethylacetamide), in the presence of a halogenated aralkyl derivative and a base (e.g. an organic base such as pyridine and triethylamine) at temperatures ranging from about 10 to 100° C. to give a 4,7-dihydro-4-oxothieno[2,3-b]pyridine-5-carboxylic acid ester derivative shown by the formula (Ia). Then, the compound (Ia) is stirred together with N-bromosuccinimide (NBS) in a solvent, which does not give undesirable effect on the reaction, (e.g. halogenated wherein $R^{1'}$ is hydrogen or an alkyl group, R' is an alkyl group, X is a leaving group, Xa is halogen, and $R^2$, $R^4$, $R^5$, $R^7$, $R^8$, $R^9$, m and n are of the same meaning as defined in the above.

The alkyl group shown by $R^{1'}$ and R' is of the same meaning as defined above.

As the leaving group shown by X, mention is made of, for example, a group which is potentially substituted by a nucleophilic reagent such as a hydrocarbon residue having a hetero atom (e.g. an oxygen atom, a sulfur atom, a nitrogen atom) being negatively charged. The preferable examples of the leaving group include halogen (e.g. iodine, bromine chlorine), alkanoyloxy (e.g. acetoxy), alkylsulfonyloxy (e.g. methanesulfonyloxy), alkyl-arylsulfonyloxy (e.g. p-toluenesulfonyloxy).

The halogen shown by Xa is fluorine, iodine, chlorine, iodine. Among these, bromine is more preferable.

[Production Method 2]

In substantially the same manner as in [production Method 1], a 2-aminothiophene derivative whose 5-position is unsubstituted (vi), which can be synthesized by the method disclosed by Karl Gewald [K. Gewald, Chem. Ber., 98, 3571–3577 (1965); K. Gewald and E. Schinke, Chem. Ber., 99, 2712–2715 (1966)] is allowed to react with diethyl ethoxymethylene malonate under heating, in accordance with the method disclosed by Kuwata et al. [German Patent 2,435,025], to give an adduct (vii). The adduct is stirred at temperatures ranging from about 10 to 60° C. in a solvent, which does not affect adversely on the reaction, (e.g. alcohols such as ethanol and methanol) in the presence of a suitable base (e.g. alkali metal hydroxide such as potassium hydroxide and sodium hydroxide to give carboxylic acid (viii). The compound (viii) is subjected to various cationoid substitution reactions and, depending on cases, to a suitable change of functional groups to introduce the substituent shown by $R^2$, which is then subjected to ring-closure reaction under heating in polyphosphoric acid ester (PPE) to give a thieno[2,3-b]pyridine derivative (ix). The compound (ix) is stirred together with a halogenated aralkyl derivative in a solvent, which does not affect adversely on the reaction, (e.g. amides such as dimethylformamide and dimethylacetamide), in the presence of a base, at temperatures ranging from about 10 to 100° C., to give a 4,7-dihydro-4-oxothieno[2,3-b]pyridine-5-carboxylic acid ester derivative shown by the formula (Ia). As the cationoid substitution reaction, mention is made of, for example, nitration (fuming nitric acid—concentrated sulfuric acid, sodium nitrate—concentrated sulfuric acid), acylation (acid chloride—aluminum chloride), formylation (phosphorus oxychloride—dimethylformamide or N-methylformanilide) and bromination (N-bromosuccinimide, bromine-pyridine). The compound (Ia) is then processed in substantially the same manner as in [Production Method 1] to produce the compounds (Ib) and (I). The Production Method 2 is shown in Scheme 2:

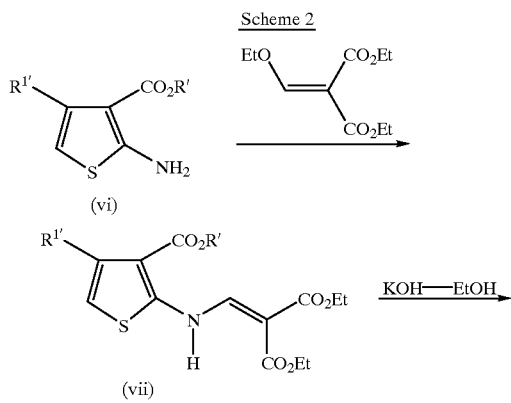

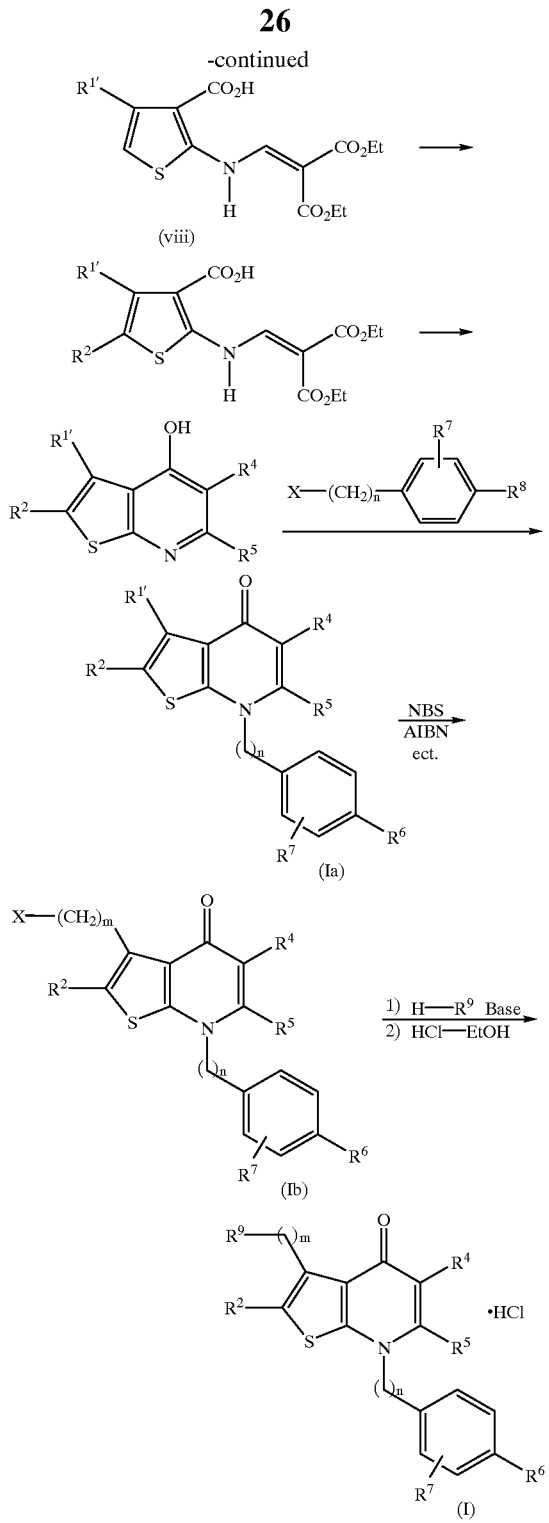

wherein each symbol has the same meaning as defined above.

[Production Method 3]

An alantoic acid derivative (x) is stirred at temperatures ranging from about 30 to 110° C. together with an equivalent or an excess amount of triphosgene relative the the compound (x) in a solvent which does not adversely affect on the reaction (e.g. ethers such as tetrahydrofuran and 1,4-dioxane) to give an isatoic acid anhydride derivative (xi). Then, a halogenated derivative shown by the formula (xii) is stirred at temperatures ranging from about 40 to 130° C. in a solvent, which does not affect adversely on the reaction, (ethers such as tetrahydrofuran and 1,4-dioxane, aromatic hydrocarbons such as benzene and toluene, amides such as N,N-dimethylformamide and N,N-dimethylacetamide, alkylsulfoxides such as dimethyl sulfoxide), in the presence of a base (e.g. alkali metal carbonate such as potassium carbonate, alkali metal hydride such as sodium hydride and potassium hydride, and alkali metal alkoxide such as potassium-butoxide), to give a substituted derivative (xiii). The derivative (xiii) is allowed to react with an equivalent or a little excess amount (e.g. about 1.1 to 1.5 equivalent) of a β-keto-acid ester derivative (xiv) relative to the compound (xiii) at temperatures ranging from 40 to 110° C. in a solvent, which does not affect adversely on the reaction, (e.g. ethers such as tetrahydrofuran and 1,4-dioxane, aromatic hydrocarbons such as benzene and toluene, amides such as N,N-dimethylformamide and N,N-dimethylacetamide, and alkyl sulfoxide such as dimethyl sulfoxide), in the presence of a base (e.g. alkali metal carbonate such as potassium carbonate, alkali metal hydride such as sodium hydride and potassium hydride, and alkali metal alkoxide such as potassium-butoxide) to give the compound (Va). The foregoing production method 3 is shown in Scheme 3:

Scheme 3

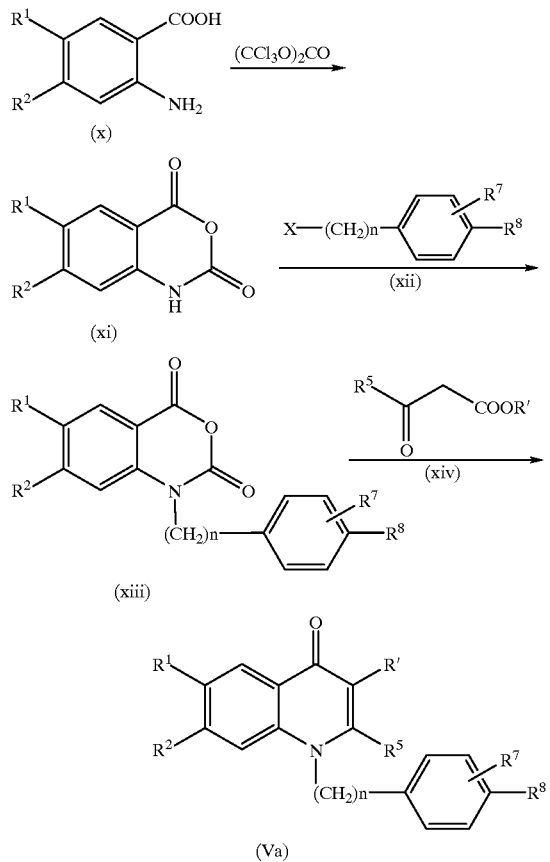

1,4-dioxane), at temperatures ranging from about 30 to 110° C. to give an acid anhydride derivative (xvi). Then, the halogenated derivative shown by (xii) is stirred in a solvent, which does not affect adversely on the reaction, (e.g. ethers such as tetrahydrofuran and 1,4-dioxane, aromatic hydrocarbons such as benzene and toluene, amides such as N,N-dimethylformamide and N,N-dimethylacetamide, and alkyl sulfoxides such as dimethyl sulfoxide), at temperatures ranging from about 40 to 130° C. in the presence of a base (e.g. alkali metal carbonate such as potassium carbonate, alkali metal hydride such as sodium hydride and potassium hydride, and alkali metal alkoxide such as potassium-butoxide) to give a substituted derivative (xvii). The derivative (xvii) is allowed to react with equivalent or a little excess amount (e.g. 1.1 to 1.5 equivalent) of a β-keto-acid ester derivative (xiv) in a solvent, which does not affect adversely on the reaction, (e.g. ethers such as tetrahydrofuran and 1,4-dioxane, aromatic hydrocarbons such as benzene and toluene, amides such as N,N-dimethylformamide and M,N-dimethylacetamide, and alkyl sulfoxides such as dimethyl sulfoxide), in the presence of a base (e.g. alkali metal carbonate such as potassium carbonate, alkali metal hydride such as sodium hydride and potassium hydride and alkali metal alkoxide such as potassium-butoxide), at temperatures ranging from about 40 to 110°C., to give the compound (Vb). The foregoing production method 4 is shown by Scheme 4:

Scheme 4

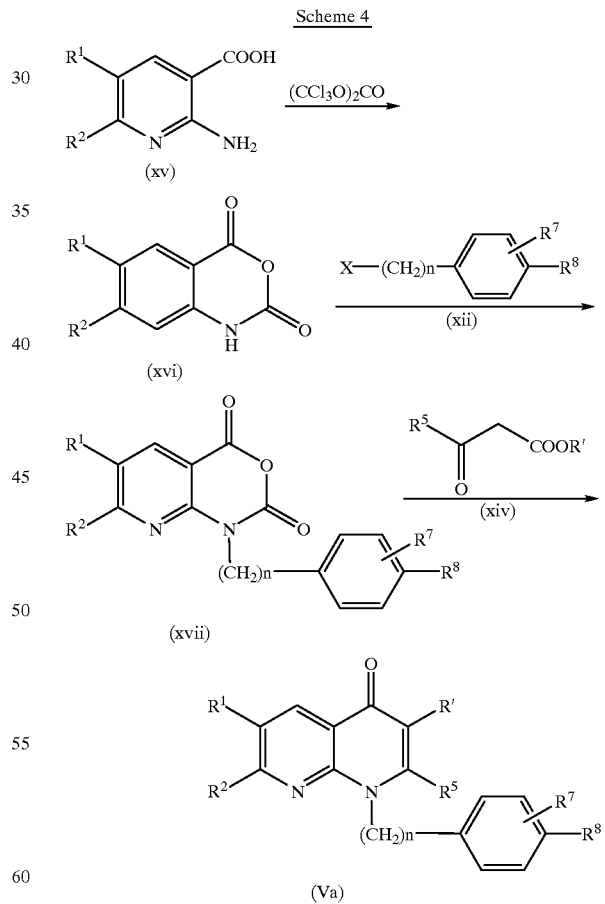

wherein each symbol is of the same meaning as defined above.

[Production Method 4]

A pyridine derivative (xv) is stirred, together with equivalent or an excess amount of triphosgene relative to the compound (xv), in a solvent, which does not affect adversely on the reaction, (e.g. ethers such as tetrahydrofuran and wherein each symbol is of the same meaning as defined above.

[Production Method 5]

In a proper solvent, which does not affect adversely on the reaction, (e.g. ethers such as tetrahydrofuran, ethyl ether and dioxane), 4,7-dihydro-4-oxothieno[2,3-b]pyridine-5-carboxylic acid ester derivative (va) is stirred together with a suitable reducing agent (e.g. lithium aluminum hydride) at temperatures ranging from about 0 to 80° C. to give a 4,7-dihydro-thieno[2,3-b]pyridine-4-one derivative shown by the formula (Ic). The said derivative is stirred, together with a suitable oxidizing agent (e.g. manganese dioxide), in a proper solvent (e.g. dichloromethane or chloroform) at temperatures ranging from about 10 to 80° C. to give a 5-formyl derivative. The derivative (Id) thus produced is stirred, together with a Grignard's reagent, at temperatures ranging from about 0 to 80°C. in a solvent, which does not affect adversely on the reaction, (e.g. ethers such as tetrahydrofuran and ethyl ether) to give a corresponding secondary alcohol derivative (Ie). The compound (Ie) is stirred, together with a suitable oxidizing agent (e.g. metal oxide such as manganese dioxide), in a proper solvent (e.g. halogenated hydrocarbons such as dichloromethane and chloroform) at temperatures ranging from about 10 to 80° C. to give a 5-carbonyl derivative (If). The foregoing production method 5 is shown in Scheme 5:

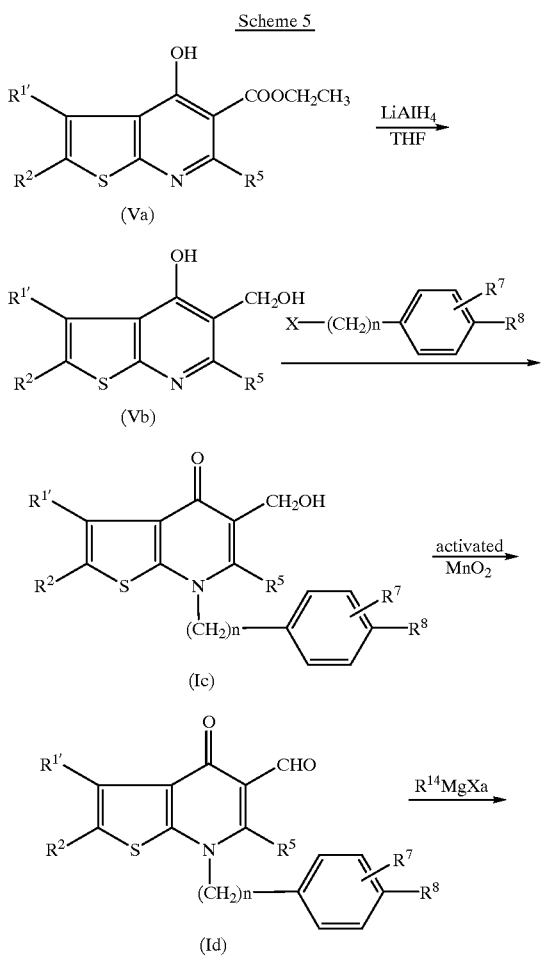

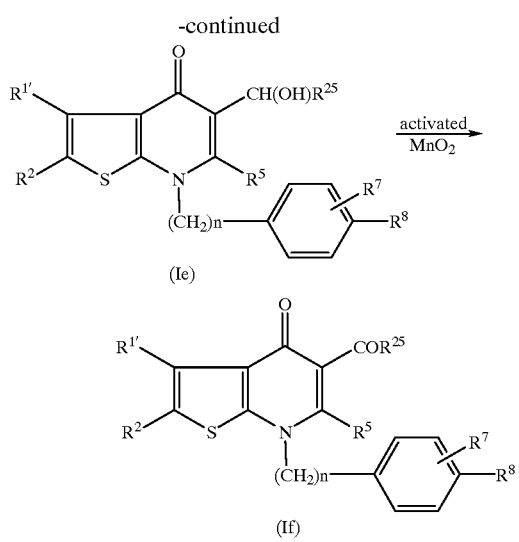

wherein $R^{25}$ is hydrocarbon residue, and other symbols are of the same meaning as defined above.

The hydrocarbon residue shown by the above $R^{25}$ is of the same meaning as the hydrocarbon residue in the carbonyl group optionally substituted with hydrocarbon residue shown by the above-described $R^4$.

[Production Method 6]

4,7-Dihydro-4-oxothieno[2,3-b]pyridine-5-carboxylic acid ester derivative (Ia') is stirred at temperatures ranging from about 10 to 100° C., together with an aluminum amide derivative previously produced from a proper aluminum reagent [(e.g. trimethyl aluminum and diisobutyl aluminum hydride (DIBAL)] and amine in a suitable solvent, which does not affect adversely on the reaction, (e.g. halogenated hydrocarbons such as dichloromethane and ethers such as tetrahydrofuran, ethyl ether and dioxane), to give a 4,7-dihydro-4-oxothieno[2,3-b]pyridine-5-carboxylic acid amide derivative (Ia"). The said derivative (Ia") is stirred, together with a Grignard's reagent, in a proper solvent, which does not affect adversely on the reaction, (e.g. tetrahydrofuran and ethyl ether) at temperatures ranging from about −78° C. to 80° C. to give a corresponding ketone derivative (If). The foregoing production method 6 is shown in Scheme 6:

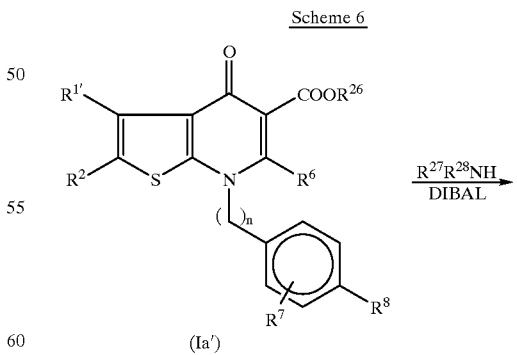

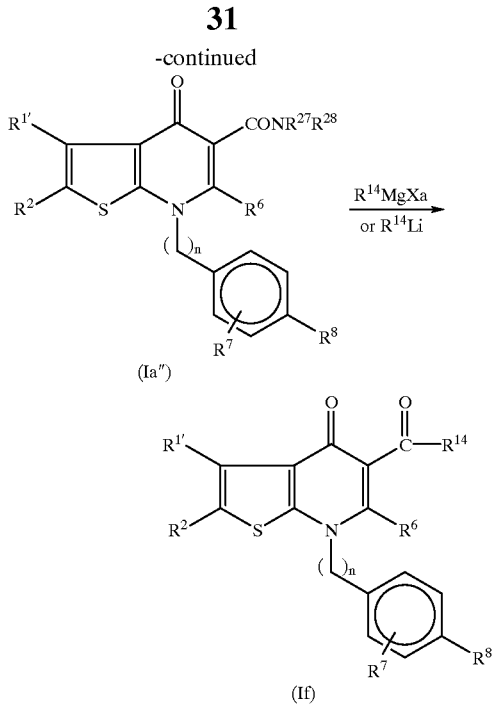

(Ia″)

(If)

wherein $R^{26}$ is alkyl or aryl; $R^{27}$ and $R^{28}$ are each hydrogen or hydrocarbon residue; and other symbols are of the same meaning as defined above.

The alkyl and aryl shown by the above $R^{26}$ are of the same meaning as defined above.

The hydrocarbon residue shown by the above $R^{27}$ and $R^{28}$ has the same meaning as the hydrocarbon residue in the carbonyl group optionally substituted with hydrocarbon residue shown by the above $R^4$.

[Production Method 7]

In a proper solvent, which does not affect adversely on the reaction, (e.g. halogenated hydrocarbons such as dichloromethane; ethers such as tetrahydrofuran, ethyl ether and dioxane; and pyridine), a 4,7-dihydro-5-hydroxymethylthieno[2,3-b]pyridine-4-one derivative (Ia) is stirred together with a suitable halogenating reagent (e.g. thionyl chloride and methanesulfonyl chloride) at temperatures ranging from about 0 to 100°C. to give a 4,7-dihydrothieno[2,3-b]pyridine one derivative (Ig). The said derivative (Ig) is stirred, together with a suitable nucleophilic reagent, in a proper solvent, which does not affect adversely on the reaction, (e.g. ethers such as tetrahydrofuran and ethyl ether; and amides such as dimethylformamide) to give a corresponding 5-substituted derivative (Ih). The above production method 7 is shown in Scheme 7:

Scheme 7

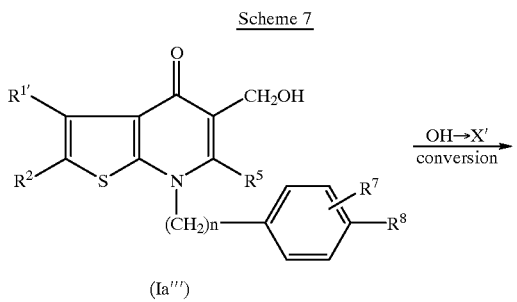

(Ia‴)

(Ig)

(Ih)

wherein X' is a leaving group, Z is an oxygen atom, a sulfur atom or a nitrogen atom optionally substituted with hydrocarbon residue, and other symbols are of the same meaning as defined above.

As the leaving group shown by the above X', mention is made of, for example, groups readily susceptible to substitution reaction by a nucleophilic reagent [e.g. the hydrocarbon residue having a heteroatom with negative electric charge (e.g. oxygen atom, sulfur atom and nitrogen atom) shown by the above $^-YR^{16}$]. More specifically, for example, aralkyloxy (e.g. acetoxy), alkylsulfonyloxy (e.g. methanesulfonyloxy) and alkyl-aryl sulfonyloxy (e.g. p-toluenesulfonyloxy) are mentioned.

The hydrocarbon residue in the nitrogen atom optionally substituted with hydrocarbon residue mentioned above has the same meaning as defined in reference to the hydrocarbon residue in the carbonyl group optionally substituted with hydrocarbon residue shown by the above-mentioned $R^4$.

[Production Method 8]

In a proper solvent, which does not affect adversely on the reaction, (e.g. ethers such as tetrahydrofuran, ethyl ether and dioxane; and pyridine), 4,7-dihydro-5-formylthieno[2,3-b]pyridine-4-one derivative (Ih) is stirred together with a suitable Wittig reagent at temperatures ranging from about 0 to 100° C. to give a 4,7-dihydrothieno[2,3-b]pyridine-4-one derivative (Ij). The said derivative (Ij) is stirred at temperatures ranging from about 10 to 100° C. together with a suitable reducing reagent [e.g. hydrogenation using, in hydrogen streams, a catalyst (e.g. palladium-carbon catalyst)] in a proper solvent, which does not affect adversely on the reaction (e.g. alcohols such as ethyl alcohol, esters such as acetic acid ethyl ester, ethers such as tetrahydrofuran, ethyl ether and dimethylformamide) to give a corresponding 5-substituted derivative (Ik). The above production method 8 is shown in Scheme 8:

Scheme 8

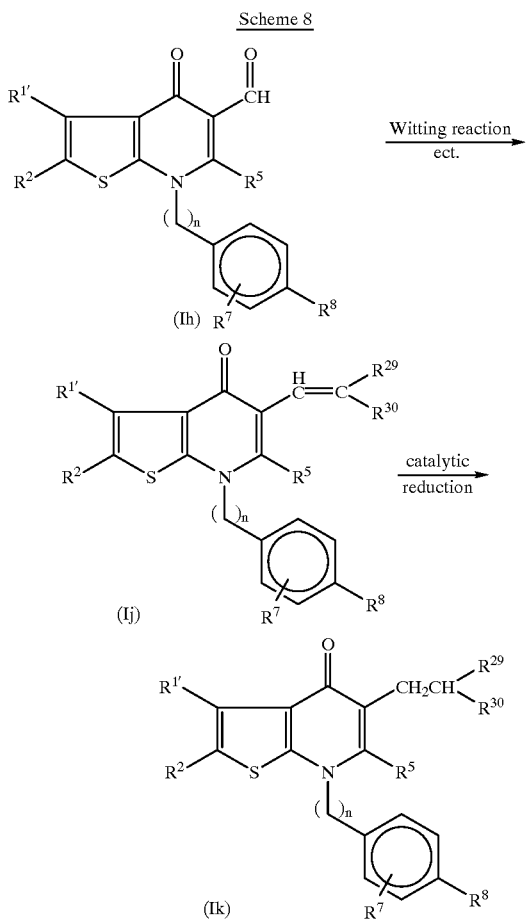

wherein $R^{29}$ and $R^{30}$ are each hydrogen or hydrocarbon residue, and other symbols are of the same meaning as defined above.

The hydrocarbon residue shown by the above-mentioned $R^{29}$ and $R^{30}$ has the same meaning as the hydrocarbon residue in the carbonyl group optionally substituted with the hydrocarbon residue shown by the above-mentioned $R^4$.

[Production Method 9]

In a proper solvent, which does not affect adversely on the reaction, (e.g. ethers such as tetrahydrofuran and dioxane; and alcohols such as ethyl alcohol), 4,7-dihydro-4-oxothieno[2,3-b]pyridine-5-carboxylic acid ester derivative (Ia') is subjected to hydrolysis under stirring at temperatures ranging from about 10 to 100° C. by adding an acid (e.g. inorganic acid such as hydrochloric acid) or an alkaline aqueous solution (e.g. 1–4N aqueous solution of alkali metal hydroxide such as sodium hydroxide, potassium hydroxide and lithium hydroxide). The resulting 5-carboxylic acid derivative is heated at temperatures ranging from about 50 to 200° C. in a proper solvent, which does not affect adversely on the reaction, to give a corresponding decarboxylated derivative (In). The foregoing production method 9 is shown by Scheme 9:

Scheme 9

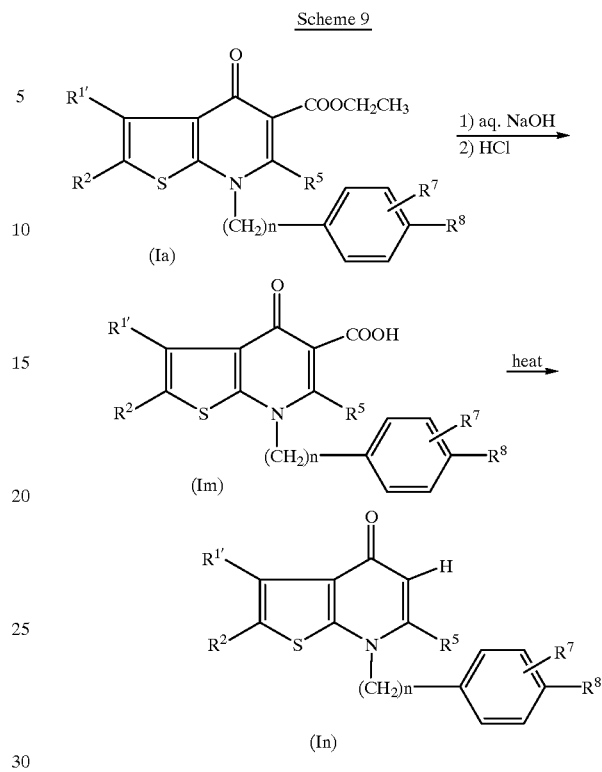

wherein each symbol is of the same meaning as defined above.

[Production Method 10]

Starting from the 2-aminothiophene derivative (ii), the urea derivative (II) was produced by, for example, the following method A or B.

1. Method A: The 2-aminothiophene derivative (ii) produced by the method described in Production Method 1 or a salt thereof is allowed to react with an isocyanate derivative. The isocyanate derivative is exemplified by derivatives represented by the formula, $R^{12}$—NCO (
wherein $R^{12}$ is of the same meaning as defined above). The reaction of the compound (ii) or a salt thereof with the isocyanate derivative is conducted in an solvent which does not adversely affect on the reaction (e.g. tetrahydrofuran, pyridine, dioxane, benzene, dichloromethane, 1,2-dichloroethane, toluene, xylene) at temperatures ranging from about 15 to about 130° C. The isocyanate derivative is employed in an amount of about 1 to 5 equivalents, preferably about 1.1 to 2.5 equivalents, relative to 1 equivalent of the compound (ii). The reaction time ranges from several hours to several days, preferably from about 15 minutes to about two days.

2. Method B: Amine [e.g. a compound represented by the formula $R^{12}$—$NH_2$ (
wherein $R^{12}$ is of the same meaning as defined above)] is subjected to addition reaction to an isocyanate derivative produced by allowing a 2-aminothiophene derivative (ii) or a salt thereof to react with phosgene or an equivalent compound thereof [e.g. diphosgene such as bis(trichloromethyl)carbonate, triphosgene such as trichloromethylchloroformate]. The reaction of the compound (ii) or a salt thereof with phosgene or an equivalent compound thereof is conducted in a solvent which does not affect adversely on the reaction (e.g. dioxane, tetrahydrofuran, benzene, toluene, xylene, 1,2-dichloroethane, chloroform) at temperatures ranging from about 40 to 120° C. Phosgene or an equivalent compound thereof is employed in an amount ranging from about 0.5 to 2 equivalents, preferably from about 0.9 to 1.1 equivalent). The reaction time ranges from several minutes to several days, preferably from about 15 minutes to about two days. The addition reaction of amine is conducted in a solvent which does not affect adversely on the reaction (e.g. pyridine, tetrahydrofuran, dioxane, benzene, dichloromethane, 1,2-dichloroethane, toluene, xylene) at temperatures ranging from about 15 to 130° C. Amine is employed in an amount ranging from about 1 to 5 equivalents, preferably from about 1.1 to 3 equivalents. The reaction time ranges from several minutes to several days, preferably from about 15 minutes to about two days.

The compound (XV) or a salt thereof thus produced is processed with a base to cause ring-closure reaction to thereby produce a thieno [2,3-d] pyrimidine derivative (XVI). The ring-closure reaction is conducted in a solvent which does not affect adversely on the reaction. The solvent is exemplified by alcohols such as methanol, ethanol or propanol, and ethers such as dioxane or tetrahydrofuran.

As the base, use is made of, for example, an alkali metal alkoxide such as sodium methylate, sodium ethylate or sodium isopropoxide, and an alkali metal hydride such as sodium hydride.

The amount of the base to be employed ranges from 1 to 5 equivalents, preferably from about 1.5 to 3 equivalents, relative to 1 equivalent of the compound (XV).

The reaction temperature ranges from about 10° C. to the boiling point of the solvent then employed, preferably from about 25° C. to the boiling point of the solvent then employed.

The reaction time ranges from several minutes to several days, preferably from about 10 minutes to two days.

The compound (XVI) and a halogenated aralkyl derivative are stirred, in the presence of a base (e.g. an organic base such as pyridine or triethylamine), in a solvent which does not affect adversely on the reaction (e.g. amides such as dimethylformamide or dimethylacetamide), at about 10 to 100° C., to produce a 2,4-dioxothieno[2,3-d]pyrimidine derivative (IIa). Subsequently, the said compound (IIa) is stirred together with N-bromosuccinimide (NBS) in a solvent which does not affect adversely on the reaction (e.g. halogenated hydrocarbons such as carbon tetrachloride or chloroform), in the presence of α, α'-azobisisobutyronitrile, to thereby produce the compound (IIb). Further, the said compound is stirred together with various amines, in the presence of a base, in a solvent which does not affect adversely on the reaction (e.g. amides such as dimethylformamide or dimethylacetamide, nitrites such as acetonitrile, alcohols such as ethanol), at temperatures ranging from about 10 to 100° C., to thereby produce the compound (II). When necessary, the said compound is made into a corresponding salt with a suitable acid (e.g. hydrochloric acid or oxalic acid).

The foregoing Production Method 10 is shown by Scheme 10:

Scheme 10

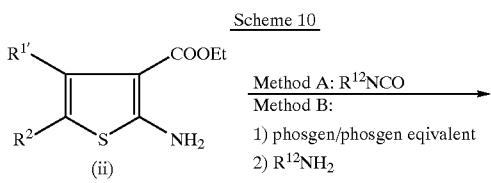

Method A: R$^{12}$NCO
Method B:
1) phosgen/phosgen eqivalent
2) R$^{12}$NH$_2$

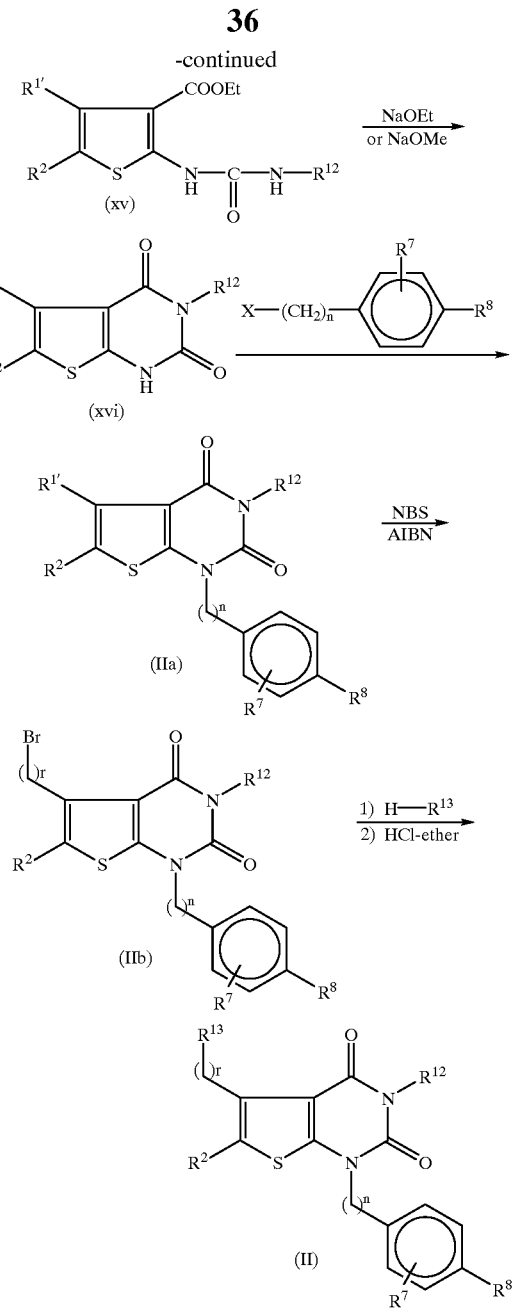

wherein each symbol is of the same meaning as defined above.

[Production Method 11]

The amino group of a 2-aminothiophene derivative (xvii) was protected (e.g. Boc), which was stirred, in accordance with the method of T. Hirohashi et al. [Ger. Pat., 2155403 (1972), among others] or the method of M. Nakanishi et al. [Jap. Pat., 73, 01664 (1973), among others], together with a halogenated acyl derivative, in the presence of a base, in a solvent which does not affect adversely on the reaction (e.g. amides such as dimethylformamide or dimethylacetamide) at temperatures ranging from about 0 to 100° C. to give a derivative (xviii), which was stirred together with a suitable salt (e.g. lithium iodide) in a suitable solvent (e.g. acetone or methyl ethyl ketone) to give a derivative (xix), which was subjected to substitution reaction with a suitable amine (e.g. ammonia) to give a derivative (xx), which was stirred in a solvent which does not affect adversely on the reaction (e.g.

toluene, dimethylformamide, dimethylacetamide, methanol or ethanol), when necessary in the presence of a suitable catalyst (e.g. sodium ethoxide or toluenesulfonic acid) at temperatures ranging from about 30 to 120° C., to cause dehydro-cyclization to thereby produce a derivative (VIIa). The said compound was stirred, together with a halogenated aralkyl derivative, in the presence of a base (e.g. organic bases including potassium carbonate, pyridine and triethylamine), in a solvent which does not affect adversely on the reaction (e.g. amides including dimethylformamide and dimethylacetamide), at temperatures ranging from about 10 to 100° C. to give a 2-oxothieno [2,3-e] azepine derivative (VIIb). Subsequently, the said compound (VIIb) was stirred together with N-bromosuccinimide (NBS) in a solvent (e.g. halogenated hydrocarbons including carbon tetrachloride and chloroform), in the presence of α, α'-azobisisobutyronitrile, at temperatures ranging from about 30 to 100° C., to give a compound (VIIc). The said compound was stirred with various amines in the presence of a base, in a solvent which does not affect adversely on the reaction (e.g. amides including dimethylformamide and dimethylacetamide, nitriles including acetonitrile, and alcohols including ethanol) at temperatures ranging from about 10 to 100°C. to give a compound (VId). When necessary, the said compound was made into a corresponding salt with a suitable acid (e.g. hydrochloric acid or oxalic acid). The foregoing Production Method 2 is shown in Scheme 11:

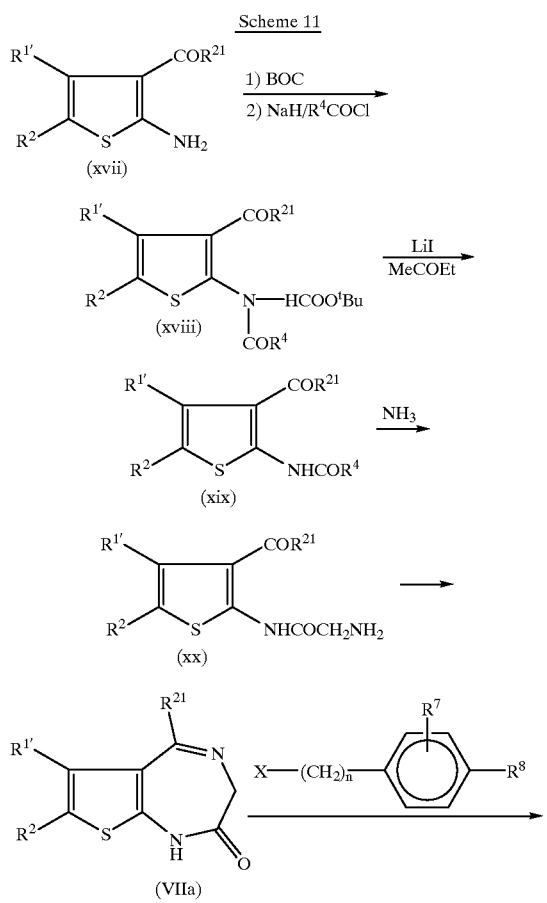

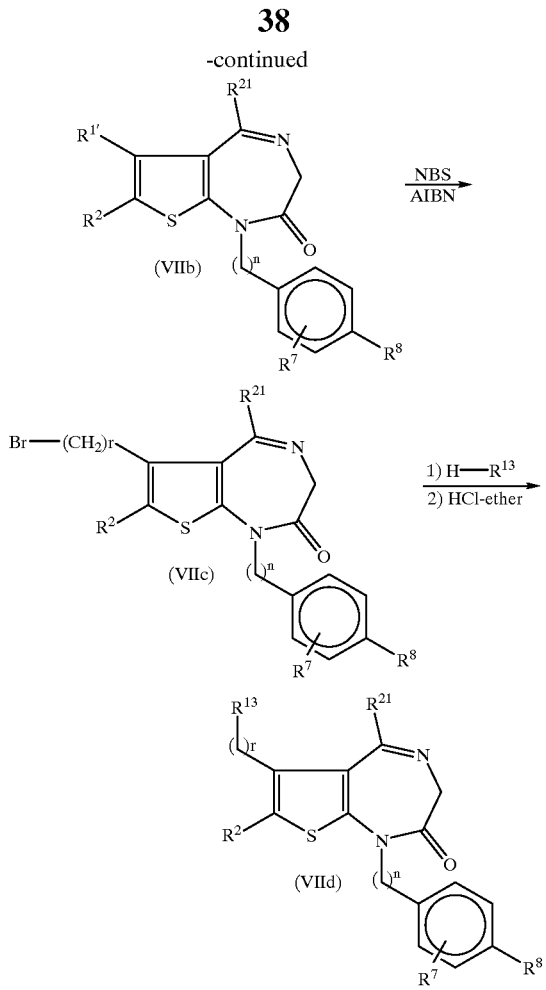

wherein each symbol is of the same meaning as defined above.

[Production Method 12]

The amino group of a 2-aminothiophene derivative producible by the method described in Production Method 1 was protected (e.g. Boc), which was stirred together with a halogenated aralkyl derivative, in the presence of a base (e.g. organic bases including potassium carbonate, pyridine and triethylamine), in a solvent which does not affect adversely on the reaction (e.g. amides including dimethylformamide and dimethylacetamide), at temperatures ranging from about 10 to 100° C., to give a derivative (xxi), which was subjected to alkali hydrolysis with a suitable alkali (e.g. sodium hydroxide) in a suitable solvent (e.g. methanol, tetrahydrofuran), and, the derivative thus produced was stirred together with DPPA in a solvent which does not affect adversely on the reaction (e.g. toluene, tetrahydrofuran, dimethylformamide, dimethylacetamide, ethanol) at temperatures ranging from about 0 to 100° C., and the resultant was made into a carbamic acid ester derivative (xxii) with a suitable alcohol (e.g.ethanol). The said derivative was stirred, in the presence of a base (e.g. sodium ethoxide), in a solvent which does not affect adversely on the reaction (e.g. dimethylformamide, dimethylacetamide), at temperatures ranging from about 0 to 100°C. to give a thieno[2,3-d]imidazol-2-one derivative (VIIe). The said compound was stirred together with a halogenated alkyl derivative, in the presence of a base, in a solvent which does not affect adversely on the reaction (e.g. amides including dimethylformamide, dimethylacetamide), at temperatures ranging from about 0 to 100° C. to give a compound (VIIf). Subsequently, the said compound (VIIf) was stirred, together with N-bromosuccinimide (NBS), in a solvent which does not affect adversely on the reaction (e.g. halogenated hydrocarbons including carbon tetrachloride and chloroform), in the presence of α,α'-azobisisobutyronitrile, at temperatures ranging from about 30 to 100° C. to give a compound (VIIg). The said compound was further stirred, together with various amine, in the presence of a base, in a solvent which does not affect adversely on the reaction (e.g. amides including dimethylformamide and dimethylacetamide, nitrites including acetonitrile, alcohols including ethanol), at temperatures ranging from about 10 to 100° C. to produce a compound (VIIh). The said compound, when necessary, was made into a corresponding salt with a suitable acid (e.g. hydrochloric acid, oxalic acid). The foregoing Production Method 12 is shown in Scheme 12:

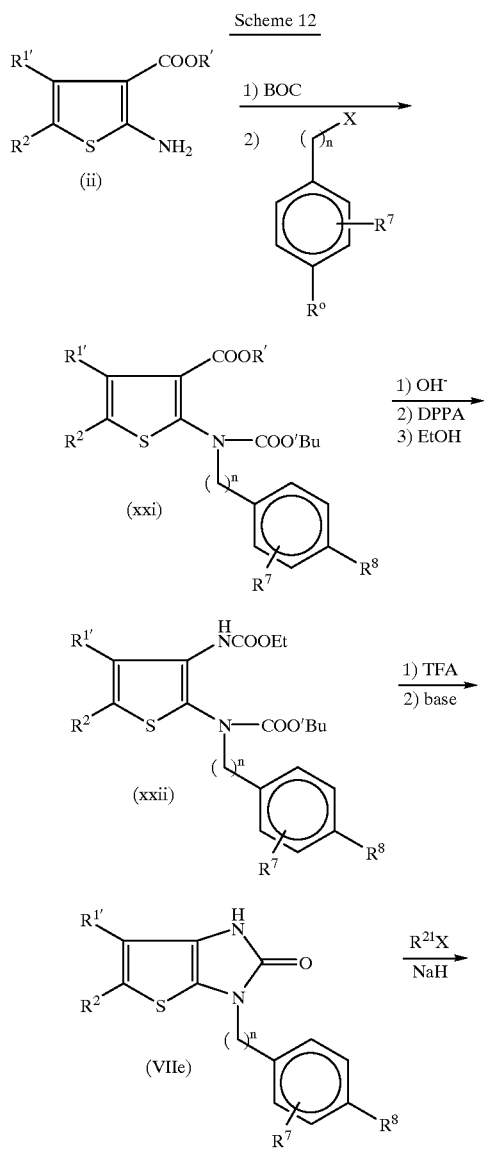

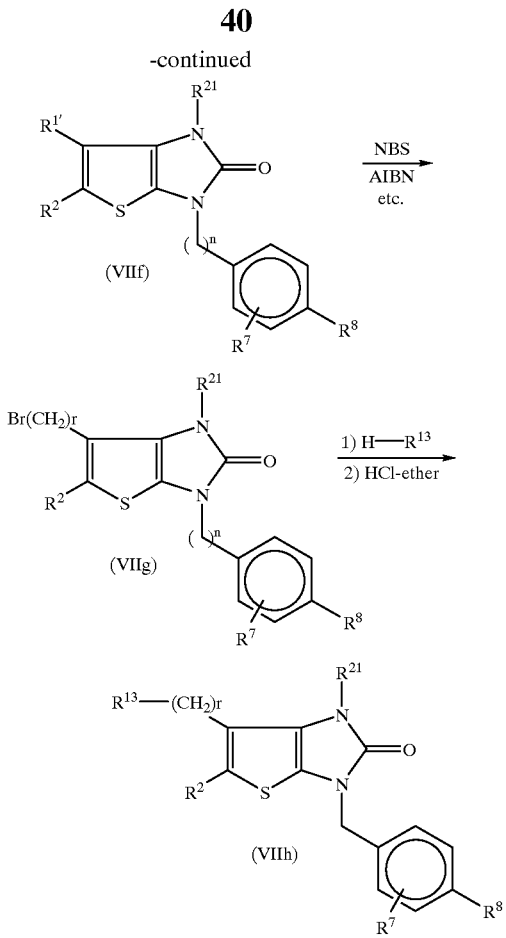

wherein each symbol is of the same meaning as defined above.

[Production Method 13]

Starting from a 2-aminothiophene derivative (ii) producible by the method described in Production Method 1 or a salt thereof, 4,5-dihydro-7-hydroxy-5-oxothieno [3,2-b] pyridine-6-carboxylic acid ethyl derivative (VIIj) was produced by the method of J. M. Barker et al. [J. Chem. Res. (M), 1980, 113; J. Chem. Res. (s), 6(1980)]. More specifically, the 2-aminothiophene derivative (ii) or a salt thereof was allowed to react with malonic acid ester to give the compound (xxii), which was stirred, in the presence of a suitable base (e.g. sodium hydride), in a solvent which does not affect adversely on the reaction (e.g. amides including dimethylformamide and dimethyl acetamide), at temperatures ranging from about 10 to 100° C. to give the derivative (VIIj). The said derivative (VIIj) was stirred, together with a halogenated aralkyl derivative, in the presence of a base (e.g. organic bases including potassium carbonate, pyridine and triethylamine), in a solvent which does not affect adversely on the reaction (e.g. amides including dimethylformamide and dimethyl acetamide), at temperatures ranging from about 10 to 100°C. to give a derivative (VIIk), and,the said derivative was stirred, together with N-bromosuccinimide (NBS), in a solvent which does not affect adversely on the reaction (e.g. halogenated hydrocarbons including carbon tetrachloride and chloroform), in the presence of α,α'-azobisisobutyronitrile, at temperatures ranging from about 30 to 100° C. to give the compound (VIIm). Further, the said compound was stirred, together with various amines, in the presence of a base, in a solvent which does not affect adversely on the reaction (e.g. amides including dimethylformamide and dimethyl acetamide, nitriles including acetonitrile, alcohols including ethanol), at temperatures ranging from about 10 to 100°C. to produce the compound (VIIn). when necessary, the said compound was made into a corresponding salt with a suitable acid (e.g. hydrochloric acid, oxalic acid).The foregoing Production Method 13 was shown in Scheme 13:

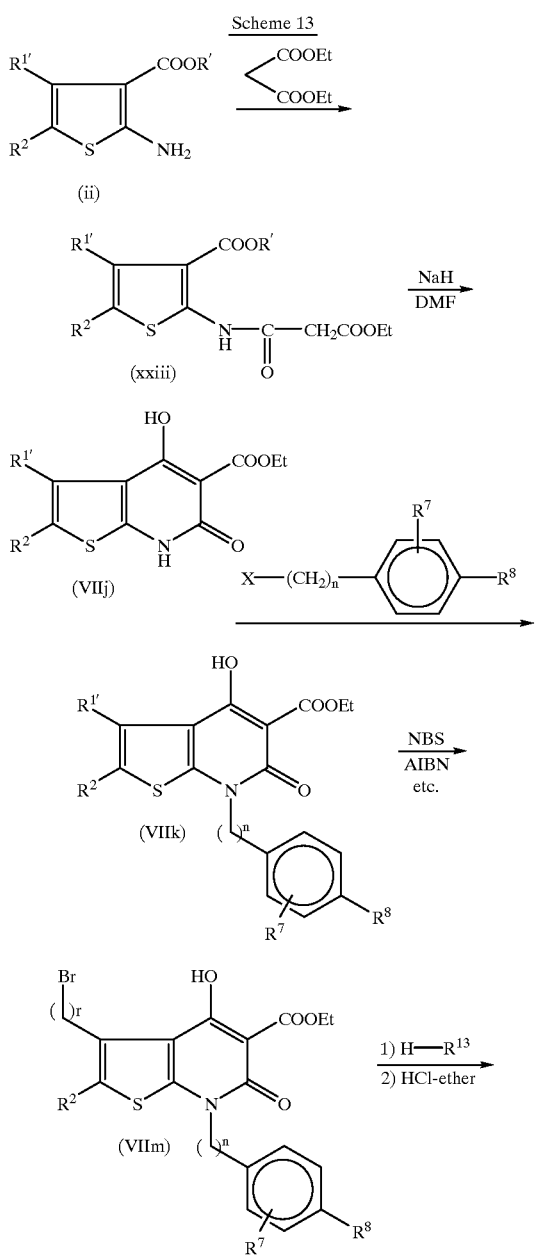

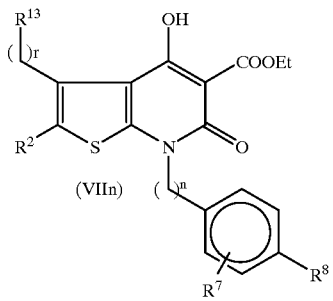

wherein each symbol is of the same meaning as defined above.

[Production Method 14]

In a suitable solvent which does not affect adversely on the reaction (e.g. halogenated hydrocarbons including dichloromethane, and ethers including tetrahydrofuran, ethyl ether and dioxane), the 1,4-dihydro-4-oxoquinoline-3-carboxylic acid ester derivative (Va') was stirred, together with an aluminum amide derivative produced from a suitable aluminum reagent (e.g. trimethyl aluminum, triethyl aluminum or diisobutyl aluminum hydride (DIBAL)] and amines, at temperatures ranging from about 10 to 100° C. to give a 1,4-dihydro-4-oxoquinoline-3-carboxylic acid amide derivative (Va"). The said derivative was stirred, together with a Grignard reagent, in a suitable solvent (e.g. tetrahydrofuran and ethyl ether) at temperatures ranging from 0 to 80° C. to give a corresponding ketone derivative (Vc). The above production method 14 is shown in Scheme 14:

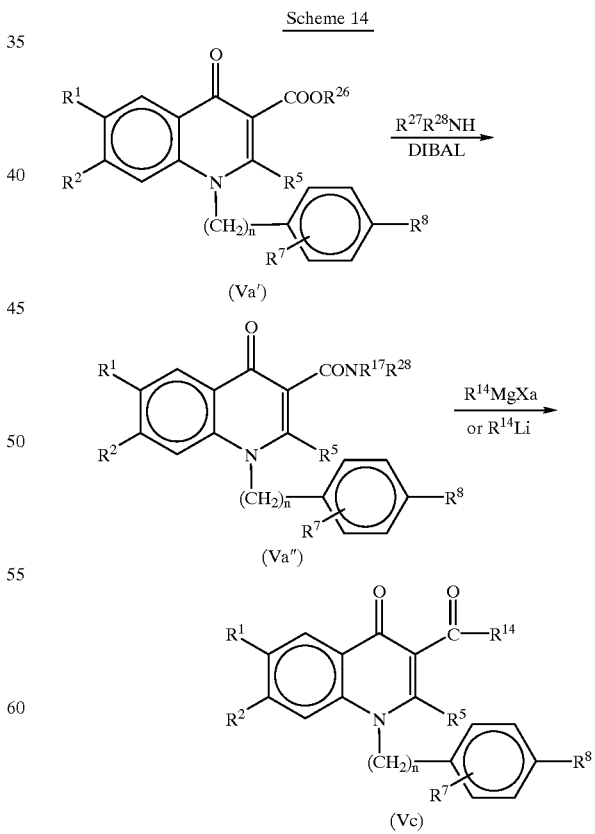

wherein $R^{26}$ is alkyl or aryl, $R^{27}$ and $R^{28}$ are each hydrogen or hydrocarbon residue, and other symbols are of the same meaning as defined in the foregoing.

The alkyl and aryl shown by the above-mentioned $R^{26}$ is of the same meaning as defined in the foregoing.

The hydrocarbon residues shown by the above-mentioned $R^{27}$ and $R^{28}$ are of the same meaning as the hydrocarbon residue in the optionally substituted carbonyl group with a hydrocarbon residue shown by the above-mentioned R'.

[Production Method 15]

In a suitable solvent which does not affect adversely on the reaction (e.g. halogenated hydrocarbons including dichloromethane, and ethers including tetrahydrofuran, ethyl ether and dioxane), 1,4-dihydro-4-oxopyrido [2,3-b] pyridine-3-carboxylic acid ester derivative (Vd) is stirred, together with an aluminum amide derivative produced from a suitable aluminum reagent [e.g. trimethyl aluminum, triethyl aluminum and diisobutyl aluminum hydride (DIBAL)] and amines, at temperatures ranging from about 10 to 100° C. to give a 1,4-dihydro-4-oxopyrido[2,3-b]pyridine-3-carboxylic acid amide derivative (Vd'). The said derivative is stirred, together with a Grignard reagent, in a suitable solvent which does not affect adversely on the reaction (e.g.tetrahydrofuran and ethyl ether), at temperatures ranging from about 0 to 80° C. to give a corresponding ketone derivative (Ve). The production method is shown in Scheme 15:

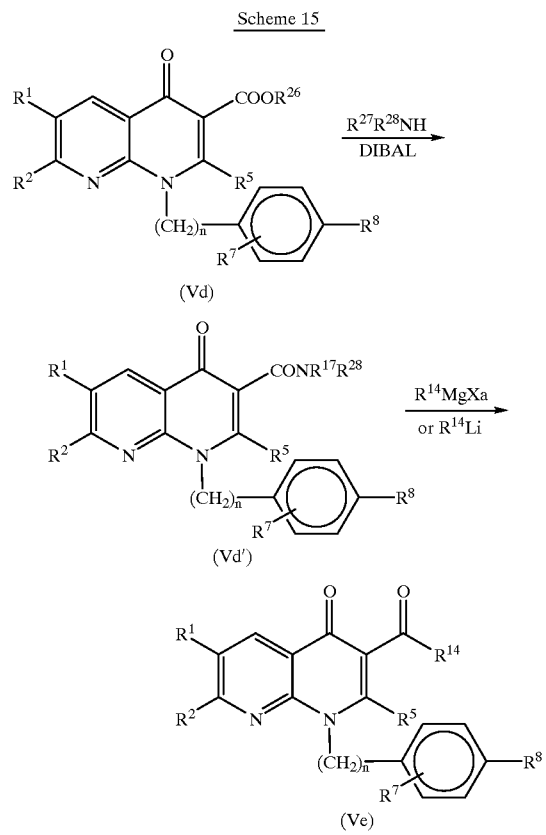

wherein $R^{26}$ is alkyl or aryl, $R^{27}$ and $R^{28}$ are each hydrogen or hydrocarbon residue, and other symbols are of the same meaning as defined above.

The alkyl and aryl shown by the above $R^{26}$ are of the same meaning as defined above.

The hydrocarbon residue shown by the above $R^{27}$ and $R^{28}$ is of the same meaning as the hydrocarbon residue in the carbonyl group optionally substituted with hydrocarbon residue shown by the above-mentioned R'.

[Production Method 16]

In a suitable solvent which does not affect adversely on the reaction (e.g. ethers including 1,2-dimethoxyethane, tetrahydrofuran and dioxane and alcohols including ethyl alcohol). To the solution is added, in the presence of equimolar to an excess amount (2 to 10 equivalents) of a suitable base (e.g. sodium carbonate), a suitable aryl boric acid derivative (e.g. phenyl boric acid, 3-methoxyphenyl boric acid and 4-ethoxycarbonyl phenyl boric acid). To the mixture is added, in the streams of an inert gas (e.g. argon gas), a suitable catalyst [e.g. palladium metal including tetrakis (triphenylphosphine) palladium]. The mixture is stirred for a period ranging from several minutes to several hours at temperatures ranging from about 10 to 100° C. Insolubles are removed to leave the desired derivative (Iq). The foregoing production method 16 is shown in Scheme 16:

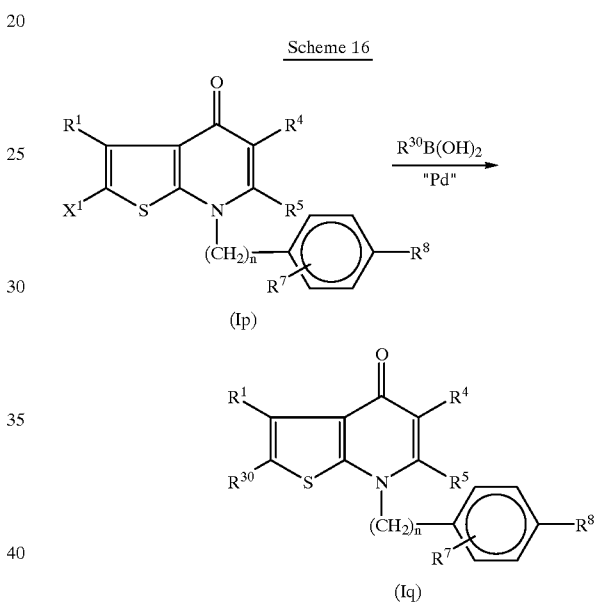

wherein $R^{30}$ is an optionally substituted aryl group, and other symbols are of the same meaning as defined above.

As salts of the compounds of this invention obtained thus above, physiologically acceptable acid addition salts are preferable. Examples of such salts include those with an inorganic acid (e.g. hydrochloric acid, hydrobromic acid, nitric acid, sulfuric acid and phosphoric acid) or those with an organic acid (e.g. formic acid, acetic acid, trifluoroacetic acid, fumaric acid, oxalic acid, tartaric acid, maleic acid, citric acid, succinic acid, malic acid, methanesulfonic acid, bezenesulfonic acid, and p-toluenesulfonic acid). Further, when the compound (I) of this invention has an acid group such as —COOH, the compound(I) may form a salt with an inorganic base (e.g. an alkali metal or alkaline earth metal such as sodium, potassium, calcium and magnesium; ammonia) or an organic base (e.g. trimethylamine, triethylamine, pyridine, picolin, ethanolamine, diethanolamine, triethanolamine, dicyclohexylamine and N,N'-dibenzylethylenediamine).

Especially preferable examples of the compounds or their salts of this invention include 3-(N-benzyl-N-methylaminomethyl)-4,7-dihydro-7-(2-methoxybenzyl)-2-(4-methoxyphenyl)-4-oxothieno[2,3-b]pyridine-5-carboxylic acid ethyl ester, (3-(N-benzyl-N- methylaminomethyl)-4,7-dihydro-7-(2-fluorobenzyl)-2-(4-methoxyphenyl)-4-oxothieno[2,3-b]pyridine-5-carboxylic acid ethyl ester, 2-(4-acetylaminophenyl)-3-(N-benzyl-N-methylaminomethyl)-4,7-dihydro-7-(2-fluorobenzyl)-4-oxothieno[2,3-b]pyridine-5-carboxylic acid ethyl ester, 5-benzylmethylaminomethyl-l-(2-chloro-6-fluorobenzyl)-2,4(1H,3H)-dioxo-6-(4-methoxyphenyl)-3-phenylthieno(2,3-d)pyrimidine, 5-benzoul-3-(N-benzyl-N-methylaminomethyl)-7-(2,6-difluorobenzyl)-4,7-dihydro-4-oxo-2-(4-propionylaminophenyl)thieno[2,3-b]pyridine, 5-benzoyl-3-(N-benzyl-N-methylaminomethyl)-7-(2,6-difluorobenzyl)-4,7-dihydro-2-(4-N'-methylureidophenyl)-4-oxothieno[2,3-b]pyridine, 3-(N-benzyl-N-methylaminomethyl)-7-(2,6-difluorobenzyl)-4,7-dihydro-5-isobutyryl-4-oxo-2-(4-propionylaminophenyl)thieno[2,3-b]pyridine, 3-(N-benzyl-N-methylaminomethyl)-7-(2,6-difluorobenzyl)-4,7-dihydro-2-5-isobutyryl-(4-N'-methylureidophenyl)-4-oxothieno[2,3-b]pyridine, 3-(N-benzyl-N-methylaminomethyl)-7-(2,6-difluorobenzyl)-4,7-dihydro-2-(4-N'-methylureidophenyl)-4-oxothieno[2,3-b]pyridine-5-(N-isopropyl)carboxamide, 3-(N-benzyl-N-methylaminomethyl)-7-(2,6-difluorobenzyl)-4,7-dihydro-2-(4-N'-methylureidophenyl)-4-oxothieno[2,3-b]pyridine-5-(N-isopropyl-N-methyl)carboxamide, 3-(N-benzyl-N-methylaminomethyl)-7-(2,6-difluorobenzyl)-4,7-dihydro-2-(4-N'-methylureidophenyl)-4-oxothieno[2,3-b]pyridine-5-(N-benzyl-N-methyl)carboxamide or their salts.

The compounds or salts thereof of the present invention produced thus above can be isolated and purified by a conventional separating means such as recrystallization, distillation and chromatography. In the case where the compound (I) is produced in the free form, it can be converted to a salt thereof by a per se conventional means or a method analogous thereto. On the contrary, when it is obtained in the form of a salt, it can be converted to its free form or to any other salt.

In the case where the compound or a salt thereof of the present invention is an optically active compound, it can be separated into d-compound and l-compound by means of a conventional optical resolution.

Since the compounds of this invention have a GnRH antagonistic activity and low in toxicity, they can be safely used for the therapy of male hormone or female hormone dependent diseases as well as the therapy of diseases caused by excess secretion of these hormones, in warm-blooded animals (e.g. human, monkey, cow, horse, dog, cat, rabbit, rat and mouse), suppressing the secretion of gonadotropic hormone by the action of GnRH receptor antagonistic action. More specifically, the compounds of this invention are effective as a prophylactic or therapeutic agent for the prevention or treatment of several hormone dependent diseases, for example, a sex hormone dependent cancer (e.g. prostate cancer, cancer of the uterine cervix, breast cancer, pituitary adenoma), benign prostatic hypertrophy, myoma of the uterus, endometriosis, precocious puberty, amenorrhea, premenstrual syndrome, polycystic ovary syndrome and acne vulgaris. And, the compounds of this invention are also effective as a fertility controlling agent in both sexes (e.g. pregnancy controlling agents and menstrual cycle controlling agents). The compounds of this invention can be further used as a contraceptive of male or female and, as an ovulation-inducing agent of female. The compound of this invention can be used as an infertility treating agent by using a rebound effect owing to a stoppage of administration thereof. Further, the compounds of this invention are useful as modulating estrous cycles in animals in the field of animal husbandry, and as an agent for improving the quality of edible meat or promoting the growth of animals. Besides, the compounds of this invention are useful as an agent of spawning promotion in fish. While the compounds of this invention can be used singly, they can also effectively be used by administering in combination with a steroidal or non-steroidal antiandrogenic agent. The compound of this invention can be used for the suppressing a passing ascent of testosterone concentration in plasma, the ascent which occurs in administration of GnRH super antagonist such as leuprorelin acetate. The compound of this invention can effectively be used by administering in combination with a chemoterapeutic agent for cancer. In treatment of prostate cancer, examples of the chemoterapeutic agent include Ifosfamide, UFT, Adriamycin, Peplomycin, Cisplatin and the like. In treatment of breast cancer, examples of the chemoterpeutic agent include Cyclophohamide, 5-FU-, UFT, Methotrexate, Adriamycin, Mitomycin C, Mitoxantrone and the like.

When the compound of this invention is employed, in the field of animal husbandry or fisheries, as prophylactic and therapeutic agents of the above-mentioned diseases, is can be administered orally or non-orally in accordance with per se known means. It is mixed with a pharmaceutically acceptable carrier and usually administered orally as a solid preparation such as tablet, capsule, granule or powder, or non-orally as intravenous, subcutaneous or intramuscular injection, or as suppository or sublingually administrable tablet. Further, it is sublingually, subcutaneously or intramuscularly administered as a prolonged release formulation such as sublingually administrable tablets, or microcapsules. The daily dose varies with the degree of affliction; age, sex, body weight and difference of sensitivity of the subject to be administered; the time and intervals of administration, properties, dosage forms and kinds of the medicinal preparation; and kinds of the effective components, and it ranges usually, though not specifically limited, from about 0.01 to 10 mg, preferably from about 0.02 to 2 mg, more preferably from about 0.01 to 1 mg, relative to 1 kg body weight of warm-blooded animals, which is administered usually once daily or by 2 to 4 divided dosages. The daily dose when used in the field of animal husbandry or fishery varies with the conditions analogous to those mentioned above, it ranges, relative to 1 kg body weight of the subject animal or fish, from about 0.001 to 5 mg, preferably from about 0.002 to 2 mg, once or 2 to 3 divided dosages.

As the above-mentioned pharmaceutically acceptable carriers, conventional various organic or inorganic carriers are used, and they are incorporated as excipients, lubricants, binders and disintegrants in solid compositions; and as solvents, solubilisers, suspending agents, isotonizing agents, buffering agents and pain-easing agents in liquid compositions. And, depending on necessity, further additives such as preservatives, anti-oxidants, coloring agents and sweeteners can also be used.

Preferable examples of the above-mentioned excipients include lactose, sugar, D-mannito, starch, crystalline cellulose and more volatile silicon dioxide. Preferable examples of above-mentioned lubricants include magnesium stearate, calcium stearate, talc and colloid silica. Preferable examples of the above-mentioned binders include crystalline cellulose, sugar, D-mannitol, dextrin, hydroxypropyl cellulose, hydroxymethyl cellulose and polyvinyl pyrrolidone. Preferable examples of the above-mentioned disintegrants include starch, carboxymethyl cellulose, carboxymethyl cellulose calcium, cross carmelose sodium, cross carmelose sodium and carboxymethyl starch sodium. Preferable examples of the above-mentioned solvents include water for injection, alcohol, propylene glycol, macrogol, sesame oil and corn oil. Preferable examples of the above-mentioned solubilizers include polyethylene glycol, propylene glycol, D-mannitol, benzyl benzoate, ethanol, tris-aminomethane, cholesterol, triethanolamine, sodium carbonate and sodium citrate. Preferable examples of the above-mentioned suspending agents include surfactants such as stearyl triethanolamine, sodium lauryl sulfate, lauryl aminopropionic acid, lecithin, benzalkonium chloride, benzetonium chloride and monostearic glyceryl ester; and hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose. Preferable examples of the above-mentioned isotonizing agents include sodium chloride, glycerin and D-mannitol. Preferable examples of the above-mentioned buffering agents include buffer solutions such as phosphate, acetate, carbonate and citrate. Preferable examples of the above-mentioned pain-easing agents include benzyl alcohol. Preferable examples of the above-mentioned preservatives include para-hydroxybenzoic acid esters, chlorobutanol, benzyl alcohol, phenethyl alcohol, dehydroacetic acid and sorbic acid. Preferable examples of the above-mentioned anti-oxidants include sulfite and ascorbic acid.

To the compound of this invention, are added, for example, a suspending agent, a solubilizer, a stabilizer, an isotonizing agent and a preservative, then the mixture is formulated, in accordance with a er se known method, into an intravenous, subcutaneous or intramuscular injection. These injections can be processed into lyophilized preparations, when necessary, by a per se known method.

Examples of the above-mentioned pharmaceutical composition are oral agents (e.g. diluted powders, granules, capsules and tablets), injections, dropping injections, external agents (e.g. transnasal preparations, percutaneous preparations, etc.), ointments (e.g. rectal ointment, vaginal ointment, etc.) and the like.

Such pharmaceutical compositions can be manufactured by a per se known method commonly used in preparing pharmaceutical compositions.

The compound of the present invention or a salt thereof can be made into injections either in a form of an aqueous injection together with dispersing agents [e.g. Tween 80 (Atlas Powder, U.S.A.), HCO 80 (Nikko Chemicals, Japan), polyethylene glycol, carboxymethylcellulose, sodium alginate, etc.], preservatives (e.g. methyl paraben, propyl paraben, benzyl alcohol, etc.), isotonizing agents (e.g. sodium chloride, mannitol, sorbitol, glucose, etc.) and the like or in a form of an oily injection by dissolving, suspending or emulsifying in plant oil (e.g. olive oil, sesame oil, cotton seed oil, corn oil, etc.), propylene glycol and the like.

In preparing a pharmaceutical composition for oral use, the compound of the present invention or a salt thereof is molded by compressing, for example, with fillers (e.g. lactose, sucrose, starch, etc.), disintegrating agents (e.g. starch, calcium carbonate, etc.), binders (e.g. starch, gum arabic, carboxymethylcellulose, polyvinylpyrrolidone, hydroxypropylcellulose, etc.) or lubricants (e.g. talc, magnesium stearate, polyethylene glycol 6000, etc.) and the like. If necessary, the composition is coated by a per se known method with an object of masking the taste, enteric coating or long-acting. Examples of the coating agent therefore are hydroxypropylmethylcellulose, ethylcellulose, hydroxymethylcellulose, hydroxypropylcellulose, polyoxyethylene glycol, Tween 80, pluronic F 68, cellulose acetate phthalate, hydroxypropylmethylcellulose phthalate, hydroxymethylcellulose acetate succinate, Eudragit (a copolymer of methacrylic acid with acrylic acid; manufactured by Rohm, Germany), red oxide of iron and the like. Subcoating layer may be provided between the enteric coating and the core according to per se known method.

In preparing an external composition, the compound of the present invention or a salt thereof as it is or a salt thereof is subjected to a per se known method to give a solid, semisolid or liquid agent for external use. For example, the solid preparation is manufactured as follows. Thus, the compound of the present invention as it is or after adding/mixing fillers (e.g. glycol, mannitol, starch, microcrystalline cullulose, etc.), thickeners (e.g. natural gums, cellulose derivatives, acrylic acid polymers, etc.) and the like thereto/therewith is made into a powdery composition. With respect to the liquid composition, an oily or aqueous suspension is manufactured by the manner nearly the same as in the case of the injection. In the case of a semisolid composition, the preferred one is an aqueous or oily gel or an ointment. Each of them may be compounded with a pH adjusting agent (e.g. carbonic acid, phosphoric acid, citric acid, hydrochloric acid, sodium hydroxide, etc.), an antiseptic agent (e.g. p-hydroxybenzoates, chlorobutanol, benzalkonium chloride, etc.) and the like.

In the manufacture of an ointment for example, the compound of the present invention or a salt thereof can be made into an oily or an aqueous solid, semisolid or liquid ointment. Examples of the oily base material applicable in the above-mentioned composition are glycerides of higher fatty acids [e.g. cacao butter, Witepsols (manufactured by Dynamite-Nobel), etc.], medium fatty acids [e.g. Miglyols (manufactured by Dynamite-Nobel), etc.] and plant oil (e.g. sesame oil, soybean oil, cotton seed oil, etc.) and the like. Examples of the aqueous base material are polyethylene glycols and propylene glycol and those of the base material for aqueous gel are natural gums, cellulose derivatives, vinyl polymers, acrylic acid polymers, etc.

BEST MODE FOR CARRYING OUT OF THE INVENTION

By way of the following Reference Examples, Working Examples and Test Examples, the present invention will be described more specifically, but they are not intended to limit the scope of this invention thereto.

$^1$H-NMR spectra were taken with the Varian GEMINI 200 (200 MHz) type spectrometer, JEOL LAMBDA300 (300 MHz) type spectrometer or the Brucker AM 500 (500 MHz) type spectrometer, employing tetramethylsilane as the internal standard. All delta values were expressed in ppm.

The symbols used in the present specification have the following meanings:

s: singlet, d: doublet, t: triplet, dt: double triplet, m: multiplet, br: broad

REFERENCE EXAMPLE 1

2-Amino-5-phenylthiophene-3-carboxylic acid ethyl ester

To a mixture of ethyl cyanoacetate (6.1 g, 50 mmol), sulfur (1.61 g, 50 mmol) triethylamine (3.5 ml, 25 mmol) and dimethylformamide (10 ml) was added dropwise, with stirring at 45° C., phenylacetaldehyde (50% diethylphthalate solution; 12.05 g, 50 mmol) for 20 minutes. The mixture was stirred for 9 hours at 45° C., and the reaction mixture was concentrated. The resulting residue was extracted with ethylacetate. The extract was washed with an aqueous sodium chloride solution, which was then dried (MgSO$_4$), followed by distilling off the solvent under reduced pressure. The residue was chromatographed on silica gel, followed by crystallization from ether-hexane to give slightly yellow plates (5.55 g, 45%), m.p.124.5–125.5° C. (value in literature reference 123–124° C.).

| Elemental Analysis for $C_{13}H_{13}NO_2S$: | | | |
|---|---|---|---|
| | C(%) | H(%) | N(%) |
| Calcd.: | 63.13; | 5.30; | 5.66 |
| Found: | 62.99; | 5.05; | 5.63 |

$^1$H-NMR (200 MHz, CDCl$_3$) δ: 1.37(3H,t,J=7.1 Hz), 4.30(2H,d,J=7.1 Hz), 5.97(2H,br), 7.17–7.46(6H,m). IR(KBr): 3448, 3320, 1667, 1590, 1549 cm$^{-1}$.

REFERENCE EXAMPLE 2

2-Amino-4-methyl-5-(4-methoxyphenyl)thiophene-3-carboxylic acid ethyl ester

A mixture of 4-methoxyphenylacetone (16.5 g, 0.10 mol), ethyl cyanoacetate (12.2 g, 0.10 mol), ammonium acetate (1.55 g, 20 mmol), acetic acid (4.6 ml, 80 mmol) and benzene (20 ml) was heated for 24 hours under reflux, while removing water produced in the reaction mixture using a Dean and Stark apparatus. After cooling, the reaction mixture was concentrated under reduced pressure. The residue was partitioned between dichloromethane and an aqueous sodium hydrogencarbonate solution. The organic layer was washed with an aqueous sodium chloride solution, which was then dried (MgSO$_4$), followed by distilling of the solvent under reduced pressure. To an ethanol (30 ml) solution of the residue were added sulfur (3.21 g, 0.10 mol) and diethylamine (10.4 ml, 0.10 mol). The mixture was stirred at 50–60° C. for 2 h and then concentrated, and the concentrate was extracted with ethyl acetate. The extract was washed with an aqueous sodium chloride solution and dried (MgSO$_4$), followed by distilling off the solvent under reduced pressure. The residue was chromatographed on silica gel, which was the crystallized from ether-hexane to give a pale yellow plates (11.5 g, 40%), m.p.79–80° C.

| Elemental Analysis for $C_{15}H_{17}NO_3S$: | | | | |
|---|---|---|---|---|
| | C(%) | H(%) | N(%) | S(%) |
| Calcd.: | 61.83; | 5.88; | 4.81; | 11.01 |
| Found: | 61.81; | 5.75; | 4.74; | 10.82 |

$^1$H-NMR (200 MHz, CDCl$_3$) δ: 1.37(3H,t,J=7.1 Hz), 2.28(3H,s), 3.83(3H,s), 4.31(2H,q,J=7.1 Hz), 6.05(2H,brs), 6.91(2H,d,J=8.8 Hz), 7.27(2H,d,J=8.8 Hz). IR(KBr): 3426, 3328, 1651, 1586, 1550, 1505, 1485 cm$^{-1}$. FAB-MS m/z: 291 (M$^+$)

REFERENCE EXAMPLE 3

Employing various acetone derivatives in place of 4-methoxyphenylacetone, compounds shown in Table 1 were produced in accordance with substantially the same manner as described in Reference Example 2.

TABLE 1

| R.Ex.3 Cpd.No. | $R^{20}$ | $R^{21}$ | Yield (%) | m.p. (° C.) |
|---|---|---|---|---|
| 1 | methyl | phenyl | 40 | 64–65 |
| 2 | methyl | 2-methoxyphenyl | 12 | 70–71 |

REFERENCE EXAMPLE 4

{3-Ethoxycarbonyl-5-(4-methoxyphenyl)-4-methylthiophen-2-yl}aminomethylene malonic acid diethyl ester To the compound produced in Reference Example 2 (10 g, 343.3 mmol) was added diethyl ehoxymethylene malonate (7.45 g, 34.5 mmol). The mixture was stirred for 2 hours at 120° C. After cooling, to the reaction mixture was added ether to precipitate crystals. The crystals were collected by filtration and washed with ether once more, followed by drying over phosphorus pentaoxide under reduced pressure to give pale yellow crystals (14.2 g, 90%), m.p.122–123° C.

$^1$H-NMR (200 MHz, CDCl$_3$) δ: 1.32(3H,t,J=7.1 Hz), 1.38(3H,t,J=7.2 Hz), 1.41(3H,t,J=7.2 Hz), 2.34(3H,s), 3.85 (3H,s), 4.25(2H,q,J=7.1 Hz), 4.38(2H,q,J=7.2 Hz), 4.45(2H, q,J=7.2 Hz), 6.95(2H,d,J=8.8 Hz), 7.31(2H,d,J=8.8 Hz), 8.22(1H,d,J=13.4 Hz), 12.74(1H,d,J=13.1 Hz). IR(KBr): 2984, 1720, 1707, 1688, 1653, 1599, 1518, 1499 cm$^{-1}$.

REFERENCE EXAMPLE 5

Employing, as starting materials, compounds produced in Reference Example 3 or commercially available various thiophene compounds, in accordance with substantially the same manner as described in Reference Example 4, the compounds shown in Table 2 were produced.

TABLE 2

| R.Ex.5 Cpd.No. | $R^{20}$ | $R^{21}$ | Yield (%) | m.p. (° C.) |
|---|---|---|---|---|
| 1 | methyl | phenyl | 92 | 108–109 |
| 2 | phenyl | methyl | 92 | 137–138 |
| 3 | methyl | H | 92 | 132–133 |
| 4 | methyl | 2-methoxyphenyl | 100 | amorphous |

REFERENCE EXAMPLE 6

{3-carboxy-5-(4-methoxyphenyl)-4-methylthiophen-2-yl}aminomethylene malonic acid diethyl ester To a solution of the compound produced in Reference Example 4 (7.0 g, 15.2 mmol) in dioxane (20 ml) was added a solution of potassium hydroxide (5.0 g, 75.7 mmol) in ethanol (30 ml) at 60–70° C. with stirring. The mixture was stirred for one hour at the same temperature range, which was allowed to stand for one hour at room temperature. To the reaction mixture was added 2N HCl (40 ml, 80 mmol) with ice-cooling. The reaction mixture was concentrated under reduced pressure. Resulting yellow precipitate was collected by filtration, which was washed with a mixture of cold water and ethanol, followed by drying over phosphorus pentaoxide under reduced pressure to give a yellow powder (6.1 g, 93%), m.p. 184–187° C.

$^1$H-NMR (200 MHz, DMSO-d$_6$) δ: 1.24(3H,t,J=7.1 Hz), 1.28(3H,t,J=7.2 Hz), 2.30(3H,s), 3.80(3H,s), 4.15(2H,q,J=7.1 Hz), 4.24(2H,q,J=7.2 Hz), 7.03(2H,d,J=8.7 Hz), 7.37 (2H,d,J=8.7 Hz), 8.08(1H,d,J=13.6 Hz), 12.41(1H,d,J=13.6 Hz). IR(KBr): 3422, 2980, 1719, 1653, 1607, 1551, 1512 cm$^{-1}$.

REFERENCE EXAMPLE 7

Employing compounds obtained in Reference Example 5 as starting materials, in accordance with substantially the same manner as Reference Example 6, the compounds shown in Table 3 were produced.

TABLE 3

| R.Ex.7 Cpd.No. | R$^{20}$ | R$^{21}$ | Yield (%) | m.p. (° C.) |
|---|---|---|---|---|
| 1 | methyl | phenyl | 98 | 181–190 |
| 2 | phenyl | methyl | 65 | 173–175 |
| 3 | methyl | H | 94 | 187–189 |
| 4 | methyl | 2-methoxyphenyl | 88 | 167–169 |

REFERENCE EXAMPLE 8

4-Hydroxy-2-(4-methoxyphenyl)-3-methylthieno[2,3-b]pyridine-5-carboxylic acid ethyl ester To polyphosphoric ester (PPE) (90 ml) was added the compound produced in Reference Example 6 (6.0 g, 13.8 mmol) in small portions at 190° C. with stirring. The mixture was stirred for 30 minutes at the same temperature. The reaction mixture was poured into ice-water, which was subjected to extraction with ethylacetate. The extract solution was washed with an aqueous sodium chloride solution, which was then dried (MgSO$_4$), followed by distilling off the solvent under reduced pressure. The residue was chromatographed on silica gel to give a yellow powder (3.65 g, 77%). As the sample for elemental analysis, the powder was recrystallized from ethanol to give yellow crystals, m.p.162–163° C.

| Elemental Analysis for C$_{18}$H$_{17}$NO$_4$S: | | | | |
|---|---|---|---|---|
| | C(%) | H(%) | N(%) | S(%) |
| Calcd.: | 62.96; | 4.99; | 4.08; | 9.34 |
| Found: | 62.89; | 5.04; | 4.01; | 9.34 |

$^1$H-NMR (200 MHz, CDCl$_3$) δ: 1.47(3H,t,J=7.1 Hz), 2.63(3H,s), 4.87(3H,s), 4.49(2H,q,J=7.1 Hz), 6.99(2H,d,J=8.8 Hz), 7.44(2H,d,J=8.8 Hz), 8.84(1H,s), 12.11(1H,s). IR(KBr): 3434, 2992, 1692, 1601, 1582, 1535, 1504 cm$^{-1}$. FAB-MS m/z: 344 (MH$^+$).

REFERENCE EXAMPLE 9

Employing compounds produced in Reference Example 7 as starting materials, in accordance with substantially the same manner as described in Reference Example 8, the compounds shown in Table 4 were produced.

TABLE 4

| R.Ex.9 Cpd.No. | R$^{20}$ | R$^{21}$ | Yield (%) | m.p. (° C.) |
|---|---|---|---|---|
| 1 | methyl | phenyl | 60 | 155–157 |
| 2 | phenyl | methyl | 69 | 146–147 |
| 3 | methyl | H | 21 | 175–177 |
| 4 | methyl | 2-methoxyphenyl | 73 | amorphous |

REFERENCE EXAMPLE 10

4-Hydroxy-2-(4-nitrophenyl)-3-methylthieno[2,3-b]pyridine-5-carboxylic acid ethyl ester To a solution of the compound 1 produced in Reference Example 9 (3.76 g, 12.0 mmol) in conc. sulfuric acid (10 ml) was added dropwise, a solution of sodium nitrate (1.27 g, 15.0 mmol) in conc. sulfuric acid (5 ml) with ice-cooling. The mixture was stirred for 30 minutes at the same temperature. The reaction mixture was poured into ice-water, which was subjected to extraction with chloroform. The extract was washed with an aqueous sodium chloride solution, which was then dried (MgSO$_4$), followed by distilling off the solvent under reduced pressure. The residue was chromatographed on silica gel to give a yellow powder, which was recrystallized from ethanol to afford yellow crystals (1.75 g, 41%), m.p.260–261° C.

| Elemental Analysis for C$_{17}$H$_{14}$N$_2$O$_5$S: | | | |
|---|---|---|---|
| | C(%) | H(%) | N(%) |
| Calcd.: | 56.98; | 3.94; | 7.82 |
| Found: | 56.66; | 3.91; | 7.86 |

$^1$H-NMR (200 MHz, CDCl$_3$) δ: 1.49(3H,t,J=7.1 Hz), 2.70(3H,s), 4.51(2H,q,J=7.1 Hz), 7.70(2H,d,J=8.8 Hz), 8.34 (2H,d,J=8.8 Hz), 8.89(1H,s), 12.27(1H,s). IR(KBr): 3002, 1692, 1605, 1514, 1350, 1290 cm$^{-1}$. FAB-MS m/z: 358 (MH$^+$).

REFERENCE EXAMPLE 11

4-Hydroxy-5-hydroxymethyl-2-(4-methoxyphenyl)-3-methylthieno[2,3-b]pyridine

To a suspension (6 ml) of lithium aluminum hydride (0.0326 g, 0.87 mmol) in anhydrous tetrahydrofuran was added dropwise a solution of the compound produced in Reference Example 8 (0.20 g, 0.58 mmol) in anhydrous tetrahydrofuran (3 ml) at room temperatures (15–35° C., the same range applies hereinafter). The mixture was then stirred for 30 minutes at room temperature, to which was added an aqueous solution of Rochelle salt. Resulting precipitate was removed by filtration. In this process, when necessary, the reaction mixture was subjected to heating under reflux to complete the reaction. The precipitate was washed with ethyl alcohol and chloroform, which was combined with the filtrate, followed by concentration under reduced pressure. The concentrate was partitioned between ethyl acetate and an aqueous sodium chloride solution. The organic layer was dried ($MgSO_4$), from which the solvent was distilled off under reduced pressure to give white crystals (0.13 g, 74%).

mp>300° C. $^1$H-NMR (200 MHz, DMSO-$d_6$) δ: 2.55(3H, s), 3.81(3H,s), 4.41(2H,s), 7.03(2H,d,J=8.8 Hz), 7.40(2H,d, J=8.8 Hz), 7.75(1H,s). IR(KBr): 3210, 2930, 1613, 1506, 1255 $cm^{-1}$. FAB-MS m/z: 302 ($MH^+$).

REFERENCE EXAMPLE 12

2-Benzoyl-4-hydroxy-3-methylthieno[2,3-b]pyridine-5-carboxylic acid ethyl ester

To a mixture of the compound 3 produced in Reference Example 7 (5.0 g, 15.3 mmol) and anhydrous aluminum chloride (8.6 g, 64.5 mmol) in nitromethane (100 ml) was added dropwise gradually, in an atmosphere of nitrogen with ice cooling, benzoyl chloride (3.6 ml, 31.0 mmol). The mixture was stirred for one hour at room temperature and, then, for 14 hours at 50° C. The reaction mixture was poured into ice-water, followed by extraction with ethyl acetate. The extract was washed with an aqueous sodium chloride solution, which was dried ($MgSO_4$), then the solvent was distilled off under reduced pressure to give a brownish powder (7.58 g). The powder was added, in small portions, to polyphosphoric acid ester (PPE), while stirring at 120° C. The mixture was stirred for 90 minutes at the same temperature, which was then poured into ice-water, followed by extraction with ethyl acetate. The extract was washed with an aqueous sodium chloride solution and dried ($MgSO_4$)$_1$ then the solvent was distilled off under reduced pressure. The residue was chromatographed on silica gel to give a yellow powder (0.82 g, 16%). As the sample for elemental analysis, the powdery product was recrystallized from chloroform-methanol to give a yellow crystals. m.p.241–243° C.

| Elemental Analysis for $C_{16}H_{15}NO_4S.0.25H_2O$: | | | |
|---|---|---|---|
| | C(%) | H(%) | N(%) |
| Calcd.: | 62.51; | 4.52; | 4.05 |
| Found: | 62.77; | 4.22; | 4.30 |

$^1$H-NMR (200 MHz, $CDCl_3$—$CD_3OD$) δ: 1.49(3H,t,J= 7.1 Hz), 2.71(3H,s), 4.53(2H,q,J=7.1 Hz), 7.49–7.70(3H,m), 8.96(1H,s). IR(KBr): 3004, 1692, 1638, 1603, 1582, 1537, 1431 $cm^{-1}$.

REFERENCE EXAMPLE 13

2-Phenylacetyl-4-hydroxy-3-methylthieno[2,3-b]pyridine-5-carboxylic acid ethyl ester Employing the compound 3 (10.0 g, 30.55 mmol) produced in Reference Example 7, in substantially the same manner as in Reference Example 12, using phenylacetyl chloride in place of benzoyl chloride, the above-titled compound (1.47 g, 14%) were produced. m.p.208–214° C.

| Elemental Analysis for $C_{19}H_{17}NO_4S.0.1EtOAc$: | | | |
|---|---|---|---|
| | C(%) | H(%) | N(%) |
| Calcd.: | 63.98; | 4.93; | 3.85 |
| Found: | 64.25; | 4.66; | 3.52 |

$^1$H-NMR (200 MHz, $CDCl_3$—$CD_3OD$) δ: 1.47(3H,t,J= 7.1 Hz), 2.99(3H,s), 4.20(2H,s), 4.49(2H,q,J=7.1 Hz), 7.26–7.41(5H,m), 8.96(1H,s), 12.50(1H,s). IR(KBr): 3424, 2986, 1694, 1601, 1580, 1535, 1495, 1439 $cm^{-1}$.

REFERENCE EXAMPLE 14

2-Bromo-4-hydroxy-3-methylthieno[2,3-b]pyridine-5-carboxylic acid ethyl ester

To a solution of the compound 3 produced in Reference Example 7 (17.8 g, 54.4 mmol) and pyridine (22 ml, 0.272 mmol) in chloroform (120 ml) was added dropwise gradually a solution of bromine (3.4 ml, 66.0 mmol) in chloroform (30 ml). The mixture was stirred for 40 minutes at room temperature, and then, the reaction mixture was concentrated under reduced pressure. To the concentrate was added dilute hydrochloric acid. The resulting crystalline precipitate was collected by filtration, which was washed with water and a small volume of cold ether, followed by drying over phosphorus pentaoxide under reduced pressure to give a brown powder (20 g). This powder was added, in small portions, to polyphosphoric acid ester (PPE) (100 ml) at 120°C. under stirring. The mixture was stirred for 90 minutes at the same temperature. The reaction mixture was then poured into ice-water, which was subjected to extraction with ethyl acetate. The extract was washed with an aqueous saline solution and dried ($MgSO_4$), then the solvent was distilled off under reduced pressure. The residue was chromatographed on silica gel to give a pale yellow powder (9.93 g, 58%). As the sample for elemental analysis,the powder was recrystallized from chloroform-methanol to give colorless needles, m.p.214–216° C.

| Elemental Analysis for $C_{11}H_{10}NO_3SBr$: | | | |
|---|---|---|---|
| | C(%) | H(%) | N(%) |
| Calcd.: | 41.79; | 3.19; | 4.43 |
| Found: | 41.55; | 3.14; | 4.53 |

$^1$H-NMR (200 MHz, $CDCl_3$-$CD_3OD$) δ: 1.47(3H,t,J=7.1 Hz), 2.60(3H,s), 4.50(2H,q,J=7.1 Hz), 8.82(1H,s). IR(KBr): 2990, 1694, 1605, 1578, 1533 $cm^{-1}$.

REFERENCE EXAMPLE 15

2-Bromo-4-hydroxy-3-methylthieno[2,3-b]pyridine-5-carboxylic acid ethyl ester (alternative method of producing the compound produced in Reference Example 14)

A mixture of the compound 3 produced in Reference Example 9 (0.24 g, 1.01 mmol), N-bromosuccinimide (10.198 g, 1.11 mol) and chloroform (10 ml) was refluxed for 3 hours. After cooling, the reaction mixture was poured into an aqueous sodium chloride solution, followed by extraction with chloroform. The extract was washed with an aqueous sodium chloride solution and dried ($MgSO_4$), then the solvent was distilled off under reduced pressure. The residue was chromatographed on silica gel to give a yellow powder, which was recrystallized from chloroform-methanol to give colorless needles (0.29 g, 91%). m.p.214–216° C.

REFERENCE EXAMPLE 16
7-Benzoyl-4,7-dihydro-2-(4-methoxyphenyl)-3-methyl-4-oxothieno[2,3-b]pyridine-5-carboxylic acid ethyl ester To a solution of the compound produced in Reference Example 8 (5 g, 14.6 mmol) in pyridine (100 ml) was added, under ice-cooling, benzoyl chloride (1.78 ml, 15.3 mmol). After stirring for 150 minutes at room temperature, to the reaction mixture was added ethanol (1 ml). The mixture was concentrated under reduced pressure. The residue was partitioned between dichloromethane and a saturated aqueous sodium chloride solution. The aqueous layer was extracted with dichloromethane. The organic layers were combined, washed with water and dried ($MgSO_4$). The solvent was distilled off, and the residue was chromatographed on silica gel, which was crystallized from ethanol to give white crystals (6.41 g, 98%), m.p.110–112° C.

| Elemental Analysis for $C_{25}H_{21}NO_5S$: | | | |
|---|---|---|---|
| | C(%) | H(%) | N(%) |
| Calcd.: | 67.10; | 4.73; | 3.13 |
| Found: | 66.95; | 4.68; | 2.93 |

$^1$H-NMR (200 MHz, $CDCl_3$) δ: 1.14(3H,t,J=7.7 Hz), 2.42(3H,s), 3.85(3H,s), 4.26(2H,q,J=7.2 Hz), 6.98(2H,d,J=6.7 Hz), 7.40(2H,d,J=8.9 Hz), 7.57(2H,t,J=7.6 Hz), 7.70 (1H,t,J=5.9 Hz), 8.27(2H,d,J=7.0 Hz), 9.14(1H,s). IR(KBr): 2972, 1717, 1607, 1580, 1522, 1502 $cm^{-1}$.

REFERENCE EXAMPLE 17
7-Benzoyl-3-bromomethyl-4,7-dihydro-2-(4-methoxyphenyl)-4-oxothieno[2,3-b]pyridine-5-carboxylic acid ethyl ester A mixture of the compound produced in Reference Example 16 (6.39 g, 14.3 mmol), N-bromosuccinimide (2.67 g, 15 mmol), α,α'-azobisisobutyronitrile (0.47 g, 2.86 mmol) and carbon tetrachloride (100 ml) was refluxed for one hour. Upon cooling, resulting insolubles were filtered off. The filtrate was diluted with chloroform. The organic layer was washed with a saturated aqueous sodium chloride solution and dried ($MgSO_4$), followed by distilling off the solvent under reduced pressure. The residue was crystallized from ethyl acetate to give colorless needles (7.02 g, 93%). m.p.124–126° C.

| Elemental Analysis for $C_{25}H_{20}NO_5SBr$: | | | |
|---|---|---|---|
| | C(%) | H(%) | N(%) |
| Calcd.: | 57.04; | 3.83; | 2.66 |
| Found: | 57.16; | 3.85; | 2.70 |

$^1$H-NMR (200 MHz, $CDCl_3$) δ: 1.14(3H,t,J=7.2 Hz), 3.88(3H,s), 4.26(2H,q,J=7.2 Hz), 4.68(2H,s), 7.04(2H,d,J=8.8 Hz), 7.53–7.75(5H,m), 8.35(2H,d,J=7.0 HZ), 9.20(1H, s).

IR(KBr): 2984, 1717, 1605, 1502 $cm^{-1}$.

REFERENCE EXAMPLE 18
3-(N-Benzyl-N-methylaminomethyl)-4-hydroxy-2-(4-methoxyphenyl)-thieno[2,3-b]pyridine-5-carboxylic acid ethyl ester A mixture of the compound produced in Reference Example 17 (6.73 g, 12.8 mmol), N-ethyldiisopropylamine (2.30 ml, 13.4 mmol), N-benzylmethylamine (1.73 ml, 13.4 mmol) and dimethylformamide (100 ml) was stirred for 40 minutes at room temperature. The solvent was distilled off under reduced pressure, and the residue was partitioned between dichloromethane and a saturated aqueous sodium chloride solution. The organic layer was washed with water and dried ($MgSO_4$). The solvent was distilled off under reduced pressure, and the residue was dissolved with a mixture of dichloromethane (100 ml) and ethanol (50 ml). To the solution was added, under ice-cooling, a solution of sodium ethoxide (0.88 g, 13 mmol) in ethanol (50 ml), and the mixture was stirred for 4 hours at room temperature. The reaction mixture was neutralized with acetic acid, then the solvent was distilled off under reduced pressure. The residue was subjected to partition between dichloromethane and water. The organic layer was washed with water and dried ($MgSO_4$), then the solvent was distilled off under reduced pressure. The residue was chromatographed on silica gel, which was crystallized from ethanol to give colorless needles (4.32 g, 73%). m.p.175–177° C.

| Elemental Analysis for $C_{26}H_{26}N_2O_4S$: | | | |
|---|---|---|---|
| | C(%) | H(%) | N(%) |
| Calcd.: | 67.51; | 5.67; | 6.06 |
| Found: | 67.43; | 5.72; | 6.06 |

$^1$H-NMR (200 MHz, $CDCl_3$) δ: 1.45(3H,t,J=7.2 Hz), 2.35(3H,s), 3.75(2H,brs), 3.89(3H,s), 3.92(2H,s), 4.44(2H, q,J=7.2 Hz), 7.01(2H,d,J=6.7 Hz), 7.21–7.37(7H,m), 8.87 (1H,s). IR(KBr): 3424, 3000, 1686, 1607, 1504 $cm^{-1}$.

REFERENCE EXAMPLE 19
2-Amino-4-methyl-5-(4-nitrophenyl)thiophene-3-carboxylic acid ethyl ester In substantially the same procedure as described in Reference Example 1, using 4-nitrophenylacetone (35.0 g, 195 mmol) in place of 4-methoxyphenyl acetone, ethyl cyanoacetate (23 g, 19.5 mmol), ammonium acetate (3.1 g, 40 mmol), acetic acid (9.1 ml, 159 mmol), sulfur (5.0 g, 160 mmol) and diethylamine (16.0 ml, 160 mmol), the titled compound was produced as colorless crystals (22.2 g, 52%). m.p.168–170°C. (recrystallized from ether-hexane).

| Elemental Analysis for $C_{14}H_{14}N_2O_4S$: | | | |
|---|---|---|---|
| | C(%) | H(%) | N(%) |
| Calcd.: | 54.89; | 4.61; | 9.14 |
| Found: | 54.83; | 4.90; | 9.09 |

$^1$H-NMR (200 MHz, $CDCl_3$) δ: 1.39(3H,t,J=7.1 Hz), 2.40(3H,s), 4.34(2H,q,J=7.1 Hz), 6.27(2H,brs), 7.48(2H,d, J=8.7 Hz), 8.23(2H,d,J=8.7 Hz). IR (KBr): 3446, 3324, 1667, 1580, 1545, 1506, 1491, 1475, 1410, 1332 $cm^{-1}$.

REFERENCE EXAMPLE 20
2,4(1H,3H)-Dioxo-5-methyl-6-(4-methoxyphenyl)-thieno[2,3-d]pyrimidin-3-acetic acid ethyl ester To a solution of the compound produced in Reference Example 1 (5.00 g, 17.20 mmol) was added ethyl isocyanatoacetate (2.90 ml, 25.80 mmol). The mixture was stirred for 6 hours at 45° C., followed by concentration under reduced pressure. The concentrate was dissolved in ethanol (6 ml), to which was added sodium ethoxide [prepared from ethanol (30 ml) and sodium (0.79 g, 34.30 mmol)]. The mixture was stirred for 24 hours at room temperature, to which was added 2N HCl (18 ml, 36 mmol). Ethanol was distilled off under reduced pressure, and the residue was subjected to filtration, which was washed with water-ethanol and dried under reduced pressure, followed by recrystallization from ethanol to give white needles (5.70 g, 89%). m.p.164–165° C.

Elemental Analysis for $C_{18}H_{18}N_2O_5S$:

|  | C(%) | H(%) | N(%) |
|---|---|---|---|
| Calcd.: | 57.74; | 4.85; | 7.48 |
| Found: | 57.78; | 5.03; | 7.45 |

$^1$H-NMR (200 MHz, CDCl$_3$) δ: 1.30(3H,t,J=7.2 Hz), 2.45(3H,s), 3.85(3H,s), 4.26(2H,q,J=7.2 Hz), 4.78(2H,s), 6.95(2H,d,J=8.5 Hz), 7.31(2H,d,J=8.8 Hz), 10.58(1H,s). IR (KBr): 2914, 1742, 1713, 1655, 1605, 1568, 1528, 1499 cm$^1$.

REFERENCE EXAMPLE 21

Employing, as starting materials, the compounds produced in Reference Examples 2, 3 and 19, compounds set forth in Table 5 were produced, in accordance with the method described in Reference Example 20.

TABLE 5

| R.Ex.21 Cpd.No. | $R^{33}$ | $R^{34}$ | Yield (%) | m.p. (° C.) |
|---|---|---|---|---|
| 1 | ethyl acetate | H | 85 | 119–120 |
| 2 | methyl | methoxy | 84 | 273–276 |
| 3 | phenyl | methoxy | 85 | >300 |
| 4 | phenyl | nitro | 84 | >300 |
| 5 | benzyl | methoxy | 92 | 241–242 |
| 6 | 4-methoxyphenyl | methoxy | 99 | >300 |
| 7 | cyclohexyl | methoxy | 84 | 275–276 |
| 8 | 2-methoxyphenyl | methoxy | 81 | 257–258 |
| 9 | 3-methoxyphenyl | methoxy | 93 | >300 |
| 10 | 2-chlorophenyl | methoxy | 95 | 285–286 |
| 11 | 3-chlorophenyl | methoxy | 97 | >300 |
| 12 | 4-chlorophenyl | methoxy | 95 | >300 |

REFERENCE EXAMPLE 22

2,4(1H,3H)-Dioxo-6-(4-nitrophenyl)-5-methylthieno[2,3-d]pyrimidin-3-acetic acid ethyl ester To the compound 1 produced in Reference Example 21 (2.20 g, 6.39 mmol) was added conc. sulfuric acid (12 ml). To the mixture was added dropwise, under ice-cooling, a solution of sodium nitrate (550 mg, 6.47 mmol) in conc. sulfuric acid, followed by stirring for one hour under ice-cooling. The reaction mixture was poured into ice-water, which was extracted with ethyl acetate. The extract was washed with an aqueous sodium chloride solution and dried (MgSO$_4$), followed by distilling off the solvent under reduced pressure. The residue was chromatographed on silica gel to give a yellowish solid (1.30 g, 52%), which was then recrystallized from ethyl acetate-hexane to yellow crystals, m.p.277–280° C.

Elemental Analysis for $C_{17}H_{15}N_3O_6S.0.4H_2O$:

|  | C(%) | H(%) | N(%) |
|---|---|---|---|
| Calcd.: | 51.48; | 4.01; | 10.59 |
| Found: | 51.64; | 3.79; | 10.61 |

$^1$H-NMR (200 MHz, CDCl$_3$) δ: 1.33(3H,t,J=7.2 Hz), 2.56(3H,s), 4.28(2H,q,J=7.2 Hz), 4.79(2H,s), 7.57(2H,d,J=8.8 Hz), 8.30(2H,d,J=8.8 Hz), 10.30(1H,s). IR (KBr): 1748, 1719, 1663, 1522, 1460 cm$^{-1}$.

REFERENCE EXAMPLE 23

2,4(1H,3H)-Dioxo-1-(2-fluorobenzyl)-6-(4-nitrophenyl)-5-methylthieno[2,3-d]pyrimidin-3-acetic acid ethyl ester To a solution of the compound produced in Reference Example 22 (700 mg, 1.80 mmol) in dimethylformamide (10 ml) were added potassium carbonate (372 mg, 2.70 mmol), potassium iodide (299 mg, 1.80 mmol) and 2-fluorobenzyl chloride (0.43 ml, 3.60 mmol). The mixture was stirred for 2 hours at room temperature. The reaction mixture was concentrated, and the concentrate was partitioned between ethyl acetate and an aqueous sodium chloride solution. The aqueous layer was extracted with ethyl acetate. The combined extract was washed with an aqueous sodium chloride solution, which was then dried (MgSO$_4$), followed by distilling off the solvent under reduced pressure. The residue was chromatographed on silica gel to give a white powder (500 mg, 56%), m.p.155–158° C.

Elemental Analysis for $C_{24}H_{20}N_3O_6SF.0.5H_2O$:

|  | C(%) | H(%) | N(%) |
|---|---|---|---|
| Calcd.: | 56.91; | 4.18; | 8.30 |
| Found: | 56.74; | 3.84; | 8.25 |

$^1$H-NMR (200 MHz, CDCl$_3$) δ: 1.32(3H,t,J=7.2 Hz), 3.84(3H,s), 4.27(2H,q,J=7.2 Hz), 4.84(2H,s), 5.30(2H,s), 7.06–7.33(4H,m), 7.54(2H,d,J=8.9 Hz), 7.27(2H,d,J=8.9 Hz). IR (KBr): 1748, 1711, 1673, 1520, 1491 cm$^{-1}$.

REFERENCE EXAMPLE 24

Starting from the compounds produced in Reference Example 21, compounds set forth in Table 6 were produced in accordance with the method described in Reference Example 23.

TABLE 6

[Structure: thieno[2,3-d]pyrimidine with CH3, R33, R34-phenyl, R35-benzyl substituents]

| Ref.Ex.24 Cpd.No. | R33 | R35 | R34 | Yield (%) | m.p. (° C.) |
|---|---|---|---|---|---|
| 1 | ethyl acetate | 2-fluoro | methoxy | 87 | 127–128 |
| 2 | methyl | 2-methoxy | methoxy | 92 | 174–175 |
| 3 | methyl | 2-fluoro | methoxy | 97 | 179–180 |
| 4 | phenyl | 2-methoxy | methoxy | 93 | 240–241 |
| 5 | phenyl | 2-fluoro | methoxy | 96 | 252–253 |
| 6 | phenyl | 2-fluoro | nitro | 87 | 294–295 |
| 7 | phenyl | 3-fluoro | methoxy | 88 | 215–217 |
| 8 | phenyl | 4-fluoro | methoxy | 66 | 209–212 |
| 9 | phenyl | 2,4-difluoro | methoxy | 73 | 227–228 |
| 10 | phenyl | 2,6-difluoro | methoxy | 87 | 291–292 |
| 11 | phenyl | 2-chloro,6-fluoro | methoxy | 91 | 287–288 |
| 12 | phenyl | 2-methyl-thio | methoxy | 81 | 239–240 |
| 13 | benzyl | 2-fluoro | methoxy | 86 | 124–126 |
| 14 | benzyl | 2,6-difluoro | methoxy | 82 | 161–163 |
| 15 | 4-methoxy-phenyl | 2-fluoro | methoxy | 87 | 270–272 |
| 16 | 4-methoxy-phenyl | 2,6-difluoro | methoxy | 83 | >300 |
| 17 | cyclohexyl | 2-fluoro | methoxy | 79 | 172–173 |
| 18 | cyclohexyl | 2,6-difluoro | methoxy | 73 | 207–208 |
| 19 | phenyl | 2,6-difluoro | nitro | 93 | 280–282 |
| 20 | 2-methoxy-phenyl | 2-fluoro | methoxy | 84 | 195–198 |
| 21 | 2-methoxy-phenyl | 2,6-difluoro | methoxy | 86 | 205–208 |
| 22 | 3-methoxy-phenyl | 2-fluoro | methoxy | 89 | 241–242 |
| 23 | 3-methoxy-phenyl | 2,6-difluoro | methoxy | 85 | 253–255 |
| 24 | 2-chloro-phenyl | 2-fluoro | methoxy | 91 | 220–221 |
| 25 | 2-chloro-phenyl | 2,6-difluoro | methoxy | 83 | 178–182 |
| 26 | 3-chloro-phenyl | 2-fluoro | methoxy | 90 | 247–248 |
| 27 | 3-chloro-phenyl | 2,6-difluoro | methoxy | 93 | 278–279 |
| 28 | 4-chloro-phenyl | 2-fluoro | methoxy | 79 | 269–270 |
| 29 | 4-chloro-phenyl | 2,6-difluoro | methoxy | 91 | >300 |

REFERENCE EXAMPLE 25

5-Bromomethyl-2,4(1H,3H)-dioxo-1-(2-fluorobenzyl)-6-(4-nitrophenyl)thieno[2,3-d]pyrimidin-3-acetic acid ethyl ester A mixture of the compound produced in Reference Example 23 (0.300 g, 0.603 mmol), N-bromosuccinimide (0.107 g, 0.603 mmol), α,α'-azobisisobutyronitrile (10 mg, 0.60 mmol) and carbon tetrachloride (15 ml) was refluxed for 2 hours. Upon cooling resulting insolubles were filtered off from the reaction mixture. The filtrate was diluted with chloroform. The organic layer was washed with an aqueous sodium chloride solution and dried (MgSO4), then the solvent was distilled off under reduced pressure. The residue was recrystallized from ethyl acetate to give colorless needles (0.284 g, 82%), m.p.165–167° C.

| Elemental Analysis for $C_{24}H_{19}N_3O_6SBrF$: | | | |
|---|---|---|---|
| | C(%) | H(%) | N(%) |
| Calcd.: | 50.01; | 3.32; | 7.29 |
| Found: | 49.87; | 3.27; | 7.23 |

$^1$H-NMR (200 MHz, CDCl$_3$) δ: 1.31(3H,t,J=7.1 Hz), 4.26(2H,q,J=7.1 Hz), 4.78(2H,s), 4.86(2H,s), 5.30(2H,s), 7.07–7.37(4H,m), 7.75(2H,d,J=8.8 Hz), 8.33(2H,d,J=8.8 Hz). IR (KBr): 1713, 1673, 1524, 1477 cm$^{-1}$.

REFERENCE EXAMPLE 26

Starting from the compounds produced in Reference Example 24, compounds set forth in Table 7 were produced in accordance with the method described in Reference Example 25.

TABLE 7

[Structure: bromomethyl-thieno[2,3-d]pyrimidine with R33, R34-phenyl, R35-benzyl substituents]

| Ref. Ex. 26 Cpd. No. | R33 | R35 | R34 | Yield (%) | m.p. (° C.) |
|---|---|---|---|---|---|
| 1 | ethyl acetate | 2-fluoro | methoxy | 70 | 152–153 |
| 2 | methyl | 2-methoxy | methoxy | 63 | 173–176 |
| 3 | methyl | 2-fluoro | methoxy | 82 | 175–177 |
| 4 | phenyl | 2-methoxy | methoxy | 93 | 240–241 |
| 5 | phenyl | 2-fluoro | methoxy | 86 | 230–233 |
| 6 | phenyl | 2-fluoro | nitro | 86 | 224–225 |
| 7 | phenyl | 3-fluoro | methoxy | 84 | 215–216 |
| 8 | phenyl | 4-fluoro | methoxy | 84 | 232–233 |
| 9 | phenyl | 2,4-difluoro | methoxy | 84 | 230–231 |
| 10 | phenyl | 2,6-difluoro | methoxy | 87 | 250–252 |
| 11 | phenyl | 2-chloro,6-fluoro | methoxy | 86 | 255–257 |
| 12 | phenyl | 2-methyl-thio | methoxy | 90 | 212–214 |
| 13 | benzyl | 2-fluoro | methoxy | 83 | 132–134 |
| 14 | benzyl | 2,6-difluoro | methoxy | 89 | 154–155 |
| 15 | 4-methoxy phenyl | 2-fluoro | methoxy | 88 | 226–228 |
| 16 | 4-methoxy phenyl | 2,6-difluoro | methoxy | 80 | 249–251 |
| 17 | cyclohexyl | 2-fluoro | methoxy | 86 | 149–151 |
| 18 | cyclohexyl | 2,6-difluoro | methoxy | 77 | 192–194 |
| 19 | phenyl | 2,6-difluoro | nitro | 94 | 228–229 |
| 20 | 2-methoxy-phenyl | 2-fluoro | methoxy | 77 | 180–181 |
| 21 | 2-methoxy-phenyl | 2,6-difluoro | methoxy | 79 | 212–214 |

TABLE 7-continued

[Structure: Br—CH₂ group on thieno[2,3-b]pyridine-dione core with R³³, R³⁴, R³⁵ substituents and CH₂-phenyl group]

| Ref. Ex. 26 Cpd. No. | R³³ | R³⁵ | R³⁴ | Yield (%) | m.p. (° C.) |
|---|---|---|---|---|---|
| 22 | 3-methoxy-phenyl | 2-fluoro | methoxy | 82 | 234–235 |
| 23 | 3-methoxy-phenyl | 2,6-difluoro | methoxy | 88 | 255–256 |
| 24 | 2-chloro-phenyl | 2-fluoro | methoxy | 85 | 175–178 |
| 25 | 2-chloro-phenyl | 2,6-difluoro | methoxy | 88 | 191–193 |
| 26 | 3-chloro-phenyl | 2-fluoro | methoxy | 81 | 243–246 |
| 27 | 3-chloro-phenyl | 2,6-difluoro | methoxy | 92 | 270–273 |
| 28 | 4-chloro-phenyl | 2-fluoro | methoxy | 84 | 271–274 |
| 29 | 4-chloro-phenyl | 2,6-difluoro | methoxy | 78 | 265–268 |

REFERENCE EXAMPLE 27

5-Benzylmethylaminomethyl-2,4(1H,3H)-dioxo-1-(2-fluorobenzyl)-6-nitrophenyl)thieno[2,3-d]pyrimidin-3-acetic acid ethyl ester hydrochloride To a solution of the compound produced in Reference Example 25 (0.270 g, 0.47 mmol) in dumethylformamide (10 ml) were added, under ice-cooling, ethyl diisopropylamine (0.12 ml, 0.710 mmol) and benzylmethyl amine (0.07 ml, 0.56 mmol). The mixture was stirred for 20 hours at room temperature. The reaction mixture was concentrated, and the concentrate was partitioned between ethyl acetate and a saturated aqueous solution of sodium hydrogencarbonate. The aqueous layer was extracted with ethyl acetate. organic layers were combined and dried ($MgSO_4$), then the solvent was distilled off under reduced pressure. The residue was chromatographed on silica gel to give a colorless oil (0.297 g, 100%). To a solution of this oil in ethyl acetate was added, under ice-cooling, 1N ethereal hydrochloric acid. The mixture was stirred for 10 minutes at the same temperature. The reaction mixture was concentrated under reduced pressure, and the concentrate was crystallized from ethyl acetate-ether to give the corresponding hydrochloride (0.084 g) as white crystals.

m.p.[hydrochloride) 120–128° C.

Elemental Analysis for $C_{32}H_{29}N_4O_6SF \cdot HCl \cdot H_2O$:

| | C(%) | H(%) | N(%) |
|---|---|---|---|
| Calcd.: | 57.27; | 4.81; | 8.35 |
| Found: | 57.23; | 4.55; | 8.42 |

¹H-NMR (200 MHz, $CDCl_3$) [free amine]δ: 1.31(3H,t,J=7.1 Hz), 2.16(3H,s), 3.61(2H,s), 3.97(2H,s), 4.27(2H,q,J=7.1 Hz), 4.87(2H,s), 5.31(2H,s), 7.10–7.35(9H,m), 7.97(2H, d,J=8.8 Hz), 8.23(2H,d,J=8.8 Hz). IR (KBr) (hydrochloride]: 1711, 1665, 1522, 1493 cm⁻¹.

WORKING EXAMPLE 1

4,7-Dihydro-7-(2-methoxybenzyl)-2-(4-methoxyphenyl)-3-methyl-4-oxothieno[2,3-b]pyridine-5-carboxylic acid ethyl ester To a suspension of sodium hydride (60% oil; 123 mg, 3.08 mmol) in dimethylformamide (3 ml) was added dropwise, in an atmosphere of nitrogen under ice-cooling, a solution of the compound produced in Reference Example 8 (1.0 g, 2.91 mmol) in dimethylformamide (20 ml). The mixture was stirred for 30 minutes under ice-cooling, to which was added dropwise a solution of 2-methoxybenzyl chloride (0.92 g, 5.87 mmol) in dimethylformamide (3 ml). The reaction mixture was stirred for 23 hours at room temperature, then for 2 hours at 70° C. The reaction mixture was then concentrated, and the concentrate was partitioned between ethyl acetate and an aqueous ammonium chloride solution. The aqueous layer was extracted with ethyl acetate. The extract was washed with an aqueous sodium chloride solution and dried ($MgSO_4$), then the solvent was distilled off under reduced pressure. The residue was chromatographed on silica gel to give a pale yellow amorphous (0.95 g, 70%). As the sample for elemental analysis, the amorphous was recrystallized from dichloromethane-ether to afford yellow prisms, m.p.165–167° C.

Elemental Analysis for $C_{26}H_{25}NO_5S \cdot 0.5H_2O$:

| | C(%) | H(%) | N(%) |
|---|---|---|---|
| Calcd.: | 66.08; | 5.55; | 2.96 |
| Found: | 66.33; | 5.44; | 2.74 |

¹H-NMR (200 MHz, $CDCl_3$) δ: 1.41(3H,t,J=7.1 Hz), 2.65(3H,s), 3.85(3H,s), 3.86(3H,s), 4.39(2H,q,J=7.1 Hz), 5.16(2H,s), 6.92–7.00(4H,m), 7.21–7.41(4H,m), 8.41(1H,s). IR(KBr): 2980, 1727, 1684, 1609, 1590, 1497, 1464 cm⁻¹.

WORKING EXAMPLE 2

Employing the compound produced in Reference Example 8 as the starting material, in accordance with substantially the same reaction as described in Working Example 1, the compounds shown in Table 8 were produced.

TABLE 8

[Structure of thieno[2,3-b]pyridine with $CH_3$, $COOC_2H_5$, $CH_3O$-phenyl, and $CH_2$-phenyl-R groups]

| W. Ex. 2 Cpd. No. | R | Yield (%) | m.p. (° C.) |
|---|---|---|---|
| 1 | H | 49 | 170–172 |
| 2 | 3-methoxy | 71 | 153–155 |
| 3 | 4-methoxy | 72 | 132–134 |
| 4 | 2-methyl | 63 | 199–201 |
| 5 | 2-acetoxy | 52 | 154–156 |
| 6 | 2-methylthio | 49 | 152–154 |

TABLE 8-continued

[Structure: thieno[2,3-b]pyridine with CH3 at 3-position, 4-methoxyphenyl at 2-position, COOC2H5 at 5-position, and N-CH2-C6H4-R]

| W. Ex. 2 Cpd. No. | R | Yield (%) | m.p. (° C.) |
|---|---|---|---|
| 7 | 4-nitro | 97 | 98–99 |
| 8 | 4-(2-cyanophenyl) | 62 | 134–136 |
| 9 | 4-(2-t-butoxycarbonyl)phenyl | 76 | 120–122 |

WORKING EXAMPLE 3

Employing the compounds produced in Reference Examples 9 and 10 as the starting materials, the compounds shown in Table 9 were produced by substantially the same procedure as described in Working Example 1.

TABLE 9

[Structure: thieno[2,3-b]pyridine with $R^{31}$, $R^{32}$, $R^{36}$ substituents and COOC2H5]

| W. Ex. 3 Cpd. No. | $R^{31}$ | $R^{32}$ | $R^{36}$ | Yield (%) | m.p. (° C.) |
|---|---|---|---|---|---|
| 1 | methyl | 4-nitrophenyl | 2-methoxybenzyl | 69 | 194–195 |
| 2 | methyl | phenyl | 2-methoxybenzyl | 91 | amorphous |
| 3 | phenyl | methyl | 2-methoxybenzyl | 73 | 184–186 |
| 4 | methyl | benzyl | 2-methoxyphenyl | 47 | 65–70 |
| 5 | methyl | phenylacetyl | 2-methoxyphenyl | 64 | 167–170 |
| 6 | methyl | 2-methoxyphenyl | 2-methoxyphenyl | 57 | 194–196 |
| 7 | methyl | bromine | 2-methoxyphenyl | 90 | 161–163 |
| 8 | methyl | 4-nitrophenyl | 2-fluorobenzyl | 90 | 184–186 |
| 9 | methyl | 4-methoxyphenyl | 2-fluorobenzyl | 81 | 117–120 |
| 10 | methyl | 4-methoxyphenyl | 2,6-difluorobenzyl | 80 | amorphous |
| 11 | methyl | 4-nitrophenyl | 2,6-difluorobenzyl | 81 | 215–217 |
| 12 | methyl | 4-nitrophenyl | 2-chloro-6-fluorobenzyl | 80 | 211–213 |
| 13 | methyl | phenyl | 2,6-difluorobenzyl | 90 | 184–186 |
| 14 | methyl | phenyl | 2-chloro-6-fluorobenzyl | 86 | 171–173 |
| 15 | methyl | 4-methoxyphenyl | 1-naphthyl | 74 | 193–195 |
| 16 | methyl | 4-methoxyphenyl | 2-methoxyphenethyl | 50 | 134–136 |
| 17 | methyl | 4-methoxyphenyl | phenethyl | 54 | 182–184 |
| 18 | methyl | 4-methoxyphenyl | 3-phenylpropyl | 62 | 147–149 |
| 19 | methyl | 4-methoxyphenyl | cinnamyl | 64 | 170–172 |
| 20 | methyl | 4-methoxyphenyl | 3-picolyl | 28 | 142–144 |
| 21 | methyl | bromine | 2-fluorobenzyl | 78 | 211–213 |
| 22 | methyl | bromine | 2,6-difluorobenzyl | 73 | 175–176 |

WORKING EXAMPLE 4

4,7-Dihydro-5-hydroxymethyl-7-(2-methoxybenzyl)-2-(4-methoxyphenyl)-3-methyl-4-oxothieno[2,3-b]pyridine To a solution of the compound produced in Reference Example 11 (0.12 g, 0.40 mmol) in dimethylformamide (10 ml) were added, at room temperature, potassium carbonate (0.083 g, 0.60 mol), 2-methoxybenzyl chloride (0.094 g, 0.60 mol) and potassium iodide (0.033 g, 0.20 mmol). The mixture was stirred for 90 minutes at room temperature, and then for 2 hours at 50° C. The reaction mixture was concentrated, and the concentrate was partitioned between dichloromethane and water. The aqueous layer was extracted with dichloromethane. The extract was washed with an aqueous sodium chloride solution, which was then dried (MgSO$_4$), then the solvent was distilled off under reduced pressure. The residue was chromatographed on silica gel to give a pale yellow amorphous, which was recrystallized from ethyl acetate to afford colorless crystals, m.p.153–156° C.

| Elemental Analysis for $C_{24}H_{23}NO_4S$: | | | |
|---|---|---|---|
| | C(%) | H(%) | N(%) |
| Calcd.: | 68.39; | 5.50; | 3.32 |
| Found: | 68.11; | 5.58; | 3.24 |

$^1$H-NMR (200 MHz, CDCl$_3$) δ: 2.67(3H,s), 3.85(3H,s), 3.86(3H,s), 4.59(2H,s), 5.12(2H,s), 6.90–7.00(4H,m), 7.15(1H,d), 7.3–7.4(3H,m), 7.45(1H,s). IR(KBr): 3400, 2936, 2838, 1618, 1547, 1504, 1249 cm$^{-1}$.

WORKING EXAMPLE 5

5-Acetoxymethyl-4,7-dihydro-7-(2-methoxybenzyl)-2-(4-methoxyphenyl)-3-methyl-4-oxothieno[2,3-b]pyridine To a solution of the compound produced in Working Example 4 in pyridine (0.400 g, 0.96 mmol) was added, at room temperature, anhydrous acetic acid (1.78 g, 19.0 mmol). The mixture was stirred for one hour at room temperature. The reaction mixture was concentrated. The concentrate was partitioned between ethyl acetate and dilute hydrochloric acid. The aqueous layer was extracted with ethyl acetate. The extract was chromatographed on silica gel to give a colorless amorphous, which was recrystallized from ethyl ether to give colorless crystals (0.46 g, 100%), m.p.158–159° C.

| Elemental Analysis for $C_{26}H_{25}NO_5S$: | | | |
|---|---|---|---|
| | C(%) | H(%) | N(%) |
| Calcd.: | 67.37; | 5.44; | 3.02 |
| Found: | 67.09; | 5.09; | 3.06 |

$^1$H-NMR (200 MHz, CDCl$_3$) δ: 2.07(3H,s), 2.67(3H,s), 3.84(3H,s), 3.86(3H,s), 5.11(2H,s), 5.12(2H,s), 6.90–7.00 (4H,m), 7.18(1H,d,J=7.7 Hz), 7.3–7.4(3H,m), 7.69(1H,s). IR(KBr): 1752, 1626, 1578, 1508, 1506, 1255 cm$^{-1}$.

WORKING EXAMPLE 6

3-Bromomethyl-4,7-dihydro-7-(2-methoxybenzyl)-2-(4-methoxyphenyl)-4-oxothieno[2,3-b]pyridine-5-carboxylic acid ethyl ester A mixture of the compound produced in Working Example 1 (0.35 g, 0.755 mmol), N-bromosuccinimide (0.135 g, 0.758 mmol), α,α'-azobis isobutyronitrile (13 mg, 0.079 mmol) and carbon tetrachloride (5 ml) was refluxed for 2 hours. Upon cooling, resulting insolubles were filtered off from the reaction mixture, and the filtrate was diluted with chloroform. The organic layer was washed with an aqueous sodium chloride solution and, then, dried (MgSO$_4$). The solvent was distilled off under reduced pressure, and the residue was recrystallized from ethyl acetate to afford colorless needles (0.272 g, 66%), m.p.200–201° C.

| Elemental Analysis for $C_{26}H_{24}NO_5SBr$: | | | |
|---|---|---|---|
| | C(%) | H(%) | N(%) |
| Calcd.: | 57.57; | 4.46; | 2.58 |
| Found: | 57.75; | 4.31; | 2.31 |

$^1$H-NMR (200 MHz, CDCl$_3$) δ: 1.40(3H,t,J=7.1 Hz), 3.86(6H,s), 4.40(2H,q,J=7.1 Hz), 5.05(2H,s), 5.16(2H,s), 6.92–7.04(4H,m), 7.23–7.28(1H,m), 7.34–7.43(1H,m), 7.57 (2H,d,J=8.9 Hz), 8.46(1H,s). IR(KBr): 2980, 1725, 1607, 1588, 1497 cm$^{-1}$.

WORKING EXAMPLE 7

Employing the compounds produced in Working Examples 3, 4, 19, 65, 66 and 73 as starting materials, in accordance with substantially the same manner as described in Working Example 6, the compounds shown by Table 10 were produced.

TABLE 10

| W. Ex. 7 Cpd. No. | $R^{31}$ | $R^{32}$ | $R^{37}$ | $R^{36}$ | Yield (%) | m.p. (° C.) |
|---|---|---|---|---|---|---|
| 1 | bromo-methyl | 4-nitro-phenyl | ethoxy-carbonyl | 2-methoxy-benzyl | 95 | 173–175 |
| 2 | bromo-methyl | 4-methoxy-phenyl | acetoxy-methyl | 2-methoxy-benzyl | 37 | 131–133 |
| 3 | bromo-methyl | phenyl | ethoxy-carbonyl | 2-methoxy-benzyl | 71 | 194–196 |
| 4 | phenyl | bromo-methyl | ethoxy-carbonyl | 2-methoxy-benzyl | 40 | amorphous |
| 5 | bromo-methyl | benzoyl | ethoxy-carbonyl | 2-methoxy-benzyl | 36 | amorphous |
| 6 | bromo-methyl | 2-methoxy-phenyl | ethoxy-carbonyl | 2-methoxy-benzyl | 55 | amorphous |
| 7 | bromo-methyl | bromide | ethoxy-carbonyl | 2-methoxy-benzyl | 59 | 174–175 |
| 8 | bromo-methyl | 3-methoxy-phenyl | ethoxy-carbonyl | 2-methoxy-benzyl | 91 | 83–86 |
| 9 | bromo-methyl | 4-nitro-phenyl | ethoxy-carbonyl | 2-fluoro-benzyl | 69 | 202–204 |
| 10 | bromo-methyl | 4-methoxy-phenyl | ethoxy-carbonyl | 2-fluoro-benzyl | 100 | amorphous |
| 11 | bromo-methyl | 4-nitro-phenyl | ethoxy-carbonyl | 2,6-difluoro-benzyl | 81 | 200–202 |
| 12 | bromo-methyl | 4-nitro-phenyl | ethoxy-carbonyl | 2-chloro-6-fluoro-benzyl | 62 | 175–177 |
| 13 | bromo-methyl | 4-methoxy-phenyl | 1-acetoxy-ethyl | 2-fluoro-benzyl | 43 | amorphous |
| 14 | bromo- | 4-nitro- | benzoyl | 2,6- | 80 | 236–238 |

TABLE 10-continued

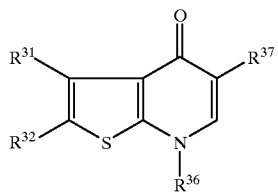

| W. Ex. 7 Cpd. No. | R³¹ | R³² | R³⁷ | R³⁶ | Yield (%) | m.p. (° C.) |
|---|---|---|---|---|---|---|
|  | methyl | phenyl |  | difluoro-benzyl |  |  |
| 15 | bromo-methyl | 4-nitro-phenyl | isobutyryl | 2,6-difluoro-benzyl | 84 | 123–124 |
| 16 | bromo-methyl | 4-methoxy-phenyl | isobutyryl | 2,6-difluoro-benzyl | 81 | 226–228 |
| 17 | bromo-methyl | 4-methoxy-phenyl | acetyl | 2-fluoro-benzyl | 75 | 186–187 |
| 18 | bromo-methyl | 4-methoxy-phenyl | propionyl | 2-fluoro-benzyl | 45 | 165–166 |
| 19 | bromo-methyl | 4-methoxy-phenyl | butyryl | 2-fluoro-benzyl | 65 | 165–166 |
| 20 | bromo-methyl | 4-methoxy-phenyl | hexanoyl | 2-fluoro-benzyl | 55 | 168–169 |
| 21 | bromo-methyl | 4-methoxy-phenyl | valeryl | 2-fluoro-benzyl | 63 | 173–174 |
| 22 | bromo-methyl | 4-methoxy-phenyl | heptonoyl | 2-fluoro-benzyl | 54 | 146–147 |
| 23 | bromo-methyl | 4-methoxy-phenyl | isovaleryl | 2-fluoro-benzyl | 74 | 187–189 |
| 24 | bromo-methyl | 4-methoxy-phenyl | benzoyl | 2-fluoro-benzyl | 75 | 145–147 |
| 25 | bromo-methyl | 4-ethoxy-carbonyl-phenyl | ethoxy-carbonyl | 2-methoxy-benzyl | 98 | 196–198 |
| 26 | bromo-methyl | 4-methoxy-phenyl | ethoxy-carbonyl | 2-fluoro-benzyl | 77 | 115–120 |
| 27 | bromo-methyl | 4-diethyl-amino-carbonyl-phenyl | ethoxy-carbonyl | 2-fluoro-benzyl | 40 | amorphous |
| 28 | bromo-methyl | 4-ethoxy-carbonyl-phenyl | benzoyl | 2,6-difluoro-benzyl | 88 | 190–192 |
| 29 | bromo-methyl | 4-butoxy-phenyl | ethoxy-carbonyl | 2-fluoro-benzyl | 40 | 138–140 |
| 30 | bromo-methyl | 4-methoxy-phenyl | cyano | 2-fluoro-benzyl | 100 | 216–218 |

WORKING EXAMPLE 8

3-Benzylaminomethyl-4,7-dihydro-7-(2-methoxybenzyl)-3-(4-methoxyphenyl)-4-oxothieno[2,3-b]pyridine-5-carboxylic acid ethyl ester hydrochloride To a solution of the compound produced in Working Example 6 (0.245 g, 0.452 mmol) in dimethylformamide (5 ml) were added, under ice-cooling, triethylamine (0.10 ml, 0.717 mmol) and benzylamine (80 μl, 0.732 mmol). The mixture was stirred for 90 minutes at room temperature. The reaction mixture was concentrated, and the concentrate was partitioned between ethyl acetate and a saturated aqueous solution of sodium hydrogen carbonate. The aqueous layer was extracted with ethyl acetate. The organic layer was dried (MgSO₄), then the solvent was distilled off under reduced pressure. The residue was chromatographed on silica gel to give a colorless oil (0.135 g, 53%). To a solution of the oily in ethanol (4 ml) was added, under ice-cooling, 1N ethanolic hydrochloric acid (0.2 ml). The mixture was stirred for 10 minutes with ice-cooling. The reaction mixture was concentrated under reduced pressure, which was crystallized from ethyl acetate and ether to give the corresponding hydrochloride (0.113 g) as white crystals, m.p.118–119° C.

| Elemental Analysis for $C_{33}H_{32}N_2O_5S \cdot HCl \cdot 0.9H_2O$: | | | |
|---|---|---|---|
|  | C(%) | H(%) | N(%) |
| Calcd.: | 63.79; | 5.64; | 4.51 |
| Found: | 64.03; | 5.44; | 4.51 |

$^1$H-NMR (200 MHz, CDCl₃) [Free amine]δ: 1.40(3H,t, J=7.1 Hz), 2.05(1H,br), 3.81(3H,s), 3.86(3H,s), 3.87(2H,s), 3.94(2H,s), 4.40(2H,q,J=7.1 Hz), 5.18(2H,s), 6.80(2H,d,J= 8.8 Hz), 6.91–6.99(2H,m), 7.20–7.42(9H,m), 8.45(1H,s). IR(KBr) [hydrochloride]: 3422, 2938, 1719, 1605, 1560, 1545, 1502, 1460 cm⁻¹.

WORKING EXAMPLE 9

Employing, as the starting material, the compound produced in Working Example 6, the compounds shown in Table 11 were produced by substantially the same procedures as described in Working Example 8.

TABLE 11

[Structure: thieno-pyridine with R$^{31}$, COOC$_2$H$_5$, 4-methoxyphenyl group on thiophene, and N-CH$_2$-(2-methoxyphenyl) substituent]

| W. Ex. 9 Cpd. No. | R$^{31}$ | Yield (%) | m.p. (° C.) |
|---|---|---|---|
| 1 | anilinomethyl | 44 | 173–174 |
| 2 | phenethylaminomethyl | 34 | 148-15 (oxalate) |
| 3 | phenylpropylaminomethyl | 36 | 116–118 (hydrochloride) |
| 4 | N'-methylpiperazinylmethyl | 63 | 138–139 |
| 5 | N'-phenylpiperazynylmethyl | 61 | 189–190 |
| 6 | 4-phenylpiperidinomethyl | 52 | 165–167 (oxalate) |
| 7 | N'-benzylpiperazinylmethyl | 86 | 109–110 (oxalate) |
| 8 | phthalimidomethyl | 46 | 221–223 |
| 9 | 1,2,3,4-tetrahydro-isoquinolylmethyl | 49 | 156–158 (hydrochloride) |
| 10 | benzhydrylaminomethyl | 52 | 133–135 (hydrochloride) |
| 11 | N-phenyl-N-benzylaminomethyl | 20 | 93–95 (hydrochloride) |
| 12 | methylaminomethyl | 100 | 118–120 (hydrobromide) |
| 13 | ethylaminomethyl | 100 | 114–116 (hydrobromide) |
| 14 | N-benzyl-N-methylaminomethyl | 69 | 96–98 (oxalate) |
| 15 | N-benzyl-N-methylaninomethyl | 77 | 147–152 (hydrochloride) |
| 16 | 2-methoxybenzylaminomethyl | 40 | 108–110 (hydrochloride) |
| 17 | 3-methylbenzylaminomethyl | 28 | 110–112 (hydrochloride) |
| 18 | 3,4-dimethoxybenzyl-aminomethyl | 10 | 129–131 (hydrochloride) |
| 19 | 2-phenylimidazo-1-ylmethyl | 49 | 130–132 |
| 20 | aminomethyl | 89 | 104–106 (hydrobromide) |
| 21 | N-benzyl-N-dimethylammonium methyl | 40 | 135–137 (bromide) |
| 22 | N-methyl-N-(2,3,4-trimethoxybenzyl)aminomethyl | 31 | 113–115 (hydrochloride) |
| 23 | N-methyl-N-(N-methylindol-3-yl)ethylaminomethyl | 43 | 151–153 (hydrochloride) |
| 24 | N-methyl-N-phenylpropylaminomethyl | 64 | 103–105 (hydrochloride) |
| 25 | N-methyl-N-(2-thiomethylbenzyl)aminomethyl | 77 | 115–117 (hydrochloride) |
| 26 | N-methyl-N-(3,5-trifluoro-methylbenzyl)aminomethyl | 53 | 130–132 (hydrochloride) |
| 27 | N-methyl-N-(2,6-dichlorobenzyl)aminomethyl | 75 | 124–126 (hydrochloride) |
| 28 | N-methyl-N-(2-nitrobenzyl)aminomethyl | 76 | 139–141 (hydrochloride) |

TABLE 11-continued

[Structure: same thieno-pyridine as above]

| W. Ex. 9 Cpd. No. | R$^{31}$ | Yield (%) | m.p. (° C.) |
|---|---|---|---|
| 29 | t-butylaminomethyl | 80 | 126–128 (hydrobromide) |
| 30 | dimethylaminomethyl | 98 | 117–119 (hydrobromide) |
| 31 | N-methyl-N-(2-chlorobenzyl)-aminomethyl | 64 | 143–145 (hydrochloride) |
| 32 | N-methyl-N-(3-chlorobenzyl)-aminomethyl | 75 | 203–205 (hydrochloride) |
| 33 | N-methyl-N-(4-chlorobenzyl)-aminomethyl | 67 | 197–199 (hydrochloride) |
| 34 | N-methyl-N-(2-fluorobenzyl)-aminomethyl | 38 | 120–122 (hydrochloride) |
| 35 | dibenzylaminomethyl | 55 | 155–157 (hydrochloride) |
| 36 | N-hydroxyethyl-N-benzyl-aminomethyl | 60 | 112–114 (hydrochloride) |
| 37 | N-ethoxycarbonylethyl-N-benzylaminomethyl | 50 | 78–80 (hydrochloride) |
| 38 | N-benzyl-N-acetamidomethyl | 17 | 78–82 (hydrochloride) |
| 39 | N-propyl-N-benzylaminomethyl | 64 | 103–107 (hydrochloride) |
| 40 | N-benzyl-N-phenethyl-aminomethyl | 67 | 105–111 (hydrochloride) |
| 41 | 2-indanylaminomethyl | 56 | 128–132 (hydrochloride) |
| 42 | N-methyl-N-(2-indanyl)aminomethyl | 24 | 121–125 (hydrochloride) |
| 43 | N-methyl-N-(3-nitrobenzyl)aminomethyl | 80 | 209–211 (hydrochloride) |
| 44 | N-methyl-N-(4-nitrobenzyl)aminomethyl | 80 | 199–201 (hydrochloride) |
| 45 | N-methyl-N-(2-phenyl-benzyl)aminomethyl | 70 | 112–114 (hydrochloride) |

WORKING EXAMPLE 10

Employing the compounds produced in Working Example 7, the compounds shown in Table 12 were produced by substantially the same procedure described in Working Example 8.

TABLE 12

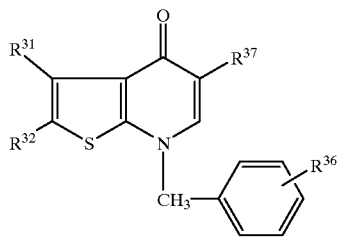

| W.Ex.10 Cpd.No. | R³¹ | R³² | R³⁵ | R³⁷ | Yield (%) | m.p. (° C.) |
|---|---|---|---|---|---|---|
| 1 | N-benzyl-N-methylamino-methyl | 4-nitro-phenyl | 2-methoxy | ethoxy-carbonyl | 73 | 124–126 (hydro-chloride) |
| 2 | N-benzyl-N-methylamino-methyl | 4-methoxy-phenyl | 2-methoxy | acetoxy-methyl | 30 | 108–117 (hydro-chloride) |
| 3 | N-benzyl-aminomethyl | phenyl | 2-methoxy | ethoxy-carbonyl | 25 | 167–169 (hydro-chloride) |
| 4 | N-benzyl-N-methylamino-methyl | phenyl | 2-methoxy | ethoxy-carbonyl | 94 | 117–120 (hydro-chloride) |
| 5 | phenyl | N-benzyl-aminomethyl | 2-methoxy | ethoxy-carbonyl | 40 | 195–197 (hydro-chloride) |
| 6 | N-benzyl-N-methylamino-methyl | benzoyl | 2-methoxy | ethoxy-carbonyl | 70 | 90–95 (hydro-chloride) |
| 7 | N-benzyl-aminomethyl | 2-methoxy-phenyl | 2-methoxy | ethoxy-carbonyl | 18 | 114–118 (hydro-chloride) |
| 8 | N-benzyl-N-methylamino-methyl | 2-methoxy-phenyl | 2-methoxy | ethoxy-carbonyl | 57 | 119–122 |
| 9 | N-benzylamino-methyl | bromine | 2-methoxy | ethoxy-carbonyl | 60 | 207–211 (oxalate) |
| 10 | N-benzyl-N-methylamino-methyl | bromine | 2-methoxy | ethoxy-carbonyl | 78 | 112–116 (oxalate) |
| 11 | N-benzyl-N-methylamino-methyl | 3-methoxy-phenyl | 2-methoxy | ethoxy-carbonyl | 71 | 115–120 (hydro-chloride) |
| 12 | N-benzyl-N-methylamino-methyl | 4-methoxy-carbonyl-phenyl | 2-methoxy | ethoxy-carbonyl | 94 | 122–125 (hydro-chloride) |
| 13 | N-benzyl-N-methylamino-methyl | 4-methoxy-phenyl | 2-fluoro | cyano | 92 | 203–206 (hydro-chloride) |

WORKING EXAMPLE 11

4,7-Dihydro-7-(2-methoxybenzyl)-2-(4-methoxyphenyl)-3-methyl-4-oxothieno[2,3-b]pyridine-N-benzylpiperazinyl-5-carboxamide To 1-benzylpiperazine (0.77 g, 4.37 mmol) was added dropwise, under ice-cooling, a toluene solution of diisobutyl aluminum hydride (1.5N, 2.9 ml, 4.37 mmol). The mixture was warmed to room temperature and stirred for 30 minutes. To this solution was, at room temperature, added a solution of the compound produced in working Example 1 (0.50 g, 1.08 mmol) in toluene (5 ml). After stirring for 15 hours at room temperature, to the reaction mixture was added methylene chloride (30 ml). The mixture was washed with water, then, dried over sodium sulfate. The solvent was distilled off under reduced pressure to leave a solid compound (1.03 g), which was recrystallized from methylene chloride-n-hexane to give the above-titled compound (0.48 g, 78%), m.p.233–235° C.

| Elemental Analysis for $C_{35}H_{35}N_5O_4S \cdot 1/2H_2O$: | | | | |
|---|---|---|---|---|
| | C(%) | H(%) | N(%) | S(%) |
| Calcd.: | 69.75; | 6.02; | 6.97; | 5.32 |
| Found: | 69.88; | 6.06; | 6.98; | 5.39 |

$^1$H-NMR (200 MHz, CDCl$_3$) δ: 2.45–2.55(4H,m), 2.63 (3H,s), 3.43–3.49(2H,m), 3.55(2H,s), 3.73–3.82(2H,m), 3.84(6H,s), 5.11(2H,s), 6.89–6.98(4H,m), 7.21–7.40(9H,m), 7.79(1H,s).

WORKING EXAMPLE 12

Employing, as the starting material, the compound produced in Working Example 1, in accordance with substantially the same procedure as described in Working Example 11, the compounds set forth in Table 13 were produced.

TABLE 13

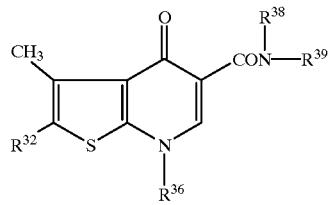

| W.Ex.12 Cpd.No. | $R^{32}$ | $R^{36}$ | $R^{38}$ | $R^{39}$ | Yield (%) | m.p. (° C.) |
|---|---|---|---|---|---|---|
| 1 | 4-methoxyphenyl | 2-methoxybenzyl | 3-pyridyl | hydrogen | 54 | 214–216 |
| 2 | 4-methoxyphenyl | 2-methoxybenzyl | dimethylaminopropyl | hydrogen | 59 | 160–164 |
| 3 | 4-methoxyphenyl | 2-methoxybenzyl | 3-pyridylmethyl | hydrogen | 60 | 168–170 |
| 4 | 4-nitrophenyl | 2,6-difluorobenzyl | methyl | methoxy | 80 | 223–224 |
| 5 | phenyl | 2,6-difluorobenzyl | methyl | methoxy | 85 | amorphous |

WORKING EXAMPLE 13

4,7-Dihydro-7-(2-methoxybenzyl)-2-(4-methoxyphenyl)-3-[N-methyl-N-(2-methoxybenzyl)aminomethyl]-4-oxothieno[2,3-b]pyridine-5-carboxylic acid ethyl ester-hydrochloride To a solution of the compound 12 produced in Working Example 9 (0.30 g, 0.52 mmol) in ethyl alcohol (5 ml) were added, at room temperature, triethylamine (0.21 g, 2.1 mmol) and 2-methoxybenzyl chloride (0.16 g, 1.0 mmol). The mixture was stirred for 60 hours at room temperature. The reaction mixture was concentrated, and the concentrate was partitioned between ethyl acetate and a saturated aqueous solution of sodium hydrogencarbonate. The aqueous layer was extracted with ethyl acetate. The combined organic layer was dried ($Na_2SO_4$), and then, the solvent was distilled off under reduced pressure. The residue was chromatographed on silica gel to give a yellow oil (0.23 g, 72%). To a solution of this oil (0.07 g, 0.10 mmol) in ethyl acetate (5 ml) was added, under ice-cooling, a 1 N ether solution of hydrogen chloride (0.2 ml, 0.20 mmol) during 5 minutes. The reaction mixture was concentrated under reduced pressure. The resulting residue was recrystallized from ethyl acetate-ether to give the corresponding hydrochloride (0.07 g, 100%) as white crystals, m.p. 107–109° C.

| Elemental Analysis for $C_{35}H_{36}N_2O_6S \cdot HCl \cdot H_2O$: | | | |
|---|---|---|---|
| | C(%) | H(%) | N(%) |
| Calcd.: | 63.01; | 5.89; | 4.20 |
| Found: | 63.57; | 6.05; | 3.88 |

$^1$H-NMR (200 MHz, $CDCl_3$) [free amine] δ: 1.39(3H,t,J=7.2 Hz), 2.38(3H,s), 3.71(3H,s), 3.85(3H,s), 3.87(3H,s), 3.88(2H,s), 4.30(2H,s), 4.39(2H,q,J=7.2 Hz), 5.21(2H,s), 6.77–7.70(12H,m), 8.44(1H,s). IR(KBr) [hydrochloride]: 3422, 2944, 1721, 1605, 1499, 1464, 1383, 1294, 1253 $cm^{-1}$. FAB-Mass m/z 613(MH)$^+$.

WORKING EXAMPLE 14

Employing, as the starting material, the compound 12 produced in Working Example 9, in accordance with substantially the same procedure as described in Working Example 13, the compounds set forth in Table 14 were produced.

TABLE 14

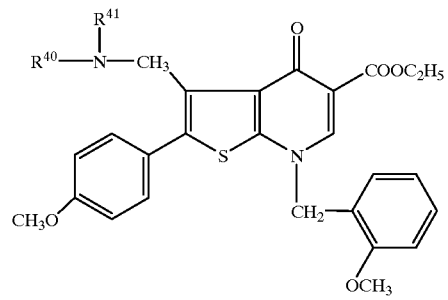

| W.Ex.14 Cpd.No. | $R^{40}$ | $R^{41}$ | Yield (%) | m.p. (° C.) |
|---|---|---|---|---|
| 1 | 2-methylbenzyl | methyl | 84 | 120–122 |
| 2 | 3-methoxybenzyl | methyl | 78 | 74–76 |
| 3 | 4-methoxybenzyl | methyl | 55 | 126–128 |
| 4 | 2,3-dimethoxybenzyl | methyl | 91 | 99–101 |
| 5 | 2-bromobenzyl | methyl | 24 | 141–143 |
| 6 | phenethyl | ethyl | 53 | 133–135 |
| 7 | 2-methoxyphenethyl | methyl | 31 | 154–156 |
| 8 | 2'-cyanobiphenyl-4-methyl | methyl | 87 | 120–122 |
| 9 | phenylcarbamoyl | methyl | 91 | 89–91 |
| 10 | 2-phenyl-2-propenyl | methyl | 13 | 152–154 |
| 11 | allyl | methyl | 36 | 138–140 |
| 12 | 3-pyridylmethyl | methyl | 20 | 160–162 |
| 13 | 1-naphthylmethyl | methyl | 47 | 161–163 |
| 14 | 2-naphthylmethyl | methyl | 47 | 148–150 |
| 15 | α-methylbenzyl | methyl | 35 | 149–151 |
| 16 | 2-hydroxybenzyl | methyl | 18 | 178–180 |
| 17 | 2-methoxycarbonylbenzyl | methyl | 36 | 129–131 |
| 18 | 2-trifluoromethylbenzyl | methyl | 33 | 129–123 |
| 19 | 2-thenyl | methyl | 26 | 133–135 |

WORKING EXAMPLE 15

2-(4-Aminophenyl)-4,7-dihydro-7-(2-methoxybenzyl)-3-(N-methyl-N-benzylaminomethyl)-4-oxothieno[2,3-b]pyridine-5-carboxylic acid ethyl ester To a solution of the compound 1 produced in Working Example 10 (0.60 g, 1.00 mmol) in methyl alcohol (10 ml) was added iron powder (0.22 g, 4.0 mmol). The mixture was vigorously stirred under ice-cooling, then the reaction mixture was poured into ice-water, which was neutralized with sodium hydrogencarbonate, followed by extraction with ethyl acetate. The organic layer was washed with an aqueous sodium chloride solution and dried ($Na_2SO_4$), and the solvent was distilled off under reduced pressure. The residue was chromatographed on silica gel, followed by crystallization from chloroform-ether to give yellow needles (0.40 g, 71%), m.p.120–122° C.

Elemental Analysis for $C_{33}H_{33}N_3O_4S.3/2H_2O$:

|  | C(%) | H(%) | N(%) |
|---|---|---|---|
| Calcd.: | 66.65; | 6.10; | 7.07 |
| Found: | 66.16; | 5.76; | 7.13 |

$^1$H-NMR (200 MHz, $CDCl_3$) [free amine] δ: 1.38(3H,t, J=7.2 Hz), 2.14(3H,s), 3.68(3H,s), 3.87(3H,s), 4.17(2H,s), 4.39(2H,q,J=7.2 Hz), 5.21(2H,s), 6.72(2H,d), 6.96(2H,t), 7.20(4H,m), 7.35(1H,t), 7.64(2H,d), 8.37(1H,s). IR(KBr) [hydrochloride]: 3454, 1690, 1603, 1499, 1386, 1317 $cm^{-1}$. FAB-Mass m/z 568(MH)$^+$.

WORKING EXAMPLE 16

4,7-Dihydro-5-hydroxymethyl-3-(N-methyl-N-benzylaminomethyl)-7-(2-methoxybenzyl)-2-(4-methoxyphenyl)-4-oxothieno[2,3-b]pyridine hydrochloride To a solution of the compound 2 produced in Working Example 10 (0.390 g, 0.67 mmol) in methyl alcohol (40 ml) was added an aqueous solution of potassium carbonate [prepared from potassium carbonate (0.185 g, 1.34 mmol) and water (8 ml)]. After stirring for 30 minutes at room temperature, the reaction mixture was then concentrated. The concentrate was partitioned between ethyl acetate and a saturated aqueous solution of sodium hydrogencarbonate. The aqueous layer was extracted with ethyl acetate. The combined organic layer was dried ($MgSO_4$), and then the solvent was distilled off under reduced pressure to give a pale yellow oil (0.36 g, 100%). To a solution of this oil (0.10 g) in tetrahydrofuran (5 ml) was added, under ice-cooling, a 1N HCl-ether solution (0.37 ml, 0.37 mmol), and the mixture was stirred for 10 minutes under ice-cooling. The reaction mixture was concentrated under reduced pressure, which was crystallized from ether to give the corresponding hydrochloride (0.105 g, 100%) as white crystals, m.p. [hydrochloride] 135–140° C.

Elemental Analysis for $C_{32}H_{33}N_2O_4SCl$:

|  | C(%) | H(%) | N(%) |
|---|---|---|---|
| Calcd.: | 66.60; | 5.76; | 4.85 |
| Found: | 66.57; | 5.90; | 4.54 |

$^1$H-NMR (500 MHz, $CDCl_3$) [free amine] δ: 2.76(3H,s), 3.86(3H,s), 3.89(3H,s), 4.37(2H,s), 4.45(1H,br s), 4.55(1H, br s), 4.77(2H,s), 5.53(2H,s), 6.94(2H,d,J=8.2 Hz), 6.98(1H, t,J=7.4 Hz), 7.06(2H,br d), 7.3–7.45(7H,m), 7.50(1H,m), 8.27(1H,s). IR(KBr) [hydrochloride]: 3388, 1607, 1499, 1460, 1253 $cm^{-1}$. FAB-Mass m/z 541(MH)$^+$.

WORKING EXAMPLE 17

4,7-Dihydro-7-(2-methoxybenzyl)-2-(4-methoxyphenyl)-3-(N-methyl-N-benzylaminomethyl)-4-oxothieno[2,3-b]pyridine-5-carboxamide hydrochloride Anhydrous ammonia (22 ml) was dissolved in toluene (5 ml) at −78° C., to which was added, at −78° C., a toluene solution of diisobutyl aluminum hydride. The mixture was then warmed to room temperature, which was stirred for further 30 minutes. To this solution was added, at room temperature, a solution of the compound 15 produced in Reference Example 9 (0.25 g, 0.425 mmol) in toluene (4 ml). The mixture was stirred for further one hour at room temperature, which was then partitioned between dichloromethane and water. The aqueous layer was extracted with dichloromethane. The combined organic layer was washed with water, followed by drying over magnesium sulfate, followed by distilling off the solvent under reduced pressure. The residue was chromatographed on silica gel to give colorless crystals. To a solution of these crystals (0.130 g, 0.23 mmol) in tetrahydrofuran (5 ml) was added, under ice-cooling, an 1N solution of hydrogen chloride in ether (0.46 ml, 0.46 mmol), and the mixture was stirred for 10 minutes under ice-cooling. The reaction mixture was concentrated under reduced pressure, which was crystallized from ether to give the corresponding hydrochloride (0.143 g, 100%) as white crystals, m.p.152–157° C.

Elemental Analysis for $C_{32}H_{32}N_3O_4SCl$:

|  | C(%) | H(%) | N(%) |
|---|---|---|---|
| Calcd.: | 66.71; | 5.60; | 4.86 |
| Found: | 66.28; | 5.80; | 4.51 |

$^1$H-NMR (500 MHz, $CDCl_3$) [free amine] δ: 2.84(3H,s), 3.87(3H,s), 3.88(3H,s), 4.35(1H,q,J=4.8 Hz), 4.6–4.8(3H, m), 5.31(2H,s), 6.09(1H,s), 6.95(1H,t,J=7.6 Hz), 6.99(1H,t, J=7.6 Hz), 7.03(2H,d,J=8.0 Hz), 7.30–7.36(4H,m), 7.40–7.50(5H,m), 8.94(1H,s), 9.70(1H,br), 11.61(1H,br). IR(KBr) [hydrochloride]: 1663, 1605, 1578, 1502, 1255 $cm^{-1}$. FAB-Mass m/z 554(MH)$^+$.

WORKING EXAMPLE 18

The compound 15 obtained in Working Example 9 was allowed to react, in substantially the same procedure as described in Working Example 17, with various amine derivatives to produce the compounds set forth in Table 15.

TABLE 15

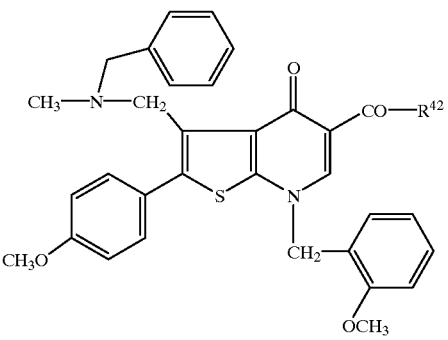

| W.Ex.18 Cpd.No. | $R^{42}$ | Yield (%) | m.p. (° C.) |
|---|---|---|---|
| 1 | N,N-dimethylamino | 51 | 136–144 (hydrochloride) |
| 2 | N'-benzylpiperazino | 26 | 168–174 (hydrochloride) |
| 3 | piperidino | 38 | 133–142 (hydrochloride) |

WORKING EXAMPLE 19

4,7-Dihydro-7-(2-methoxybenzyl)-2-(3-methoxyphenyl)-3-methyl-oxothieno[2,3-b]pyridine-5-carboxylic acid ethyl ester To a mixture of the compound 7 produced in Working Example 3 (0.615 g, 1.41 mmol), 3-methoxyphenyl boric acid (9.321 g, 2.11 mmol), 2M sodium carbonate (3.53 ml, 7.06 mmol) and 1,2-dimethoxyethane (30 ml) was added, in an atmosphere of argon, tetrakis (triphenylphosphine) palladium (O) (0.163 g, 0.141 mmol), and the mixture was refluxed for 24 hours. After cooling, to the reaction mixture was added ethyl acetate. Insolubles were filtered off with celite. The filtrate was partitioned between ethyl acetate and an aqueous sodium chloride solution. The aqueous layer was extracted with ethyl acetate. The combined organic layer was washed with a saturated aqueous sodium chloride solution and dried over magnesium sulfate. The solvent was distilled off under reduced pressure, and the residue was chromatographed on silica gel to give white amorphous (0.446 g, 68%).

| Elemental Analysis for $C_{26}H_{25}NO_5S.0.5H_2O$: | | | |
|---|---|---|---|
| | C(%) | H(%) | N(%) |
| Calcd.: | 66.08; | 5.55; | 2.96 |
| Found: | 66.33; | 5.40; | 2.91 |

$^1$H-NMR (200 MHz, $CDCl_3$) δ: 1.41(3H,t,J=7.1 Hz), 2.69(3H,s), 3.84(3H,s), 3.87(3H,s), 4.39(2H,q,J=7.1 Hz), 5.16(2H,s), 6.87–7.02(5H,m), 7.22–7.42(3H,m), 8.42(1H,s). IR(KBr): 3440, 2938, 1727, 1688, 1607, 1493, 1465 cm$^{-1}$.

WORKING EXAMPLE 20

4,7-Dihydro-2-(4-methoxyphenyl)-3-(N-methyl-N-benzylaminomethyl)-7-(2-methylthiobenzyl)-4-oxothieno[2,3-b]pyridine-5-carboxylic acid ethyl ester hydrochloride A mixture of the compound produced in Reference Example 18 (0.12 g, 0.26 mmol), $K_2CO_3$ (54 mg, 0.39 mmol), 2-methylthiobenzyl chloride (54 mg, 0.31 mmol), KI (18 mg, 0.1 mmol) and dimethylformamide (3 ml) was stirred for 2 hours at 50° C. After cooling, the solvent was distilled off under reduced pressure. The residue was chromatographed on silica gel, which was dissolved in ethyl acetate (20 ml). To the solution was added an 1N hydrogen chloride solution in ether (0.33 ml), which was concentrated under reduced pressure. The concentrate was crystallized from ether to give the corresponding hydrochloride as pale yellow crystals (0.1 g, 64%), m.p.118–120°C.

| Elemental Analysis for $C_{34}H_{34}N_2O_4S_2.HCl.0.4H_2O$: | | | |
|---|---|---|---|
| | C(%) | H(%) | N(%) |
| Calcd.: | 63.57; | 5.62; | 4.36 |
| Found: | 63.81; | 5.82; | 4.49 |

$^1$H-NMR (200 MHz, $CDCl_3$) δ: 1.38(3H,t,J=7.1 Hz), 2.52(3H,s), 2.94(3H,s), 3.88(3H,s), 4.38(3H,q, like,J=7.1 Hz), 4.60(1H brs), 4.75(2H,brs), 5.39(2H,s), 7.04(2H,d,J=8.7 Hz), 7.23–7.53(11H,m), 8.39(1H,s), 11.82(1H,brs). IR(KBr): 3406, 2980, 1719, 1605, 1502 cm$^{-1}$.

WORKING EXAMPLE 21

Employing, as the starting material, the compound produced in Reference Example 18, reactions were conducted with various halogen compounds in substantially the same manner as described in Working Example 20 to produce the compounds set forth in Table 16.

TABLE 16

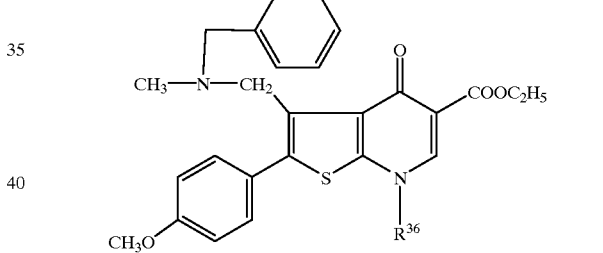

| W.Ex.21 Cpd.No. | $R^{36}$ | Yield (%) | m.p. (° C.) |
|---|---|---|---|
| 1 | 3-methoxybenzyl | 65 | 109–113 (hydrochloride) |
| 2 | 4-methoxybenzyl | 65 | 200–204 (hydrochloride) |
| 3 | 2-fluorobenzyl | 61 | 203–207 (hydrochloride) |
| 4 | 1-naphthylmethyl | 62 | 187–192 (hydrochloride) |
| 5 | 2-naphthylmethyl | 77 | 122–125 (hydrochloride) |
| 6 | 2-methoxyphenethyl | 57 | 76–81 (hydrochloride) |
| 7 | 2-trifluoromethyl-benzyl | 66 | 189–194 (hydrochloride) |

WORKING EXAMPLE 22

4,7-Dihydro-5-formyl-7-(2-methoxybenzyl)-2-(4-methoxyphenyl)-3-(N-methyl-N-benzylaminomethyl)-4-oxothieno[2,3-b]pyridine To a solution of the compound produced in Working Example 16 (0.54 g, 0.10 mmol) in chloroform (10 ml) was added active manganese dioxide (0.27 g), and the mixture was stirred for one hour at room temperature. The reaction mixture was filtered with celite, and then celite was washed with chloroform. The combined filtrate was concentrated. The concentrate was chromatographed on silica gel to give a yellow solid, which was recrystallized from ethyl acetate-ether to give white crystals (0.014 g, 25%), m.p.181–185° C.

| Elemental Analysis for $C_{32}H_{30}N_2O_4S.0.8SiO_2$: | | | |
|---|---|---|---|
| | C(%) | H(%) | N(%) |
| Calcd.: | 65.51; | 5.15; | 4.77 |
| Found: | 63.25; | 5.13; | 5.25 |

$^1$H-NMR (200 MHz, CDCl$_3$) δ: 2.40(3H,s), 3.85(3H,s), 3.87(3H,s), 3.8–4.0(2H,br), 4.33(2H,s), 5.23(2H,s), 6.9–7.1 (5H,m), 7.2–7.4(7H,m), 7.64(1H,d,J=7.9 Hz), 8.31(1H,s), 10.45(1H,s). IR(KBr): 2934, 1688, 1603, 1502, 1386, 1255 cm$^{-1}$. FAB-Mass m/z 539(MH)$^+$.

WORKING EXAMPLE 23

2-(4-Acetylaminophenyl)-4,7-dihydro-7-(2-methoxybenzyl)-3-(N-methyl-N-benzylaminomethyl)-4-oxothieno[2,3-b]pyridine-5-carboxylic acid ethyl ester To a solution of the compound produced in Working Example 15 (0.11 g, 0.20 mmol) were added, with ice-cooling, acetic anhydride (1 ml) and pyridine (0.29 g, 10.0 mmol). The mixture was stirred for 8 hours at room temperature. The reaction mixture was poured into a saturated aqueous solution of sodium hydrogencarbonate, which was extracted with dichloromethane. The extract was washed with an aqueous sodium chloride solution and dried (Na$_2$SO$_4$), followed by distilling off the solvent under reduced pressure. The residue was chromatographed on silica gel, followed by recrystalization from ether to give white crystalline powder (0.07 g, 58%), m.p.161–163° C.

$^1$H-NMR (500 MHz, DMSO-d$_6$) δ: 1.35(3H,t,J=7.2 Hz), 2.10(3H,s), 2.58(3H,s), 3.82(3H,s), 4.2–4.4(4H,m), 4.42 (1H,d), 4.58(1H,d), 5.51(2H,s), 6.70(1H,t), 7.05(1H,d), 7.1–7.3(1H,m), 7.3–7.5(7H,m), 7.68(1H,s), 7.78(2H,d), 8.88(1H,s), 10.33(1H,s). IR(KBr): 3258, 1717, 1686, 1605, 1495, 1317, 1253 cm$^{-1}$. FAB-Mass m/z 610(MH)$^+$. Working Example 24

4,7-Dihydro-2-(4-formylaminophenyl)-7-(2-methoxybenzyl)-3-(N-methyl-N-benzylaminomethyl)-4-oxothieno[2,3-b]pyridine-carboxylic acid ethyl ester To a solution of the compound produced in Working Example 15 (0.23 g, 4.00 mmol) in dichloromethane (5 ml) was added, with ice-cooling, a mixture of acetic acid anhydride and formic acid [prepared by adding, under ice-cooling, formic acid (99%, 6.00 mmol) to acetic anhydride (0.41 g, 4.00 mmol), followed by stirring for 2 hours at 60° C.]. The mixture was stirred for 8 hours at room temperature.

The reaction mixture was poured into a saturated aqueous solution of sodium hydrogencarbonate, which was extracted with dichloromethane. The extract was washed with an aqueous sodium chloride solution and dried (Na$_2$SO$_4$), then the solvent was distilled off under reduced pressure. The residue was chromatographed on silica gel, followed by recrystalization from chloroform-ether to give white needles (0.17 g, 72%), m.p.185–187° C.

| Elemental Analysis for $C_{34}H_{33}N_3O_5S.0.5H_2O$: | | | |
|---|---|---|---|
| | C(%) | H(%) | N(%) |
| Calcd.: | 67.53; | 5.67; | 6.95 |
| Found: | 67.04; | 5.28; | 6.97 |

$^1$H-NMR (200 MHz, CDCl$_3$) δ: 1.38(3H,t,J=7.2 Hz), 2.13(3H,s), 3.65(2H,s), 3.87(3H,s), 4.17(2H,s), 4.38(2H,q), 5.18(2H,s), 6.97(1H,t), 7.1–7.3(8H,m), 7.38(1H,t), 7.5–7.7 (2H,m), 7.8–7.9(2H,m), 8.40(1H,s), 8.44(1H,s). IR(KBr): 3336, 2978, 1723, 1605, 1495, 1439, 1305 cm$^{-1}$. FAB-Mass m/z 596(MH)$^+$.

WORKING EXAMPLE 25

Employing, as the starting compounds, the compound produced in Reference Example 11 and derived from the compound in Reference Example 18 with reduction in accordance with substantially the same method as described in Reference Example 11, in accordance with substantially the same method as described in Working Example 4, the compound shown in Table 17 was produced.

TABLE 17

| W.Ex.25 Cpd.No. | R$^{31}$ | R$^{32}$ | R$^{36}$ | Yield (%) | m.p. (° C.) |
|---|---|---|---|---|---|
| 1 | methyl | 4-methoxy-phenyl | 2-fluoro-benzyl | 76 | 184–185 |
| 2 | N-methyl-N-benzyl-aminomethyl | 4-methoxy-phenyl | 2-fluoro-benzyl | 92 | amorphous |

WORKING EXAMPLE 26

Employing, as the starting compound, the compound produced in Working Example 7, in accordance with substantially the same method as described in Working Example 8, the compounds shown in Table 18 were produced.

TABLE 18

[Structure: CH₃—N—CH₂(Ph) attached to thienopyridine core with R³², S, N-R³⁶, and COOCH₂CH₃ group]

| W. Ex. 26 Cpd. No. | R³² | R³⁶ | Yield (%) | m.p. (° C.) |
|---|---|---|---|---|
| 1 | 4-nitrophenyl | 2-fluoro-benzyl | 83. | 140–144 |
| 2 | 4-nitrophenyl | 2,6-difluoro-benzyl | 91 | 145–147 |
| 3 | 4-nitrophenyl | 2-chloro-6-fluorobenzyl | 78 | 175–177 |

WORKING EXAMPLE 27

Employing, as the starting compound, the compound produced in Working Example 26, in accordance with substantially the same reaction as described in Working Example 15, the compounds shown in Table 19 were produced.

TABLE 19

[Structure: same as above with CH₃—N—CH₂(Ph), R³², S, N-R³⁶, and COOCH₂CH₃]

| W. Ex. 27 Cpd. No. | R³² | R³⁶ | Yield (%) | m.p. (° C.) |
|---|---|---|---|---|
| 1 | 4-aminophenyl | 2-fluorobenzyl | 79 | 158–160 |
| 2 | 4-aminophenyl | 2,6-difluoro-benzyl | 96 | 195–196 |
| 3 | 4-aminophenyl | 2-chloro-6-fluorobenzyl | 71 | 144–146 |

WORKING EXAMPLE 28

4,7-Dihydro-7-(2-fluorobenzyl)-5-formyl-2-(4-methoxyphenyl)-3-methyl-4-oxothieno[2,3-b]pyridine:

The compound produced in Working Example 25 (4.10 g) was stirred for one hour at room temperature together with manganese dioxide (20.5 g) in chloroform (120 ml). The reaction mixture was filtered with celite. The filtrate was concentrated to dryness, the concentrate was chromatographed on silica gel, followed by recrystalization from methylene chloride-ethyl acetate to give colorless crystals (3.72 g, yield 83%).

¹H-NMR (200 MHz, CDCl₃) δ ppm: 2.66(3H,s), 3.85(3H, s), 5.26(2H,s), 6.96(2H,d), 7.1–7.4(6H,m), 8.17(1H,s), 10.44(1H,s).

WORKING EXAMPLE 29

4,7-Dihydro-7-(2-fluorobenzyl)-5-(1-hydroxyethyl)-2-(4-methoxyphenyl)-3-methyl-4-oxothieno[2,3-b]pyridine:

The compound produced in Working Example 28 (1.0 g) was dissolved in anhydrous tetrahydrofuran (50 ml). To the solution was added, with ice-cooling, methyl magnesium bromide (0.35 g), and the mixture was warmed to room temperature,followed by stirring for further 3 hours. The reaction mixture was filtered with celite. The filtrate was concentrated to dryness. To the residue were added a saturated aqueous solution of ammonium chloride (20 ml) and ethyl acetate (20 ml), then the mixture was stirred. The aqueous layer was extracted with ethyl acetate (20 ml). The combined organic layer was dried. The solvent was distilled off under reduced pressure. The residue was chromatographed on silica gel to give a yellow amorphous (1.10 g, yield 100%).

¹H-NMR (200 MHz, CDCl₃) δ ppm: 1.55(3H,d), 2.66 (3H,s), 3.84(3H,s), 4.94(1H,q), 5.20(2H,s), 6.95(2H,d), 7.1–7.2(3H,m), 7.3–7.4(3H,m), 7.44(1H,s).

WORKING EXAMPLE 30

The compound produced in Working Example 28 was subjected to reactions, in accordance with substantially the same manner as described in Working Example 29, with various Grignard's reagents in place of methyl magnesium bromide, to give the compounds set forth in Table 20.

TABLE 20

[Structure: CH₃ on thiophene ring, 4-methoxyphenyl substituent, thienopyridine core with N-CH₂-phenyl-R group and CH(OH)R' group]

| W. Ex. 30 Cpd. No. | R | R' | Yield (%) | m.p. (° C.) |
|---|---|---|---|---|
| 1 | 2-methoxy | methyl | 100 | amorphous |
| 2 | 2-fluoro | ethyl | 97 | amorphous |
| 3 | 2-fluoro | n-propyl | 92 | amorphous |
| 4 | 2-fluoro | phenyl | 71 | amorphous |
| 5 | 2-fluoro | isopropyl | 85 | amorphous |
| 6 | 2-fluoro | n-butyl | 95 | amorphous |
| 7 | 2-fluoro | sec-butyl | 72 | amorphous |
| 8 | 2-fluoro | t-butyl | 77 | amorphous |
| 9 | 2-fluoro | n-pentyl | 75 | amorphous |
| 10 | 2-fluoro | cyclopentyl | 75 | amorphous |
| 11 | 2-fluoro | n-hexyl | 68 | amorphous |
| 12 | 2-fluoro | cyclohexyl | 100 | amorphous |
| 13 | 2-fluoro | 4-fluoro-phenyl | 92 | amorphous |
| 14 | 2-fluoro | benzyl | 46 | amorphous |

WORKING EXAMPLE 31

5-Acetyl-4,7-dihydro-7-(2-fluorobenzyl)-2-(4-methoxyphenyl)-3-methyl-4-oxothieno[2,3-b]pyridine The compound produced in Working Example 29 (0.50 g) was stirred for 3 hours at 40° C. together with manganese dioxide in chloroform (50 ml). The reaction mixture was filtrated with celite. The filtrate was concentrated to dryness. The residue was recrystallized from hexane-ethyl acetate to give colorless crystals (0.35 g, yield 70%), m.p.215–216° C.

| Elemental Analysis for $C_{24}H_{20}NO_3S$: | | | |
|---|---|---|---|
| | C(%) | H(%) | N(%) |
| Calcd.: | 68.44; | 4.78; | 3.33 |
| Found: | 68.35; | 4.70; | 3.41 |

$^1$H-NMR (200 MHz, CDCl$_3$) δ ppm: 2.66(3H,s), 2.78(3H,s), 3.85(3H,s), 5.25(2H,s), 6.96(2H,d), 7.1–7.5(6H,m), 8.37 (1H,s). FAB-Mass m/z 422(MH)$^+$.

WORKING EXAMPLE 32

Employing the compound produced in Working Example 30, in accordance with substantially the same procedure as described in Working Example 31, the compounds set forth in Table 21 were produced.

TABLE 21

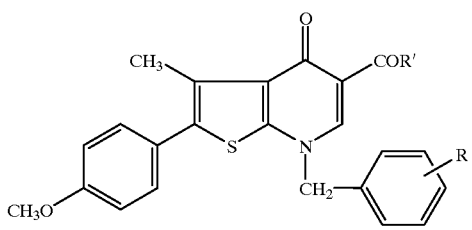

| W. Ex. 32 Cpd. No. | R | R' | Yield (%) | m.p. (° C.) |
|---|---|---|---|---|
| 1 | 2-methoxy | methyl | 80 | 156–157 |
| 2 | 2-fluoro | ethyl | 67 | 180–181 |
| 3 | 2-fluoro | n-propyl | 65 | 170–171 |
| 4 | 2-fluoro | phenyl | 84 | 183–184 |
| 5 | 2-fluoro | isopropyl | 70 | 172–174 |
| 6 | 2-fluoro | n-butyl | 83 | 162–163 |
| 7 | 2-fluoro | sec-butyl | 75 | 132–133 |
| 8 | 2-fluoro | t-butyl | 44 | 141–144 |
| 9 | 2-fluoro | n-pentyl | 88 | 145–147 |
| 10 | 2-fluoro | cyclopentyl | 62 | 182–183 |
| 11 | 2-fluoro | n-hexyl | 66 | 125–126 |
| 12 | 2-fluoro | cyclohexyl | 69 | 191–192 |
| 13 | 2-fluoro | 4-fluoro-phenyl | 86 | 187–188 |

WORKING EXAMPLE 33

5-Acetyl-3-bromomethyl-4,7-dihydro-7-(2-fluorobenzyl)-2-(4-methoxyphenyl)-4-oxothieno[2,3-b]pyridine The compound produced in Working Example 31 (0.32 g) was dissolved in carbon tetrachloride (60 ml). The solution was refluxed for 2 hours together with N-bromosuccinimide (0.144 g) and α,α'-azobisisobutyronitrile (0.013 g). After cooling, to the reaction mixture was added chloroform. The mixture was washed with a saturated aqueous solution of sodium hydrogencarbonate (20 ml). The organic layer was dried. The solvent was distilled off under reduced pressure. The residue was chromatographed on silica gel to give a yellow amorphous, which was recrystallized from chloroform-isopropyl ether-ethyl acetate to give colorless needles (0.29 g, yield 75%), m.p.226–228° C.

$^1$H-NMR (200 MHz, CDCl$_3$) δ ppm: 2.81(3H,s), 3.86(3H,s), 5.03(2H,s), 5.26(2H,s), 7.03(2H,d), 7.1–7.5(4H,m), 7.55 (2H,d), 8.38(1H,s).

WORKING EXAMPLE 34

Employing the compounds produced in Working Example 32 as the starting materials, in accordance with substantially the same reactions as described in Working Example 33, the compounds set forth in Table 22 were produced.

TABLE 22

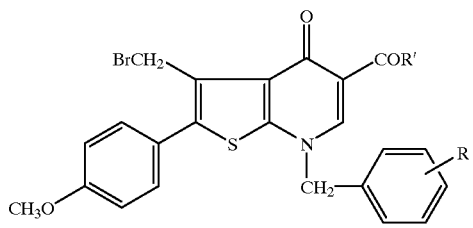

| W. Ex. 34 Cpd. No. | R | R' | Yield (%) | m.p. (° C.) |
|---|---|---|---|---|
| 1 | 2-methoxy | methyl | 68 | 206–208 |
| 2 | 2-fluoro | ethyl | 48 | 186–187 |
| 3 | 2-fluoro | n-propyl | 65 | 165–166 |
| 4 | 2-fluoro | phenyl | 75 | 145–147 |
| 5 | 2-fluoro | isopropyl | 81 | 123–124 |
| 6 | 2-fluoro | n-butyl | 63 | 173–174 |
| 7 | 2-fluoro | sec-butyl | 68 | 146–148 |
| 8 | 2-fluoro | t-butyl | 80 | 98–99 |
| 9 | 2-fluoro | isobutyl | 74 | 187–189 |
| 10 | 2-fluoro | n-pentyl | 55 | 168–169 |
| 11 | 2-fluoro | cyclopentyl | 45 | 166–167 |
| 12 | 2-fluoro | n-hexyl | 54 | 146–147 |
| 13 | 2-fluoro | cyclohexyl | 61 | 169–170 |
| 14 | 2-fluoro | 4-fluoro-phenyl | 94 | 135–136 |

WORKING EXAMPLE 35

5-Acetyl-4,7-dihydro-7-(2-fluorobenzyl)-2-(4-methoxyphenyl)-3-(N-methyl-N-benzylaminomethyl)-4-oxothieno[2,3-b]pyridine The compound produced in Working Example 33 (0.25 g) was dissolved in dimethylformamide (20 ml). To the solution were added, at room temperature, diisopropyl ethylamine (0.079 g) and N-benzylmethylamine (0.074 g). The mixture was stirred for 90 minutes at room temperature. The reaction mixture was concentrated to dryness under reduced pressure. The residue was partitioned between ethyl acetate (100 ml) and a saturated aqueous solution of sodium hydrogencarbonate (50 ml). The aqueous layer was extracted with ethyl acetate (100 ml). The combined organic layer was dried. The solvent was distilled off, and the residue was chromatographed on silica gel to give a yellow amorphous (0.27 g). The amorphous was dissolved in methylene chloride (5 ml), to which was added, with ice-cooling, an IN solution of hydrogen chloride in ether (1 ml). The resulting crystalline precipitate was collected by filtration to give a titled compound (0.22 g, yield 77%), m.p.185–193° C.

| Elemental Analysis for $C_{32}H_{30}N_2O_3SClF.2H_2O$: | | | |
|---|---|---|---|
| | C(%) | H(%) | N(%) |
| Calcd.: | 62.68; | 5.59; | 4.57 |
| Found: | 63.16; | 5.62; | 4.56 |

$^1$H-NMR (200 MHz, CDCl$_3$) δ ppm: 2.80(3H,s), 2.87(3H,s), 3.88(3H,s), 4.3–4.44(1H,m), 4.6–4.8(3H,m), 5.35(2H,s), 7.03(2H,d), 7.2–7.5(11H,m), 8.48(1H,s), 11.8(1H,br S). FAB-Mass m/z 541(MH)$^+$.

WORKING EXAMPLE 36

Employing the compounds produced in Working Example 34 as starting materials, in accordance with substantially the same reactions as described in Working Example, the compounds set forth in Table 23 were produced.

TABLE 23

| W. Ex. 36 Cpd. No. | R | R' | Yield (%) | m.p. (° C.) |
|---|---|---|---|---|
| 1 | 2-methoxy | methyl | 100 | 124–130 |
| 2 | 2-fluoro | ethyl | 83 | 163–172 |
| 3 | 2-fluoro | n-propyl | 62 | 145–150 |
| 4 | 2-fluoro | phenyl | 50 | 154–161 |

WORKING EXAMPLE 37

4,7-Dihydro-7-(2-fluorobenzyl)-3-(N-methyl-N-benzylaminomethyl)-2-(4-N'-methylureidophenyl)-4-oxothieno[2,3-b]pyridine-5-carboxylic acid ethyl ester To a solution of the compound produced in Working Example 26 (0.11 g, 0.20 mmol) in tetrahydrofuran (5 ml) was added pyridine (0.5 ml). To the mixture was added dropwise, with ice-cooling, methyl isocyanate (0.064 ml). The mixture was stirred for 4 hours at room temperature. The reaction mixture was then concentrated under reduced pressure. The concentrate was dissolved in chloroform, which was washed with an aqueous sodium chloride solution and dried ($Na_2SO_4$). The solvent was distilled off under reduced pressure., and the residue was chromatographed on silica gel, followed by recrystalization from ethanol-ethyl acetate to give white needles (0.09 g, 73%), m.p. 216–220° C.

Elemental Analysis for $C_{34}H_{33}N_4O_4SF \cdot 2H_2O$:

| | C(%) | H(%) | N(%) |
|---|---|---|---|
| Calcd.: | 62.95; | 5.75; | 8.64 |
| Found: | 63.22; | 5.60; | 8.39 |

$^1$H-NMR (500 MHz, DMSO-$d_3$) δ: 1.44(3H,t), 2.25(3H, br s), 2.84(3H,s), 4.35(2H,br s), 4.43(2H,q), 4.90(2H,br s), 5.62(2H,s), 7.20–7.32(7H,m), 7.45–7.60(6H,m), 8.85(1H,s). IR(KBr): 3308, 1698, 1605, 1499, 1319, 1236, 1183 cm$^{-1}$. Mass m/z 613(MH)$^+$.

WORKING EXAMPLE 38

Employing the compounds produced in Working Example 27 as starting materials, in accordance with substantially the same reactions as described in Working Examples 23, 24 and 37, the compounds set forth in Table 24 were produced as the corresponding hydrochlorides.

TABLE 24

| W. Ex. 38 Cpd. No. | $R^{21}$ | $R^{22}$ | Yield (%) | m.p. (° C.) |
|---|---|---|---|---|
| 1 | 4-acetyl-aminophenyl | 2-fluorobenzyl | 84 | 118–120 |
| 2 | 4-propionyl-aminophenyl | 2-fluorobenzyl | 74 | 221–223 |
| 3 | 4-isobutyryl-aminophenyl | 2-fluorobenzyl | 72 | 118–192 |
| 4 | 4-benzoyl-aminophenyl | 2-fluorobenzyl | 53 | 141–143 |
| 5 | 4-methane-sulfonamido-phenyl | 2-fluorobenzyl | 95 | >300 |

WORKING EXAMPLE 39

5-Benzylmethylaminomethyl-2,4(1H,3H)-dioxo-1-(2-fluorobenzyl)-6-(4-methoxyphenyl)-3-phenylthieno[2,3-d]pyrimidine hydrochloride To a solution of the compound 15 produced in Reference Example 29 (0.150 g, 0.310 mmol) in dimethylformamide (10 ml), with ice-cooling, were added ethyldiisopropylamine (0.08 ml, 0.460 mmol) and methylbenzylamine (0.05 ml, 0.370 mmol). After stirring for 2 hours at room temperature, the reaction mixture was concentrated. The residue was partitioned between ethyl acetate and a saturated aqueous solution of sodium bicarbonate. The aqueous layer was extracted with ethyl acetate. The combined organic layer was dried (MgSO$^4$). The solvent was distilled off under reduced pressure, and the residue was chromatographed on silica gel to give a colourless oil (0.159 g, 97%). To the solution of this oil in ethyl acetate (4 ml) was added, with ice-cooling, an iN solution of hydrogen chloride in ether (0.3 ml). After stirring for 10 minutes under ice-cooling, the reaction mixture was concentrated with reduced pressure. The residue was crystallized from ethyl acetate-ether to give a titled hydrochloride (0.144 g) as white crystals. m.p. [hydrochloride] 140–143° C.

Elemental Analysis for $C_{35}H_{30}N_3O_3SF \cdot HCl \cdot H_2O$:

| | C(%) | H(%) | N(%) |
|---|---|---|---|
| Calcd.: | 65.05; | 5.14; | 6.50 |
| Found: | 65.14; | 5.03; | 6.37 |

$^1$H-NMR (200 MHz, CDCl$_3$) [free amine] δ: 2.07(3H,s), 3.57(2H,s), 3.86(3H,s), 3.90(3H,s), 5.30(2H,s), 6.94(2H,d, J=8.8 Hz), 7.05–7.60(14H,m), 7.66(2H,d,J=8.8 Hz). IR(KBr) [hydrochloride]: 1711, 1665, 1543, 1477 cm$^{-1}$.

WORKING EXAMPLE 40

Starting from the compounds produced in Reference Example 28,-compounds set forth in Table 25 were produced in accordance with the method described in Working Example 39.

TABLE 25

| W. Ex. 40 Cpd. No. | R³³ | R³⁵ | R³⁴ | Yield (%) | m.p. (° C.) |
|---|---|---|---|---|---|
| 1 | methyl | 2-methoxy | methoxy | 46 | 119–122 |
| 2 | methyl | 2-fluoro | methoxy | 97 | 128–131 |
| 3 | phenyl | 2-methoxy | methoxy | 95 | 97–105 |
| 4 | phenyl | 2-fluoro | nitro | 100 | 140–143 |
| 5 | phenyl | 3-fluoro | methoxy | 97 | 152–156 |
| 6 | phenyl | 4-fluoro | methoxy | 100 | 165–170 |
| 7 | phenyl | 2,4-difluoro | methoxy | 77 | 155–160 |
| 8 | phenyl | 2,6-difluoro | methoxy | 100 | 160–162 |
| 9 | phenyl | 2-chloro, 6-fluoro | methoxy | 98 | 150–155 |
| 10 | phenyl | 2-methyl-thio | methoxy | 76 | 152–158 |
| 11 | benzyl | 2-fluoro | methoxy | 89 | 128–134 |
| 12 | benzyl | 2,6-difluoro | methoxy | 100 | 123–127 |
| 13 | 4-methoxy phenyl | 2-fluoro | methoxy | 93 | 150–155 |
| 14 | 4-methoxy phenyl | 2,6-difluoro | methoxy | 84 | 153–157 |
| 15 | cyclohexyl | 2-fluoro | methoxy | 93 | 144–150 |
| 16 | cyclohexyl | 2,6-difluoro | methoxy | 97 | 145–150 |
| 17 | phenyl | 2,6-difluoro | nitro | 93 | 155–160 |
| 18 | 2-methoxy-phenyl | 2-fluoro | methoxy | 93 | 152–153 |
| 19 | 2-methoxy-phenyl | 2,6-difluoro | methoxy | 100 | 148–150 |
| 20 | 3-methoxy-phenyl | 2-fluoro | methoxy | 92 | 155–158 |
| 21 | 3-methoxy-phenyl | 2,6-difluoro | methoxy | 91 | 160–163 |
| 22 | 2-chloro-phenyl | 2-fluoro | methoxy | 97 | 147–152 |
| 23 | 2-chloro-phenyl | 2,6-difluoro | methoxy | 98 | 150–155 |
| 24 | 3-chloro-phenyl | 2-fluoro | methoxy | 100 | 148–153 |
| 25 | 3-chloro-phenyl | 2,6-difluoro | methoxy | 100 | 152–157 |
| 26 | 4-chloro-phenyl | 2-fluoro | methoxy | 91 | 161–164 |
| 27 | 4-chloro-phenyl | 2,6-difluoro | methoxy | 86 | 145–146 |

WORKING EXAMPLE 41
3-Cyanomethyl-4,7-dihydro-7-(2-fluorobenzyl)-2-(4-methoxyphenyl)-4-oxothieno[2,3-b]pyridine-5-carboxylic acid ethyl ester To a suspension of the compound produced in Working Example 7 (Compound No.10) (0.80 g, 1.51 mmol) in dimethyl sulfoxide (DMSO) was added, at room temperature, sodium cyanide (0.084 g, 1.66 mmol). The reaction mixture was heated up to 60° C., which was stirred for further 4 hours. After cooling to room temperature, the reaction mixture was poured into water. The mixture was extracted with ethyl acetate (50 ml×2). The extract was washed with water, which was then dried. The resulting solution was evaporated to dryness to leave a pale yellow oil (0.77 g). This product was used in the following working example 42 without purification.

WORKING EXAMPLE 42
4,7-Dihydro-3-ethoxycarbonylmethyl-7-(2-fluorobenzyl)-2-(4-methoxyphenyl)-4-oxothieno[2,3-b]pyridine-5-carboxylic acid ethyl ester To a solution of the compound produced in Working Example 41 (0.77 g) in anhydrous ethanol (250 ml) was added dropwise carefully, at room temperature, conc. sulfuric acid (50 drops). The reaction mixture was refluxed for 15 hours. The reaction mixture was neutralized, with ice-cooling, with an excess volume of an aqueous solution of sodium hydrogencarbonate, which was extracted with ethyl acetate (500 ml×3). The extract was washed with water and dried., followed by concentration under reduced pressure to give a brownish solid (0.72 g). This solid was chromatographed on silica gel to give crystals, followed by recrystallization from ethyl acetate-hexane to give colorless crystals (0.28 g, overall yield 35%), m.p.199–201° C.

| Elemental Analysis for $C_{28}H_{26}NO_6SF.0.7H_2O$: | | | |
|---|---|---|---|
| | C(%) | H(%) | N(%) |
| Calcd.: | 62.72; | 5.02; | 2.61 |
| Found: | 62.57; | 4.84; | 2.53 |

$^1$H-NMR (300 MHz, CDCl$_3$) δ: 1.38(3H,t,J=7.2 Hz), 2.68(3H,t,J=7.2 Hz), 3.84(3H,s), 4.04(2H,s), 4.16(2H,q,J=7.2 Hz), 4.37(2H,q,J=7.2 Hz), 5.23(2H,s), 6.92–7.42(8H,m), 8.36(1H,s). IR (KBr): 3430, 1727, 1611, 1502, 1255, 1183, 1033, 762, 520 cm$^{-1}$.

WORKING EXAMPLE 43
4,7-Dihydro-7-(2-fluorobenzyl)-3-hydroxyethyl-2-(4-methoxyphenyl)-4-oxothieno[2,3-b]pyridine-5-carboxylic acid ethyl ester To a solution of the compound (0.21 g) produced in Working Example 42 in anhydrous tetrahydrofuran (THF) was added, under ice-cooling, lithium aluminum hydride. The reaction mixture was allowed to warm to room temperature, and stirred for further one hour, which was poured into a saturated aqueous solution of ammonium chloride, followed by extraction with ethyl acetate (100 ml×3). The extract was washed with a saturated aqueous solution of ammonium chloride, and dried, followed by filtration. The filtrate was concentrated under reduced pressure to give a solid, which was chromatographed on silica gel to give a pale yellow amorphous (0.16 g, 66%).

$^1$H-NMR (300 MHz, CDCl$_3$) δ: 0.90(3H,t,J=7.2 Hz), 1.70(1H,br s), 3.29(2H,t,J=6.0 Hz), 3.84(3H,s), 4.20–4.23 (2H,m), 4.37(2H,q,J=7.2 Hz), 5.29(2H,s), 6.93–7.34(8H,m), 8.45(1H,s). FAB-Mass m/z 482(MH)$^+$.

WORKING EXAMPLE 44
4,7-Dihydro-7-(2-fluorobenzyl)-2-(4-methoxyphenyl)3-(N-methyl-N-benzylaminoethyl)-4-oxothieno[2,3-b]pyridine-5-carboxylic acid ethyl ester To a solution of the compound produced in Working Example 43 (0.08 g, 0.67 mmol) in methylene chloride (5 ml) was added, with ice-cooling, an excess volume of phorphorus tribromide (0.5 ml). The reaction mixture was allowed to warm to room temperature and stirred for further one hour, to which was added ethyl acetate (20 ml). The mixture was washed with water and dried. The filtrate was concentrated under reduced pressure to give a solid. This solid was dissolved in dimethylformamide (DMF) (5 ml), to which were added an excess amount of diisopropyl ethylamine (100 mg) and N-benzylmethyl amine (100 mg). The reaction mixture was stirred for further one hour, to which was added ethyl acetate (20 ml), followed by washing with a saturated aqueous solution of sodium hydrogencarbonate and a saturated aqueous sodium chloride solution, and, then, drying. The dried solution was concentrated under reduced pressure to give a solid, which was chromatographed on silica gel to give a pale yellow amorphous (0.005 g, 4%).

$^1$H-NMR (300 MHz, CDCl$_3$) δ: 1.40(3H,t,J=7.2 Hz), 2.70(3H,s), 3.30–3.60(4H,m), 3.83(3H,s), 4.06(2H,s), 4.40(2H,q,J=7.2 Hz), 5.28(2H,s), 6.56–7.51(13H,m), 8.45(1H, s). FAB-Mass m/z 585(MH)$^+$.

WORKING EXAMPLE 45

5-(1-Acetoxyethyl)-4,7-dihydro-7-(2-fluorobenzyl)-2-(4-methoxyphenyl)-3-methyl-4-oxothieno[2,3-b]pyridine To a solution of the compound produced in Working Example 29 (0.55 g, 1.32 mmol) in pyridine (25 ml) was added, under ice-cooling, anhydrous acetic acid (2.69 g, 26.3 mmol). The reaction mixture was allowed to warm to room temperature, which was stirred for further 24 hours. The reaction mixture was concentrated under reduced pressure. The concentrate was partitioned between ethyl acetate (50 ml) and 1N HCl (10 ml). The aqueous layer was extracted with ethyl acetate. The combined organic layer was washed with a saturated aqueous sodium chloride solution, and then dried. The dried solution was concentrated under reduced pressure to give a solid, which was chromatographed on silica gel to give a pale yellow solid (0.67 g), which was recrystallized from ethyl acetate-hexane to give colorless needles (0.492 g, 81%), m.p.145–146° C.

$^1$H-NMR (200 MHz, CDCl$_3$) δ: 1.56(3H,d,J=6.5 Hz), 2.07(3H,s), 2.66(3H,s), 3.04(3H,s), 5.19(2H,s), 6.13(1H,q,J=6.5 Hz), 6.94(2H,d,J=8.8 Hz), 7.10–7.50(6H,m), 7.53(1H, s).

WORKING EXAMPLE 46

5-(1-Acetoxyethyl)-4,7-dihydro-7-(2-fluorobenzyl)-2-(4-methoxyphenyl)-3-(N-methyl-N-benzylaminomethyl)-4-oxothieno[2,3-b]pyridine To a solution of the compound 13 produced in Working Example 7 (0.15 g, 0.28 mmol) in dimethylformamide (DMF) (15 ml) were added, at room temperature, ethyl diisopropylamine (0.094 g, 0.34 mmol) and N-benzylmethyl amine (0.041 g, 0.34 mmol). After stirring for one hour, the reaction mixture was concentrated under reduced pressure. The concentrate was partitioned between ethyl acetate (50 ml) and a saturated aqueous solution of sodium hydrogencarbonate (10 ml). The aqueous layer was extracted with ethyl acetate. The combined organic layer was washed with a saturated aqueous sodium chloride solution, which was then dried. The dried solution was concentrated under reduced pressure to give a solid, which was chromato graphed on silica gel to give a pale yellow solid (0.05 g), which was recrystallized from ethyl acetate-diethyl ether to give colorless crystals (0.05 g, 29%), m.p.183–187° C.

| Elemental Analysis for C$_{34}$H$_{33}$N$_2$O$_4$SF.2H$_2$2H$_2$O: | | | |
|---|---|---|---|
| | C(%) | H(%) | N(%) |
| Calcd.: | 65.79; | 6.00; | 4.51 |
| Found: | 63.69; | 5.55; | 5.02 |

$^1$H-NMR (500 MHz, CDCl$_3$) δ: 1.59(3H,d,J=6.9 Hz), 2.09(3H,s), 2.88(3H,d,J=4.7 Hz), 3.88(3H,s), 4.40(1H,m), 4.5–4.7(3H,m), 5.46(2H,s), 6.16(1H,m), 7.08(2H,d,J=7.2 Hz), 7.16(1H,t,J=9.5 Hz), 7.22(1H,t,J=7.6 Hz), 7.3–7.4(3H, m), 7.4–7.5(6H,m), 7.97(1H,s). FAB-Mass m/z 585(MH)$^+$.

WORKING EXAMPLE 47

Starting from the compound produced in Working Example 7, compounds set forth in Table 26 were produced in accordance with substantially the same method as described in Working Example 46.

TABLE 26

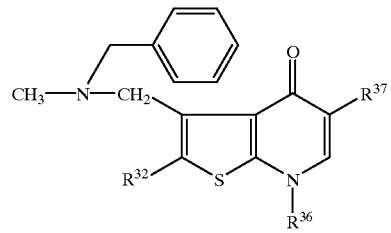

| W. Ex. 47 Cpd. No. | R$^{32}$ | R$^{36}$ | R$^{37}$ | Yield (%) | m.p. (° C.) |
|---|---|---|---|---|---|
| 1 | 4-nitrophenyl | 2,6-difluoro-benzyl | benzoyl | 83 | 197–199 |
| 2 | 4-nitrophenyl | 2,6-difluoro-benzyl | isobutyryl | 66 | 151–152 |
| 3 | 4-ethoxy-carbonyl-phenyl | 2,6-difluoro-benzyl | benzoyl | 87 | 175–180 (hydro-chloride) 169–171 (free base) |
| 4 | 4-butoxy-phenyl | 2-fluoro-benzyl | ethoxy-carbonyl | 72 | 200–202 |

WORKING EXAMPLE 48

4,7-Dihydro-7-(2-fluorobenzyl)-5-(1-hydroxyethyl)-2-(4-methoxyphenyl)-3-(N-methyl-N-benzylaminomethyl)-4-oxothieno[2,3-b]pyridine To a solution of the compound produced in Working Example 46 (0.15 g, 0.28 mmol) in methanol (5 ml) was added an aqueous solution of potassium carbonate (prepared by dissolving 0.012 g of potassium carbonate in 1 ml of water). After stirring for 3 hours, the reaction mixture was concentrated under reduced pressure. The concentrate was partitioned between ethyl acetate (20 ml) and a saturated aqueous solution of sodium hydrogencarbonate (10 ml). The aqueous layer was extracted with ethyl acetate. The combined organic layer was washed with a saturated aqueous sodium chloride solution, and then dried. The dried solution was concentrated under reduced pressure to give a solid (0.018 g, 77%), m.p.183–187° C.

| Elemental Analysis for $C_{32}H_{31}N_2O_3SF.H_2O$: | | | |
|---|---|---|---|
| | C(%) | H(%) | N(%) |
| Calcd.: | 68.55; | 5.93; | 5.00 |
| Found: | 68.69; | 5.79; | 4.92 |

$^1$H-NMR (500 MHz, CDCl$_3$) δ: 1.56(3H,d,J=6.4 Hz), 2.16(3H,s), 3.68(2H,br), 3.86(3H,s), 4.17(2H,s), 4.7–4.9 (1H,br s), 4.97(1H,q,J=6.4 Hz), 5.22(2H,s), 6.95(2H,d,J=6.9 Hz), 7.1–7.3(5H,m), 7.13–7.18(3H,m), 7.37(1H,m), 7.46 (1H,s), 7.74(2H,d,J=8.6 Hz). FAB-Mass m/z 543(MH)$^+$.

WORKING EXAMPLE 49

Starting from the compound produced in Working Example 27, the compounds set forth in Table 27 were produced in accordance with substantially the same methods described in Working Examples 23, 24 and 37.

TABLE 27

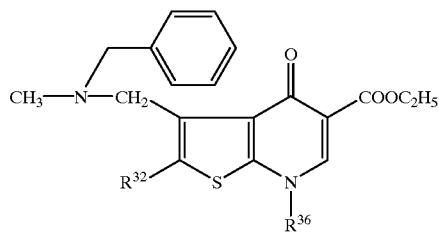

| W. Ex. 49 Cpd. No. | R$^{32}$ | R$^{36}$ | Yield (%) | m.p. (° C.) |
|---|---|---|---|---|
| 1 | 4-N'-methyl-ureidophenyl | 2-chloro-6-fluorobenzyl | 63 | 199–200 |
| 2 | 4-N'-methyl-ureidophenyl | 2-chloro-6-fluorobenzyl | 30 | 182–184 |
| 3 | 4-propionyl-aminophenyl | 2-chloro-6-fluorobenzyl | 46 | 172–173 |
| 4 | 4-N'-methyl-ureidophenyl | 2,6-difluoro-benzyl | 79 | 214–215 |
| 5 | 4-propionyl-aminophenyl | 2,6-difluoro-benzyl | 100 | 100–102 |
| 6 | 4-N'-methylthio-ureidophenyl | 2,6-difluoro-benzyl | 74 | 215–217 |
| 7 | 4-(2-methoxy-propionyl-amino)phenyl | 2,6-difluoro-benzyl | 62 | 110–112 |
| 8 | 4-n-butyryl-aminophenyl | 2-fluoro-benzyl | 48 | 203–204 |
| 9 | 4-valeryl-aminophenyl | 2-fluoro-benzyl | 47 | 206–208 |
| 10 | 4-ethoxy-carbonylamino-phenyl | 2-fluoro-benzyl | 40 | amorphous |
| 11 | 4-N'-methyl-thioureido-phenyl | 2-fluoro-benzyl | 59 | 204–205 |
| 12 | 4-N'-phenyl-ureidophenyl | 2-fluoro-benzyl | 48 | 205–207 |

WORKING EXAMPLE 50

4,7-Dihydro-7-(2,6-difluorobenzyl)-3-(N-methyl-N-benzylaminomethyl)-2-(4-nitrophenyl)-4-oxothieno[2,3-b]pyridine-5-(N-isopropyl)carboxamide To a solution of isopropylamine (0.296 g, 5 mmol) in anhydrous methylene chloride (5 ml) was added dropwise at 0° C. a hexane solution of trimethyl aluminum (15%, 2.41 ml, 5.0 mmol) in hexane. The mixture was allowed to warm to room temperature and stirred for further one hour. To this solution was added, with ice-cooling (0° C.), a solution of the compound 2 produced in Working Example 26 (0.12 g, 0.25 mmol) in anhydrous methylene chloride (3 ml), over a period of 30 minutes. The mixture was stirred for further one hour at room temperature, to which was added chloroform (50 ml), and the mixture was washed with water. The combined organic layer was dried over sodium sulfate, which was concentrated to give a solid. The solid was recrystallized from chloroform-ethyl acetate-ethyl ether to give colorless crystals (0.096 g, 70%), m.p.200–202° C.

$^1$H-NMR (500 MHz, CDCl$_3$) (free amine) δ: 1.30(6H,d, J=6.7 Hz), 2.15(3H,s), 3.66(2H,s), 4.18(2H,s), 4.18–4.31 (1H,m), 5.32(2H,s), 7.00(2H,t,J=7.26 Hz), 7.13–7.25(5H, m), 7.42(1H,t,J=7.3 Hz), 8.02(2H,d,J=8.9 Hz), 8.26(2H,d, J=8.9 Hz), 8.73(1H,s), 10.02(1H,d,J=9.1 Hz). IR (KBr): 2974, 1661, 1597, 1547, 1497, 1346, 1212, 1035 cm$^{-1}$. FAB-Mass m/z 617(MH)$^+$.

WORKING EXAMPLE 51

Starting from the compounds produced in Working Examples 26, 27, 37, 38 and 49, compounds set forth in Table 28 and Table 29 were produced in accordance with substantially the same procedure as described in Working Example 50.

TABLE 28

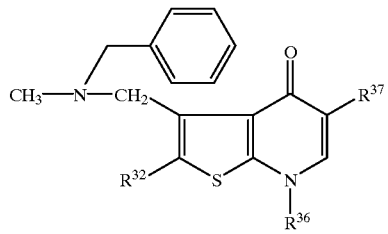

| W. Ex. 51 Cpd. No. | R$^{32}$ | R$^{36}$ | R$^{37}$ | Yield (%) | m.p. (° C.) |
|---|---|---|---|---|---|
| 1 | 4-N'-methyl-ureidophenyl | 2,6-difluoro-benzyl | N-isopropyl-N-methyl carbox-amide | 76 | 133–135 (184–186 as hydro-chloride) |
| 2 | 4-N'-methyl-ureidophenyl | 2,6-difluoro-benzyl | N-methyl-O-methyl-hydro-xamic acid | 80 | 138–140 |
| 3 | 4-propionyl-aminophenyl | 2,6-difluoro-benzyl | N,N-dimethyl-carbox-amide | 55 | 110–112 |
| 4 | 4-propionyl-aminophenyl | 2,6-difluoro-benzyl | pyrroli-dinyl amide | 43 | 130–132 |
| 5 | 4-propionyl-aminophenyl | 2,6-difluoro benzyl | N',N'-dimethyl amino-1,3-propyl-carbox-amide | 46 | 90–92 |
| 6 | 4-propionyl-aminophenyl | 2,6-difluoro-benzyl | N-methyl-N-butyl-carbox-amide | 28 | 120–122 |

TABLE 28-continued

| W. Ex. 51 Cpd. No. | R³² | R³⁶ | R³⁷ | Yield (%) | m.p. (° C.) |
|---|---|---|---|---|---|
| 7 | 4-N'-methyl-ureidophenyl | 2,6-difluoro-benzyl | N-methyl-N-benzyl-carbox-amide | 27 | 135–137 (179–181 as hydro-chloride) |
| 8 | 4-N'-methyl ureidophenyl | 2,6-difluoro-benzyl | N-isopropyl-carbox-amide | 55 | 148–150 |
| 9 | 4-nitro-phenyl | 2,6-difluoro-benzyl | 4-methyl-O-methyl-hydro-xamic acid | 96 | 100–102 |
| 10 | 4-propionyl-aminophenyl | 2,6-difluoro-benzyl | N-isopropyl-carbox-amide | 56 | 144–146 |
| 11 | 4-propionyl-aminophenyl | 2,6-difluoro-benzyl | N-butyl-carbox-amide | 32 | 107–109 |
| 12 | 4-N'-methyl-ureidophenyl | 2-chloro-6-fluorobenzyl | N-isopropyl-carbox-amide | 77 | 172–174 |
| 13 | 4-propionyl-aminophenyl | 2-chloro-6-fluorobenzyl | N-isopropyl-carbox-amide | 75 | 120–122 |
| 14 | 4-propionyl-aminophenyl | 2-chloro-6-fluorobenzyl | N-butyl-carbox-amide | 40 | 105–107 |
| 15 | 4-acetyl-aminophenyl | 2-fluoro-benzyl | N-isopropyl-carbox-amide | 83 | 184–186 |
| 16 | 4-propionyl-aminophenyl | 2,6-difluoro-benzyl | N-methyl-O-methyl-hydro-xamic acid | 74 | amor-phous |
| 17 | 4-N'-methyl-ureidophenyl | 2,6-difluoro-benzyl | N-methyl-N-(2-pyridyl)-carbox-amido | 54 | 156–158 (hydro-chloride) |
| 18 | 4-propionyl-aminophenyl | 2,6-difluoro-benzyl | N-methyl-N-(2-pyridyl)-carbox-amido | 85 | 148–150 (hydro-chloride) |
| 19 | 4-N'-methyl-ureidophenyl | 2,6-difluoro-benzyl | N-ethyl-N-benzyl-carboxy-amide | 26 | 125–127 (hydro-chloride) |

TABLE 29

| W. Ex. 51 Cpd. No. | R³¹ | R³² | R³⁶ | R³⁷ | Yield (%) | m.p. (° C.) |
|---|---|---|---|---|---|---|
| 20 | methyl | bromine | 2,6-difluoro-benzyl | N-methyl-O-methyl-carbo-hydro-xiamic acid | 87 | 192–194 |

WORKING EXAMPLE 52

5-Benzoyl-(2,6-difluorobenzyl)-4-7-dihydro-7,3-methyl-2-(4-nitrophenyl)-4-oxothieno[2,3-b]pyridine The compound 4 produced in Working Example 12 (3.93 g, 7.87 mmol) was dissolved in anhydrous tetrahydrofuran (THF) under mild heating. To this solution was added dropwise, while keeping at 0° C., a solution of phenyl magnesium bromide in THF (1M, 15.7 ml, 15.7 mmol), over a period of 10 minutes. The mixture was stirred for further one hour. The reaction mixture was partitioned between ethyl acetate (300 ml) and water (50 ml). The aqueous layer was again extracted with ethyl acetate. The combined organic layer was dried over magnesium sulfate, which was concentrated under reduced pressure. The concentrate was chromatographed on silica gel to give yellow crystals (3.00 g, 74%), which was recrystallized from ethyl acetate - hexane; m.p.114–116° C.

Elemental Analysis for $C_{26}H_{18}N_2O_4SF_2.0.7H_2O$:

|  | C(%) | H(%) | N(%) |
|---|---|---|---|
| Calcd.: | 63.56; | 3.70; | 5.29 |
| Found: | 63.83; | 3.95; | 5.08 |

$^1$H-NMR (500 MHz, CDCl$_3$) δ: 2.68(3H,s), 5.30(2H,s), 7.02(2H,t,J=8.1 Hz), 7.43(3H,t,J=7.2 Hz), 7.52–7.63(3H, m), 7.86(2H,d,J=7.5 Hz), 7.99(1H,s), 8.30(2H,d,J=8.7 Hz). IR (KBr): 3422, 3068, 1665, 1615, 1491, 1473, 1346, 853 cm$^{-1}$. FAB-Mass m/z 517(MH)$^+$.

WORKING EXAMPLE 53

Starting from the compounds produced in Working Example 51, compounds set forth in Table 30 were produced in accordance with substantially the same procedure as described in Working Example 52.

TABLE 30

[Structure: thieno[2,3-b]pyridin-4-one core with substituents R31, R32, R36, R37, S, N, O]

| W. Ex. 53 Cpd. No. | R32 | R31 | R36 | R37 | Yield (%) | m.p. (° C.) |
|---|---|---|---|---|---|---|
| 1 | 4-nitro-phenyl | N-methyl-N-benzyl-amino-methyl | 2,6-difluoro-benzyl | iso-butyryl | 10 | 236–238 (hydrochloride) |
| 2 | phenyl | N-methyl-N-benzyl-amino-methyl | 2,6-difluoro-benzyl | iso-butyryl | 52 | 204–205 |
| 3 | bromine | methyl | 2,6-difluoro-benzyl | benzoyl | 87 | 229–230 |

WORKING EXAMPLE 54

2-(4-Aminophenyl)-5-benzoyl-7-(2,6-difluorobenzyl)-4,7-dihydro-3-(N-methyl-N-benzylaminomethyl)-4-oxo-thieno[2,3-b]pyridine To a mixture of the compound 1 produced in Working Example 47 (0.30 g, 0.47 mmol) in ethyl alcohol (6 ml) was added one drop of conc. HCl, which made the mixture into a homogeneous solution. To the solution were added dropwise iron powder (0.105 g, 2.0 mmol) and conc. HCl (0.39 ml, 4.7 mmol). After stirring for 5 hours at room temperature, the reaction mixture was filtrated with celite. To the filtrate was added a small volume of aqueous ammonia, which was concentrated under reduced pressure. The concentrate was poured into ice-water, which was neutralized with sodium hydrogencarbonate, followed by extraction with ethyl acetate. The combined organic layer was washed with an aqueous sodium chloride solution, followed by drying (MgSO$_4$). The solvent was distilled off under reduced pressure. The residue was chromatographed on silica gel, followed by recrystallization from isopropyl ether to give yellow needles (0.24 g, 84%), m.p.126–128° C.

| Elemental Analysis for C$_{36}$H$_{29}$N$_3$O$_2$SF$_2$.1/2H$_2$O: | | | |
|---|---|---|---|
| | C(%) | H(%) | N(%) |
| Calcd.: | 68.93; | 5.04; | 6.70 |
| Found: | 68.71; | 5.18; | 6.62 |

$^1$H-NMR (300 MHz, CDCl$_3$) δ: 2.13(3H,s), 3.65(2H,s), 3.87(2H,br s), 4.14(2H,s), 5.28(2H,s), 6.74(2H,d,J=8.7 Hz), 7.00(2H,t,J=7.8 Hz), 7.16–7.24(5H,m), 7.36–7.46(3H,m), 7.53(1H,t,J=7.2 Hz), 7.62(2H,d,J=8.4 Hz), 7.89(2H,d,J=7.2 Hz), 7.94(1H,s). IR (KBr): 3358, 1607, 1495, 1473, 1035 cm$^{+1}$. FAB-Mass m/z 606(MH)$^+$.

WORKING EXAMPLE 55

2-(4-Aminophenyl)-7-(2,6-difluorobenzyl)-4,7-dihydro-5-isobutyryl-3-(N-methyl-N-benzylaminomethyl)-4-oxothieno[2,3-b]pyridine To a solution of the compound 2 produced in Working Example 47 (0.25 g, 0.415 mmol) in methanol (5 ml) were added dropwise, under ice-cooling, iron powder (0.093 g, 1.66 mmol) and conc. HCl (0.8 ml). After stirring for one hour at room temperature, the reaction mixture was filtrated with celite. To the filtrate was added a saturated aqueous solution of sodium hydrogencarbonate (10 ml), which was extracted with methylene chloride (30 ml×3). The combined extract solution was washed with water and dried (MgSO$_4$), then the solvent was distilled off under reduced pressure. The residue was chromatographed on silica gel to give a pale yellow amorphous (0.203 g, 86%).

$^1$H-NMR (300 MHz, CDCl$_3$) δ: 1.18(6H,d), 2.11(3H,s), 3.65(2H,s), 3.85(2H,br s), 4.17(2H,s), 4.18(1H,m), 5.25(2H,s), 6.73(2H,d), 6.95(2H,t), 7.10–7.26(5H,m), 7.42(1H,m), 7.58(2H,d), 8.27(1H,s).

WORKING EXAMPLE 56

5-Benzoyl-7-(2,6-difluorobenzyl)-4,7-dihydro-3-(N-methyl-N-benzylaminomethyl)-2-(4-propionylamidophenyl)-4-oxothieno[2,3-b]pyridine The compound produced in Working Example 54 (0.14 g, 0.23 mmol) was dissolved in anhydrous methylene chloride (2 ml). To the solution was added, with ice-cooling (0° C.), triethylamine (0.038 ml). After stirring for a while, to the mixture was added propionyl chloride (0.021 ml, 0.243 mmol). The mixture was then stirred for further 40 minutes with ice-cooling (0° C.). The reaction mixture was partitioned between methylene chloride (25 ml) and an highly dilute aqueous solution of sodium hydrogencarbonate (1 ml). The aqueous layer was again extracted with methylene chloride (25 ml). The combined organic layer was washed with an aqueous sodium chloride solution and dried (MgSO$_4$), then the solvent was distilled off under reduced pressure to give a solid. The solid was recrystallized from ethyl acetate-isopropyl ether to give yellow needles (0.10 g, 65%), m.p.226–228° C.

| Elemental Analysis for C$_{39}$H$_{33}$N$_3$O$_3$SF$_2$.0.7H$_2$O: | | | |
|---|---|---|---|
| | C(%) | H(%) | N(%) |
| Calcd.: | 69.46; | 5.14; | 6.23 |
| Found: | 69.60; | 5.18; | 6.04 |

This compound was dissolved in ethyl acetate, to which was added saturated solution of HCl in ether (an equimolar to a little excess amount) to give crystals. The crystals were recrystallized from isopropyl ether to give pale yellow needles (0.095 g, 61%), m.p.218–220° C.

| Elemental Analysis for C$_{39}$H$_{33}$N$_3$O$_3$SF$_2$.HCl.3.5H$_2$O: | | | |
|---|---|---|---|
| | C(%) | H(%) | N(%) |
| Calcd.: | 61.53; | 5.43; | 5.52 |
| Found: | 61.83; | 5.33; | 5.30 |

$^1$H-NMR (300 MHz, DMSO-d$_6$) δ: 1.11(3H,t,J=7.2 Hz), 1.93(3H,s), 2.35(2H,q,J=7.5 Hz), 3.44(2H,s), 4.00(2H,s), 5.62(2H,s), 7.11–7.25(6H,m), 7.43–7.72(10H,m), 7.79(2H,d,J=7.5 Hz), 8.40(1H,s), 10.03(1H,s). IR (KBr): 3422, 3068, 1603, 1502, 1473, 1035 cm$^{-1}$. FAB-Mass m/z 662(MH)$^+$.

WORKING EXAMPLE 57

Starting from the compounds produced in Working Examples 54 and 55, compounds set forth in Table 31 were produced in accordance with substantially the same procedures as described in Working Examples 56 and 23, 4, 27 and 38.

TABLE 31

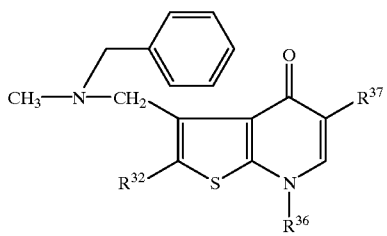

| W. Ex. 57 Cpd. No. | $R^{32}$ | $R^{36}$ | $R^{37}$ | Yield (%) | m.p. (° C.) | m.p. (° C.) (HCL salt) |
|---|---|---|---|---|---|---|
| 1 | 4-(N'-methyl-ureidophenyl) | 2,6-difluoro-benzyl | benzoyl | 68 | 238–240 | 230–231 |
| 2 | 4-propionyl-aminophenyl | 2,6-difluoro-benzyl | iso-butyryl | 64 | 201–204 | 207–214 |
| 3 | 4-(N'-methyl-ureidophenyl) | 2,6-difluoro-benzyl | iso-butyryl | 55 | 207–210 | 222–226 |
| 4 | 4-ethane-sulfonamido-phenyl | 2,6-difluoro-benzyl | benzoyl | 49 | — | 185–187 |
| 5 | 4-isobutyryl-aminophenyl | 2,6-difluoro-benzyl | benzoyl | 79 | — | 216–218 |
| 6 | 4-(N',N'-dimethyl-ureidophenyl) | 2,6-difluoro-benzyl | benzoyl | 73 | — | 180–183 |
| 7 | 4-(N'-isopropyl-ureidophenyl) | 2,6-difluoro-benzyl | benzoyl | 65 | 245–247 | — |
| 8 | 4-pyrrolidine-carbox-amidephenyl | 2,6-difluoro-benzyl | benzoyl | 65 | — | 176–178 |
| 9 | 4-(2,2,2-trifluoro-ethoxy-carboxylamino-chenyl) | 2,6-difluoro-benzyl | benzoyl | 70 | — | 232–234 |
| 10 | 4-isobutyryl-aminophenyl | 2,6-difluoro-benzyl | iso-butyryl | 73 | — | 192–197 |

WORKING EXAMPLE 58

5-Benzoyl-7-(2,6-difluorobenzyl)-4,7-dihydro-3-(N-methyl-N-benzylaminomethyl)-2-(4-nitrophenyl)-4-oxothieno[2,3-b]pyridine The compound 9 produced in Working Example 51 (1.91 g, 3.09 mmol) was dissolved in anhydrous tetrahydrofuran (THF) (30 ml) with warming. To the solution was added dropwise, under ice-cooling (0° C.), a solution of phenyl magnesium bromide in THF (1M, 6.18 ml, 6.2 mmol), over a period of 10 minutes. After stirring for one hour under ice-cooling, the reaction mixture was partitioned between ethyl acetate (100 ml) and HCl (0.5N, 100 ml). The organic layer was again washed with a saturated aqueous sodium chloride solution (100 ml). The organic layer was dried ($MgSO_4$), then the solvent was distilled off under reduced pressure. The residue was chromatographed on silica gel to give yellow crystals (1.00 g, 51%), followed by recrystallization from isopropyl ether to give yellow needles, m.p.197–199° C.

| Elemental Analysis for $C_{36}H_{27}N_3O_4SF_2.0.7H_2O$: | | | |
|---|---|---|---|
| | C(%) | H(%) | N(%) |
| Calcd.: | 66.70; | 4.42; | 6.48 |
| Found: | 66.59; | 4.48; | 6.42 |

$^1$H-NMR (300 MHz, $CDCl_3$) δ: 2.17(3H,s), 3.61(2H,s), 4.16(2H,s), 5.30(2H,s), 7.03(2H,t,J=8.1 Hz), 7.19–7.25(5H, m), 7.40–7.47(3H,m), 7.56(1H,t,J=7.5 Hz), 7.88(2H,d,J=6.9 Hz), 7.96(1H,s), 8.10(2H,d,J=8.7 Hz), 8.28(2H,d,J=8.7 Hz). IR (KBr): 3430, 1663, 1611, 1518, 1473, 1348, 853 cm$^{-1}$. FAB-Mass m/z 636(MH)$^+$.

WORKING EXAMPLE 59

Starting from the compounds 2, 9 and 16 produced in Working Example 51, compounds set forth in Table 32 were produced in accordance substantially the same procedure as described in Working Example 58. This method is an alternative method of producing the compounds described in Working Examples 56 and 57.

TABLE 32

[Structure: thieno[2,3-b]pyridine core with substituents R31, R32, R36, R37, with carbonyl (O) at position 4]

| W. Ex. 59 Cpd. No. | $R^{31}$ | $R^{32}$ | $R^{36}$ | $R^{37}$ | Yield (%) | m.p. (° C.) (HCl salt) |
|---|---|---|---|---|---|---|
| 1 | N-methyl-N-benzyl-aminomethyl | 4-pro-pionyl-amino-phenyl | 2,6-difluoro-benzyl | iso-butyryl | 29 | 207–214 |
| 2 | N-methyl-N-benzyl-amino-methyl | 4-(N'-methyl-ureido-phenyl) | 2,6-difluoro-benzyl | iso-butyryl | 30 | 222–226 |
| 3 | N-methyl-N-benzyl-amino-methyl | 4-pro-pionyl-amino-phenyl | 2,6-difluoro-benzyl | benzoyl | 45 | 218–220 |
| 4 | N-methyl-N-benzyl-amino-methyl | 4-(N'-methyl-ureido-phenyl) | 2,6-difluoro-benzyl | benzoyl | 34 | 230–232 |

WORKING EXAMPLE 60
6-(4-Aminophenyl)-2,4(1H,3H)-dioxo-1-(2-fluorobenzyl)-3-phenyl-5-(N-methyl-N-benzylaminomethyl)thieno[2,3-d]pyrimidine The compound 4 produced in Working Example 40 (0.15 g, 0.247 mmol) was dissolved in ethanol (15 ml), to which was added 10% palladium-carbon (15 mg). The mixture was hydrogenized for 8 hours at room temperature under atmospheric pressure in an atmosphere of hydrogen. The reaction mixture was filtrated with celite, and the filtrate was concentrated under reduced pressure. The concentrate was chromatographed on silica gel to give a yellow crystalline amorphous (0.046 g, 32%).
$^1$H-NMR (300 MHz, CDCl$_3$) δ: 2.05(3H,s), 3.57(2H,s), 3.81(2H,br s), 3.89(2H,s), 5.29(2H,s), 6.69(2H,d,J=8.7 Hz), 7.05–7.56(16H,m). FAB-Mass m/z 577(MH)$^+$.

WORKING EXAMPLE 61
6-(4-Acetylaminophenyl)-2,4(1H,3H)-dioxo-1-(2-fluorobenzyl)-5-(N-methyl-N-benzylaminomethyl)-3-phenylthieno[2,3-d]pyrimidine The compound produced in Working Example 60 (0.63 g, 0.11 mmol) was dissolved in anhydrous pyridine (5 ml), to which was added acetic anhydride (0.01 ml, 0.11 mmol). The mixture was stirred for 2 hours at room temperature. The reaction mixture was concentrated under reduced pressure. The concentrate was partitioned between methylene chloride (30 ml) and a saturated aqueous sodium chloride solution (10 ml). The aqueous layer was again extracted with methylene chloride (30 ml). The combined organic layer was dried over magnesium sulfate, which was concentrated under reduced pressure. The concentrate was chromatographed on silica gel to give a colorless solid (0.01 g, 15%).
$^1$H-NMR (300 MHz, CDCl$_3$) δ: 2.06(3H,s), 2.19(3H,s), 3.57(2H,s), 3.90(2H,s), 5.30(2H,s), 7.04–7.57(16H,s), 7.70 (2H,d,J=8.4 Hz).

WORKING EXAMPLE 62
4,7-Dihydro-7-(2-fluorobenzyl)-2-(4-hydroxyphenyl)-3-methyl-4-oxothieno[2,3-b]pyridine-5-caraboxylic acid ethyl ester To a solution of the compound No. 3 produced in Working Example 65 (1.30 g, 2.70 mmol) in tetrahydrofurane (80 ml) was added 1M solution of hydrogen chloride in ether (81 ml, 81 mmol) with ice-cooling. After stirring at room temperature for 60 hours, the reaction mixture was concentrated under reduced pressure. The resulting residue was partitioned between ethyl acetate (100 ml) and saturated aqueous sodium chloride solution (50 ml), and then aqueous layer was extracted with ethyl acetate (50 ml). The combined organic layer was dried over Na$_2$SO$_4$, followed by distilling off the solvent under reduced pressure. The resulting residual solid was recrystallized from ethyl acetate-ethanol to give yellow needles (0.81 g, 69%), m.p. 225–227° C.

| Elemental Analysis for C$_{24}$H$_{20}$NO$_4$SF.0.1H$_2$O: | | | |
|---|---|---|---|
| | C(%) | H(%) | N(%) |
| Calcd.: | 65.62; | 4.63; | 3.19 |
| Found: | 65.46; | 4.65; | 3.33 |

$^1$H-NMR (300 MHz, CDCl$_3$) δ: 1.30(3H,t,J=7.0 Hz), 4.24(2H,q,J=7.0 Hz), 5.52(2H,s), 6.84(2H,d,J=8.4 Hz), 7.20–7.46(6H,m), 8.65(1H,s), 9.75(1H,s). IR(KBr): 3856, 1711, 1611, 1589, 1510, 1493, 1448 cm$^{-1}$. FAB-Mass m/z 438(MH)$^+$.

WORKING EXAMPLE 63
4,7-Dihydro-7-(2-fluorobenzyl)-2-(4-hydroxyphenyl)-3-(N-methyl-N-benzylaminomethyl)-4-oxothieno[2,3-b]pyridine-5-caraboxylic acid ethyl ester Employing the compound No. 26 produced in Working Example 7 (0.26 g, 0.46 mmol), N-methylbenzylamine (0.072 ml, 0.56 mmol) and N-ethyldiisopropylamine (0.12 ml, 0.69 mmol) as a starting material, in accordance with substantially the same manner as described in Working Example 8, a yellow amorphous was produced (0.24 g). To the solution of this amorphous in ethanol (6 ml) was added iN hydrochloric acid (4 ml, 4 mmol) and then stirred at room temperature for 2 hours. To the reaction mixture was added 1 N hydrochloric acid (8ml, 8 mmol) and then stirred at room temperature for 19 hours. To the reaction mixture was added a water containing sodium bicarbonate (1.01 g, 12.0 mmol), followed by extraction with ethyl acetate (30 ml×3). The combined organic layer was dried over Na$_2$SO$_4$, followed by distilling off the solvent under reduced pressure. The resulting residue was chromatographed on silica gel to give a colourless oil (0.15 g, 58%). To a solution of this oil in ethanol (3 ml) was added an 1M solution of hydrogen chloride in ether (0.35 ml, 0.35 mmol) with ice-cooling, and then the mixture was stirred with ice-cooling for 10 minutes. The reaction mixture was concentrated under reduced pressure, the resulting residue was recrystallized from ether to give a white powder (0.116 g, total yield 41%) as a hydrochloride, m.p. 231–235° C.

| Elemental Analysis for $C_{32}H_{29}N_2O_4SF.HCl.1.5H_2O$: | | | |
|---|---|---|---|
| | C(%) | H(%) | N(%) |
| Calcd.: | 61.98; | 5.36; | 4.52 |
| Found: | 61.99; | 5.23; | 4.55 |

$^1$H-NMR (300 MHz, CDCl$_3$) δ: 1.39(3H,t,J=7.1 Hz), 2.53(3H,br s), 4.09(2H,br s), 4.38(2H,q,J=7.1 Hz), 4.39(2H, br s), 5.46(2H,s), 7.05(2H,d,J=8.5 Hz), 7.13–7.51(11H,m), 8.57(1H,s). IR(KBr): 3422, 2988, 1719, 1695, 1605, 1543, 1504, 1458 cm$^{-1}$.

WORKING EXAMPLE 64

2-(4-n-Butoxyphenyl)-4,7-dihydro-7-(2-fluorobenzyl)-3-methyl-4-oxothieno[2,3-b]pyridine-5-caraboxylic acid ethyl ester To a solution of the compound produced in Working Example 62 (0.30 g, 0.686 mmol) in DMF (10 ml) was added sodium hydride (30 mg, 0.75 mmol) with ice-cooling, and then the mixture was stirred at room temperature for one hour. To this solution was added n-butyl iodied (0.19 g, 1.03 mmol), and then stirred at room temperature for 15 hours. The reaction mixture was concentrated under reduced pressure. The residue was partitioned between ethyl acetate (100 ml) and a saturated aqueous sodium chloride solution (50 ml), and then the aqueous layer was extracted with ethyl acetate (50 ml). The combined organic layer was dried over Na$_2$SO$_{41}$ followed by distilling off the solvent under reduced pressure. The resulting residual solid was recrystallized from ethyl acetate-n-hexane to give colourless crystals (0.33 g, 97%), m.p. 119–121° C.

| Elemental Analysis for $C_{28}H_{28}NO_4SF.0.2H_2O$: | | | |
|---|---|---|---|
| | C(%) | H(%) | N(%) |
| Calcd.: | 67.64; | 5.76; | 2.82 |
| Found: | 67.36; | 5.69; | 2.68 |

FAB-Mass m/z 494(MH)$^+$.

WORKING EXAMPLE 65

Employing the compound No. 7 produced in Working Example 3 as well as the compound No. 3 produced in Working Example 53, as the starting materials, in accordance with substantially the same procedure as described in Working Example 19, the compounds shown in Table 33 were produced.

TABLE 33

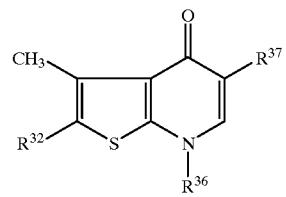

| W. Ex. 65 Cpd. No. | R$^{32}$ | R$^{36}$ | R$^{37}$ | Yield (%) | m.p. (° C.) |
|---|---|---|---|---|---|
| 1 | 4-(4-nitro-benzyloxy-carbonyl)phenyl | 2-fluoro-benzyl | ethoxy-carbonyl | 62 | 188–190 |
| 2 | 4-ethoxy-carbonylphenyl | 2,6-difluoro-benzyl | benzoyl | 64 | 221–223 |
| 3 | 4-methoxy-methoxyphenyl | 2-fluoro-benzyl | ethoxy-carbonyl | 80 | 112–113 |
| 4 | 4-ethoxy-carbonyl-phenyl | 2-methoxy-benzyl | ethoxy-carbonyl | 78 | 171–172 |

WORKING EXAMPLE 66

5-Benzoyl-7-(2,6-difluorobenzyl)-4,7-dihydro-2-(4-N-ethylaminocaraboxyphenyl)-3-(N-methyl-N-benzylaminomethyl)-4-oxothieno[2,3-b]pyridine A solution of the compound No. 3 produced in Working Example 47 (0.15 g, 0.226 mmol) in ethanol (3 ml) and THF (3 ml) was treated with an 1N aqueous sodium hydroxide solution (1.2 ml, 1.2 mmol) to give a carboxylic acid derivative. To a solution of this resulting carboxylic acid derivative in THF (5 ml) were added triethylamine (0.084 ml, 0.60 mmol) and isobutyl chloroformate with ice-cooling in an atmosphere of nitrogen, and then the mixture was stirred with ice-cooling for one hour and at room temperature for and half one hour. To this solution was added 70% aqueous ethyl amine solution (0.16 ml, 2.48 mmol) dropwise with ice-cooling, and then the mixture was stirred with ice-cooling for 30 minutes and at room temperature for 2 hours. The reaction mixture was partitioned between a saturated aqueous sodium chloride solution (50 ml) and ethyl acetate (50 ml), and then the aqueous layer was extracted with ethyl acetate (50 ml). The combined organic layer was dried over Na$_2$SO$_{41}$ followed by distilling off the solvent under reduced pressure. The resulting residue was chromatographed on silica gel to give a pale yellow amorphous (0.095 g, 63%). To a solution of this amorphous in methylene chloride (4 ml) was added an 1M solution of hydrogen chloride in ether (0.29 ml, 0.29 mmol) with ice-cooling, and then the mixture was stirred with ice-cooling for 10 minutes. The reaction mixture was concentrated under reduced pressure to give a residue, which was crystallized from methylene chloride-ethyl acetate-ether to give pale yellow powder (0.088 g, total yield 56%) as a hydrochloride, m.p. 156–160° C.

| Elemental Analysis for $C_{39}H_{33}N_3O_3SF_2 \cdot HCl \cdot 1.8H_2O$: | | | |
|---|---|---|---|
| | C(%) | H(%) | N(%) |
| Calcd.: | 64.11; | 5.19; | 5.75 |
| Found: | 63.88; | 4.90; | 5.59 |

$^1$H-NMR (300 MHz, CDCl$_3$) [free amine] δ: 1.28(3H,t, J=7.2 Hz), 2.13(3H,br s), 3.49–3.58(2H,m), 3.62(2H,br s), 4.16(2H,br s), 5.30(2H,s), 6.23(1H,br s), 6.99–7.05(2H,m), 7.17–7.26(5H,m), 7.39–7.58(4H,m), 7.83–7.97(7H,m). IR(KBr)[hydrochloride]: 3386, 3064, 1655, 1630, 1605, 1543, 1508, 1497, 1473 cm$^{-1}$. FAB-Mass m/z 662(MH)$^+$.

WORKING EXAMPLE 67

Employing the compound Nos. 3 and 4 produced in Working Example 47, as the starting materials, in accordance with substantially the same procedure as described in Working Example 66, the compounds shown in Table 34 were produced.

TABLE 34

| W. Ex. 67 Cpd. No. | R$^{32}$ | R$^{31}$ | R$^{37}$ | R$^{36}$ | Yield (%) | m.p. (hydro-chloride) (° C.) |
|---|---|---|---|---|---|---|
| 1 | 4-N,N-diethyl-amino-car-boxy-phenyl | N-methyl-N-benzyl-amino-methyl | ethoxy-carbonyl | 2-fluoro-benzyl | 80 | 110–113° C. |
| 2 | 4-N-propyl-amino-car-boxy-phenyl | N-methyl-N-benzyl-amino-methyl | benzoyl | 2,6-difluoro-benzyl | 75 | 153–157 |
| 3 | 4-N-allyl-amino-car-boxy-phenyl | N-methyl-N-benzyl-amino-methyl | benzoyl | 2,6-difluoro-benzyl | 69 | 152–156 |

WORKING EXAMPLE 68

4,7-Dihydro-5-ethoxymethyl-7-(2-fluorobenzyl)-2-(4-methoxyphenyl)-3-(N-methyl-N-benzylaminomethyl)-4-oxothieno[2,3-b]pyridine hydrochloride To a solution of the compound No. 2 produced in Working Example 25 (0.23 g, 0.435 mmol) in anhydrous THF (5 ml) was added sodium hydride (19 mg, 0.475 mmol) in an atmosphere of nitrogen with ice-cooling, and then the mixture was stirred at 0° C. for 30 minutes. To this mixture was added ethyl iodide (0.038 ml, 0.475 mmol), and then allowed to warm to room temperature. After stirring at room temperature for 2 hours, to the reaction mixture was added ethyl iodide (0.038 ml, 0.475 mmol) and then stirred for 19 hours. To the reaction mixture was added a saturated aqueous ammonium chloride solution, and then the mixture was partitioned between ethyl acetate (30 ml) and a saturated aqueous sodium bicarbonate solution (30 ml). The aqueous layer was extracted with ethyl acetate. The combined organic layers were dried over Na$_2$SO$_4$, followed by distilling off the solvent under reduced pressure. The resulting residue was chromatographed on silica gel to give a white solid (0.09 g, 37%). To a solution of this solid in methylene chloride (4 ml) was added an 1M solution of hydrogen chloride in ether (0.2 ml, 0.2 mmol) with ice-cooling, and then the mixture was stirred with ice-cooling for 10 minutes. The reaction mixture was concentrated under reduced pressure to give a residue, which was crystallized from methylene chloride-ethyl acetate-ether to give white powder (0.058 g) as a hydrochloride, m.p. 200–204° C.

| Elemental Analysis for $C_{33}H_{33}N_2O_3SF \cdot HCl \cdot 0.5H_2O$: | | | |
|---|---|---|---|
| | C(%) | H(%) | N(%) |
| Calcd.: | 65.82; | 5.86; | 4.65 |
| Found: | 66.01; | 5.67; | 4.62 |

$^1$H-NMR (300 MHz, CDCl$_3$) δ: 1.28(3H,t,J=7.0 Hz), 2.15(3H,br s), 2.86(2H,br s), 3.68(2H,q,J=7.0 Hz), 3.86(3H,s), 4.21(2H,br s), 4.57(2H,s), 5.31(2H,br s), 7.00–7.69(14H, m). FAB-Mass m/z 557(MH)$^+$.

WORKING EXAMPLE 69

5-Benzyloxymethyl-4,7-dihydro-7-(2-fluorobenzyl)-2-(4-methoxyphenyl)-3-(N-methyl-N-benzylaminomethyl)-4-oxothieno[2,3-b]pyridine hydrochloride Employing the compound No. 2 produced in Working Example 25, as the starting materials, and benyl chloride in place of ethyl iodide, in accordance with substantially the same procedure as described in working Example 68, the titled compound was produced as a pale yellow crystalline powder (0.10 g, 79%), m.p. 77–83° C.

WORKING EXAMPLE 70

4,7-Dihydro-5-ethylthiomethyl-7-(2-fluorobenzyl)-2-(4-methoxyphenyl)-3-(N-methyl-N-benzylaminomethyl)-4-oxothieno[2,3-b]pyridine hydrochloride To a solution of the compound No. 2 produced in Working Example 25 (0.15 g, 0.284 mmol) in anhydrous THF (5 ml) were added tributylphosphine (0.36 mg, 1.44 mmol) and diethyldisulfide (0.18 ml, 1.46 mmol) and the mixture was refluxed for 5 hours. To this mixture were added tributylphosphine (0.72 ml, 2.88 mmol) and diethyldisulfide (0.36 ml, 2.92 mmol), and the mixture was refluxed for 3 days. After cooling, the reaction mixture was partitioned between ethyl acetate (50 ml) and a saturated aqueous sodium chloride solution (50 ml). The aqueous layer was extracted with ethyl acetate (50 ml). The combined organic layer was dried over Na$_2$SO$_4$, followed by distilling off the solvent under reduced pressure. The resulting residue was chromatographed on silica gel to give a white solid (0.124 g, 76%). To a solution of this solid in methylene chloride (3 ml) was added an 1M solution of hydrogen chloride in ether (0.45 ml, 0.45 mmol) with ice-cooling, and then the mixture was stirred with ice-cooling for 10 minutes. The reaction mixture was concentrated under reduced pressure to give a residue, which was crystallized from methylene chloride-ethyl acetate-ether to give white powder (0.09 g) as a hydrochloride, m.p. 213–217° C.

Elemental Analysis for $C_{33}H_{33}N_2O_2S_2F.HCl.H_2O$:

|  | C(%) | H(%) | N(%) |
|---|---|---|---|
| Calcd.: | 63.19; | 5.78; | 4.47 |
| Found: | 63.21; | 5.69; | 4.59 |

$^1$H-NMR (300 MHz, CDCl$_3$) δ: 1.27(3H,t,J=7.4 Hz), 2.23(3H,br s), 2.56(2H,q,J=7.4 Hz), 3.76(2H,s), 3.79(2H, br), 3.86(3H,s), 4.25(2H,br s), 5.25(2H,s), 6.97(2H,d,J=8.6 Hz), 7.12–7.39(10H,m), 7.71(2H,br s). IR(KBr): 3480, 2966, 1609, 1520, 1458 cm$^{-1}$. FAB-Mass m/z 573(MH)$^+$.

WORKING EXAMPLE 71

7-(2,6-Difluorobenzyl)-4,7-dihydro-6-isobutyl-3-(N-methyl-N-benzylaminomethyl)-4-oxo-2-(4-propionylaminophenyl)thieno[2,3-b]pyridine-5-carboxylic acid ethyl ester hydrochloride To a mixture of the compound No. 5 produced in Working Example 49 (0.10 g, 0.159 mmol) and copper iodide (0.095 g, 0.5 mmol) was added isobutylmagnesium bromide (0.5 ml, 1 mmol) with ice-cooling. To the mixture was added anhydrous THF (20 ml) with ice-cooling and the mixture was stirred for one hour. The reaction mixture was poured into a saturated aqueous ammonium chloride solution, and the mixture was extracted with ethyl acetate (50 ml×3). The combined organic layers was dried over Na$_2$SO$_4$, followed by distilling off the solvent under reduced pressure. The resulting brown oil (0.124 g) was dissolved methylene chloride (5 ml), to this solution was added dichlorodicyanoquinone (0.0207 g, 0.091 mmol) and the mixture was stirred with ice-cooling for 2 hours. The reaction mixture was partitioned between chloroform (50 ml) and water (30 ml). The aqueous layer was extracted with chloroform (50 ml). The combined organic layer was dried over Na$_2$SO$_4$, followed by distilling off the solvent under reduced pressure to give a brown oil (0.02 g, 32%). The oil was crystallized from ethyl acetate-n-hexane to give dark brown crystals, m.p. 135–137° C.

Elemental Analysis for $C_{39}H_{41}N_3O_4SF_2.C_8H_7Cl_2N_2O_2.1.4NaCl$:

|  | C(%) | H(%) | N(%) |
|---|---|---|---|
| Calcd.: | 58.49; | 4.91; | 6.35 |
| Found: | 58.34; | 5.01; | 6.75 |

$^1$H-NMR (300 MHz, CDCl$_3$) δ: 1.07(6H,br s), 1.23(3H,br s), 1.46(3H,t,J=6.3 Hz), 2.10(1H,br s), 2.30–2.96(7H,m), 4.30–4.53(6H,m), 5.55(2H,br s), 6.94–7.90(12H,m). IR(KBr): 3428, 2970, 2214, 1725, 1688, 1628, 1589, 1504, 1470, 1386, 1152, 1025, 789, 748, 700 cm$^{-1}$. FAB-Mass m/z 686(MH)$^+$.

WORKING EXAMPLE 72

5-Cyano-4,7-dihydro-7-(2-fluorobenzyl)-2-(4-methoxyphenyl)-3-methyl-4-oxothieno[2,3-b]pyridine A mixture of the compound No. 6 produced in Working Example 12 (0.435 g, 1.03 mmol) and phosphorus oxychloride (0.145 ml, 1.56 mmol) was refluxed for one hour. After cooling, the reaction mixture was partitioned between chloroform and aqueous solution of sodium bicarbonate, and then aqueous layer was extracted with chloroform. The combined organic layer was washed with aqueous sodium chloride solution and dried over MgSO$_4$, followed by distilling off the solvent under reduced pressure. The resulting residue was chromatographed on silica gel, followed by recrystallization from ethyl acetate-isopropylether to give pale yellow crystals (0.225 g, 70%), m.p. 215–216° C.

WORKING EXAMPLE 73

5-Ethylsulfinylmethyl-4,7-dihydro-7-(2-fluorobenzyl)-2-(4-methoxyphenyl)-3-(N-methyl-N-benzylaminomethyl)-4-oxothieno[2,3-b]pyridine hydrochloride To a solution of the compound produced in Working Example 71 (0.15 g, 0.26 mmol) in methylenechloride (4 ml) was added 1M hydrogen chloride solution in ether (0.29 ml, 0.29 mmol) with ice-cooling and the mixture was stirred for 5 minutes with ice-cooling. The mixture was concentrated under reduced pressure to give a yellow amorphous. To an ice-cooled solution of this amorphous in methylene chloride (5 ml) was added dropwise a solution of m-chloroperbenzoic acid (45 mg, 0.26 mmol) in methylene chloride (5 ml) over a period of 10 minutes. After being stirred at 0° C. for 1.5 hours and at room temperature for 1.5 hours, the reaction mixture was partitioned between chloroform and an aqueous solution of sodium bicarbonate. The aqueous layer was separated and extracted with chloroform. The combined organic layer was washed with an aqueous sodium chloride solution and dried over MgSO$_4$, followed by distilling off the solvent under reduced pressure. The resulting residue was chromatographed on silica gel to give a pale yellow syrup (60 mg, 38.9%). To an ice-cooled solution of this syrup (50 mg, 0.085 mmol) in methylene chloride (4 ml) was added an 1M solution of hydrogen chloride in ether (0.13 ml, 0.13 mmol), and then the mixture was stirred with ice-cooling for 5 minutes. The reaction mixture was concentrated under reduced pressure to give a residue, which was recrystallized from ether to give yellow powders (37 mg, 53%) as a hydrochloride, m.p. 216–219° C.

WORKING EXAMPLE 74

6-(Aminophenyl)-2,4(1H,3H)-dioxo-1-(2,6-difluorobenzyl)-5-(N-methyl-N-benzylaminomethyl)-3-phenylthieno[2,3-d]pyrimidine Employing the compound No. 17 produced in Working Example 40, as the starting material, in accordance with substantially the same procedure as described in Working Example 60, the titled compound was produced as a crystalline amorphous (yield 65%).

$^1$H-NMR (300 MHz, CDCl$_3$) δ: 2.05(3H,s), 3.56(2H,s), 3.81(2H,br s), 3.88(2H,s), 5.36(2H,s), 6.71(2H,d,J=8.7 Hz), 6.91(2H,t,J=8.7 Hz), 7.21–7.53(13H,m).

WORKING EXAMPLE 75

Employing the compound produced in Working Example 60, as the starting material, in accordance with substantially the same procedure as described in Working Example 61, the following compounds were produced.

No. 1: 2,4(2H,3H)-Dioxo-1-(2-fluorobenzyl)-5-(N-methyl-N-benzylaminomethyl)-3-phenyl-6-(4-propionylaminophenyl)thieno[2,3-d]pyrimidine hydrochloride (yield: 86%, m.p. 172–175° C.).

No. 2: 2,4(2H,3H)-Dioxo-1-(2-fluorobenzyl)-6-(4-isobutyrylaminophenyl)-5-(N-methyl-N-benzylaminomethyl)-3-phenylthieno[2,3-d]pyrimidine hydrochloride (yield: 77%, m.p. 185–188° C.).

No. 3: 2,4(2H,3H)-Dioxo-1-(2-fluorobenzyl)-6-(4-methoxyacetylaminophenyl)-5-(N-methyl-N-benzylaminomethyl)-3-phenylthieno[2,3-d]pyrimidine hydrochloride (yield: 88%, m.p. 157–162° C.).

WORKING EXAMPLE 76

Using the compound produced in Working Example 8 (100 mg), lactose (165 mg), corn starch (5 mg), polyvinyl alcohol (4 mg) and magnesium stearate (1 mg), a tablet was prepared by a conventional method.

WORKING EXAMPLE 77

The compound produced in Working Example 8 (5 g) was dissolved in distilled water for injection to make the whole volume 100 ml. The solution was subjected to sterilized filtration with 0.22 μm membrane filter (manufactured by Sumitomo Electric Industries, Ltd. or by Zartolius, Inc.), 2 ml each of which was distributed to sterilized vials, followed by lyophilization by a conventional means to give lyophilized injectable solution of 100 mg/vial.

WORKING EXAMPLE 78

Using the compound 15 produced in Working Example 9 (100 mg), lactose (165 mg), corn starch (25 mg), polyvinyl alcohol (4 mg) and magnesium stearate (1 mg), a tablet was prepared by a conventional method.

WORKING EXAMPLE 79

The compound 15 produced in Working Example 9 (5 g) was dissolved in distilled water for injection to make the whole volume 100 ml. This solution was subjected to sterilized filtration with 0.22 μm membrane filter (manufactured by Sumitomo Electric Industries, Ltd. or Zartolius, Inc.), 2 ml each of which was distributed to sterilized vials, followed by lyophilization by a conventional means to prepare lyophilized injectable solution of 100 mg/vial.

WORKING EXAMPLE 80

Using the compound 3 produced in Working Example 21 (100 mg), lactose (165 mg), corn starch (25 mg), polyvinyl alcohol (4 mg) and magnesium stearate (1 mg), a tablet was prepared by a conventional method.

WORKING EXAMPLE 81

The compound 3 produced in Working Example 21 (5 g) was dissolved in distilled water for injection to make the whole volume 100 ml. This solution was subjected to sterilized filtration with 0.22 μm membrane filter (manufactured by Sumitomo Electric Industries, Ltd. or Zartolius, Inc.), 2 ml each of which was distributed to sterilized vials, followed by lyophilization by a conventional means to prepare lyophilized injectable solution of 100 mg/vial.

WORKING EXAMPLE 82

Using the compound produced in Working Example 23 (100 mg), lactose (165 mg), corn starch (25 mg), polyvinyl alcohol (4 mg) and magnesium stearate (1 mg), a tablet was prepared by a conventional method.

WORKING EXAMPLE 83

The compound produced in Working Example 23 (5 g) was dissolved in distilled water for injection to make the whole volume 100 ml. This solution was subjected to sterilized filtration with 0.22 μm membrane filter (manufactured by Sumitomo Electric Industries, Ltd. or Zartolius Inc.), 2 ml each of which was distributed to sterilized vials, followed by lyophilization by a conventional means to prepare lyophilized injectable solution of 100 mg/vial.

WORKING EXAMPLE 84

Using the compound produced in Working Example 56 (100 mg), lactose (165 mg), corn starch (25 mg), polyvinyl alcohol (4 mg) and magnesium stearate (1 mg), tablets are prepared by a conventional method.

WORKING EXAMPLE 85

In distilled water for injection is dissolved the compound produced in Working Example 56 (5 g) to make the whole volume 100 ml. This solution is subjected to sterilized filtration through a membrane filter of 0.22 μm thick (manufactured by Sumitomo Electric Industries, Ltd. or Zartolius Inc., 2 ml each of which was divided into sterilized vials, followed by lyophilization to prepare a lyophilized injectable composition of 100 mg/vial.

WORKING EXAMPLE 86

Using the compound 2 produced in Working Example 57 (100 mg), lactose (165 mg), cornstarch (25 mg), polyvinyl alcohol (4 mg) and magnesium stearate (1 mg), tablets are prepared by a conventional method.

WORKING EXAMPLE 87

The compound 2 produced in Working Example 57 (5 g) is dissolved in distilled water for injection to make the whole volume 100 ml. This solution was subjected to sterilized filtration through 0.22 μm membrane filter (manufactured by Sumitomo Electric Industries, Ltd. or Zartolius Inc.), 2 ml each of which was divided into sterilized vials, followed by lyophilization to prepare a lyophilized injectable composition of 100 mg/vial.

WORKING EXAMPLE 88

The compound 3 produced in Working Example 57 (100 mg), lactose (165 mg), cornstarch (25 mg), polyvinyl alcohol (4 mg) and magnesium stearate (1 mg), tablets are prepared by a conventional method.

WORKING EXAMPLE 89

The compound 3 produced in Working Example 57 (5 g) is dissolved in distilled water for injection to make the whole volume 100 ml. This solution is subjected to sterilized filtration through 0.22 μm membrane filter (manufactured by Sumitomo Electric Industries, Ltd, or Zartolius Inc.), 2 ml each of which is divided into sterilized vials, followed by lyophilization to prepare a lyophilized injectable composition of 100 mg/vial.

WORKING EXAMPLE 90

The compound 7 produced in Working Example 51 (5 g) is dissolved in distilled water for injection to make the whole volume 100 ml. This solution is subjected to sterilized filtration through 0.22 μm membrane filter (manufactured by Sumitomo Electric Industries, Ltd. or Zartolius Inc.), 2 ml each of which is distributed to sterilized vials, followed by lyophilization to prepare a lyophilized injectable composition of 100 mg/vial.

WORKING EXAMPLE 91

The compound 8 produced in Working Example 51 (5 g) is dissolved in distilled water for injection to make the whole volume 100 ml. This solution is subjected to sterilized filtration through 0.22 μm membrane filter (manufactured by Sumitomo Electric Industries, Ltd. or Zartolius Inc.), 2 ml each of which is divided into sterilized vials, followed by lyophilization to prepare a lyophilized injectable composition of 100 mg/vial.

WORKING EXAMPLE 92

| | | |
|---|---|---|
| (1) Compound produced in working Example 56 | 5 | g |
| (2) Lactose.crystalline cellulose (granules) | 330 | g |
| (3) D-mannitol | 29 | g |
| (4) Low-substituted hydroxypropyl cellulose | 20 | g |
| (5) Talc | 25 | g |
| (6) Hydroxypropyl cellulose | 50 | g |
| (7) Aspartame | 3 | g |
| (8) Dipotassium glycyrrhetinate | 3 | g |
| (9) Hydroxypropylmethyl cellulose 2910 | 30 | g |
| (10) Titanium oxide | 3.5 | g |
| (11) Yellow iron sesquioxide | 0.5 | g |
| (12) Light silicic acid anhydride | 1 | g |

In refined water were suspended or dissolved (1), (3), (4), (5), (7) and (8). The nuclear granule of (2) was coated with the suspension or solution to prepare raw fine granules, which were coated with (9)–(11) to prepare coated fine granules, which were mixed with (12), to give 500 g of fine granules containing 1% of the compound produced in Working Example 56. 500 mg each of thus-prepared fine granules was packed.

TEST EXAMPLE 1
Preparation of $^{125}$I-leuprorelin

Ten μl of a $3\times10^{-4}$M aqueous solution of leuprorelin and 10 μl of 0.01 mg/ml lactoperoxidase in 0.1M HEPES buffer (pH 7.4) were taken into a tube, to which was added 10 μl [37 MBq in 0.1M HEPES buffer (pH 7.4)] of an Na$^{125}$I solution. The mixture was stirred, to which was added 10 μl of 0.001% $H_2O_2$, then reaction was allowed to proceed for 20 minutes at room temperature. To the reaction mixture was added 700 μl of a 0.05% TFA solution to stop the reaction. The product was purified by means of reversed phase HPLC. Conditions of HPLC are as follows. $^{125}$I-leuprorelin was eluted at a retention time of 26 to 27 minutes.

| | |
|---|---|
| Column: | TSK gel ODS-80 ™CTR (4.6 mm × 10 cm) |
| Eluent: | Solvent A (0.05% TFA) |
| | Solvent B (40% CH$_3$CN-0.05% TFA) |
| | 0 minute (100% Solvent A) - 3 minutes (100% Solvent A) - 7 minutes (50% Solvent A + 50% Solvent B) - 40 minutes (100% Solvent B) |
| Elution temp.: | room temperature |
| Flow rate: | 1 ml/min. |

TEST EXAMPLE 2
Preparation of membrane fraction of rat pituitary anterior lobes of containing GnRH receptors Forty Wister rats (8 week old, male) were killed and the pituitary anterior lobes were collected and washed with an ice-cooled homogenate buffer (25 mM Tris (tris (hydroxymethyl)aminomethane)-HCl, 0.3M saccharose, 1 mM EGTA (glycoletherdiamine tetraacetate), 0.25 mM PMSF (phenylmethylsulfonyl fluoride), 10 U/ml aprotinin, 1 μg/ml pepstatin, 20 μg/ml leupeptin, 100 μg/ml phosphoramidon, 0.03% sodium azide, pH 7.5). The pituitary gland was suspended in 2 ml of the homogenate buffer, which was homogenated with a Polytron homogenizer. Centrifugal separation was conducted for 15 minutes at 700 ×g. The supernatant was collected into an ultracentrifuge tube, which was subjected to centrifuge for one hour at 100,000 ×g to give membrane fraction as precipitate. This precipitate was suspended in 2 ml of an assay buffer (25 mM Tris-HCl, 1 mM EDTA (ethylenediamine tetraacetate), 0.1% BSA (bovine serum albumin), 0.25 mM PMSF, 1 μg/ml pepstatin, 20 μg/ml leupeptin, 100 μg/ml phosphoramidon, 0.03% sodium azide, pH 7.5), which was subjected to centrifugal separation for one hour at 100,000 ×g. The membrane fraction recovered as precipitate was again suspended in 10 ml of the assay buffer, which was distributed into vials and stored at –80° C. until used.

TEST EXAMPLE 3

Preparation of membrane fraction of CHO (Chinese Hamster Ovary) cells containing human GnRH receptors CHO cells ($10^9$) expressing human GnRH receptors were suspended in a phosphate-buffered saline supplemented with 5 mM EDTA (PBS-EDTA). The suspension was subjected to centrifugal separation for 5 minutes at 100 ×g. To the pellet of cells was added 10 ml of a homogenate buffer for cells (10 mM NaHCO$_3$, 5 mM EDTA, pH 7.5), which was homogenated by using a Polytron homogenizer. Centrifugal separation was conducted for 15 minutes at 400 ×g. The supernatant was taken into an ultracentrifugal tube, which was subjected to centrifuge for one hour at 100,000 ×g to give precipitate of the membrane fraction. The precipitate was suspended in 2 ml of the assay buffer, which was centrifuged for one hour at 100,000 ×g. The membrane fraction recovered as precipitate was again suspended in 20 ml of the assay buffer, which was distributed to vials and stored at –80° C. until used.

TEST EXAMPLE 4
Determination of inhibitory rate of $^{125}$I-leuprorelin binding Membrane fractions of rat pituitary and CHO cells expressing human GnRH receptors prepared in Test Examples 2 and 3 were respectively diluted with an assay buffer to 200 μg/ml and 188 μl each was distributed into tubes. In the case where the membrane fraction of rat pituitary anterior lobes were used, 2 μl of 0.1 mM of the compound dissolved in 60% DMSO (dimethyl sulfoxide) and 10 μl of 38 nM $^{125}$I-leuprorelin were added simultaneously. In the case where the CHO cell membrane fraction expressing human GnRH receptors, 2 μl of 2 mM of the compound dissolved in 60% DMSO and 10 μl of 38 nM $^{125}$I-leuprorelin were added simultaneously. For determining the amount of maximum binding, a solution for reaction supplemented with 2 μl of 60% DMSO and 10 μl of 38 nM $^{125}$I-leuprorelin was prepared. And, for determining the amount of non-specific binding, a solution for reaction supplemented with 2 μl of 100 μM leuprorelin dissolved in 60% DMSO and 10 μl of 38nM $^{125}$I-leuprorelin were also prepared simultaneously.

In the case where the membrane fraction of rat pituitary anterior lobes were used, reaction was allowed to proceed at 4° C. for 90 minutes, while in the case where the CHO cell membrane faction expressing human GnRH receptor was used, reaction was allowed to proceed at 25° C. for 60 minutes. The reaction mixtures were respectively subjected to filtration under sucking with Whatman glass filter (GF-F) processed with polyethylenimine. After completing the filtration, radioactivity of the $^{125}$I-leuprorelin remaining on the filter paper was measured with a γ-counter.

By calculation of (TB-SB)/(TB-NSB)×100 (SB: radioactivity obtained when a compound was added, TB: maximum binding radioactivity, NSB: non-specific binding ratio activity, the binding inhibitory rate (%) of each test compound was determined. Besides, the inhibitory rates were determined by changing the concentrations of test compounds, and the concentration of a test compound inhibiting the (TB-NSB) by 50% (IC$_{50}$ value) was calculated by way of Hill plot. The results are shown in Table 32.

TABLE 32

$^{125}$I-leuprorelin binding inhibitory rate

| Test compound | Binding inhibitory rate (%) | | IC$_{50}$ value ($\mu$M) | |
|---|---|---|---|---|
| | rat(1 $\mu$M) | human(20 $\mu$M) | rat | human |
| Compound of W.Ex.1 | | 67 | | 13 |
| Compound of W.Ex.9 (Compound No.14) | 46 | 112 | 1 | 0.08 |
| Compound of W.Ex.9 (Compound No.15) | 36 | 114 | 1.9 | 0.08 |
| Compound of W.Ex.21 (Compound No.3) | 35 | 106 | 2 | 0.03 |
| Compound of W.Ex.23 | | 107 | | 0.01 |

TEST EXAMPLE 5
Inhibition of LH/FSH secretion by primary cultured cells of rat pituitary anterior lobes.

Anterior lobes of pituitary glands from 40 Wistar rats (8-week old, male) was put into a petri dish containing buffer A (0.7 mM sodium dihydrogen phosphate, 137 mM sodium chloride, 5 mM potassium chloride, 25 mM HEPES, 50 $\mu$g/ml gentamicin sulfate), which was once washed with the buffer A, then the anterior lobes were divided into four portions, followed by further washing twice. A portion of thus-washed rat pituitary anterior lobes were put into a conical flask with a stopper containing enzyme solution I (buffer A containing 0.4% collagenase, 0.4% BSA (bovine serum albumin), 10 $\mu$g/ml deoxyribonuclease and 0.2% glucose. The mixture was incubated for one hour at 37° C. with shaking. After sucking and discharging with a pipette repeatedly the tissue fragments were dispersed. The dispersion was transferred to a centrifugal tube, which was then centrifuged for 6 minutes to remove the supernatant. To the remainder was added enzyme solution II (enzyme solution A containing 10% pancreatin), and the mixture was incubated for 8 minutes at 37° C., to which was added 2 ml of FCS (fetal calf serum). The mixture was again centrifuged for 6 minutes at 480 xg, and the supernatant was removed. The remainder was suspended in 10 ml of culture medium I (Dulbecco modified Eagle's medium containing 10% FCS, 20 mM HEPES, 50 U/ml penicillin G, 50 $\mu$g/ml streptomycin, and 3.7 g/l sodium hydrogencarbonate), which was subjected to filtration with nylon mesh. The material collected by the filtration was washed twice with 10 ml each portion of the culture medium I, followed by allowing the cells to be suspended in the culture medium I at a cell density of 5×10$^5$/ml. One ml each of the cell suspension was distributed to each well of a 24-well plate, which was incubated for 3 days in a CO$_2$ incubator at 37° C. under an atmosphere of 5% CO$_2$—95% air, to which was added 2 ml of the culture medium II (Culture medium I without 10% FCS), followed by incubation for one hour. The culture medium was removed. To each well of the 24-well plate was added 800 $\mu$l of fresh culture medium II, followed by addition of 20 $\mu$M solution (100 $\mu$l) of the compound 15 produced in Working Example 9 dissolved in 0.2% (v/v) dimethyl sulfoxide and 100 $\mu$l of 5 nM GnRH simultaneously. The culture in the absence of the compound was employed as the control. After incubation at 37° C. for 3 hours, 500 $\mu$l of the culture supernatant was recovered, which was subjected to centrifuge for 10 minutes at 1000 xg to collect the supernatant. The concentrations of LH and FSH in the supernatant were determined by using the radio immunoassay kit (Amersham Inc.).

By calculating in accordance with the formula; 100-(LH or FSH concentration in the presence of the compound)/(LH or FSH concentration of the control culture)×100, the inhibiting rate (%) of LH or FSH secretion by each compound was determined. The compound 15 inhibited the LH secretion by 28±9.0% (p<0.01, n=3), and inhibited the FSH secretion by 20±10% (p<0.01, n=3).

From the foregoing results, the compound 15 produced in Working Example 9 was shown to have a GnRH antagonistic activity.

TEST EXAMPLE 6
Suppression of testosterone concentration in rat plasma

The compound 15 produced in Working Example 9 was dissolved in vehicle I (20% propylene glycol –80% physiological saline). The solution was administered once subcutaneously to male SD rats (8-week old, n=5). The dosage was 30 mg per 1 kg of body weight. Animals administered with the vehicle alone were used as control. At 24 hours after the administration, blood was collected from jugular vein under anesthesia with ether. To the blood were immediately added ethylenediamine tetracetate (EDTA) at a final concentration of 3 mg/ml and aprotinin at a final concentration of 300 KIU/ml. The mixture was centrifuged for 15 minutes at 3000 xg, and the concentration of testosterone in the plasma was measured by the radio immunoassay.

The rate of testosterone suppression (%) of the test compound was determined by the formula; 100-(concentration of plasma testosterone in the test group)/(concentration of plasma testosterone in the control group)×100.

The compound 15 produced in Working Example 9 showed suppression rate of 38±9.7% (p <0.05).

TEST EXAMPLE 7
Suppression of testosterone concentration in mouse plasma

The compound produced in Working Example 56 was dissolved in vehicle II (0.5% methylcellulose dissolved in distilled water). The solution was administered orally once a day during successive 3 days to male ICR mice (10-week old, n=12). The dosage was 30 mg per 1 kg of body weight. ICR mice administered with vehicle alone were used as control (n=15). At 24 hours after the administration, blood was collected from jugular vein under anesthesia with ether. To the blood were immediately added ethylenediamine tetracetate (EDTA) at a final concentration of 3 mg/ml and aprotinin at a final concentration of 300 KIU/ml. The mixture was centrifuged for 15 minutes at 3000 xg, and the concentration of testosterone in the plasma was measured by the radio immunoassay.

The rate of testosterone suppression (%) of the test compound was determined by the formula; 100-(concentration of plasma testosterone in the test group)/(concentration of plasma testosterone in the control group)×100.

The compound produced in Working Example 56 showed a suppression rate of 85±9.7% (p<0.05).

The gonadotropin-releasing hormone antagonistic agent of the present invention is effective as a prophylactic or therapeutic agent for the prevention or treatment of several hormone dependent diseases, for example, a sex hormone dependent cancer (e.g. prostatic cancer, pituitary adenoma , cancer of the uterine cervix, breast cancer), prostatic hypertrophy, myoma of the uterus, endometriosis, precocious puberty, amenorrhea syndrome, polycystic ovary syndrome and acne vulgaris, or as a fertility controlling agent (e.g. a contraceptive agent) infertility treating agent, a menstruation controlling agent. Further, in the field of animal husbandry, the gonaolotropin-releasing hormone antagonistic agent of the present invention is effective as agents of controlling oestrus in animals, improving the quality of edible meat, growth regulation of animals, and also a spawning-accelerating agent in the field of fisheries.

INDUSTRIAL APPLICABILITY

A gonadotropin-releasing hormone antagonistic composition of the present invention is effective as a propylactic or therapeutic agent for the prevention or treatment of several hormone dependent diseases, for example, a sex hormone dependent cancer (e.g. prostatic cancer, cancer of uterine cervix, breast cancer, pituitary adenoma), benign prostatic hypertrophy, myoma of the uterus, endometriosis, precocious puberty, amenorrhea, premenstrual syndrome, polycystic ovary syndrome and acne vulgaris; is effective as a fertility controlling agent in both sexes (e.g. a pregnancy controlling agent and a menstrual cycle controlling agent); can be used as a contraceptive of male or female, as an ovulation-inducing agent of female; can be used as an infertility treating agent by using a rebound effect owing to a stoppage of administration thereof; is useful as modulating estrous cycles in animals in the field of animal husbandry, as an agent fro improving the quality of edible meat or promoting the growth of animals; is useful as an agent of spawning promotion in fish.

The substituent designations of the formulae of the second embodiment are specific to the second embodiment and may be the same or different than the substituent designations according to the first embodiment.

TECHNICAL FIELD OF THE SECOND EMBODIMENT

A second embodiment of the present invention relates to novel thienopyrimidine derivatives and salts thereof. The second embodiment further relates to methods for manufacturing the thienopyrimidine derivatives and the salts thereof, and pharmaceutical compositions containing the thienopyrimidine derivatives.

BACKGROUND ART OF THE SECOND EMBODIMENT

Secretion of anterior pituitary hormone is controlled by peripheral hormones secreted from target organs for the respective hormones and by secretion-accelerating or -inhibiting hormone from the hypothalamus, which is the upper central organ of the anterior lobe of the pituitary (in this specification, these hormones are collectively called "hypothalamic hormone"). At the present stage, as hypothalamic hormones, nine kinds of hormones including, for example, thyrotropin releasing hormone (TRH) or gonadotropin releasing hormone {GnRH: sometimes called LH-RH (luteinizing hormone releasing hormone)} have been confirmed (cf. Seirigaku 2, compiled by M. Iriku and K Toyama, published by Bunkohdo, p610–618, 1986). These hypothalamic hormones are assumed to show their actions via the receptor which is considered to exist in the anterior lobe of the pituitary (cf. ibid), and studies of receptor genes specific to these hormones, including those of humans, have been developed (Receptor Kiso To Rinshô, compiled by H. Imura, et al., published by Asakura Shoten, p297–304, 1993). Accordingly, antagonists or agonists specifically and selectively acting on these receptors control the action of action of hypothalamic hormone and the secretion of anterior pituitary hormone. As a result, they are expected to be useful as prophylactic and therapeutic agents of anterior pituitary hormone dependent diseases.

Leuprorelin acetate (Fujino et al., Biological and Biophysical Research Communications, Vol.60, 00.406–413, 1974; Oliver, R. T. D. et al., British Journal of Cancers, Vol.59, p.823, 1989; and Toguchi et al., Journal of International Medical Research, Vol.18, pp.35–41), which is a highly potent derivative of gonadotropic hormone-releasing hormone, one of the hypothalamic hormones, (hereinafter sometimes abbreviated as GnRH) (Schally A. V. et at., Journal of Biological Chemistry, Vol. 246, pp.7230–7236, 1971; and Burgus, R. et al., Proceeding of Natural Academic Science, USA, Vol.69, pp278–282, 1972), by administration of multiple doses, lowers release of gonadotropic hormone in the pituitary, causing a lowering of reactivity of gonadotropic hormone in the sperm and ovary tissue to suppress secretion of testosterone and estrogen. Leuprorelin acetate has, therefore, been known to show antitumor activity on such hormone-dependent cancers as prostate cancer, and has been widely used in the clinical field. Leuprorelin acetate has been widely used clinically also as a therapeutic agent of e.g. endometriosis and precocious puberty. The high antitumor activity of leuprorelin acetate is assumed to be due to its high resistance, as compared with natural GnRH, against protease,and to its high affinity for GnRH receptor causing desensitization of GnRH due to decrease in number of receptors. However, as leuprorelin acetate is an ultra-agonist of GnRH receptors, it has been known that, immediately after the first administration; a transient aggravation accompanied with a rise of serum testosterone concentration due to pituitary-gonadotropic action (acute action) is observed. Under these circumstances, GnRH antagonistic drugs which are expected to have substantially the same therapeutic effects as described above but not to cause the above-mentioned transient pituitary-gonadotropic action (acute action) have been desired. As compounds having such GnRH antagonistic activity, a number of compounds including, for example, derivatives of GnRH such as straight-chain peptides, (U.S. Pat. Nos. 5,140,009 and 5,171, 835), cyclic hexapeptide derivatives [Japanese Patent Application Laid-open No. 61(1986)-191698] or bicyclic peptide derivatives [Journal of medicinal chemistry, Vol.36, pp.3265–3273, 1993] have been disclosed. These compounds are, however, all peptides, which leave many problems including, for example, dosage forms, stability of drugs, durability of actions and stability on metabolism. For solving these problems, orally administrable GnRH antagonistic drugs, especially non-peptide ones, are strongly desired. At the present stage, however, no report on non-peptide GnRH antagonistic drugs has been made.

An object of the second embodiment invention lies in providing novel compounds having excellent gonadotropic hormone releasing hormone antagonistic activity as well as excellent gonadotropic hormone releasing hormone antagonistic agents.

DISCLOSURE OF THE SECOND EMBODIMENT

Thus, the second embodiment of the present invention provides (1). a novel thienopyrimidine derivative (I) of the formula:

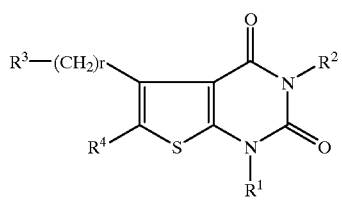

(I)

wherein $R^1$ is hydrogen, an alkyl group or a group of the formula:

Q—(CH$_2$)p— in which Q is (1) an aryl group which may be substituted by one or more of (i) halogen, (ii) nitro, (iii) cyano, (iv) amino, (v) an optionally substituted carboxyl, (vi) alkylenedioxy and (vii) a group of the formula: —A—R$^5$ in which A is a chemical bond or a spacer group and R is an alkyl group, (2) an optionally substituted cycloalkyl group or (3) an optionally substituted heterocyclic group, and p is an integer of 0 to 3;

$R^2$ is hydrogen, an alkyl group which may be substituted by alkoxy, an optionally substituted aryl group, an optionally substituted aralkyl group or an optionally substituted cycloalkyl group;

$R^3$ is an optionally substituted amino group; r is an integer of 0 to 3; and $R^4$ is an optionally substituted aryl group; or a salt thereof;

(2). A compound according to the item (1), wherein the spacer group represented by A is —O— or —S(O)m— in which m is an integer of 0 to 2;

(3). A compound according to the item (1), wherein $R^1$ is a group of the formula:

Q—(CH$_2$)p— in which Q is an aryl group which may be substituted by one or more of (i) halogen and (ii) a group of the formula: —A—R$^5$ in which A is —O— or —S(O)m— wherein m is an integer of 0 to 2 and R$^5$ is an alkyl group; and p is an integer of 0 to 3;

(4). A compound according to the item (1), wherein $R^2$ is (1) an alkyl group which may be substituted by alkoxy, (2) an aryl group which may be substituted by one or more of (i) amino, (ii) acyl, (iii) carbamoyl, (iv) carboxy, (v) nitro, (vi) hydroxy, (vii) alkoxy group which may be substituted by alkoxy, (viii) halogen and (ix) a group of the formula: —S(O)n—R$^6$ in which n is an integer of 0 to 2 and R$^6$ is an alkyl group, (3) an aralkyl group which may be substituted by halogen or (4) a cycloalkyl group;

(5). A compound according to the item (4), wherein $R^2$ is (1) an alkyl group which may be substituted by alkoxy, (2) an aryl group which may be substituted by one or more of (i) hydroxy, (ii) alkoxy group which may be substituted by alkoxy, (iii) halogen and (iv) a group of the formula: —S(O)n—R$^6$ in which n is an integer of 0 to 2 and R$^6$ is an alkyl group, (3) an aralkyl group or (4) a cycloalkyl group;

(6). A compound according to the item (4), wherein $R^2$ is an aryl group which may be substituted by one or more of (1) an alkoxy group which may be substituted by alkoxy, (2) halogen and (3) a group of the formula: —S(O)n—R$^6$ in which n is an integer of 0 to 2 and R$^6$ is an alkyl group;

(7). A compound according to the item (1), wherein $R^3$ is an optionally substituted amino group of the formula:

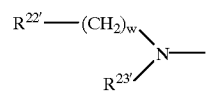

wherein $R^{22'}$ is (1) an aryl group which may be substituted by one or more of (i) amino, (ii) acyl, (iii) carbamoyl, (iv) carboxy, (v) nitro, (vi) hydroxy, (vii) alkoxy group which may be substituted by alkoxy, (viii) halogen, (ix) alkyl and (x) a group of the formula: —S(O)n—R$^6$ in which n is an integer of 0 to 2 and R$^6$ is an alkyl group, (2) a heterocyclic group which may be substituted by one or more of (i) amino, (ii) acyl, (iii) carbamoyl, (iv) carboxy, (v) nitro, (vi) hydroxy, (vii) alkoxy group, (viii) halogen, (ix) alkyl and (x) a group of the formula: —S(O)n—R$^6$ in which n is an integer of 0 to 2 and R$^6$ is an alkyl group, (3) an aralkyl group which may be substituted by halogen, (4) a group of the formula:

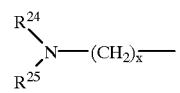

wherein $R^{24}$ is hydrogen, an alkyl group or an aryl group, $R^{25}$ is hydrogen or an alkyl group and $R^{24}$ and $R^{25}$ may form a 5 to 7 membered cyclic amino group containing the adjacent nitrogen atom which may be optionally substituted and x is an integer of 0 to 3 or (5) an alkyl group which may be substituted by alkylthio, w is an integer of 0 to 3; and $R^{23'}$ is hydrogen or an alkyl group;

(8). A compound according to the item (1), wherein $R^3$ is an optionally substituted amino group of the formula:

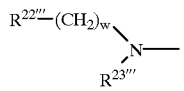

wherein $R^{22'''}$ is (1) an aryl group which may be substituted by alkylthio, (2) a heterocyclic group, (3) a group of the formula:

wherein $R^{24'}$ is hydrogen or alkyl, $R^{25'}$ is hydrogen or alkyl, and $R^{24'}$ and $R^{25'}$ may form a 5 to 7 membered cyclic amino group containing the adjacent nitrogen atom or (4) an alkyl group which may be-substituted by alkylthio, w is an integer of 0 to 3; and $R^{23'''}$ is hydrogen or an alkyl group;

(9). A compound according to the item (1), wherein $R^4$ is an aryl group which may be substituted by one or more of (1) an optionally substituted amino group, (2) acyl, (3) an optionally substituted carbamoyl group, (4) carboxy, (5) nitro, (6) hydroxy, (7) an optionally substituted alkoxy group and (8) an optionally substituted alkenyl group;

(10). A compound according to the item (1), wherein $R^4$ is an aryl group which may be substituted by one or more of (1) a group of the formula:

wherein $R^{11'}$ is (i) hydrogen, (ii) alkyl, (iii) an optionally substituted alkoxy group, (iv) an optionally substituted acyl group or (v) a group of the formula: —S(O)n—$R^6$ in which n is an integer of 0 to 2, and $R^6$ is an alkyl group and $R^{12'}$ is hydrogen or alkyl, (2) acyl, (3) carbamoyl, (4) N-mono or di-alkylcarbamoyl, (5) nitro, (6) alkoxy which may be further substituted by one or more of alkoxy, alkanoyl, oxo, hydroxy, cycloalkyl and halogen, (7) alkenyl which may be further substituted by alkoxycarbonyl or alkylcarbonyl and (8) alkenyloxy;

(11). A compound according to the item (1), wherein $R^4$ is an aryl group which may be substituted by one or more of (1) a group of the formula:

wherein $R^{11''}$ is (i) hydrogen, (ii) alkyl, (iii) alkoxy which may be substituted by halogen or alkoxy, (iv) formyl, (v) alkanoyl which may be substituted by halogen or alkoxy, (vi) benzoyl or (vii) a group of the formula: —S(O)n—$R^6$ in which n is an integer of 0 to 2 and $R^6$ is an alkyl group and $R^{12''}$ is hydrogen or alkyl, (2) alkoxy which may be substituted by alkoxy, alkanoyl or cycloalkyl, (3) N-mono or di-alkylcarbamoyl, (4) nitro, (5) alkenyl which may be substituted by alkoxy-carbonyl or alkylcarbonyl or (6) alkenyloxy;

(12). A compound according to the item (1), which is 2,4(1H,3H)-dioxo-6-(4-methoxyphenyl)-3-phenyl-1-(2-chloro-6-fluorobenzyl)-5-(N-benzyl-N-methylaminomethyl)thieno[2,3-d]pyrimidine or its salt;

(13). A compound according to the item (1), which is 2,4(1H,3H)-dioxo-1-(2,6-difluorobenzyl)-6-(4-propionylaminophenyl)-5-(N-benzyl-N-methylaminomethyl)-3-(3-methoxyphenyl)thieno[2,3-d]pyrimidine or its salt;

(14). A compound according to the item (1), which is 2,4(1H,3H)-dioxo-1-(2,6-difluorobenzyl)-6-(4-isobutyrylaminophenyl)-5-(N-benzyl-N-methylaminomethyl)-3-(3-methoxyphenyl)thieno[2,3-d]pyrimidine or its salt;

(15). A method for producing a compound of the formula (I):

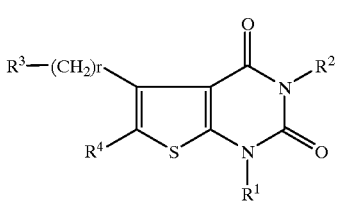

wherein $R^1$, $R^2$, $R^3$, $R^4$ and r have the same meaning as defined above or a salt thereof, which comprises reacting a compound of the formula:

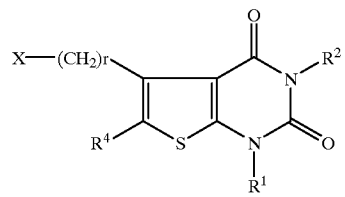

wherein $R^1$, $R^2$, $R^4$ and r have the same meaning as defined above, X is a leaving group, or a salt thereof with compound of the formula:

wherein $R^3$ has the same meaning as defined above, or a salt thereof;

(16). A pharmaceutical composition, which comprises a compound as defined in the item (1) and a carrier, excipient or diluent therefor;

(17). A composition according to the item (16), which is a gonadotropin-releasing hormone antagonistic composition;

(18). A composition according to the item (16), which is a composition for preventing or treating a sex hormone dependent disease;

(19). A method for antagonizing gonadotropin-releasing hormone in a mammal, which comprises administering an effective amount of a compound as defined in the item (1) to a mammal suffering from a gonadotropin-releasing hormone derived disorder;

(20). A method according to the item (19), wherein the gonadotropin-releasing hormone derived disorder is a sex hormone dependent disease;

(21). A compound as defined in the item (1) for medicinal use;

(22). Use of a compound as defined in the item (1) for producing a gonadotropin-releasing hormone antagonistic composition for antagonizing gonadotropin-releasing hormone in a mammal suffering from a gonadotropin-releasing hormone derived disorder;

(23). Use according to the item (22), wherein the gonadotropin-releasing hormone derived disorder is a sex hormone dependent disease;

The nucleus of the present compound, 2,4(1H,3H)-dioxo-thieno[2,3-d]pyrimidine, is shown below;

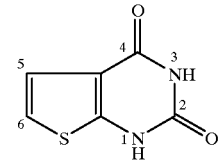

As the alkyl group shown by $R^1$, $R^5$ and alkyl which may be substituted by alkoxy shown by $R^2$ mention is made of, for example, $C_{1-6}$ alkyl (e.g. methyl, ethyl, propyl, isopropyl, butyl, sec-butyl, t-butyl, pentyl, hexyl). Among these, alkyl group having one to three carbon atoms is preferable.

As the aryl group shown by Q or in the optionally substituted aryl group shown by $R^2$ and $R^4$, mention is made of, for example, mono cyclic- or condensed polycyclic-aromatic hydrocarbon residues. Preferable example of them includes $C_{6-14}$ aryl such as phenyl, naphthyl, anthryl, phenanthryl, acenaphthylenyl and the like. Among these, phenyl, 1-naphthyl and 2-naphthyl are more preferable.

The number of substituents on the aryl group is one or more, preferably one to three. Examples of the substituents on the aryl group shown by $R^2$ and $R^4$ include (1) $C_{1-6}$ alkyl (e.g. methyl, ethyl, n-propyl, isopropyl, n-butyl, isobutyl, pentyl, hexyl. The alkyl may be substituted by alkyl-carbonyl or alkoxy-carbonyl), (2) an optionally substituted alkenyl group such as $C_{2-6}$ alkenyl (e.g. vinyl, allyl, 1-butenyl, 2-butenyl), which may be substituted by one or more of $C_{1-10}$ acyl or $C_{1-6}$ alkoxy-carbonyl, (3) $C_{2-6}$ alkynyl (e.g. ethynyl, propargyl, 2-butynyl, 5-hexynyl), (4) $C_{3-7}$ cycloalkyl (e.g. cyclopropyl, cyclobutyl, cyclopentyl, cyclohexyl), (5) $C_{6-14}$ aryl (e.g. phenyl, naphthyl) which may be substituted by one or more of (i) halogen, (ii) alkyl, (iii) alkoxy which may be further substituted by alkoxy, (iv) nitro, (v) cyano, (vi) a group $-S(O)_n-R^6$ wherein n is an integer of 0 to 2 and $R^6$ shows alkyl or amino, (vii) amino, (viii) acyl, (ix) carbamoyl, (x) carboxy and (xi) hydroxy, (6) heterocyclic group, for example, 5- to 9-membered aromatic heterocyclic group having 1 to 4 hetero atoms selected from a nitrogen atom, an oxygen atom and a sulfur atom (e.g. furyl, thienyl, pyrrolyl, thiazolyl, imidazolyl, pyrazolyl, pyridyl), or 5- to 9-membered nonaromatic heterocyclic group having 1 to 4 hetero atoms selected from a nitrogen atom, an oxygen atom and a sulfur atom (e.g. oxiranyl, azetidinyl, oxetanyl, thietanil, pyrrolidinyl, tetrahydrofuryl, thioranyl, piperidinyl, tetrahydropyranyl, morpholinyl, thiomorpholinyl, piperazinyl), these heterocyclic group may be substituted by one or more of (i) halogen, (ii) alkyl, (iii) amino, (iv) acyl, (v) carbamoyl, (vi) carboxy, (vii) nitro, (viii) hydroxy, (ix) alkoxy and (x) a group of the formula: $-S(O)_n-R^6$ in which n is an integer of 0 to 2 and $R^6$ is alkyl group, (7) $C_{7-13}$ aralkyl (e.g. benzyl, phenethyl, benzhydryl) which may be substituted by one or more of halogen, (8) an optionally substituted amino group such as a group of the formula:

wherein $R^{11}$ denotes hydrogen; alkyl, e.g. $C_{1-6}$ alkyl which may be substituted by hydroxy; acyl (e.g. $C_{1-6}$ alkyl-carbonyl, formyl; arylcarbonyl) which may be substituted by one or more of halogen or alkoxy; optionally substituted alkoxy group as mentioned below; $C_{3-7}$ cycloalkyl which may be substituted by one or more of hydroxy; a group of the formula: $-S(O)n-R^6$ in which n is an integer of 0 to 2 and $R^6$ is alkyl group and $R^{12}$ denotes hydrogen or $C_{1-6}$ alkyl, (9) a group of the formula:

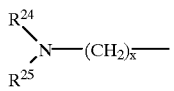

wherein $R^{24}$ is hydrogen, alkyl group or aryl group, $R^{25}$ is hydrogen or alkyl group and $R^{24}$ and $R^{25}$ may form an optionally substituted 5 to 7 membered cyclic amino group containing the adjacent nitrogen atom and x is an integer of 0 to 3, (10) amidino, (11) acyl (e.g. $C_{1-8}$ alkanoyl such as formyl, acetyl, propionyl, butyryl, octanoyl; $C_{1-8}$ alkoxy-carbonyl such as methoxycarbony, ethoxycarbonyl, propoxycarbonyl, butoxycarbonyl; $C_{6-14}$ aryl-carbonyl such as benzoyl; $C_{8-11}$ aralkylcarbonyl such as benzylcarbonyl; $C_{7-12}$ aralkyloxy-carbonyl such as benzyloxycarbonyl) which may be optionally substituted by one or more of substituents (e.g. halogen, alkylthio, alkoxy, oxo, hydroxy), (12) an optionally substituted carbamoyl group, e.g. carbamoyl, N-monosubstituted carbamoyl {e.g. N-($C_{1-7}$ alkyl)carbamoyl such as methylcarbamoyl, ethylcarbamoyl, propylcarbamoyl, isopropylcarbamoyl}, N,N-disubstituted carbamoyl [e.g. N,N-di($C_{1-6}$ alkyl)carbamoyl such as dimethylcarbamoyl, diethylcarbamoyl, N-ethyl-N-methylcarbamoyl, N-propyl-N-methylcarbamoyl}, (13) sulfamoyl, (14) N-monosubstituted sulfamoyl {e.g. N-($C_{1-6}$ alkyl)sulfamoyl such as methylsulfamoyl, ethylsulfamoyl, propylsulfamoyl}, (15) N,N-disubstituted sulfamoyl {e.g. N,N-di($C_{1-6}$ alkyl)sulfamoyl such as dimethylsulfamoyl, diethylsulfamoyl}, (16) carboxy, (17) $C_{1-3}$ alkoxy-carbonyl (e.g. methoxycarbonyl, ethoxycarbonyl, propoxycarbonyl), (18) hydroxyl, (19) an optionally substituted alkoxy group, e.g. $C_{1-6}$ alkoxy (e.g. methoxy, ethoxy, propoxy, isopropoxy, butoxy, isobutoxy, sec-butoxy, t-butoxy, pentyloxy, hexyloxy) which may have one or more of substituent (e.g. $C_{1-6}$ alkanoyl which is the same as above, $C_{1-3}$ alkyl, halogen, $C_{1-3}$ alkylthio, $C_{1-3}$ alkoxy, oxo, hydroxy, $C_{3-7}$ cycloalkyl which is the same as above), (20) $C_{2-4}$ alkenyloxy (e.g. vinyloxy, allyloxy), (21) $C_{3-7}$ cycloalkyloxy (e.g. cyclopropyloxy, cyclopentyloxy, cyclohexyloxy), (22) $C_{7-13}$ aralkyloxy (e.g. benzyloxy, benzhydryloxy), (23) $C_{6-14}$ aryloxy (e.g. phenyloxy, naphthyloxy), (24) mercapto, (25) $C_{7-13}$ aralkylthio (e.g. benzylthio, benzhydrylthio), (26) $C_{6-14}$ arylthio (e.g. phenylthio, naphthylthio), (27) a group of the formula: $-S(O)n-R^6$ in which n is an integer of 0 to 2 and $R^6$ is alkyl group (e.g. methylthio, ethylthio, propylthio, methylsulfinyl, ethylsulfinyl, propylsulfinyl, methylsulfonyl, ethylsulfonyl, propylsulfonyl), (28) CI3 alkylenedioxy (e.g. methylenedioxy, ethylenedioxy, propylenedioxy), (29) sulfo, (30) cyano, (31) azide, (32) nitro, (33) nitroso, (34) halogen (e.g. fulorine, chlorine, bromine iodine), and the like.

As the cycloalkyl in the optionally substituted cycloalkyl shown by Q of $R^1$ and $R^2$, mention is made of, for example, $C_{3-10}$ cycloalkyl and $C_{3-10}$ bicycloalkyl. The preferable examples of them include cyclopropyl, cyclobutyl, cyclopentyl, cyclohexyl, cycloheptyl, cyclooctyl, bicyclo[2,2,1]heptyl, bicyclo[2,2,2]octyl, bicyclo[3,2,1]octyl, bicyclo[3,2,1]nonyl, bicyclo(4,2,1lnonyl, bicyclo[4,3,1]decyl. Among these, cyclopentyl and cyclohexyl are more preferable. The substituents are of the same meaning as definede in the substituents which aryl, shown by $R^2$ and $R^4$, may have. Preferred examples of the substituents are alkyl, alkoxy or halogen.

As the heterocyclic group in the optionally substituted heterocyclic group shown by Q of $R^1$, mention is made of, for example, 5- to 13-membered aromatic heterocyclic group having one to four hetero atom(s) selected from an oxygen atom, a sulfur atom and a nitrogen atom; or saturated or unsaturated non-aromatic heterocyclic group.

Examples of the aromatic heterocyclic group include an aromatic monocyclic heterocyclic group (e.g. furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl), an aromatic condensed-ring heterocyclic group {e.g. benzofuranyl, isobenzofuranyl, benzo[b]thienyl, indolyl, isoindolyl, 1H-indazolyl, benzoimidazolyl, benzoxazolyl, 1,2-benzoisoxazolyl, benzothiazolyl, 1,2-binzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyridazinyl, 1,2–4-tiazolo[4,3-a]pyridyl, 1,2,4-triazolo[4,3-b]pyridazinyl}. Examples of the non-aromatic heterocyclic group include oxylanyl, azetizinyl, oxethanyl, thiethanyl, pyrrolidinyl, tetrahydrofuranyl, thiolanyl, piperidyl, tetrahydropyranyl, morpholinyl, thiomorpholinyl, piperazinyl. Among these, furyl, thienyl, thiazolyl, imidazolyl, pyrazolyl, pyridyl, pyrimidyl, benzofuryl, indolyl and quinolyl are preferable.

The heterocyclic group may have one or more substituents, preferably one to three substituents. The substituents are of the same meaning as defined in the optionally substituted aryl shown by $R^2$ and $R^4$. Preferred examples of the substituents are halogen, alkyl, alkylthio or alkoxy.

As the halogen, as the substituent of the aryl shown by Q, mention is made of fluorine, chlorine, bromine, iodine.

As the substituents of the optionally substituted carboxyl of the aryl group shown by Q, mention is made of alkyl, cycloalkyl, aryl, aralkyl and heterocyclic group which are of the same meaning as defined above and below.

As the lower alkylenedioxy as the substituent of aryl group shown by Q, mention is made of, for example, $C_{1-6}$ alkylenedioxy. Examples of the alkylenedioxy includes methylenedioxy, ethylenedioxy, propylenedioxy, 2,2-dimethylmetylenedioxy.

As the spacer group shown by the symbol "A", mention is made of, for example, $C_{1-4}$ alkylene (e.g. methylene, ethylene), $C_{2-6}$ alkenylene (e.g. vinylene, butadienylene); a group of the formula: —(CH$_2$)cNR$^{26}$— in which c is 0 to 3, $R^{26}$ is hydrogen, $C_{1-6}$ alkyl (e.g. methyl, ethyl, butyl); a group of the formula: —CO—; a group of the formula: —CONR$^{27}$— in which $R^{27}$ is hydrogen, $C_{1-6}$ alkyl (Examples of the alkyl are made of those mentioned above), $C_{3-7}$ cycloalkyl (Examples of the cycloalkyl are made of those mentioned above), $C_{6-14}$ aryl (Examples of the aryl are made of those mentioned above), a heterocyclic group (Examples of the heterocyclic group are made of those mentioned above); a group of the formula: —S(O)$_m$— wherein m is an integer of 0 to 2; —O—; a group of the formula; —NR$^{27}$S(O)$_z$— wherein z is an integer of 0 to 2, $R^{27}$ is of the same meaning as defined in the above.

As the alkoxy which may be the substituent of the alkyl group shown by $R^2$, mention is made of $C_{1-6}$ alkoxy.

As the aralkyl in the optionally substituted aralkyl shown by $R^2$, mention is made of, for example, aryl-alkyl. The aryl is of the same meaning as defined above. Examples of the alkyl include $C_{1-6}$ alkyl such as methyl, ethyl, propyl, butyl, pentyl, hexyl. The substituents on the aralkyl shown by $R^2$ are of the same meaning as defined in the substituents which aryl group shown by $R^2$ and $R^4$ may have.

As the optionally substituted amino group shown by $R^3$, mention is made of, for example, (1) a group of the formula:

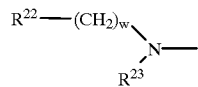

wherein $R^{22}$ is an alkyl, cycloalkyl, aryl or heterocyclic group and these groups may optionally be substituted, w is an integer of 0 to 3, $R^{23}$ is hydrogen or an optionally substituted alkyl, or (2) hexamethylenetetraamino. The substituents on the alkyl, cycloalkyl, aryl and heterocyclic groups in the above $R^{22}$ and $R^{23}$ are of the same meaning as defined in the substitution on any group shown by $R^2$ and $R^4$ as mentioned above.

As the preferable spacer group represented by A in the definition of the substituents on the aryl group of Q in $R^1$, mention is made of —O— or —S(O)m— in which m is an integer of 0 to 2.

As preferred examples of the above group $R^1$, mention is made of the group of the formula: Q—(CH$_2$)p— wherein Q and p has the same meaning as defined above.

As preferred examples of the above group $R^1$, mention is made of hydrogen or a group of the formula: —(CH$_2$)$_p$Q' wherein Q' denotes an aryl group which may be substituted by halogen, nitro, cyano, amino or a group of the formula: —A'—R (wherein A' denotes —O— or —S— and $R^{5'}$ denotes alkyl), and p has the same meaning as defined above.

As more preferred examples of the above group $R^1$, mention is made of a group of the formula:

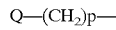

in which Q is an aryl group which may be substituted by one or more of (i) halogen and (ii) a group of the formula: —A—$R^5$ in which A is —O— or —S(O)m— in which m is an integer of 0 to 2 and $R^5$ is alkyl group; and p is an integer of 0 to 3.

As still more preferable examples of the group $R^1$, mention is made of $C_{6-14}$ aryl-methyl which may be substituted by halogen or a group —A"—$R^{5"}$ wherein A" is —O— or —S— and $R^{5"}$ is alkyl.

As especially preferable example of the group $R^1$, mention is made of the group Q'''—(CH$_2$)p— wherein Q''' is an aryl group which may be substituted by halogen and p is an integer of 0 to 3.

As preferred examples of the group $R^2$, mention is made of (1) an alkyl group which may be substituted by alkoxy, (2) an aryl group which may be substituted by one or more of (i) amino, (ii) acyl, (iii) carbamoyl, (iv) carboxy, (v) nitro, (vi) hydroxy, (vii) alkoxy group which may be substituted by alkoxy, (viii) halogen and (iv) a group of the formula: —S(O)n—$R^6$ in which n is an integer of 0 to 2 and $R^6$ is alkyl group, (3) an aralkyl group which may be substituted by halogen or (4) cycloalkyl group.

As more preferred examples of the group $R^2$, mention is made of (1) $C_{1-6}$ alkyl which may be substituted by $C_{1-3}$ alkoxy, (2) $C_{6-14}$ aryl which may be substituted by one or more of amino, acyl, carbomoyl, carboxyl, nitro, hydroxy, $C_{1-3}$ alkoxy, sulfo, halogen and a group of the formula: —S(O)$_n$—$R^6$ wherein n is an integer of 0 to 2 and $R^6$ is $C_{1-3}$ alkyl, or (3) $C_{3-10}$ cycloalkyl.

As further more preferred examples of the group $R^2$, mention is made of (1) an alkyl group which may be substituted by alkoxy, (2) an aryl group which may be substituted by one or more of (i) hydroxy, (ii) alkoxy group which may be substituted by alkoxy, (iii) halogen and (iv) a group of the formula: —S(O)n—R$^6$ in which n is an integer of 0 to 2 and R$^6$ is an alkyl group, (3) aralkyl group or (4) a cycloalkyl group.

As more preferable examples of the group R$^2$, mention is made of (1) C$_{1-6}$ alkyl which may be substituted by C$_{1-3}$ alkoxy, (2) C$_{6-14}$ aryl which may be substituted by one or more of C$_{1-3}$ alkoxy and a group of the formula: —S(O)n—R$^6$ wherein n is an integer of 0 to 2 and R$^6$ is C$_{1-3}$ alkyl, or (3) C$_{3-10}$ cycloalkyl.

As the most preferred examples of the group R$^2$, mention is made of the aryl group which may be substituted by one or more of (1) an alkoxy group which may be substituted by alkoxy, (2) halogen and (3) a group of the formula: —S(O)n—R$^5$ in which n is an integer of 0 to 2 and R$^5$ is an alkyl group.

As preferred examples of the above group R$^3$, mention is made of hexamethylenetetraamino or a substituted amino group of the formula:

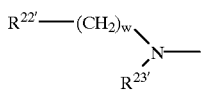

wherein R$^{22'}$ is (1) an aryl group which may be substituted by one or more of (i) amino, (ii) acyl, (iii) carbamoyl, (iv) carboxy, (v) nitro, (vi) hydroxy, (vii) alkoxy group which may be substituted by alkoxy, (viii) halogen, (ix) alkyl or (x) a group of the formula: —S(O)n—R$^6$ in which n is an integer of 0 to 2 and R$^6$ is alkyl group, (2) heterocyclic group which may be substituted by one or more of (i) amino, (ii) acyl, (iii) carbamoyl, (iv) carboxy, (v) nitro, (vi) hydroxy, (vii) alkoxy, (viii) halogen, (ix) alkyl or (x) a group of the formula: —S(O)n—R$^6$ in which n is an integer of 0 to 2 and R$^6$ is alkyl group, (3) an aralkyl group which may be substituted by halogen, (4) a group of the formula:

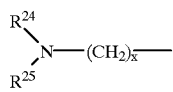

wherein R$^{24}$ is hydrogen, an alkyl group or an aryl group, R$^{25}$ is hydrogen or an alkyl group and R$^{24}$ and R$^{25}$ may form an optionally substituted 5 to 7 membered cyclic amino group containing the adjacent nitrogen atom and x is an integer of 0 to 3 or (5) an alkyl group which may be substituted by alkylthio, w is an integer of 0 to 3; and R$^{23'}$ is hydrogen or an alkyl group.

As more preferred examples of the above group R$^3$, mention is made of hexamethylenetetraamino or a group of the formula

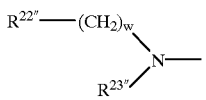

(wherein R$^{22''}$ denotes (1) alkyl, (2) phenyl which may be substituted by one or more of halogen, nitro, alkyl and a group of the formula: —S(O)$_n$—R$^6$ wherein n is an integer of 0 to 2 and R$^6$ is an alkyl group or an amino group, (3) a heterocyclic group which may be substituted by one or more of halogen and alkyl or (4) N-alkylcarbamoyl, w is an integer of 0 to 3; R$^{23''}$ denotes hydrogen or alkyl).

As more preferred examples of the above R$^3$, mention is made of a substituted amino group of the formula:

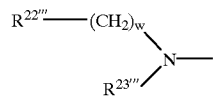

wherein R$^{22'''}$ is (1) aryl group which may be substituted by alkylthio, (2) heterocyclic group, (3) a group of the formula:

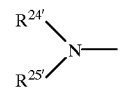

wherein R$^{24'}$ is hydrogen or alkyl and R$^{25'}$ is hydrogen or alkyl and R$^{24'}$ and R$^{25'}$ may form a 5 to 7 membered cyclic amino group containing the adjacent nitrogen atom or (4) an alkyl group which may be substituted by alkylthio, w is an integer of 0 to 3; and R$^{23'''}$ is hydrogen or an alkyl group.

As preferred examples of the above group R$^3$, mention is made of a group of the formula:

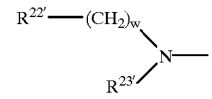

(wherein R$^{22'}$ is phenyl or pyridyl, these groups being unsubstituted or substituted by a group of the formula: —S(O)$_n$—R in which n is an integer of 0 to 2 and R$^6$ is an alkyl group, w is an integer of 0 to 3. R$^{23'}$ is hydrogen or an alkyl group).

As preferred examples of the group R$^4$, mention is made of the aryl group which may be substituted by one or more of (1) an optionally substituted amino group, (2) acyl, (3) an optionally substituted carbamoyl group, (4) carboxy, (5) nitro, (6) hydroxy, (7) an optionally substituted alkoxy group and (8) an optionally substituted alkenyl group.

As more preferred examples of the above group R$^4$, mention is made of the aryl group which may be substituted by one or more of (1) a group of the formula:

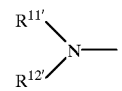

wherein R$^{11'}$ is (i) hydrogen, (ii) alkyl, (iii) an optionally substituted alkoxy group, (iv) an optionally substituted acyl group or (v) a group of the formula: —S(O)n—R$^6$ in which n is an integer of 0 to 2 and R$^6$ is an alkyl group and R$^{12'}$ is hydrogen or an alkyl group, (2) acyl, (3) carbamoyl, (4) N-mono or di-alkylcarbamoyl, (5) nitro, (6) alkoxy which may be substituted by one or more of alkoxy, alkanoyl, oxo, hydroxy, cycloalkyl and halogen, (7) alkenyl which may be substituted by alkoxycarbonyl or alkylcarbonyl and (8) alkenyloxy.

Further preferred examples of the above group R$^4$, mention is made of the aryl group which may be substituted by one or more of (1) a group of the formula:

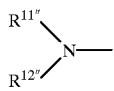

wherein $R^{11''}$ is (i) hydrogen, (ii) alkyl, (iii) alkoxy which may be substituted by halogen or alkoxy, (iv) formyl, (v) alkanoyl which may be substituted by helogen or alkoxy, (vi) benzoyl or (vii) a group of the formula: —S(O)n—$R^6$ in which n is an integer of 0 to 2 and $R^6$ is an alkyl group and $R^{12''}$ is hydrogen or alkyl, (2) alkoxy which may be substituted by alkoxy, alkanoyl or cycloalkyl, (3) N-mono or di-alkylcarbamoyl, (4) nitro, (5) alkenyl which may be substituted by alkoxycarbonyl or alkylcarbonyl or (6) alkenyloxy.

Further preferred examples of the aryl group in the above optionally substituted aryl $R^4$, mention is made of phenyl. As the preferred examples of the substituents on the aryl group shown by $R^4$, mention is made of amino, acyl, carbamoyl, N-monosubstituted alkylcarbamoyl, carboxyl, nitro, hydroxy, $C_{1-3}$ alkoxy which may be substituted by $C_{1-3}$ alkoxy, a group of the formula:

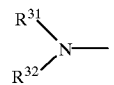

(wherein $R^{31}$ denotes $C_{1-6}$ alkyl; $C_{1-3}$ alkoxy which may be substituted by $C_{1-3}$ alkoxy; or formyl, $R^{32}$ denotes hydrogen or $C_{1-6}$ alkyl), or $C_{2-4}$ alkenyl which may be substituted by alkoxy-carbonyl or alkyl-carbonyl.

As a more preferred example of aryl in the optionally substituted aryl of the group $R^4$, mention is made of phenyl. As more preferred examples of the substituents on the aryl group shown by $R^4$, mention is made of amino; acyl; N-substituted alkylcarbamoyl; nitro; $C_{1-3}$ alkoxy which may be substituted by $C_{1-3}$ alkoxy; a group of the formula;

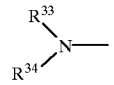

(wherein $R^{33}$ denotes $C_{1-6}$ alkyl, $C_{1-3}$ acyl which may be substituted by $C_{1-3}$ alkoxy; $C_{1-3}$ alkoxy which may be substituted by $C_{1-4}$ acyl; benzoyl; or formyl, $R^{34}$ denotes hydrogen or $C_{1-6}$ alkyl), $C_{2-4}$ alkenyl which may be substituted by $C_{1-3}$ alkoxy-carbonyl or $C_{1-3}$ alkylcarbonyl.

In the above each groups, the number of the substituents is preferably 1 to 3. r is preferably 1, p is preferably 1, and w is preferably 1.

As the 5 to 7 membered cyclic amino group containing nitrogen atom, mention is made of pyrrolidinyl, pyrrolinyl, pyrrolyl, pyrazolidinyl, pyrazolinyl, pyrazolyl, imidazolidinyl, imidazolinyl, imidazolyl, 1,2,3-triazinyl, 1,2,3-triazolidinyl, 1,2,3-triazolyl, 1,2,3,4-tetrazolyl, piperidinyl, piperazinyl, hexamethyleneamino, oxazolidino, morpholino, thiazolidino or thiomorpholino. As more preferable cyclic amino group, mention is made of pyrolidinyl, pyrazolinyl, pyrazolyl, piperidinyl, piperazinyl, morpholino and thiomorpholino.

The cyclic amino group may be substituted. The examples of the substituents includes $C_{1-6}$ alkyl, $C_{6-14}$ aryl, $C_{7-10}$ aralkyl, benzhydryl, $C_{1-6}$ alkyl-carbonyl, $C_{6-14}$ aryl-carbonyl, $C_{1-6}$ alkoxy-carbonyl. As the preferable substituent, mention is made of $C_{1-6}$ alkyl, preferably $C_{1-3}$ alkyl.

As the preferable alkyl in the above definition, mention is made of, for example, $C_{1-10}$ alkyl. Examples of the alkyl includes methyl, ethyl, propyl, isopropyl, butyl, isobutyl, sec-butyl, t-butyl, pentyl, isopentyl, neopentyl and hexyl. Among these, alkyl having one to six carbon atoms is more preferable, and alkyl having one to three carton atoms in still preferable.

As the acyl, mention is made of $C_{1-10}$ acyl and the examples of the acyl are for example alkanoyl, arylcarbonyl, aralkyl-carbonyl and aralkyloxy-carbonyl which are mentioned above.

As the preferable acyl and alkanoyl in the above definition, mention is made of alkyl-carbonyl, and alkyl is of the same meaning as defined above.

As the preferable alkoxy in the above adefinition, mention is made of $C_{1-6}$ alkoxy, and examples of the alkoxy includes methoxy, ethoxy, propoxy, isopropoxy, butoxy, isobutoxy, sec-butoxy, t-butoxy, pentyloxy, isopentyloxy, neopentyloxy, hexyloxy. Among these, alkoxy having 1 to 3 carbon atoms is preferable.

As the preferable alkenyl in the above definition, mention is made of $C_{2-4}$ alkenyl. Examples of the alkenyl includes vinyl, allyl, 1-butenyl, 2-butenyl.

As the preferable aryl in the above definition, mention is made of $C_{6-14}$ aryl. Examples of the aryl includes phenyl, naphthyl.

As the preferable aralkyl in the above definition, mention is made of $C_{7-10}$ aralkyl. Examples of the aralkyl includes benzyl, phenethyl.

As the halogen, mention is made of fluorine, chlorine, bromine, iodine.

The compounds (I) of the present invention can be produced easily by per se known methods, as exemplified by the following production methods, or a similar method thereto.

1. Method A: In accordance with the method disclosed by K. Gewald, E. Schinke and H. Bøttcher, Chem. Ber., 99, 94–100 (1966), an adequate ketone or aldehyde having an active methylene (i) is allowed to react with a cyanoacetic acid ester derivative and sulfur to convert into a 2-aminothiophene derivative (ii). More specifically, in the case of using ketone ($R^{3'}{\neq}H$), it is subjected to heating under reflux together with a cyanoacetic acid ester derivative, in the presence of acetic acid and ammonium acetate, in a proper solvent such as toluene to give an alkylidene cyanoacetic acid ester derivative, which is then heated in an adequate solvent, for example, ethanol in the presence of sulfur and a base to afford a 2-aminothiophene derivative (ii). And, in the case of using aldehyde ($R^{3'}{=}H$), it is heated in a proper solvent, for example, dimethylformamide, in the presence of a cyanoacetic acid ester derivative, sulfur and a base to give a 2-aminothiophene derivative (ii).

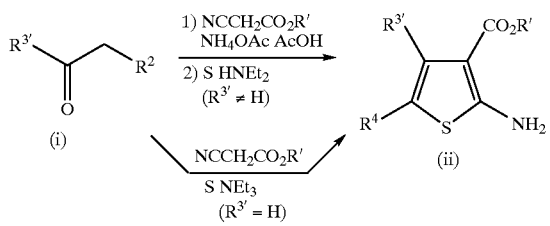

The 2-aminothiophene derivative (ii) produced by the method described in Production Method 1 or a salt thereof is allowed to react with an isocyanate derivative. The isocyanate derivative is exemplified by derivatives represented by the formula, $R^2$—NCO (wherein $R^2$ is of the same meaning as defined above). The reaction of the compound (ii) or a salt thereof with the isocyanate derivative is conducted in an solvent which does not adversely affect the reaction (e.g. tetrahydrofuran, pyridine, dioxane, benzene, dichloromethane, 1,2-dichloroethane, toluene, xylene) at temperatures ranging from about 15 to about 130° C. The isocyanate derivative is employed in an amount of about 1 to 5 equivalents, preferably about 1.1 to 2.5 equivalents, relative to 1 equivalent of the compound (ii). The reaction time ranges from several hours to several days, preferably from about 15 minutes to about two days.

2. Method B: Amine [e.g. a compound represented by the formula $R^2$—$NH_2$ (wherein $R^2$ is of the same meaning as defined above)] is subjected to addition reaction to an isocyanate derivative produced by allowing a 2-aminothiophene derivative (ii) or a salt thereof to react with phosgene or an equivalent compound thereof [e.g. diphosgene such as bis(trichloromethyl)carbonate, triphosgene such as trichloromethylchloroformate]. The reaction of the compound (ii) or a salt thereof with phosgene or an equivalent compound thereof is conducted in a solvent which does not affect adversely the reaction (e.g. dioxane, tetrahydrofuran, benzene, toluene, xylene, 1,2-dichloroethane, chloroform) at temperatures ranging from about 40 to 120°C. Phosgene or an equivalent compound thereof is employed in an amount ranging from about 0.5 to 2 equivalents, preferably from about 0.9 to 1.1 equivalent). The reaction time ranges from several minutes to several days, preferably from about 15 minutes to about two days. The addition reaction of amine is conducted in a solvent which does not affect adversely the reaction (e.g. pyridine, tetrahydrofuran, dioxane, benzene, dichloromethane, 1,2-dichloroethane, toluene, xylene) at temperatures ranging from about 15 to 130° C. Amine is employed in an amount ranging from about 1 to 5 equivalents, preferably from about 1.1 to 3 equivalents. The reaction time ranges from several minutes to several days, preferably from about 15 minutes to about two days.

The compound (XV) or a salt thereof thus produced is processed with a base to cause ring-closure reaction to thereby produce a thieno [2,3-d] pyrimidine derivative (XVI). The ring-closure reaction is conducted in a solvent which does not affect adversely the reaction. The solvent is exemplified by alcohols such as methanol, ethanol or propanol, and ethers such as dioxane or tetrahydrofuran. As the base, use is made of, for example, an alkali metal alkoxide such as sodium methylate, sodium ethylate or sodium isopropoxide, and an alkali metal hydride such as sodium hydride. The amount of the base to be employed ranges from 1 to 5 equivalents, preferably from about 1.5 to 3 equivalents, relative to 1 equivalent of the compound (XV). The reaction temperature ranges from about 10° C. to the boiling point of the solvent then employed, preferably from about 25° C. to the boiling point of the solvent then employed. The reaction time ranges from several minutes to several days, preferably from about 10 minutes to two days.

The compound (XVI) and a halogenated aralkyl derivative are stirred, in the presence of a base (e.g. an organic base such as pyridine or triethylamine), in a solvent which does not affect adversely the reaction (e.g. amides such as dimethylformamide or dimethylacetamide), at about 10 to 100° C., to produce a 2,4-dioxothieno[2,3-d]pyrimidine derivative (IIa). Subsequently, the compound (IIa) is stirred together with N-bromosuccinimide (NBS) in a solvent which does not affect adversely the reaction (e.g. halogenated hydrocarbons such as carbon tetrachloride or chloroform), in the presence of α, α'-azobisisobutyronitrile, to thereby produce the compound (II). Further, the compound (II) is stirred together with various amines, in the presence of a base, in a solvent which does not affect adversely the reaction (e.g. amides such as dimethylformamide or dimethylacetamide, nitrites such as acetonitrile, alcohols such as ethanol), at temperatures ranging from about 10 to 100° C. for 0.5 to 8 hours, to thereby produce the compound (I). When necessary, the compound (I) is made into a corresponding salt with a suitable acid (e.g. hydrochloric acid or oxalic acid).

The foregoing production method is shown by the following scheme 1:

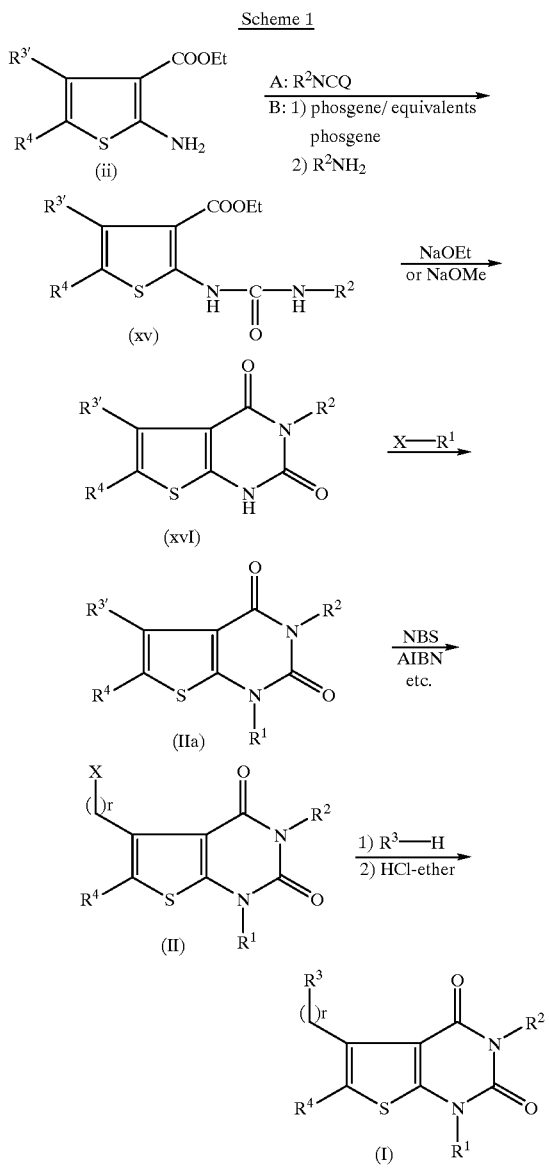

The respective groups described in the above scheme have the same meaning as defined above. X denotes a leaving group.

As the leaving group shown by the above X, mention is made of, for example, groups readily susceptible to substitution reaction by a nucleophilic reagent (e.g. the hydrocarbon residue having a hetero-atom with negative electric charge (e.g. oxygen atom,sulfur atom and nitrogen atom). More specifically, for example, halogen atom (e.g. iodide, bromide, chloride), alkanoyloxy (e.g. acetoxy, alkylsulfonyloxy (e.g. methanesulfonyloxy) and alkyl-aryl sulfonyloxy (e.g. p-toluenesulfonyloxy) are mentioned.

3. Method C: In place of the production method from the compound (ii) to the compound (IIa) in the above scheme 1, any per se conventional methods can be employed for example the following processes for producing the compound (IIa) from the compound (ii). Namely, the compound (ii) is dissolved in an appropriate solvent, e.g. methanol, ethanol, which does not adversely affect the reaction, 2N sodium hydroxide is added, and the mixture is reacted at room tempereture to heating (till about 100° C.) for one to 12 hours. The obtained compound wherein —COOEt is converted to —COOH is dissolved in an appropriate solvent, e.g. dioxane, and to the solution is added an equivalent amount of triphosgene and the mixture is reacted at a temperature of 80 to 150° C. for one to 10 hours under stirring. The obtained 1-hydroxy oxazine compound is treated in a manner similar to that of the reaction of the compound (XVI) to the compound (IIa) as mentioned above. Thus obtained oxazine compound to which the group $R^1$ is introduced at 1-position is dissolved in an appropriate solvent, e.g. dichloromethane, to the solution is added an equivalent amount to a small excess amount of an amine, e.g. ammonium, alkylamine, arylamine, and the mixture is reacted at a room temperature to heating (till 100° C.) for 1 to 12 hours under stirring. Then, to the reaction mixture is added triphosgene again and triethylamine as a base, the mixture is reacted at about 100° C. under reflux for 1 to 6 hours, to give a compound of the formula (IIa).

4. Other methods:

The substituents on the compound (I) can be converted to other substituents by er se known and conventional methods. Examples of the methods are shown below.

(i) The nitro group as the substituent can be converted to an amino group when the starting compound is dissolved in an appropriate solvent, e.g. ethanol, methanol, and (a) to the solution is added palladium-carbon, and the mixture is reacted at room temperature for one to 12 hours under the hydrogen atmosphere, or (b) to the solution is added iron powder and hydrochloric acid, and the mixture is reacted at room temperature for one to 12 hours.

(ii) The amino group can be converted to an acylated amino group in that the starting compound is dissolved in an appropriate solvent, e.g. tetrahydrofuran, dimethylsulfoxide, to the solution is added potassium carbonate, pyridine and triethylamine as a base and acid anhydride or acid halide. The mixture is reacted at a room temperature for one to 10 hours under stirring.

(iii) From an amino compound, a compound having the amino group is converted to alkenyl-amino compound. For example, the starting compound is dissolved in an appropriate solvent, e.g. acetic acid, dimethylformamide, dichloromethane, tetrahydrofuran, dioxane, acetonitrile, to the solution is added diazonizing agent, e.g. sodium nitrite, isoamyl nitrite, to the mixture is added palladium catalyst, e.g. bis(dibenzylideneacetone)palladium and one to excess equivalents of alkenyl derivative, and the mixture is stirred at room temperature to heating (80°C.) for one to 12 hours.

(iv) A carbon atom can be introduced to the amino group, for example, to the starting compound in an appropriate solvent, e.g. acetic acid, dimethylformamide, dichloromethane, tetrahydrofuran, dioxane, is added an acrylic acid derivative or oxirane derivative, e.g. epoxide compound. The mixture is stirred at 0 to 80° C. for 6 to 24 hours.

(v) A sulfur atom can be introduced to the amino group in the compound, for example, to the starting compound in an appropriate solvent, e.g. pyridine, dimethylformamide, dichloromethane, tetrahydrofuran, ethylether, dioxane, is added halide of sulfur compound. The mixture is stirred at 0 to 80° C. for 6 to 24 hours.

(vi) The substituent, formyl group, can be converted to methyl group in that a starting compound is dissolved in an appropriate solvent, e.g. tetrahydrofuran, and to the mixture is added an organic borane, derivative, e.g. dimethylsulfide borane, and the mixture is reacted at room temperature to heating under reflux for a several hours, e.g. one to 3 hours.

(vii) From methoxy derivative, actonyloxy derivative can be prepared in that the starting material is dissolved in an appropriate solvent, e.g. dichloromethane, to the solution is added one to excess equivalents of Lewis acid, e.g. aluminium chloride, and thiol compound or sulfide compound (e.g. dimethylsulfide), and the mixture is reacted at ice-cooling to room temperature for one to 10 hours, and then the obtained hydroxy derivative is dissolved in an appropriate solvent, e.g. dimethylformamide, to the solution is added a base, e.g. sodium hydroxide or potassium carbonate, and an alkyl halide. The mixture is reacted at a room temperature for one to 12 hours.

(viii) A group of methoxy can be changed to isopropoxy in that the starting material is dissolved in an appropriate solvent, e.g. dichloromethane, to the solution is added one to excess equivalents of Lewis acid, e.g. aluminum chloride, and thiol compound or sulfide compound, e.g. dimethylsulfide, and the mixture is reacted at room temperature to ice-cooling for one to 10 hours.

(ix) An aminocarbonyl group can be introduced in that a starting compound having halogen atom is dissolved in an appropriate solvent, e.g. dimethoxyethane, to the solution is added arylborric acid derivative, a base, e.g. sodium carbonate, a palladium compound e.g. tetrakis (triphenylphosphine)palladium(O), as a catalyst and the mixture is refluxed 1 to 6 hours.

(x) An alkylthio compound can be converted to an alkylsulfinyl compound or an alkylsulfonyl compound by reacting a starting compound with an oxidizing agent, e.g. metachloroperbenzoic acid, in an appropriate solvent, e.g. dichloromethahe, at ice-cooling to heating. When heating harder or treating with an excess amount of oxidizing agent, an alkylsulfonyl compound is obtained.

As salts of the compounds (I) of this invention obtained thus above, physiologically acceptable acid addition salts are preferable. Examples of such salts include those with an inorganic acid (e.g. hydrochloric acid, hydrobromic acid, nitric acid, sulfuric acid and phosphoric acid) or those with an organic acid (e.g. formic acid, acetic acid, trifluoroacetic acid, fumaric acid, oxalic acid, tartaric acid, maleic acid, citric acid, succinic acid, malic acid, methanesulfonic acid, bezenesulfonic acid, and p-toluenesulfonic acid). Further, when the compound (I) of this invention has an acid group such as —COOH, the compound(I) may form a salt with an inorganic base (e.g. an alkali metal or alkaline earth metal such as sodium, potassium, calcium and magnesium; ammonia) or an organic base (e.g. trimethylamine, triethylamine, pyridine, picolin, ethanolamine, diethanolamine, triethanolamine, dicyclohexylamine and N,N'-dibenzylethylenediamine).

The compounds (I) or salts thereof of the present invention produced above can be isolated and purified by a conventional separating means such as recrystallization, distillation and chromatography. In the case where the compound (I) is produced in the free form, it can be converted to a salt thereof by a per se conventional means or a method analogous thereto. On the contrary, when it is obtained in the form of a salt, it can be converted to its free form or to any other salt.

In the case where the compound (I) or a salt thereof of the present invention is an optically active compound, it can be separated into d-form and l-form by means of a conventional optical resolution.

Since the compounds (I) of this invention have a GnRH antagonistic activity and low in toxicity, they can be safely used for the therapy of male hormone or female hormone dependent diseases as well as the therapy of diseases caused by excess secretion of these hormones, in mammalian animals (e.g. human, monkey, cow, horse, dog, cat, rabbit, rat, mouse, etc.), suppressing the secretion of gonadotropic hormone by the action of GnRH receptor antagonistic action. More specifically, the compounds of this invention are effective as a prophylactic or therapeutic agent for the prevention or treatment of several hormone dependent diseases, for example, a sex hormone dependent cancer (e.g. prostate cancer, cancer of the uterine cervix, breast cancer, pituitary adenoma), benign prostatic hypertrophy, myoma of the uterus, endometriosis, precocious puberty, amenorrhea, premenstrual syndrome, polycystic ovary syndrome and acne vulgaris. And, the compounds of this invention are also effective as a fertility controlling agent in both sexes (e.g. pregnancy controlling agents and menstrual cycle controlling agents). The compounds of this invention can be further used as a contraceptive of male or female and, as an ovulation-inducing agent of female. The compound of this invention can be used as an infertility treating agent by using a rebound effect owing to a stoppage of administration thereof. Further, the compounds of this invention are useful as modulating estrous cycles in animals in the field of animal husbandry, and as an agent for improving the quality of edible meat or promoting the growth of animals. Besides, the compounds of this invention are useful as an agent of spawning promotion in fish. While the compounds of this invention can be used singly, they can also effectively be used by administering in combination with a steroidal or non-steroidal antiandrogenic agent. The compound of this invention can be used for the suppressing a passing ascent of testosterone concentration in plasma, the ascent which occurs in administration of GnRH super antagonist such as leuprorelin acetate. The compound of this invention can effectively be used by administering in combination with a chemoterapeutic agent for cancer. In treatment of prostate cancer, examples of the chemoterapeutic agent include Ifosfamide, UFT, Adriamycin, Peplomycin, Cisplatin and the like. In treatment of breast cancer, examples of the chemoterpeutic agent include Cyclophohamide, 5-FU-, UFT, Methotrexate, Adriamycin, Mitomycin C, Mitoxantrone and the like.

The present compounds (I) shows sufficient GnRH activity through subcutaneous or oral administration, is stably absorbed through oral administration and shows GnRH activity over a long time.

When the compound (I) of this invention is employed, in the field of animal husbandry or fisheries, as prophylactic and therapeutic agents of the above-mentioned diseases, is can be administered orally or non-orally in accordance with per se known means. It is mixed with a pharmaceutically acceptable carrier and usually administered orally as a solid preparation such as tablet, capsule, granule or powder, or non-orally as intravenous, subcutaneous or intramuscular injection, or as suppository or sublingually administrable tablet. Further, it is sublingually, subcutaneously or intramuscularly administered as a prolonged release formulation such as sublingually administrable tablets, or microcapsules. The daily dose of the present compound (I) varies with the degree of affliction; age, sex, body weight and difference of sensitivity of the subject to be administered; the time and intervals of administration, properties, dosage forms and kinds of the medicinal preparation; and kinds of the effective components, and it ranges usually, though not specifically limited, from about 0.01 to 10 mg, preferably from about 0.02 to 2 mg, more preferably from about 0.01 to 1 mg, relative to 1 kg body weight of mammalian animals, which is administered usually once daily or by 2 to 4 divided dosages. The daily dose when used in the field of animal husbandry or fishery varies with the conditions analogous to those mentioned above, it ranges, relative to 1 kg body weight of the subject animal or fish, from about 0.001 to 5 mg, preferably from about 0.002 to 2 mg, once or 2 to 3 divided dosages.

As the above-mentioned pharmaceutically acceptable carriers, conventional various organic or inorganic carriers are used, and they are incorporated as excipients, lubricants, binders and disintegrants in solid compositions; and as solvents, solubilisers, suspending agents, isotonizing agents, buffering agents and pain-easing agents in liquid compositions. And, depending on necessity, further additives such as preservatives, anti-oxidants, coloring agents and sweeteners can also be used.

Preferable examples of the above-mentioned excipients include lactose, sugar, D-mannito, starch, crystalline cellulose and more volatile silicon dioxide. Preferable examples of above-mentioned lubricants include magnesium stearate, calcium stearate, talc and colloid silica. Preferable examples of the above-mentioned binders include crystalline cellulose, sugar, D-mannitol, dextrin, hydroxypropyl cellulose, hydroxymethyl cellulose and polyvinyl pyrrolidone. Preferable examples of the above-mentioned disintegrants include starch, carboxymethyl cellulose, carboxymethyl cellulose calcium, cross carmelose sodium, cross carmelose sodium and carboxymethyl starch sodium. Preferable examples of the above-mentioned solvents include water for injection, alcohol, propylene glycol, macrogol, sesame oil and corn oil. Preferable examples of the above-mentioned solubilizers include polyethylene glycol, propylene glycol, D-mannitol, benzyl benzoate, ethanol, tris-aminomethane, cholesterol, triethanolamine, sodium carbonate and sodium citrate. Preferable examples of the above-mentioned suspending agents include surfactants such as stearyl triethanolamine, sodium lauryl sulfate, lauryl aminopropionic acid, lecithin, benzalkonium chloride, benzetonium chloride and monostearic glyceryl ester; and hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose. Preferable examples of the above-mentioned isotonizing agents include sodium chloride, glycerin and D-mannitol. Preferable examples of the above-mentioned buffering agents include buffer solutions such as phosphate, acetate, carbonate and citrate. Preferable examples of the above-mentioned pain-easing agents include benzyl alcohol. Preferable examples of the above-mentioned preservatives include para-hydroxybenzoic acid esters, chlorobutanol, benzyl alcohol, phenethyl alcohol, dehydroacetic acid and sorbic acid. Preferable examples of the above-mentioned anti-oxidants include sulfite and ascorbic acid.

To the compound (I) of this invention, are added, for example, a suspending agent, a solubilizer, a stabilizer, an isotonizing agent and a preservative, then the mixture is formulated, in accordance with a per se known method, into an intravenous, subcutaneous or intramuscular injection. These injections can be processed into lyophilized preparations, when necessary, by a per se known method.

Examples of the above-mentioned pharmaceutical composition are oral agents (e.g. diluted powders, granules, capsules and tablets), injections, dropping injections, external agents (e.g. transnasal preparations, percutaneous preparations, etc.), ointments (e.g. rectal ointment, vaginal ointment, etc.) and the like.

Such pharmaceutical compositions can be manufactured by a per se known method commonly used in preparing pharmaceutical compositions.

The compound (I) of the present invention or a salt thereof can be made into injections either in a form of an aqueous injection together with dispersing agents [e.g. Tween 80 (Atlas Powder, U.S.A.), HCO 80 (Nikko Chemicals, Japan), polyethylene glycol, carboxymethylcellulose, sodium alginate, etc.], preservatives (e.g. methyl paraben, propyl paraben, benzyl alcohol, etc.), isotonizing agents (e.g. sodium chloride, mannitol, sorbitol, glucose, etc.) and the like or in a form of an oily injection by dissolving, suspending or emulsifying in plant oil (e.g. olive oil, sesame oil, cotton seed oil, corn oil, etc.), propylene glycol and the like.

In preparing a pharmaceutical composition for oral use, the compound (I) of the present invention or a salt thereof is molded by compressing, for example, with fillers (e.g. lactose, sucrose, starch, etc.), disintegrating agents (e.g. starch, calcium carbonate, etc.), binders (e.g. starch, gum arabic, carboxymethylcellulose, polyvinylpyrrolidone, hydroxypropylcellulose, etc.) or lubricants (e.g. talc, magnesium stearate, polyethylene glycol 6000, etc.) and the like. If necessary, the composition is coated by a per se known method with an object of masking the taste, enteric coating or long-acting. Examples of the coating agent therefore are hydroxypropylmethylcellulose, ethylcellulose, hydroxymethylcellulose, hydroxypropylcellulose, polyoxyethylene glycol, Tween 80, pluronic F 68, cellulose acetate phthalate, hydroxypropylmethylcellulose phthalate, hydroxymethylcellulose acetate succinate, Eudragit (a copolymer of methacrylic acid with acrylic acid; manufactured by Rohm, Germany), red oxide of iron and the like. Subcoating layer may be provided between the enteric coating and the core according to per se known method.

In preparing an external composition, the compound (I) of the present invention or a salt thereof as it is or a salt thereof is subjected to a per se known method to give a solid, semisolid or liquid agent for external use. For example, the solid preparation is manufactured as follows. Thus, the compound of the present invention as it is or after adding/mixing fillers (e.g. glycol, mannitol, starch, microcrystalline cullulose, etc.), thickeners (e.g. natural gums, cellulose derivatives, acrylic acid polymers, etc.) and the like thereto/therewith is made into a powdery composition. With respect to the liquid composition, an oily or aqueous suspension is manufactured by the manner nearly the same as in the case of the injection. In the case of a semisolid composition, the preferred one is an aqueous or oily gel or an ointment. Each of them may be compounded with a pH adjusting agent (e.g. carbonic acid, phosphoric acid, citric acid, hydrochloric acid, sodium hydroxide, etc.), an antiseptic agent (e.g. p-hydroxybenzoates, chlorobutanol, benzalkonium chloride, etc.) and the like.

In the manufacture of an ointment for example, the compound (I) of the present invention or a salt thereof can be made into an oily or an aqueous solid, semisolid or liquid ointment. Examples of the oily base material applicable in the above-mentioned composition are glycerides of higher fatty acids [e.g. cacao butter, Witepsols (manufactured by Dynamite-Nobel), etc.], medium fatty acids [e.g. Miglyols (manufactured by Dynamite-Nobel), etc.] and plant oil (e.g. sesame oil, soybean oil, cotton seed oil, etc.) and the like. Examples of the aqueous base material are polyethylene glycols and propylene glycol and those of the base material for aqueous gel are natural gums, cellulose derivatives, vinyl polymers, acrylic acid polymers, etc.

BEST MODE FOR CARRYING OUT OF THE INVENTION

By way of the following Reference Examples and Working Examples, the present invention will be described more specifically, but they are not intended to limit the scope of this invention thereto.

$^1$H-NMR spectra were taken with the Varian GEMINI 200 (200 MHz) type spectrometer, JEOL LAMBDA300 (300 MHz) type spectrometer or the Brucker AM 500 (500 MHz) type spectrometer, employing tetramethylsilane as the internal standard. All delta values were expressed in ppm.

The symbols used in the present specification have the following meanings:

s: singlet, d: doublet, t: triplet, dt: double triplet, m: multiplet, br: broad

REFERENCE EXAMPLE 1

Production of 2-amino-5-phenylthiophene-3-carboxylic acid ethyl ester:

To a mixture of ethyl cyanoacetate (6.1 g, 50 mmol), sulfur (1.61 g, 50 mmol) triethylamine (3.5 ml, 25 mmol) and dimethylformamide (10 ml) was added dropwise, with stirring at 45° C., phenylacetaldehyde (50% diethylphthalate solution; 12.05 g, 50 mmol) for 20 minutes. The mixture was stirred for 9 hours at 45° C., and the reaction mixture was concentrated. The resulting residue was extracted with ethylacetate. The extract was washed with an aqueous sodium chloride solution, which was then dried ($MgSO_4$), followed by distilling off the solvent under reduced pressure. The residue was chromatographed on silica gel, followed by crystallization from ether-hexane to give slightly yellow plates (5.55 g, 45%), m.p.124.5–125.5° C. (value in literature reference 123–124° C.).

| Elemental Analysis for $C_{13}H_{13}NO_2S$: | | | |
|---|---|---|---|
| | C(%) | H(%) | N(%) |
| Calcd.: | 63.13; | 5.30; | 5.66 |
| Found: | 62.99; | 5.05; | 5.63 |

$^1$H-NMR (200 MHz, $CDCl_3$) δ: 1.37(3H,t,J=7.1 Hz), 4.30(2H,d,J=7.1 Hz), 5.97(2H,br), 7.17–7.46(6H,m). IR(KBr): 3448, 3320, 1667, 1590, 1549 $cm^{-1}$.

REFERENCE EXAMPLE 2

Production of 2-amino-4-methyl-5-(4-methoxyphenyl) thiophene-3-carboxylic acid ethyl ester:

A mixture of 4-methoxyphenylacetone (16.5 g, 0.10 mol), ethyl cyanoacetate (12.2 g, 0.10 mol), ammonium acetate (1.55 g, 20 mmol), acetic acid (4.6 ml, 80 mmol) and benzene (20 ml) was heated for 24 hours under reflux, while removing water produced in the reaction mixture using a Dean and Stark apparatus. After cooling, the reaction mixture was concentrated under reduced pressure. The residue was partitioned between dichloromethane and an aqueous sodium hydrogencarbonate solution. The organic layer was washed with an aqueous sodium chloride solution, which was then dried (MgSO$_4$), followed by distilling of the solvent under reduced pressure. To an ethanol (30 ml) solution of the residue were added sulfur (3.21 g, 0.10 mol) and diethylamine (10.4 ml, 0.10 mol). The mixture was stirred at 50–60° C. for 2 h and then concentrated, and the concentrate was extracted with ethyl acetate. The extract was washed with an aqueous sodium chloride solution and dried (MgSO$_4$), followed by distilling off the solvent under reduced pressure. The residue was chromatographed on silica gel, which was the crystallized from ether-hexane to give a pale yellow plates (11.5 g, 40%), m.p.79–80° C.

| Elemental Analysis for $C_{15}H_{17}NO_3S$: | | | |
|---|---|---|---|
| C(%) | H(%) | N(%) | S(%) |
| Calcd.: 61.83; | 5.88; | 4.81; | 11.01 |
| Found: 61.81; | 5.75; | 4.74; | 10.82 |

$^1$H-NMR (200 MHz, CDCl$_3$) δ: 1.37(3H,t,J=7.1 Hz), 2.28(3H,s), 3.83(3H,s), 4.31(2H,q,J=7.1 Hz), 6.05(2H,brs), 6.91(2H,d,J=8.8 Hz), 7.27(2H,d,J=8.8 Hz). IR(KBr): 3426, 3328, 1651, 1586, 1550, 1505, 1485 cm$^{-1}$. FAB-MS m/z: 291 (M$^+$).

REFERENCE EXAMPLE 3

Employing various acetone derivatives in place of 4-methoxyphenylacetone, compounds shown in Table 1 are produced in accordance with substantially the same manner as described in Reference Example 2.

TABLE 1

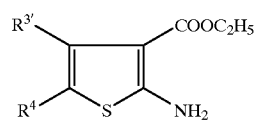

| Ref. Ex. 3 Cpd. No. | R$^{3'}$ | R$^4$ | Yield (%) | m.p. (° C.) |
|---|---|---|---|---|
| 1 | methyl | phenyl | 40 | 64–65 |
| 2 | methyl | 2-methoxyphenyl | 12 | 70–71 |
| 3 | methyl | brom | | |

REFERENCE EXAMPLE 4

Production of 2-amino-4-methyl-5-(4-nitrophenyl) thiophene-3-carboxylic acid ethyl ester:

In substantially the same procedure as described in Reference Example 1, using 4-nitrophenylacetine (35.0 g, 195 mmol) in place of 4-methoxyphenyl acetone, ethyl cyanoacetate (23 g, 19.5 mmol), ammonium acetate (3.1 g, 40 mmol), acetic acid (9.1 ml, 159 mmol), sulfur (5.0 g, 160 mmol) and diethylamine (16.0 ml, 160 mmol), the titled compound was produced as colorless crystals (22.2 g, 52%). m.p.168–170° C. (recrystallized from ether-hexane).

| Elemental Analysis for $C_{14}H_{14}N_2O_4S$: | | |
|---|---|---|
| C(%) | H(%) | N(%) |
| Calcd.: 54.89; | 4.61; | 9.14 |
| Found: 54.83; | 4.90; | 9.09 |

$^1$H-NMR (200 MHZ, CDCl$_3$) δ: 1.39(3H,t,J=7.1 Hz), 2.40(3H,s), 4.34(2H,q,J=7.1 Hz), 6.27(2H,brs), 7.48(2H,d, J=8.7 Hz), 8.23(2H,d,J=8.7 Hz). IR (KBr): 3446, 3324, 1667, 1580, 1545, 1506, 1491, 1475, 1410, 1332 cm$^{-1}$.

REFERENCE EXAMPLE 5

Production of 2,4(1H,3H)-dioxo-5-methyl-6-(4-methoxyphenyl)-thieno[2,3-d]pyrimidin-3-acetic acid ethyl ester:

To a solution of the compound produced in Reference Example 1 (5.00 g, 17.20 mmol) was added ethyl isocyanatoacetate (2.90 ml, 25.80 mmol). The mixture was stirred for 6 hours at 45° C., followed by concentration under reduced pressure. The concentrate was dissolved in ethanol (6 ml), to which was added sodium ethoxide {prepared from ethanol (30 ml) and sodium (0.79 g, 34.30 mmol)}. The mixture was stirred for 24 hours at room temperature, to which was added 2N HCl (18 ml, 36 mmol). Ethanol was distilled off under reduced pressure, and the residue was subjected to filtration, which was washed with water-ethanol and dried under reduced pressure, followed by recrystallization from ethanol to give white needles (5.70 g, 89%). m.p.164–165° C.

| Elemental Analysis for $C_{18}H_{18}N_2O_5S$: | | |
|---|---|---|
| C(%) | H(%) | N(%) |
| Calcd.: 57.74; | 4.85; | 7.48 |
| Found: 57.78; | 5.03; | 7.45 |

$^1$H-NMR (200 MHz, CDCl$_3$) δ: 1.30(3H,t,J=7.2 Hz), 2.45(3H,s), 3.85(3H,s), 4.26(2H,q,J=7.2 Hz), 4.78(2H,s), 6.95(2H,d,J=8.5 Hz), 7.31(2H,d,J=8.8 Hz), 10.58(1H,s). IR (KBr): 2914, 1742, 1713, 1655, 1605, 1568, 1528, 1499 cm$^{-1}$.

REFERENCE EXAMPLE 6

Employing, as starting materials, the compounds which are produced in Reference Examples 2, 3 or 4, compounds which are produced in accordance with the method described in Reference Example 5 are set forth in Table 2.

TABLE 2

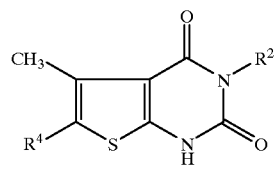

| Ref. Ex. 6 Cpd. No. | R$^2$ | R$^4$ | Yield (%) | m.p. (° C.) |
|---|---|---|---|---|
| 1 | (ethoxycarbonyl)methyl | phenyl | 85 | 119–120 |

TABLE 2-continued

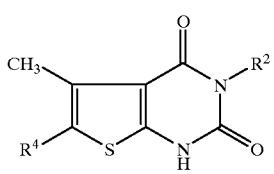

| Ref. Ex. 6 Cpd. No. | $R^2$ | $R^4$ | Yield (%) | m.p. (°C.) |
|---|---|---|---|---|
| 2 | methyl | 4-methoxyphenyl | 84 | 273–276 |
| 3 | phenyl | 4-methoxyphenyl | 85 | >300 |
| 4 | phenyl | 4-nitrophenyl | 84 | >300 |
| 5 | benzyl | 4-methoxyphenyl | 92 | 241–242 |
| 6 | 4-methoxyphenyl | 4-methoxyphenyl | 99 | >300 |
| 7 | cyclohexyl | 4-methoxyphenyl | 84 | 275–276 |
| 8 | 2-methoxyphenyl | 4-methoxyphenyl | 81 | 257–258 |
| 9 | 3-methoxyphenyl | 4-methoxyphenyl | 93 | >300 |
| 10 | 2-chlorophenyl | 4-methoxyphenyl | 95 | 285–286 |
| 11 | 3-chlorophenyl | 4-methoxyphenyl | 97 | >300 |
| 12 | 4-chlorophenyl | 4-methoxyphenyl | 95 | >300 |
| 13 | 3-methoxyphenyl | bromo | 100 | 245–247 |
| 14 | 3-isopropoxyphenyl | bromo | | |
| 15 | 3-isopropoxyphenyl | 4-methoxyphenyl | | |
| 16 | 3-methoxymethoxyphenyl | 4-nitrophenyl | 86 | 263–267 |

REFERENCE EXAMPLE 7

Production of 2,4(1H,3H)-dioxo-6-(4-nitrophenyl)-5-methylthieno[2,3-d]pyrimidin-3-acetic acid ethyl ester:

To the compound 1 produced in Reference Example 6 (2.20 g, 6.39 mmol) was added conc. sulfuric acid (12 ml). To the mixture was added dropwise, under ice-cooling, a solution of sodium nitrate (550 mg, 6.47 mmol) in conc. sulfuric acid, followed by stirring for one hour under ice-cooling. The reaction mixture was poured into ice-water, which was extracted with ethyl acetate. The extract was washed with an aqueous sodium chloride solution and dried (MgSO$_4$), followed by distilling off the solvent under reduced pressure. The residue was chromatographed on silica gel to give a yellowish solid (1.30 g, 52%), which was then recrystallized from ethyl acetate-hexane to yellow crystals, m.p.277–280° C.

Elemental Analysis for $C_{17}H_{15}N_3O_6S.0.4H_2O$:

| | C(%) | H(%) | N(%) |
|---|---|---|---|
| Calcd.: | 51.48; | 4.01; | 10.59 |
| Found: | 51.64; | 3.79; | 10.61 |

$^1$H-NMR (200 MHz, CDCl$_3$) δ: 1.33(3H,t,J=7.2 Hz), 2.56(3H,s), 4.28(2H,q,J=7.2 Hz), 4.79(2H,s), 7.57(2H,d,J=8.8 Hz), 8.30(2H,d,J=8.8 Hz), 10.30(1H,s). IR (KBr): 1748, 1719, 1663, 1522, 1460 cm$^{-1}$.

REFERENCE EXAMPLE 8

Production of 2,4(1H,3H)-dioxo-1-(2-fluorobenzyl)-6-(4-nitrophenyl)-5-methylthieno[2,3-d]pyrimidin-3-acetic acid ethyl ester:

To a solution of the compound produced in Reference Example 7 (700 mg, 1.60 mmol) in dimethylformamide (10 ml) were added potassium carbonate (372 mg, 2.70 mmol), potassium iodide (299 mg, 1.80 mmol) and 2-fluorobenzyl chloride (0.43 ml, 3.60 mmol). The mixture was stirred for 2 hours at room temperature. The reaction mixture was concentrated, and the concentrate was partitioned between ethyl acetate and an aqueous sodium chloride solution. The aqueous layer was extracted with ethyl acetate. The combined extract was washed with an aqueous sodium chloride solution, which was then dried (MgSO$_4$), followed by distilling off the solvent under reduced pressure. The residue was chromatographed on silica gel to give a white powder (500 mg, 56%). m.p.155–158° C.

Elemental Analysis for $C_{24}H_{20}N_3O_6SF.0.5H_2O$:

| | C(%) | H(%) | N(%) |
|---|---|---|---|
| Calcd.: | 56.91; | 4.18; | 8.30 |
| Found: | 56.74; | 3.84; | 8.25 |

$^1$H-NMR (200 MHz, CDCl$_3$) δ: 1.32(3H,t,J=7.2 Hz), 3.84(3H,s), 4.27(2H,q,J=7.2 Hz), 4.84(2H,s), 5.30(2H,s), 7.06–7.33(4H,m), 7.54(2H,d,J=8.9 Hz), 7.27(2H,d,J=8.9 Hz). IR (KBr): 1748, 1711, 1673, 1520, 1491 cm$^{-1}$.

REFERENCE EXAMPLE 9

Starting from the compounds which are produced in Reference Example 6, compounds which are produced in accordance with the method described in Reference Example 8 are set forth in Table 3.

TABLE 3

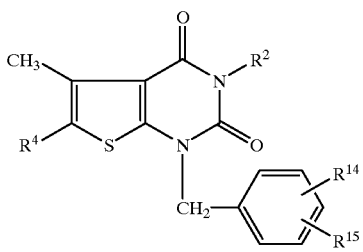

| Ref. Ex. 9 Cpd. No. | $R^2$ | $R^{14}$, $R^{15}$ | $R^4$ | Yield (%) | m.p. (° C.) |
|---|---|---|---|---|---|
| 1 | (ethoxycarbonyl)methyl | 2-fluoro | 4-methoxyphenyl | 87 | 127–128 |
| 2 | methyl | 2-methoxy | 4-methoxyphenyl | 92 | 174–175 |
| 3 | methyl | 2-fluoro | 4-methoxyphenyl | 97 | 179–180 |
| 4 | phenyl | 2-methoxy | 4-methoxyphenyl | 93 | 240–241 |
| 5 | phenyl | 2-fluoro | 4-methoxyphenyl | 96 | 252–253 |
| 6 | phenyl | 2-fluoro | 4-nitrophenyl | 87 | 294–295 |
| 7 | phenyl | 3-fluoro | 4-methoxyphenyl | 88 | 215–217 |
| 8 | phenyl | 4-fluoro | 4-methoxyphenyl | 66 | 209–212 |
| 9 | phenyl | 2,4-difluoro | 4-methoxyphenyl | 73 | 227–228 |
| 10 | phenyl | 2,6-difluoro | 4-methoxyphenyl | 87 | 291–292 |
| 11 | phenyl | 2-chloro, 6-fluoro | 4-methoxyphenyl | 91 | 287–288 |
| 12 | phenyl | 2-methylthio | 4-methoxyphenyl | 81 | 239–240 |
| 13 | benzyl | 2-fluoro | 4-methoxyphenyl | 86 | 124–126 |
| 14 | benzyl | 2,6-difluoro | 4-methoxyphenyl | 82 | 161–163 |
| 15 | 4-methoxyphenyl | 2-fluoro | 4-methoxyphenyl | 87 | 270–272 |
| 16 | 4-methoxyphenyl | 2,6-difluoro | 4-methoxyphenyl | 83 | >300 |
| 17 | cyclohexyl | 2-fluoro | 4-methoxyphenyl | 79 | 172–173 |
| 18 | cyclohexyl | 2,6-difluoro | 4-methoxyphenyl | 73 | 207–208 |
| 19 | phenyl | 2,6-difluoro | 4-nitrophenyl | 93 | 280–282 |
| 20 | 2-methoxyphenyl | 2-fluoro | 4-methoxyphenyl | 84 | 195–198 |
| 21 | 2-methoxyphenyl | 2,6-difluoro | 4-methoxyphenyl | 86 | 205–208 |
| 22 | 3-methoxyphenyl | 2-fluoro | 4-methoxyphenyl | 89 | 241–242 |
| 23 | 3-methoxyphenyl | 2,6-difluoro | 4-methoxyphenyl | 85 | 253–255 |
| 24 | 2-chlorophenyl | 2-fluoro | 4-methoxyphenyl | 91 | 220–221 |
| 25 | 2-chlorophenyl | 2,6-difluoro | 4-methoxyphenyl | 83 | 118–182 |
| 26 | 3-chlorophenyl | 2-fluoro | 4-methoxyphenyl | 90 | 247–248 |
| 27 | 3-chlorophenyl | 2,6-difluoro | 4-methoxyphenyl | 93 | 278–279 |
| 28 | 4-chlorophenyl | 2-fluoro | 4-methoxyphenyl | 79 | 269–270 |
| 29 | 4-chlorophenyl | 2,6-difluoro | 4-methoxyphenyl | 91 | >300 |
| 30 | 3-methoxyphenyl | 2,6-difluoro | bromo | 89 | 261–262 |
| 31 | 3-isopropoxyphenyl | 2,6-difluoro | bromo | | |
| 32 | 3-isopropoxyphenyl | 2,6-difluoro | 4-methoxyphenyl | | |

REFERENCE EXAMPLE 10

Production of 5-bromomethyl-2,4(1H,3H)-dioxo-1-(2-fluorobenzyl)-6-(4-nitrophenyl)thieno[2,3-d]pyrimidin-3-acetic acid ethyl ester:

A mixture of the compound produced in Reference Example 8 (0.300 g, 0.603 mmol), N-bromosuccinimide (0.107 g, 0.603 mmol), α,α'-azobisisobutyronitrile (10 mg, 0.60 mmol) and carbon tetrachloride (15 ml) was refluxed for 2 hours. Upon cooling resulting insolubles were filtered off from the reaction mixture. The filtrate was diluted with chloroform. The organic layer was washed with an aqueous sodium chloride solution and dried (MgSO$_4$), then the solvent was distilled off under reduced pressure. The residue was recrystallized from ethyl acetate to give colorless needles (0.284 g, 82%), m.p.165–167° C.

| Elemental Analysis for C₂₄H₁₉N₃O₆SBrF: | | | |
|---|---|---|---|
| | C (%) | H (%) | N (%) |
| Calcd. | 50.01 | 3.32 | 7.29 |
| Found | 49.87 | 3.27 | 7.23 |

$^1$H-NMR (200 MHz, CDCl$_3$) δ: 1.31(3H,t,J=7.1 Hz), 4.26(2H,q,J=7.1 Hz), 4.78(2H,s), 4.86(2H,s), 5.30(2H,s), 7.07–7.37(4H,m), 7.75(2H,d,J=8.8 Hz), 8.33(2H,d,J=8.8 Hz). IR (KBr): 1713, 1673, 1524, 1477 cm$^{-1}$.

REFERENCE EXAMPLE 11

Starting from the compounds which is produced in Reference Example 9, compounds which are produced in accordance with the method described in Reference Example 10 are set forth in Table 4. The compounds 30 to 33 is produced from the compounds 30 or 31 of Reference Example 9 by the method of Example 18.

TABLE 4

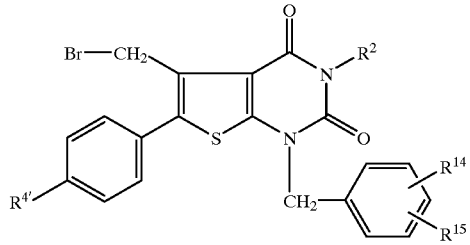

| Ref. Ex. 11 Cpd. No. | R² | R¹⁴, R¹⁵ | R⁴' | Yield (%) | m.p. (° C.) |
|---|---|---|---|---|---|
| 1 | (ethoxy-carbonyl)-methyl | 2-fluoro | methoxy | 70 | 152–153 |
| 2 | methyl | 2-methoxy | methoxy | 63 | 173–176 |
| 3 | methyl | 2-fluoro | methoxy | 82 | 175–177 |
| 4 | phenyl | 2-methoxy | methoxy | 93 | 240–241 |
| 5 | phenyl | 2-fluoro | methoxy | 86 | 230–233 |
| 6 | phenyl | 2-fluoro | nitro | 86 | 224–225 |
| 7 | phenyl | 3-fluoro | methoxy | 84 | 215–216 |
| 8 | phenyl | 4-fluoro | methoxy | 84 | 232–233 |
| 9 | phenyl | 2,4-difluoro | methoxy | 84 | 230–231 |
| 10 | phenyl | 2,6-difluoro | methoxy | 87 | 250–252 |
| 11 | phenyl | 2-chloro, 6-fluoro | methoxy | 86 | 255–257 |
| 12 | phenyl | 2-methylthio | methoxy | 90 | 212–214 |
| 13 | benzyl | 2-fluoro | methoxy | 83 | 132–134 |
| 14 | benzyl | 2,6-difluoro | methoxy | 89 | 154–155 |
| 15 | 4-methoxyphenyl | 2-fluoro | methoxy | 88 | 226–228 |
| 16 | 4-methoxyphenyl | 2,6-difluoro | methoxy | 80 | 249–251 |
| 17 | cyclohexyl | 2-fluoro | methoxy | 86 | 149–151 |
| 18 | cyclohexyl | 2,6-difluoro | methoxy | 77 | 192–194 |
| 19 | phenyl | 2,6-difluoro | nitro | 94 | 228–229 |
| 20 | 2-methoxyphenyl | 2-fluoro | methoxy | 77 | 180–181 |
| 21 | 2-methoxyphenyl | 2,6-difluoro | methoxy | 79 | 212–214 |
| 22 | 3-methoxyphenyl | 2-fluoro | methoxy | 82 | 234–235 |
| 23 | 3-methoxyphenyl | 2,6-difluoro | methoxy | 88 | 255–256 |
| 24 | 2-chlorophenyl | 2-fluoro | methoxy | 85 | 175–178 |
| 25 | 2-chlorophenyl | 2,6-difluoro | methoxy | 88 | 191–193 |
| 26 | 3-chlorophenyl | 2-fluoro | methoxy | 81 | 243–246 |
| 27 | 3-chlorophenyl | 2,6-difluoro | methoxy | 92 | 270–273 |
| 28 | 4-chlorophenyl | 2-fluoro | methoxy | 84 | 271–274 |
| 29 | 4-chlorophenyl | 2,6-difluoro | methoxy | 78 | 265–268 |
| 30 | 3-methoxyphenyl | 2,6-difluoro | propyl-amino-carbonyl | | |
| 31 | 3-methoxyphenyl | 2,6-difluoro | isopropyl-amino-carbonyl | | |
| 32 | 3-isopropoxyphenyl | 2,6-difluoro | propyl-amino-carbonyl | | |
| 33 | 3-isopropoxyphenyl | 2,6-difluoro | isopropyl-amino-carbonyl | | |
| 34 | 3-isopropoxyphenyl | 2,6-difluoro | methoxy | | |

REFERENCE EXAMPLE 12

Production of 5-(N-benzyl-N-methylaminomethyl)-2,4(1H, 3H)-dioxo-1-(2-fluorobenzyl)-6-(4-nitrophenyl)thieno[2,3-d]pyrimidin-3-acetic acid ethyl ester hydrochloride:

To a solution of the compound produced in Reference Example 10 (0.270 g, 0.47 mmol) in dymethylformamide (10 ml) were added, under ice-cooling, ethyl diisopropylamine (0.12 ml, 0.710 mmol) and benzylmethyl amine (0.07 ml, 0.56 mmol). The mixture was stirred for 20 hours at room temperature. The reaction mixture was concentrated, and the concentrate was partitioned between ethyl acetate and a saturated aqueous solution of sodium hydrogencarbonate. The aqueous layer was extracted with ethyl acetate. Organic layers were combined and dried (MgSO$_4$), then the solvent was distilled off under reduced pressure. The residue was chromatographed on silica gel to give a colorless oil (0.297 g, 100%). To a solution of this oil in ethyl acetate was added, under ice-cooling, 1N solution of hydrogen chloride in ether. The mixture was stirred for 10 minutes at the same temperature. The reaction mixture was concentrated under reduced pressure, and the concentrate was crystallized from ethyl acetate-ether to give the corresponding hydrochloride (0.084 g) as white crystals.

m.p. 120–128° C.

Elemental Analysis for C₃₂H₂₉N₄O₆SF.HCl.H₂O:

|  | C (%) | H (%) | N (%) |
|---|---|---|---|
| Calcd. | 57.27 | 4.81 | 8.35 |
| Found | 57.23 | 4.55 | 8.42 |

IR (KBr): 1711, 1665, 1522, 1493 cm$^{-1}$.

REFERENCE EXAMPLE 13

Production of 3-isobutyl-2,4(1H,3H)-dioxo-5-methyl-6-(4-methoxyphenyl)thieno[2,3-d]pyrimidine:

A mixture of isovaleric acid (1.15 ml, 10.03 mmol), diphenylphosphoryl azide (2.83 g, 10.30 mmol), triethylamine (1.45 ml, 10.03 mmol) and benzene (15 ml) was heated for one and half hour under reflux, to emerge isobutyl isocyanate. To the resultant mixture, the compound produced in Reference Example 2 (2.00 g, 6.85 mmol) and benzene (5 ml) were added, and the mixture was heated under reflux for 4 days. The reaction mixture was subjected to distribution procedure with ethyl acetate and an aqueous sodium chloride solution. The water layer was extracted with ethyl acetate, and the combined extracts were washed with an aqueous sodium chloride solution and dried with MgSO₄, and the solvent was removed under reduced pressure. The residue was chromatographed on silica gel to obtain white powders (2.64 g, 99%). The obtained urea derivative was dissolved in ethanol (30 ml), 28% sodium methoxide (3.93 g, 20.37 mmol) was added to the solution, the mixture was stirred at room temperature for 16 hours, 1N hydrochloric acid (22 ml, 22 mmol) was added. The solvent, ethanol, was distilled off under reduced pressure. The resulting residue was filtrated, washed with water-ethanol, dried under reduced pressure, and then crystallized from ethanol, to give white needles (1.61 g, 70%).

m.p. 215–216° C.

Elemental Analysis for C₁₆H₂₀N₂O₃S:

|  | C (%) | H (%) | N (%) |
|---|---|---|---|
| Calcd. | 62.77 | 5.85 | 8.13 |
| Found | 62.75 | 5.82 | 8.04. |

$^1$H-NMR (300 MHz, CDCl₃) δ: 0.96(6H,d,J=6.8 Hz), 2.20(1H,sept,J=6.8 Hz), 2.50(3H,s), 3.85–3.87(5H,m), 6.96 (2H,d,J=8.8 Hz), 7.33(2H,d,J=8.8 Hz), 9.50(1H,s). IR (KBr) :1711, 1657, 1537, 1499, 1458 cm$^{-1}$.

REFERENCE EXAMPLE 14

Employing the compounds which are produced in Reference Example 2 or 4 as a starting material, compounds which are produced in accordance with the method described in Reference Example 13 are set forth in Table 5.

TABLE 5

| Ref. Ex. 14 Cpd. No. | R² | R⁴' | Yield (%) | m.p. (° C.) |
|---|---|---|---|---|
| 1 | methoxyethyl | methoxy | 95 | 131–233 |
| 2 | 3,5-dimethoxyphenyl | methoxy | 87 | >300 |
| 3 | 3,5-dimethoxyphenyl | nitro | 85 | >300 |

REFERENCE EXAMPLE 15

Production of 2-amino-4-methyl-5-(4-methoxyphenyl)thiophene-3-carboxylic acid:

To an ethanol solution (60 ml) of the compound (3.0 g, 10.3 mmol) produced in Reference Example 2, 2N sodium hydroxide (20.0 ml, 40.0 mmol) was added and the mixture was heated under reflux for 1.5 hours. After cooling, 2N hydrochloric acid (20.0 ml, 40.0 mmol) was added to the reaction mixture to neutralize the solution, and the solution was extracted with ethyl acetate. The organic layer was washed with an aqueous sodium chloride solution, and then dried with MgSO₄. The solvent was distilled off under reduced pressure, and the residue was washed with ether-hexane to give pale yellowish powder (2.2 g, 91%). m.p. 142–145° C.

$^1$H-NMR (200 MHz, DMSO-d₆) δ: 2.22(3H,s), 3.79(3H, s), 6.98(2H,d,J=8.8 Hz), 7.25(2H,d,J=8.8 Hz), 7.39(2H,s). IR (KBr): 3470, 1647, 1576, 1508, 1475 cm$^{-1}$.

REFERENCE EXAMPLE 16

Production of 2,4(1H)-dioxo-6-(4-methoxyphenyl)-5-methylthieno[2,3-d]oxazine:

To a dioxane solution (10 ml) of the compound (6.00 g, 22.8 mmol) produced in Reference Example 15, triphosgene (6.76 g, 22.8 mmol) was added, and the mixture was stirred at 100° C. for 4 hours. After the reaction, the reaction solution was concentrated, then the residue was filtered and washed with ether to give pale yellowish powder (596 g, 90%) was obtained. m.p. 209–210° C.

$^1$H-NMR (200 MHz, DMSO-d₆) δ: 2.36(3H,s), 3.82(3H, s), 7.06(2H,d,J=8.8 Hz), 7.41(2H,d,J=8.8 Hz), 10.50(1H,s). IR (KBr): 1779, 1709, 1533, 1497 cm$^{-1}$.

REFERENCE EXAMPLE 17

Production of 2,4(1H)-dioxo-1-(2-fluorobenzyl)-6-(4-methoxyphenyl)-5-methylthieno[2,3-d]oxazine:

To a dimethylformamide (30 ml) solution of the compound (4.80 g, 16.59 mmol) produced in Reference Example 16, potassium carbonate (3.43 g, 24.88 mmol), potassium iodide (2.75 g, 16.59 mmol) and 2-fluorobenzylchloride (2.96 ml, 24.88 mmol) were added, and the mixture was stirred at room temperature for 2 hours. The reaction mixture was concentrated, the residue was subjected to distribution with ethyl acetate and an aqueous sodium chloride solution. The aqueous layer was extracted with ethyl acetate, the extracts were combined and washed with an aqueous sodium chloride solution and dried with MgSO₄, and the solvent was distilled off under reduced pressure. The obtained residue was subjected to purification by silica gel column chromatography to give white crystals (4.87 g, 74%). m.p. 162–163° C.

¹H-NMR (200 MHz, CDCl₃) δ: 2.43(3H,s), 3.84(3H,s), 5.21(2H,s), 6.95(2H,d,J=8.8 Hz), 7.05–7.44(6H,m). IR (KBr): 1769, 1719, 1562, 1531, 1493 cm⁻¹. FAB-MS m/z: 398.1(MH⁺).

REFERENCE EXAMPLE 18
Production of 2,4(1H)-dioxo-1-(2,6-difluorobenzyl)-6-(4-methoxyphenyl)-5-methylthieno[2,3-d]oxazine:

In substantially the same procedure as described in Reference Example 17, using 2,6-difluorobenzylchloride (1.18 g, 7.26 mmol) in place of 2-fluorobenzylchloride, from the compound (2.00 g, 6.91 mmol) obtained in Reference Example 17, potassium carbonate (0.95 g, 6.91 mmol) and potassium iodide (1.15 g, 6.91 mmol), the titled compound was produced as colorless crystals (2.34 g, 82%). m.p. 189–190° C. (recrystallized from ethyl acetate-hexane).

¹H-NMR (300 MHz, CDCl₃) δ: 2.42(3H,s), 3.84(3H,s), 5.27(2H,s), 6.90–6.96(4H,m), 7.24–7.36(3H,m). IR (KBr): 1775, 1731, 1528, 1468 cm⁻¹.

REFERENCE EXAMPLE 19
Production of 2,4-(1H,3H)-dioxo-1-(2-fluorobenzyl)-6-(4-methoxyphenyl)-3-(3-methoxypropyl)-5-methylthieno[2,3-d]pyrimidine:

To a dichloromethane (12 ml) solution of the compound obtained in Reference Example 17, 3-methoxypropylamine (0.17 ml, 1.67 mmol) was added under ice-cooling, and the mixture was stirred at room temperature for 1 hour. The residue obtained by concentrating the reaction mixture was subjected to distribution with dichloromethane and an aqueous sodium chloride solution. The aqueous layer was extracted with dichloromethane, the extracts were combined, the extracts was washed with an aqueous sodium chloride solution and dried with MgSO₄, and then the solvent was distilled off. Thus obtained residue was purified by silica gel column chromatography to give a white powder (524 mg, 78%). The obtained amine derivative was dissolved in tetrahydrofuran (20 ml), and to this solution triphosgene (351 mg, 1.18 mmol) and triethylamine (0.15 ml, 2.37 mmol) was added, and the mixture was stirred for 1.5 hours under heating. After cooling, the reaction mixture was extracted with ethyl acetate, the organic layer was washed with an aqueous sodium chloride solution and dried with MgSO₄, and the solvent was distilled off under reduced pressure. Thus obtained residue was purified by silica gel chromatography, and after drying it was subjected to recrystallization with ethyl acetate-hexane to give a white crystalline plate (398 mg, 72%).
m.p. 113–115° C.

Elemental Analysis for C₂₅H₂₅N₂O₄SF:

|  | C (%) | H (%) | N (%) |
|---|---|---|---|
| Calcd. | 64.09 | 5.38 | 5.98 |
| Found | 63.89 | 5.39 | 5.92. |

¹H-NMR (300 MHz, CDCl₃) δ: 2.00(2H,quint,J=6.7 Hz), 2.50(3H,s), 3.34(3H,s), 3.50(2H,t,J=6.7 Hz), 3.83(3H,s), 4.18(2H,t,J=6.7 Hz), 5.26(2H,s), 6.93(2H,d,J=8.8 Hz), 7.07–7.12(2H,m), 7.24–7.29(4H,m). IR (KBr): 1700, 1659, 1473 cm⁻¹.

REFERENCE EXAMPLE 20
Employing the compounds which are produced in Reference Example 18 as a starting material, compounds which are produced in accordance with the method described in Reference Example 15 are set forth in Table 6.

TABLE 6

[Chemical structure with substituents: CH₃, R², CH₃O, CH₂, R¹⁴, R¹⁵]

| Ref. Ex. 20 Cpd. No. | R¹⁴, R¹⁵ | R² | Yield (%) | m.p. (° C.) |
|---|---|---|---|---|
| 1 | 2,6-difluoro | methoxypropyl | 76 | 173–174 |
| 2 | 2,6-difluoro | 3-methyl-thiophenyl | 39 | 243–245 |

REFERENCE EXAMPLE 21
Production of 2,4(1H,3H)-dioxo-3-phenyl-5-methyl-6-(4-methoxyphenyl)thieno[2,3-d]pyrimidine:

To a pyridine (30 ml) solution of the compound (5.00 g, 16.32 mmol) obtained in Reference Example 4, phenylisocyanate (2.66 ml, 24.48 mmol) was added. The mixture was stirred at 45° C. for 6 hours, the reaction mixture was concentrated under reduced pressure to give a residue. The residue was dissolved in ethanol (6 ml). To the solution was added 28% sodium methoxide (7.86 g, 40.80 mmol), the mixture was stirred at room temperature for 2 hours, to the resultant was added 2N hydrochloric acid (25 ml, 50 mmol), and the solvent, ethanol, was distilled off under reduced pressure. Thus obtained residue was subjected to filtration, washed with water-ethanol, dried under reduced pressure, and recrystallized by ethanol to give yellow power (6.09 g, 98%).
m.p.>300° C.

Elemental Analysis for C₁₉H₁₃N₃O₄S.0.3H₂O:

|  | C (%) | H (%) | N (%) |
|---|---|---|---|
| Calcd. | 59.30 | 3.56 | 10.92 |
| Found | 59.56 | 3.52 | 10.93. |

¹H-NMR (300 MHz, OMSO-d₆) δ: 2.50(3H,s), 7.31–7.46 (5H,m), 7.78(2H,d,J=8.8 Hz), 8.32(2H,d,J=8.8 Hz), 12.50 (1H,s). IR (KBr): 1715, 1657, 1593, 1510 cm⁻¹.

REFERENCE EXAMPLE 22
Production of 2,4(1H,3H)-dioxo-5-methyl-3-(3-methoxyphenyl)-6-(4-methoxyphenyl)thieno[2,3-d]pyrimidine:

In substantially the same procedure as described in Reference Example 21, using 3-methoxyphenylisocyanate (1.57 ml, 12.0 mmol) in place of phenylisocyanate, from the compound (3.06 g, 10.00 mmol) obtained in Reference Example 4 and 28% sodium methoxide (4.82 g, 25.00 mmol), the titled compound was produced as colorless crystals (3.15 g, 77%). m.p.>300° C.

| Elemental Analysis for $C_{20}H_{15}N_3O_5S$: | | | |
|---|---|---|---|
| | C (%) | H (%) | N (%) |
| Calcd. | 58.67 | 3.69 | 10.26 |
| Found | 58.76 | 3.67 | 10.32 |

$^1$H-NMR (300 MHz, CDCl$_3$) δ: 2.50(3H,s), 3.78(3H,s), 6.87(1H,d,J=8.1 Hz), 6.92(1H,s), 7.00(1H,d,J=8.1 Hz), 7.38 (1H,t,J=8.1 Hz), 7.77(1H,d,J=8.7 Hz), 8.31(2H,d,J=8.7 Hz), 12.48(1H,s). IR (KBr): 1717, 1661, 1593, 1510, 1429 cm$^{-1}$.

REFERENCE EXAMPLE 23

Production of 2,4(1H,3H)-dioxo-1-(2,6-difluorobenzyl)-5-methyl-3-(3-methylsulfinylphenyl)-6-(4-methoxyphenyl) thieno[2,3-d]pyrimidine:

To a dichloromethane (20 ml) solution of the compound 2 (200 mg, 0.37 mmol) obtained in Reference Example 20 (Table 6), m-chloroperbenzoic acid (129 mg, 0.37 mmol) was added under ice-cooling. The mixture was stirred for 30 minutes, and the reaction mixture was subjected to distribution with dichloromethane and an aqueous sodium chloride solution. The aqueous layer was extracted with dichloromethane, the combined extracts were dried with an aqueous sodium chloride solution and dried with MgSO$_4$, and the solvent was distilled off under reduced pressure. Thus obtained residue was purified by silica gel column chromatography to give white powders (183 mg, 89%). m.p. 267–268° C.

$^1$H-NMR (300 MHz, CDCl$_3$) δ: 2.46(3H,s), 2.79(3H,s), 3.85(3H,s), 5.35(2H,s), 6.90–6.97(4H,m), 7.33–7.72(7H,m). IR (KBr): 1717, 1667, 1628, 1562, 1533 cm$^{-1}$. FAB-MS m/z: 553.1(MH$^+$).

REFERENCE EXAMPLE 24

Production of 2,4(1H,3H)-dioxo-1-(2,6-difluorobenzyl)-5-methyl-3-(3-methylsulfonylphenyl)-6-(4-methoxyphenyl) thieno[2,3-d]pyrimidine:

In substantially the same procedures as described in Reference Example 23, using m-chloroperbenzoic acid (62 mg, 0.18 mmol) again, from the compound (100 mg, 0.18 mmol) obtained in Reference Example 23, the titled compound was produced as colorless crystals (98 mg, 95%). m.p. 256–257° C.

$^1$H-NMR (300 MHz, CDCl$_3$) δ: 2.46(3H,s), 3.10(3H,s), 3.85(3H,s), 5.36(2H,s), 6.90–6.97(4H,m), 7.29–8.01(7H,m). IR (KBr): 1719, 1665, 1531, 1473 cm$^{-1}$. FAB-MS m/z: 569.1(MH$^+$).

REFERENCE EXAMPLE 25

Employing the compounds which are produced in accordance with the methods of Reference Example 13, 14, 21 or 22 as a starting material, compounds which are produced in accordance with the method described in reference Example 17 are set forth in Table 7.

TABLE 7

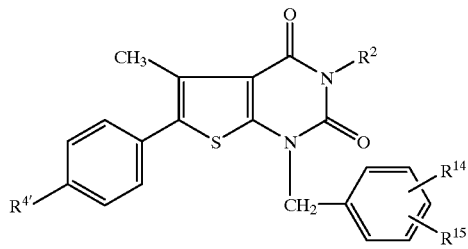

| Ref. Ex. 25 Cpd. No. | R$^2$ | R$^{14}$, R$^{15}$ | R$^{4'}$ | Yield (%) | m.p. (° C.) |
|---|---|---|---|---|---|
| 1 | isobutyl | 2-fluoro | methoxy | 80 | 136–138 |
| 2 | isobutyl | 2,6-difluoro | methoxy | 73 | 121–122 |
| 3 | methoxyethyl | 2-fluoro | methoxy | 74 | 102–104 |
| 4 | methoxyethyl | 2,6-difluoro | methoxy | 86 | 152–153 |
| 5 | 3,5-dimethoxyphenyl | 2-fluoro | methoxy | 76 | 250–252 |
| 6 | 3,5-dimethoxyphenyl | 2,6-difluoro | methoxy | 90 | 270–272 |
| 7 | 3,5-dimethoxyphenyl | 2,6-difluoro | nitro | 95 | 257–258 |
| 8 | phenyl | 2,6-difluoro | nitro | 93 | 280–282 |
| 9 | 3-methoxyphenyl | 2,6-difluoro | nitro | 84 | 231–234 |
| 10 | 3-isopropoxy-phenyl | 2,6-difluoro | nitro | | |
| 11 | 3-methoxy-methoxyphenyl | 2,6-difluoro | nitro | 88 | 209–210 |

REFERENCE EXAMPLE 26

Production of 2,4(1H,3H)-dioxo-1-(2-fluorobenzyl)-5-bromomethyl-6-(4-methoxyphenyl)-3-(3-methoxypropyl) thieno[2,3-d]pyrimidine:

A mixture of the compound (270 mg, 0.576 mmol) obtained in Reference Example 19, N-bromosuccinimide (103 mg, 0.576 mmol), α,α'-azobisisobutylonitrile 10 mg, 0.058 mmol) and carbon tetrachloride (10 ml) was heated under reflux. After cooling, insolubles were removed by filtration, the filtrate was diluted with chloroform. The organic layer was washed with an aqueous sodium chloride solution and dried with MgSO$_4$, and then the solvent was distilled off under reduced pressure. Thus obtained residue was recrystallized by ethyl acetate to give colorless powders (294 mg, 93%). m.p. 105–107° C.

$^1$H-NMR (300 MHz, CDCl$_3$) δ: 2.01(2H,quint,J=6.7 Hz), 3.33(3H,s), 3.50(2H,t,J=6.7 Hz), 3.85(3H,s), 4.21(2H,t,J=6.7 Hz), 4.81(2H,s), 5.27(2H,s), 6.98(2H,d,J=8.8 Hz), 7.09–7.34(4H,m), 7.49(2H,d,J=8.8 Hz). IR (KBr): 1713, 1661, 1628, 1541 cm$^{-1}$. FAB-MS m/z: 548.1(MH$^+$).

REFERENCE EXAMPLE 27

Employing the compounds which are produced in Reference Examples 19, 20, 23, 24 or 25 as starting materials, compounds which are produced in accordance with the method described in Reference Example 26 are set forth in Table 8.

residue was partitioned between ethyl acetate and a saturated aqueous solution of sodium bicarbonate. The aqueous layer was extracted with ethyl acetate. The combined organic layer was dried (MgSO$_4$). The solvent was distilled off under reduced pressure, and the residue was chromatographed on silica gel to give a colourless oil (0.159 g, 97%). To the solution of this oil in ethyl acetate (4 ml) was added, with ice-cooling, an iN solution of hydrogen chloride in ether (0.3 ml). After stirring for 10 minutes under ice-cooling, the reaction mixture was concentrated with reduced pressure. The residue was crystallized from ethyl acetate-ether to give

TABLE 8

| Ref. Ex. 27 Cpd. No. | R$^2$ | R$^{14}$, R$^{15}$ | R$^{4'}$ | Yield (%) | m.p. (° C.) |
|---|---|---|---|---|---|
| 1 | methoxypropyl | 2,6-difluoro | methoxy | 77 | 166–167 |
| 2 | 3-methyl-mercaptophenyl | 2,6-difluoro | methoxy | 90 | 228–230 |
| 3 | 3-methyl-sulfonylphenyl | 2,6-difluoro | methoxy | 85 | 272–273 |
| 4 | 3-methyl-sulfonylphenyl | 2,6-difluoro | methoxy | 100 | 261–263 |
| 5 | isobutyl | 2-fluoro | methoxy | 79 | 125–127 |
| 6 | isobutyl | 2,6-difluoro | methoxy | 88 | 155–157 |
| 7 | methoxylethyl | 2-fluoro | methoxy | 87 | 152–153 |
| 8 | methoxylethyl | 2,6-difluoro | methoxy | 88 | 150–151 |
| 9 | 3,5-dimethoxy-phenyl | 2-fluoro | methoxy | 76 | 234–238 |
| 10 | 3,5-dimethoxy-phenyl | 2,6-difluoro | methoxy | 86 | 251–253 |
| 11 | 3,5-dimethoxy-phenyl | 2,6-difluoro | nitro | 91 | 245–247 |
| 12 | phenyl | 2,6-difluoro | nitro | 94 | 228–229 |
| 13 | 3-methoxyphenyl | 2,6-difluoro | nitro | 91 | 253–254 |
| 14 | 3-isopropoxy-phenyl | 2,6-difluoro | nitro | | |
| 15 | 3-methoxy-methoxyphenyl | 2,6-difluoro | nitro | 97 | 207–209 |

EXAMPLE 1

Production of 2,4(1H,3H)-dioxo-6-(4-methoxyphenyl)-3-phenyl-1-(2-fluorobenzyl)-5-(N-benzyl-N-methylaminomethyl)thieno[2,3-d]pyrimidine hydrochloride:

To a solution of the compound 5 produced in Reference Example 11 (0.150 g, 0.310 mmol) in dimethylformamide (10 ml), with ice-cooling, were added ethyldiisopropylamine (0.08 ml, 0.460 mmol) and methylbenzylamine (0.05 ml, 0.370 mmol). After stirring for 2 hours at room temperature, the reaction mixture was concentrated. The a titled hydrochloride (0.144 g) as white crystals. m.p. 140–143° C. Elemental Analysis for C$_{35}$H$_{30}$N$_3$O$_3$SF.H$_2$O: C(%); H(%); N(%); Calc.: 65.05; 5.14; 6.50; Found: 65.14; 5.03; 6.37; IR(KBr) 1711, 1665, 1543, 1477 cm$^{-1}$.

EXAMPLE 2

Starting from the compounds which are produced in Reference Example 11, compounds which are produced in accordance with the method described in Example 1 are set forth in Table 9.

TABLE 9

| Ex. 2 Cpd. No. | R² | R¹⁴, R¹⁵ | R⁴' | R | Yield (%) | m.p. (° C.) |
|---|---|---|---|---|---|---|
| 1 | methyl | 2-methoxy | methoxy | phenyl | 46 | 119–122 |
| 2 | methyl | 2-fluoro | methoxy | phenyl | 97 | 128–131 |
| 3 | phenyl | 2-methoxy | methoxy | phenyl | 95 | 97–105 |
| 4 | phenyl | 2-fluoro | nitro | phenyl | 100 | 140–143 |
| 5 | phenyl | 3-fluoro | methoxy | phenyl | 97 | 152–156 |
| 6 | phenyl | 4-fluoro | methoxy | phenyl | 100 | 165–170 |
| 7 | phenyl | 2,4-difluoro | methoxy | phenyl | 77 | 155–160 |
| 8 | phenyl | 2,6-difluoro | methoxy | phenyl | 100 | 160–162 |
| 9 | phenyl | 2-chloro, 6-fluoro | methoxy | phenyl | 98 | 150–155 |
| 10 | phenyl | 2-methyl-thio | methoxy | phenyl | 76 | 152–158 |
| 11 | benzyl | 2-fluoro | methoxy | phenyl | 89 | 128–134 |
| 12 | benzyl | 2,6-difluoro | methoxy | phenyl | 100 | 123–127 |
| 13 | 4-methoxy phenyl | 2-fluoro | methoxy | phenyl | 93 | 150–155 |
| 14 | 4-methoxy phenyl | 2,6-difluoro | methoxy | phenyl | 84 | 153–157 |
| 15 | cyclohexyl | 2-fluoro | methoxy | phenyl | 93 | 144–150 |
| 16 | cyclohexyl | 2,6-difluoro | methoxy | phenyl | 97 | 145–150 |
| 17 | phenyl | 2,6-difluoro | nitro | phenyl | 93 | 155–160 |
| 18 | 2-methoxy-phenyl | 2-fluoro | methoxy | phenyl | 93 | 152–153 |
| 19 | 2-methoxy-phenyl | 2,6-difluoro | methoxy | phenyl | 100 | 148–150 |
| 20 | 3-methoxy-phenyl | 2-fluoro | methoxy | phenyl | 92 | 155–158 |
| 21 | 3-methoxy-phenyl | 2,6-difluoro | methoxy | phenyl | 91 | 160–163 |
| 22 | 2-chloro-phenyl | 2-fluoro | methoxy | phenyl | 97 | 147–152 |
| 23 | 2-chloro-phenyl | 2,6-difluoro | methoxy | phenyl | 98 | 150–155 |
| 24 | 3-chloro-phenyl | 2-fluoro | methoxy | phenyl | 100 | 148–153 |
| 25 | 3-chloro-phenyl | 2,6-difluoro | methoxy | phenyl | 100 | 152–157 |
| 26 | 4-chloro-phenyl | 2-fluoro | methoxy | phenyl | 91 | 161–164 |
| 27 | 4-chloro-phenyl | 2,6-difluoro | methoxy | phenyl | 86 | 145–146 |
| 28 | 3-methoxy-phenyl | 2,6-difluoro | propyl-amino-carbonyl | phenyl | | |
| 29 | 3-methoxy-phenyl | 2,6-difluoro | isopropyl-amino-carbonyl | phenyl | | |
| 30 | 3-isopropoxy-phenyl | 2,6-difluoro | propyl-amino-carbonyl | phenyl | | |
| 31 | 3-isopropoxy-phenyl | 2,6-difluoro | isopropyl-amino-carbonyl | phenyl | | |
| 32 | 3-methoxy-phenyl | 2,6-difluoro | methoxy | phenyl | 91 | 160–163 |
| 33 | 3-isopropoxy-phenyl | 2,6-difluoro | methoxy | phenyl | | |

TABLE 9-continued

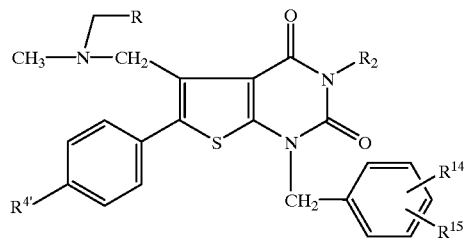

| Ex. 2 Cpd. No. | R² | R¹⁴, R¹⁵ | R⁴' | R | Yield (%) | m.p. (° C.) |
|---|---|---|---|---|---|---|
| 34 | 3-methoxy-phenyl | 2,6-difluoro | methoxy | 2-methylthio-phenyl | | |
| 35 | 3-methoxy-phenyl | 2,6-difluoro | methoxy | 2-pyridyl | | |
| 36 | phenyl | 2,6-difluoro | methoxy | 2-methyl-thiophenyl | | |
| 37 | phenyl | 2,6-difluoro | methoxy | 2-pyridyl | | |
| 38 | phenyl | 2,6-difluoro | methoxy | dimethyl-aminomethyl | | |
| 39 | phenyl | 2,6-difluoro | methoxy | diethyl-aminomethyl | | |
| 40 | phenyl | 2,6-difluoro | methoxy | 1-pyrrolidinyl-methyl | | |

EXAMPLE 3

Production of 6-(4-aminophenyl)-2,4(1H,3H)-dioxo-1-(2-fluorobenzyl)-3-phenyl-5-(N-methyl-N-benzylaminomethyl)thieno[2,3-d]pyrimidine:

The compound 4 produced in Example 2 (0.15 g, 0.247 mmol) was dissolved in ethanol (15 ml), to which was added 10% palladium-carbon (15 mg). The mixture was hydrogenized for 8 hours at room temperature under atmospheric pressure in an atmosphere of hydrogen. The reaction mixture was filtrated with celite, and the filtrate was concentrated under reduced pressure. The concentrate was chromatographed on silica gel to give a yellow crystalline amorphous (0.046 g, 32%).

$^1$H-NMR (300 MHz, CDCl$_3$) δ: 2.05(3H,s), 3.57(2H,s), 3.81(2H,br s), 3.89(2H,s), 5.29(2H,s), 6.69(2H,d,J=8.7 Hz), 7.05–7.56(16H,m). FAB-Mass m/z 577(MH)⁺.

EXAMPLE 4

Production of 6-(aminophenyl)-2,4-(1H,3H)-dioxo-1-(2,6-difluorobenzyl)-5-(N-methyl-N-benzylaminomethyl)-3-phenylthieno[2,3-d]pyrimidine:

Starting from the compound No. 17 produced in Example 2, the titled compound as crystalline amorphous (65%) was produced in accordance with the method described in Example 3.

$^1$H-NMR (300 MHz, CDCl$_3$) δ: 2.05(3H,s), 3.56(2H,s), 3.81(2H,br s), 3.88(2H,s), 5.36(2H,s), 6.71(2H,d,J=8.7 Hz), 6.91(2H,t,J=8.7 Hz), 7.21–7.53(13H,m).

EXAMPLE 5

Production of 6-(4-acetylaminophenyl)-2,4(1H,3H)-dioxo-1-(2-fluorobenzyl)-5-(N-methyl-N-benzylaminomethyl)-3-phenylthieno[2,3-d]pyrimidine:

The compound produced in Example 3 (0.63 g, 0.11 mmol) was dissolved in anhydrous pyridine (5 ml), to which was added acetic anhydride (0.01 ml, 0.11 mmol). The mixture was stirred for 2 hours at room temperature. The reaction mixture was concentrated under reduced pressure. The concentrate was partitioned between methylene chloride (30 ml) and a saturated aqueous sodium chloride solution (10 ml). The aqueous layer was again extracted with methylene chloride (30 ml). The combined organic layer was dried over magnesium sulfate, which was concentrated under reduced pressure. The concentrate was chromatographed on silica gel to give a colorless solid (0.01 g, 15%).

$^1$H-NMR (300 MHz, CDCl$_3$) δ: 2.06(3H,s), 2.19(3H,s), 3.57(2H,s), 3.90(2H,s), 5.30(2H,s), 7.04–7.57(16H,s), 7.70 (2H,d,J=8.4 Hz).

EXAMPLE 6

Employing the compound produced in Example 3, as the starting material, in accordance with substantially the same procedure as described in Example 5, the following compounds were produced.

No. 1: 2,4(2H,3H)-Dioxo-1-(2-fluorobenzyl)-5-(N-methyl-N-benzylaminomethyl)-3-phenyl-6-(4-propionylaminophenyl)thieno[2,3-d]pyrimidine hydrochloride (yield: 86%, m.p. 172–175° C.)

No. 2: 2,4(2H,3H)-Dioxo-1-(2-fluorobenzyl)-6-(4-isobutyrylaminophenyl)-5-(N-methyl-N-benzylaminomethyl)-3-phenylthieno[2,3-d]pyrimidine hydrochloride (yield: 77%, m.p. 185–188° C.)

No. 3: 2,4(2H,3H)-Dioxo-1-(2-fluorobenzyl)-6-(4-methoxyacetylaminophenyl)-5-(N-methyl-N-benzylaminomethyl)-3-phenylthieno[2,3-d]pyrimidine hydrochloride (yield: 88%, m.p. 157–162° C.)

EXAMPLE 7

Production of 2,4(1H,3H)-dioxo-1-(2-fluorobenzyl)-5-(N-benzyl-N-methylaminomethyl)-6-(4-methoxyphenyl)-3-(3-methoxypropyl)thieno[2,3-d]pyrimidine:

To a dimethylformamide (10 ml) solution of the compound (284 mg, 0.519 mmol) obtained in Reference Example 26 were added ethyldiisopropylamine (0.140 ml, 0.780 mmol) and methylbenzylamine (0.080 ml, 0.620 mmol). The mixture was stirred at room temperature for 2 hours, the reaction mixture was concentrated, and the obtained residue was subjected to distribution with ethyl acetate and saturated sodium bicarbonate. The aqueous layer was extracted with ethyl acetate. The extract and the organic layer were combined, dried with $MgSO_4$, and the solvent was distilled off under reduced pressure. Thus obtained residue was purified by silica gel column chromatography to give colorless oily substance (280 mg, 92%). The oily substance was dissolved in ethyl acetate (4 ml), and to the solution 1N solution of hydrogen chloride in ether (0.3 ml) under ice-cooling. The mixture was stirred under ice-cooling, and the reaction mixture was concentrated under reduced pressure. The residue was subjected to crystallization with ethyl acetate-ether to give a hydrochloride of the titled compound (220 mg) was obtained as white crystals.

m.p. 95–100° C.

Elemental Analysis for $C_{35}H_{34}N_3O_4SF.1.0HCl.0.5H_2O$:

|  | C (%) | H (%) | N (%) |
|---|---|---|---|
| Calcd. | 62.60 | 5.73 | 6.64 |
| Found | 62.73 | 5.67 | 6.56. |

IR (KBr): 1702, 1657, 1562, 1543, 1489 $cm^{-1}$.

EXAMPLE 8

Starting from the compounds which are produced in Reference Example 27, compounds which are produced in accordance with the method described in Example 7 are set forth in Table 10. The compound 19 and 20 are produced by hydrolyzing the compound 21 to produce the compound 22, and by reacting the compound 22 with alkyl halide in the presence of a base.

TABLE 10

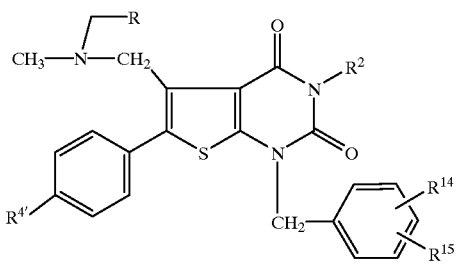

| Ex.8 Cpd.No. | $R^2$ | $R^{14}, R^{15}$ | $R^{4'}$ | R | Yield (%) | m.p. (° C.) |
|---|---|---|---|---|---|---|
| 1 | methoxypropyl | 2,6-difluoro | methoxy | phenyl | 69 | 95–100 |
| 2 | 3-methyl-thiophenyl | 2,6-difluoro | methoxy | phenyl | 94 | 139–144 |
| 3 | 3-methyl-sulfinylphenyl | 2,6-difluoro | methoxy | phenyl | 93 | 153–156 |
| 4 | 3-methyl-sulfonylphenyl | 2,6-difluoro | methoxy | phenyl | 98 | 155–159 |
| 5 | isobutyl | 2-fluoro | methoxy | phenyl | 100 | 150–153 |
| 6 | isobutyl | 2,6-difluoro | methoxy | phenyl | 98 | 165–167 |
| 7 | methoxyethyl | 2-fluoro | methoxy | phenyl | 95 | 154–156 |
| 8 | methoxyethyl | 2,6-difluoro | methoxy | phenyl | 91 | 126–130 |
| 9 | 3,5-dimethoxy-phenyl | 2-fluoro | methoxy | phenyl | 90 | 140–145 |
| 10 | 3,5-dimethoxy-phenyl | 2,6-difluoro | mthoxy | phenyl | 91 | 146–148 |
| 11 | 3,5-dimethoxy-phenyl | 2,6-difluoro | nitro | phenyl | 97 | 142–146 |
| 12 | phenyl | 2,6-difluoro | nitro | phenyl | 93 | 152–153 |
| 13 | 3-methoxy-phenyl | 2,6-difluoro | nitro | phenyl | 82 | 142–144 |
| 14 | 3-isopropoxy-phenyl | 2,6-difluoro | nitro | phenyl | 70 | amorphous (80–90) |
| 15 | 3-isopropoxy-phenyl | 2,6-difluoro | nitro | 2-thiomethyl-phenyl |  |  |
| 16 | 3-isopropoxy-phenyl | 2,6-difluoro | nitro | 2-pyridyl |  |  |
| 17 | 3-methoxy-phenyl | 2,6-difluoro | nitro | 2-thiomethyl- |  |  |

TABLE 10-continued

[Structure: CH₃-N(R)-CH₂- substituent on thieno[2,3-d]pyrimidine-2,4-dione core with R² on N, R⁴' on phenyl, and CH₂-phenyl(R¹⁴,R¹⁵) group]

| Ex.8 Cpd.No. | $R^2$ | $R^{14}, R^{15}$ | $R^{4'}$ | R | Yield (%) | m.p. (°C.) |
|---|---|---|---|---|---|---|
| 18 | 3-methoxy-phenyl | 2,6-difluoro | nitro | phenyl 2-pyridyl | | |
| 19 | 3-ethoxyphenyl | 2,6-difluoro | nitro | phenyl | 93 | 171–176 |
| 20 | 3-propoxy-phenyl | 2,6-difluoro | nitro | phenyl | 86 | 149–151 |
| 21 | 3-methoxy-methoxyphenyl | 2,6-difluoro | nitro | phenyl | 86 | 110–120 |
| 22 | 3-hydroxy-phenyl | 2,6-difluoro | nitro | phenyl | 86 | 207–209 |
| 23 | 3-methoxy-phenyl | 2,6-difluoro | nitro | diethyl-aminomethyl | | |
| 24 | 3-methoxy-phenyl | 2,6-difluoro | nitro | dimethyl-aminomethyl | | |
| 25 | 3-methoxy-phenyl | 2,6-difluoro | nitro | 1-pyrroli-dinylmethyl | | |

EXAMPLE 9

Production of 6-(4-aminophenyl)-2,4(1H,3H)-dioxo-1-(2,6-difluorobenzyl)-5-(N-benzyl-N-methylaminomethyl)-3-(3-methoxyphenyl)thieno[2,3-d]pyrimidine hydrochloride:

To a formic acid (200 ml) solution of the compound 13 produced in Example 8, 50% paradium-carbon powder (0.90 g) was added under ice-cooling, and the mixture was stirred for 2 hours in a hydrogen atmosphere at room temperature. The reaction mixture was concentrated, and the residue was subjected to distribution with dichloromethan and saturated sodium bicarbonate. The aqueous layer was extracted with dichloromethane, and the extract was combined with the organic layer. The mixture was dried with $MgSO_4$, and the solvent was distilled off under reduced pressure. The residue was purified by silica gel column chromatography to give colorless powders (5.13 g, 60%). Thus obtained compound (100 mg) was dissolved in ethyl acetate (4 ml), and to the solution was added 1N solution of hydrogen chloride in ether (0.3 ml) under ice-cooling and the mixture was stirred for 10 minutes under ice-cooling. The reaction mixture was concentrated under reduced pressure, and the residue was crystallized from ethyl acetate-ether to give hydrochloride of the titled compound (95 mg) was obtained as white crystals.

m.p. 162–165° C.

Elemental Analysis for $C_{35}H_{30}N_4O_3SF_2 \cdot 2.0HCl \cdot 1.0H_2O$:

| | C (%) | H (%) | N (%) |
|---|---|---|---|
| Calcd. | 58.74 | 4.79 | 7.83 |
| Found | 58.44 | 4.72 | 7.66. |

IR (KBr): 1715, 1659, 1537, 1473 $cm^{-1}$.

EXAMPLE 10

Starting from the compounds which are produced in Example 8, compounds which are produced in accordance with the method described in Example 9 are set forth in Table 11.

TABLE 11

[Structure: similar core with NH₂-phenyl substituent and CH₂-phenyl(R¹⁴,R¹⁵) group]

| Ex.10 Cpd. No. | $R^2$ | $R^{14}, R^{15}$ | R | Yield (%) | m.p. (°C.) |
|---|---|---|---|---|---|
| 1 | 3,5-dimethoxy-phenyl | 2,6-difluoro | phenyl | 69 | 95–100 |
| 2 | phenyl | 2,6-difluoro | phenyl | 94 | 139–144 |
| 3 | 3-isopropoxy-phenyl | 2,6-difluoro | phenyl | 77 | 138-140 |
| 4 | 3-isopropoxy-phenyl | 2,6-difluoro | 2-methylthio-phenyl | | |
| 5 | 3-isopropoxy-phenyl | 2,6-difluoro | 2-pyridyl | | |
| 6 | 3-methoxyphenyl | 2,6-difluoro | 2-methylthio-phenyl | | |
| 7 | 3-methoxyphenyl | 2,6-difluoro | 2-pyridyl | | |
| 8 | 3-ethoxyphenyl | 2,6-difluoro | phenyl | 67 | 169–172 |
| 9 | 3-propoxyphenyl | 2,6-difluoro | phenyl | 73 | 115–120 |

TABLE 11-continued

[Chemical structure: thieno[2,3-d]pyrimidine with CH₃-N(R)-CH₂- group, NH₂-phenyl substituent, R² on N, and CH₂-phenyl(R¹⁴, R¹⁵) group]

Ex.10

| Cpd. No. | R² | R¹⁴, R¹⁵ | R | Yield (%) | m.p. (° C.) |
|---|---|---|---|---|---|
| 10 | 3-methoxyphenyl | 2,6-difluoro | diethylaminomethyl | | |
| 11 | 3-methoxyphenyl | 2,6-difluoro | dimethylaminomethyl | | |
| 12 | 3-methoxyphenyl | 2,6-difluoro | 1-pyrrolidinylmethyl | | |

EXAMPLE 11

Production of 2,4(1H,3H)-dioxo-1-(2,6-difluorobenzyl)-5-(N-benzyl-N-methylaminomethyl)-6-(4-formamidophenyl)-3-phenylthieno[2,3-d]pyrimidine:

Formic acid (0.5 ml, 13.3 mmol) was added to acetic anhydride (1.0 ml, 10.6 mmol) under ice-cooling, the mixture was stirred for one hour at 50° C. to give formic acid-acetic acid anhydride. To a tetrahydrofuran (10 ml) solution of the compound 2 (200 mg, 0.34 mmol) obtained in Example 10 was added the formic acid-acetic acid anhydride (0.3 ml) under ice-cooling and the mixture was stirred for 30 minutes. The mixture was stirred for one hour. The reaction mixture was concentrated under reduced pressure. The residue was purified by silica gel column chromatography to give colorless solid substance (125 mg) of the titled compound.

m.p. 194–196° C.

Elemental Analysis for $C_{35}H_{30}N_4O_3SF_2.0.5H_2O$:

| | C (%) | H (%) | N (%) |
|---|---|---|---|
| Calcd. | 66.55 | 4.63 | 8.87 |
| Found | 66.74 | 4.56 | 8.88. |

$^1$H-NMR (300 MHz, CDCl$_3$) δ: 3.57(2H,s), 3.90(2H,s), 5.37(2H,s), 6.90–7.30(12H,m), 7.34–7.79(6H,m), 8.42(1H,s). IR (KBr): 1715, 1665, 1531, 1467 cm$^{-1}$.

EXAMPLE 12

Starting from the compounds which are produced in Example 9 or 10, compounds which are produced in accordance with the method described in Example 11 are set forth in Table 12.

TABLE 12

[Chemical structure: thieno[2,3-d]pyrimidine with CH₃-N(R)-CH₂- group, CHO-NH-phenyl substituent, R² on N, and CH₂-phenyl(R¹⁴, R¹⁵) group]

Ex.12

| Cpd. No. | R² | R¹⁴, R¹⁵ | R | Yield (%) | m.p. (° C.) |
|---|---|---|---|---|---|
| 1 | 3,5-dimethoxyphenyl | 2,6-difluoro | phenyl | 55 | 239–243 |
| 2 | 3-methoxyphenyl | 2,6-difluoro | phenyl | 56 | 213–215 |
| 3 | 3-isopropoxyphenyl | 2,6-difluoro | phenyl | | |
| 4 | 3-isopropoxyphenyl | 2,6-difluoro | 2-methylthiophenyl | | |
| 5 | 3-isopropoxyphenyl | 2,6-difluoro | 2-pyridyl | | |
| 6 | 3-methoxyphenyl | 2,6-difluoro | 2-methylthiophenyl | | |
| 7 | 3-methoxyphenyl | 2,6-difluoro | 2-pyridyl | | |

EXAMPLE 13

Production of 2,4(1H,3H)-dioxo-1-(2,6-difluorobenzyl)-5-(N-benzyl-N-methylaminomethyl)-6-(4-methylaminophenyl)-3-(3-methoxyphenyl)thieno[2,3-d]pyrimidine hydrochloride:

To a tetrahydrofuran (30 ml) solution of the compound 2 (730 mg, 1.12 mmol) obtained in Example 12 was added dimethylsulfid borane (0.28 ml, 2.8 mmol) under ice-cooling, and the mixture was heated for 2 hours under reflux. After adding hydrochloric acid (pH<2) and then heating under reflux for 1 hour, the resultant was concentrated and the residue was subjected to distribution with dichloromethane and saturated sodium bicarbonate. The aqueous layer was extracted with dichloromethane, the extract was combined with organic layer, the mixture was dried with MgSO$_4$ and the solvent was distilled off under reduced pressure. The residue was purified by silica gel column chromatography to give colorless powder (610 mg, 85%). To the ethyl acetate (4 ml) solution of thus obtained compound was added 1N solution of hydrogen chloride in ether (0.3 ml under ice-cooling, and the mixture was stirred for 10 minutes under ice-cooling. The residue obtained by concentrating the reaction mixture under reduced pressure was subjected to crystallization to give white crystals (95 mg) of hydrochloride of the titled compound.

m.p. 155–160° C.

Elemental Analysis for $C_{35}H_{30}N_4O_3SF_2.2.0HCl.0.5AcOEt.3.0H_2O$:

| | C (%) | H (%) | N (%) |
|---|---|---|---|
| Calcd. | 56.36 | 5.47 | 6.91 |
| Found | 56.08 | 5.22 | 6.86. |

IR (KBr): 1715, 1663, 1607, 1543, 1475 cm$^{-1}$.

EXAMPLE 14

Production of 2,4(1H,3H)-dioxo-1-(2,6-difluorobenzyl)-6-(4-propionylaminophenyl)-5-(N-benzyl-N-methylaminomethyl)-3-(3-methoxyphenyl)thieno[2,3-d]pyrimidine hydrochloride:

To a dichloromethane (10 ml) solution of the compound (250 mg, 0.38 mmol) obtained in Example 9 were added triethylamine (0.053 mg, 0.38 mmol) and propionyl chloride (0.033 ml, 0.38 mmol) under ice-cooling, and the mixture was stirred one hour. The reaction mixture was subjected to distribution with dichloromethane and saturated sodium bicarbonate. The aqueous layer was extracted with dichloromethane, the extracts were combined, the combined extracts were washed with an aqueous solution of sodium chloride and dried with $MgSO_4$, and the solvent was distilled off under reduced pressure. The residue was purified by silica gel column chromatography to give colorless oily substance (220 mg, 82%). To an ethyl acetate (4 ml) solution of thus obtained acyl derivative was added 1N solution of hydrogen chloride in ether (0.3 ml) under ice-cooling and the mixture was stirred for 10 minutes under ice-cooling. The reaction mixture was concentrated under reduced pressure, the residue was crystallized to give white crystals of hydrochloride (213 mg) of the titled compound.

m.p. 218–224° C. IR (KBr): 1713, 1665, 1601, 1543, 1475 $cm^{-1}$.

EXAMPLE 15

Starting from the compounds which are produced in Example 9 or 10, compounds which are produced in accordancd with the method described in Example 14 are set forth in Table 13.

TABLE 13

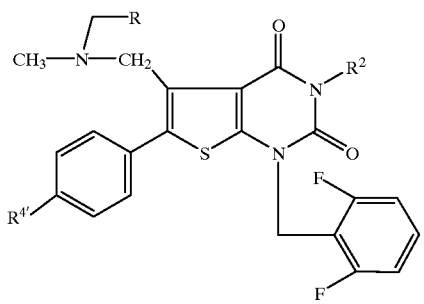

| Ex.15 Cpd. No. | $R^2$ | $R^{4'}$ | R | Yield (%) | m.p. (° C.) |
|---|---|---|---|---|---|
| 1 | 3-methoxyphenyl | isobutyryl-amino | phenyl | 85 | 170–173 |
| 2 | phenyl | isobutyryl-amino | phenyl | 67 | 185–190 |
| 3 | 3,5-dimethoxy-phenyl | propionyl-amino | phenyl | 82 | 218–224 |
| 4 | 3,5-dimethoxy-phenyl | isobutynyl-amino | phenyl | 76 | 240–245 |
| 5 | 3-methoxyphenyl | N-methyl-N-propionyl-amino | phenyl | 84 | 138–143 |
| 6 | 3-methoxyphenyl | N-methyl-N-isobutyryl-amino | phenyl | 91 | 146–152 |
| 7 | phenyl | propionyl-amino | phenyl | 78 | 197–202 |
| 8 | phenyl | butyryl-amino | phenyl | 76 | 169–170 |

TABLE 13-continued

| Ex.15 Cpd. No. | $R^2$ | $R^{4'}$ | R | Yield (%) | m.p. (° C.) |
|---|---|---|---|---|---|
| 9 | phenyl | benzoyl-amino | phenyl | 81 | 167–169 |
| 10 | 3-methoxyphenyl | propionyl-amino | phenyl | 83 | 170–175 |
| 11 | 3-isopropoxy-phenyl | isobutyryl-amino | phenyl | | |
| 12 | 3-isopropoxy-phenyl | isobutyryl-amino | 2-methylthio-phenyl | | |
| 13 | 3-isopropoxy-phenyl | isobutyryl-amino | 2-pyridyl | | |
| 14 | 3-methoxyphenyl | isobutyryl-amino | 3-methylthio-phenyl | | |
| 15 | 3-methoxyphenyl | isobutyryl-amino | 2-pyridyl | | |
| 16 | 3-isopropoxy-phenyl | propionyl-amino | phenyl | 94 | 179–181 |
| 17 | 3-ethoxyphenyl | propionyl-amino | phenyl | 67 | 164–168 |
| 18 | 3-propoxyphenyl | propionyl-amino | phenyl | 87 | 165–170 |
| 19 | 3-methoxyphenyl | ethylsul-fonylamino | phenyl | | |
| 20 | 3-methoxyphenyl | trifluoro-acetylamino | phenyl | | |
| 21 | 3-methoxyphenyl | isobutyryl-amino | diethylamino-methyl | | |
| 22 | 3-methoxyphenyl | isobutyryl-amino | dimethylamino-methyl | | |
| 23 | 3-methoxyphenyl | isobutyryl-amino | 1-pyrrolidinyl-methyl | | |

EXAMPLE 16

In substantially the same procedure as described in Example 14, using the compound which are obtained in Example 9 or 10 and anhydrous trifluoro acetic acid in place of propionyl chloride, trifluoroacetylamino derivative are obtained. To the derivative is added halogeno derivative (e.g. propyl bromide, isopropyl bromide) in the presence of an appropriate base (e.g. potassium carbonate) in a solvent (e.g. dimethylformamide) which does not affect the reaction, the mixture is stirred for 1 to 6 hours at room temperature. To the reaction mixture is added 2N aqueous sodium hydroxide solution for hydrolysis for 1 to 2 hours to give compounds set forth in Table 14.

TABLE 14

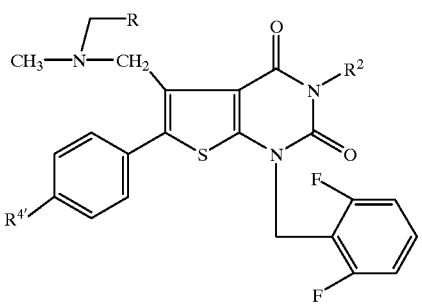

Ex.16

| Cpd.No. | R² | R⁴' | R |
|---|---|---|---|
| 1 | 3-methoxyphenyl | propylamino | phenyl |
| 2 | 3-methoxyphenyl | isopropylamino | phenyl |
| 3 | 3-isopropoxy-phenyl | propylamino | phenyl |
| 4 | 3-isopropoxy-phenyl | isopropylamino | phenyl |
| 5 | 3-isopropoxy-phenyl | propylamino | 2-methylthio-phenyl |
| 6 | 3-isopropoxy-phenyl | propylamino | 2-pyridyl |
| 7 | 3-isopropoxy-phenyl | isopropylamino | 2-methylthio-phenyl |
| 8 | 3-isopropoxy-phenyl | isopropylamino | 2-pyridyl |
| 9 | 3-methoxyphenyl | ethylamino | phenyl |
| 10 | 3-isopropoxy-phenyl | ethylamino | phenyl |
| 11 | 3-methoxyphenyl | isopropylamino | 2-methylthio-phenyl |
| 12 | 3-methoxyphenyl | isopropylamino | 2-pyridyl |
| 13 | 3-methoxyphenyl | propylamino | 2-methylthio-phenyl |
| 14 | 3-methoxyphenyl | propylamino | 2-pyridyl |
| 15 | 3-methoxyphenyl | propylamino | diethylaminomethyl |

TABLE 15

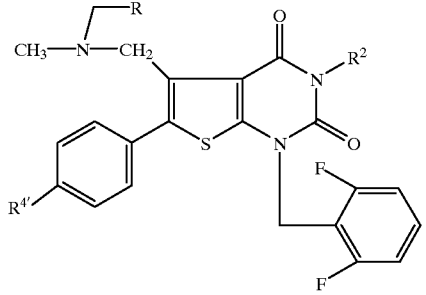

Ex.17

| Cpd.No. | R² | R⁴' | R |
|---|---|---|---|
| 1 | 3-methoxyphenyl | ethoxycarbonyl-vinyl | phenyl |
| 2 | 3-methoxyphenyl | ethoxycarbonyl-vinyl | 2-methylthio-phenyl |
| 3 | 3-methoxyphenyl | ethoxycarbonyl-vinyl | 2-pyridyl |
| 4 | 3-methoxyphenyl | propionylvinyl | phenyl |
| 5 | 3-methoxyphenyl | propionylvinyl | 2-methylthio-phenyl |
| 6 | 3-methoxyphenyl | propionylvinyl | 2-pyridyl |
| 7 | 3-isopropoxy-phenyl | ethoxycarbonyl-vinyl | phenyl |
| 8 | 3-isopropoxy-phenyl | propionylvinyl | phenyl |
| 9 | 3-isopropoxy-phenyl | ethoxycarbonyl-vinyl | 2-methylthio-phenyl |
| 10 | 3-isopropoxy-phenyl | ethoxycarbonyl-vinyl | 2-pyridyl |
| 11 | 3-isopropoxy-phenyl | propionylvinyl | 2-methylthio-phenyl |
| 12 | 3-isopropoxy-phenyl | propionylvinyl | 2-pyridyl |
| 13 | 3-methoxyphenyl | propionylvinyl | dimethyl-aminomethyl |
| 14 | 3-methoxyphenyl | propionylvinyl | 1-pyrrolidinyl-methyl |
| 15 | 3-methoxyphenyl | propionylvinyl | diethylamino-methyl |

EXAMPLE 17

Employing the compounds which are obtained in Example 9 or 10 as starting compounds, the compounds set forth in Table 15 are produced by reacting the starting compounds with isoamyl nitrite, vinyl compound and palladium compound (e.g. tetrakistri-phenylphosphine palladium, dibenzylideneacetone palladium) in acetic acid under stirring at a room temperature or under heating for 1 to 6 hours.

EXAMPLE 18

To a mixture of the compound 30 or 31 which are obtained in Reference Example 9, a small amount of arylborric acid derivative, 2M aqueous sodium carbonate solution and 1,2-dimethoxyethane, is added a catalytic amount of tetrakis(triphenylphosphine)palladium(0), and thus obtained mixture is stirred under reflux for 2 hours. To the resulting compound, N-methylbenzylamino group is introduced in accordance with the method described in Reference Example 26 and Example 1 to give compounds set forth in Table 16.

TABLE 16

[Structure: thiophene-pyrimidinedione with CH₃—N(CH₂Ph)—CH₂ group, R⁴'-phenyl, and 2,6-difluorobenzyl-N substituent, with R² on N]

| Ex.18 Cpd.No. | R² | R⁴' |
|---|---|---|
| 1 | 3-methoxyphenyl | propylaminocarbonyl |
| 2 | 3-isopropoxyphenyl | propylaminocarbonyl |
| 3 | 3-methoxyphenyl | isopropylaminocarbonyl |
| 4 | 3-isopropoxyphenyl | isopropylaminocarbonyl |
| 5 | 3-methoxyphenyl | ethylaminocarbonyl |
| 6 | 3-methoxyphenyl | N-methyl-N-propyl-aminocarbonyl |

EXAMPLE 19

To the compounds which are obtained in Example 2, 3 equivalents of dimethylsulfide and 3 equivalents of aluminium chloride are added in dichloromethane under ice-cooling. The mixture is stirred for 1 to 4 hours to give $R^4$ phenol derivative. Thus obtained compound, a small amount of an alkyl halide (e.g. chloro acetone) and a base (e.g. potassium carbonate) are mixed in dimethylformamide to produce compounds set forth in Table 17.

TABLE 17

[Structure: thiophene-pyrimidinedione with CH₃—N(R)—CH₂ group, R⁴'-phenyl, and 2,6-difluorobenzyl-N substituent, with R² on N]

| Ex.19 Cpd.No. | R² | R⁴' | R |
|---|---|---|---|
| 1 | phenyl | acetonyloxy | phenyl |
| 2 | phenyl | acetonyloxy | 2-methylthio-phenyl |
| 3 | phenyl | acetonyloxy | 2-pyridyl |
| 4 | phenyl | acetonyloxy | diethylamino-methyl |
| 5 | phenyl | acetonyloxy | dimethylamino-methyl |
| 6 | phenyl | acetonyloxy | 1-pyrrolidinyl-methyl |
| 7 | phenyl | allyloxy | phenyl |
| 8 | phenyl | propoxy | phenyl |
| 9 | phenyl | isobutoxy | phenyl |

TABLE 17-continued

| Ex.19 Cpd.No. | R² | R⁴' | R |
|---|---|---|---|
| 10 | phenyl | cyclopropyl methoxy | phenyl |
| 11 | phenyl | allyloxy | diethylamino-methyl |
| 12 | phenyl | propoxy | diethylamino-methyl |

EXAMPLE 20

Using the compound produced in Example 4 (100 mg), lactose (165 mg), corn starch (5 mg), polyvinyl alcohol (4 mg) and magnesium stearate (1 mg), a tablet is prepared by a conventional method.

EXAMPLE 21

The compound produced in Example 4 (5 g) is dissolved in distilled water for injection to make the whole volume 100 ml. The solution is subjected to sterilized filtration with 0.22 μm membrane filter (manufactured by Sumitomo Electric Industries, Ltd. or by Zartolius, Inc.), 2 ml each of which is distributed to sterilized vials, followed by lyophilization by a conventional means to give lyophilized injectable solution of 100 mg/vial.

EXAMPLE 22

Using the compound 1 produced in Example 15 (100 mg), lactose (165 mg), corn starch (25 mg), polyvinyl alcohol (4 mg) and magnesium stearate (1 mg), a tablet is prepared by a conventional method.

Example 23

The compound 1 produced in Example 15 (5 g) is dissolved in distilled water for injection to make the whole volume 100 ml. This solution is subjected to sterilized filtration with 0.22 μm membrane filter (manufactured by Sumitomo Electric Industries, Ltd. or Zartolius, Inc.), 2 ml each of which is distributed to sterilized vials, followed by lyophilization by a conventional means to prepare lyophilized injectable solution of 100 mg/vial.

EXAMPLE 24

| (1) | Compound produced in Example 4 or the compound 1 of Example 15 | 5 g |
|---|---|---|
| (2) | Lactose.crystalline cellulose (granules) | 330 g |
| (3) | D-mannitol | 29 g |
| (4) | Low-substituted hydroxypropyl cellulose | 20 g |

-continued

| | | |
|---|---|---|
| (5) | Talc | 25 g |
| (6) | Hydroxypropyl cellulose | 50 g |
| (7) | Aspartame | 3 g |
| (8) | Dipotassium glycyrrhetinate | 3 g |
| (9) | Hydroxypropylmethyl cellulose 2910 | 30 g |
| (10) | Titanium oxide | 3.5 g |
| (11) | Yellow iron sesquioxide | 0.5 g |
| (12) | Light silicic acid anhydride | 1 g |

In refined water are suspended or dissolved (1), (3), (4), (5), (7) and (8). The nuclear granule of (2) is coated with the suspension or solution to prepare raw fine granules, which are coated with (9)–(11) to prepare coated fine granules, which are mixed with (12), to give 500 g of fine granules containing 1% of the compound produced in Example 4 or the compound 1 of Example 15. 500 mg each of thus-prepared fine granules is packed.

INDUSTRIAL APPLICABILITY

A thienopyrimidine derivative (I) of the present invention is effective as a propylactic or therapeutic agent for the prevention or treatment of several hormone dependent diseases, for example, a sex hormone dependent cancer (e.g. prostatic cancer, cancer of uterine cervix, breast cancer, pituitary adenoma), benign prostatic hypertrophy, myoma of the uterus, endometriosis, precocious puberty, amenorrhea, premenstrual syndrome, polycystic ovary syndrome and acne vulgaris; is effective as a fertility controlling agent in both sexes (e.g. a pregnancy controlling agent and a menstrual cycle controlling agent); can be used as a contraceptive of male or female, as an ovulation-inducing agent of female; can be used as an infertility treating agent by using a rebound effect owing to a stoppage of administration thereof; is useful as modulating estrous cycles in animals in the field of animal husbandry, as an agent for improving the quality of edible meat or promoting the growth of animals; and is useful as an agent of spawning promotion in fish.

What is claimed is:

1. A compound of the formula:

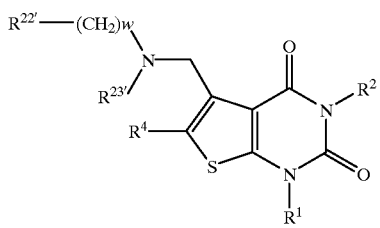

wherein $R^1$ is benzyl substituted by 1 or 2 substituents selected from the group consisting of halogen and $C_{1-3}$ alkoxy;

$R^2$ is $C_{1-6}$ alkyl, benzyl, $C_{3-10}$ cycloalkyl, or phenyl unsubstituted or substituted by a $C_{1-3}$ alkoxy or halogen;

$R^{22'}$ is $C_{6-14}$ aryl;

w is an integer of 0 to 3;

$R^{23'}$ is hydrogen or a $C_{1-6}$ alkyl group; and $R^4$ is phenyl substituted by (i) a group of the formula;

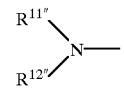

wherein $R^{11''}$ is a $C_{1-10}$ alkyl-carbonyl group and $R^{12''}$ is hydrogen or (ii) a $C_{1-3}$ alkoxy, or a pharmaceutically acceptable salt thereof.

2. A compound according to claim 1, which is 2,4(1H,3H)-dioxo-6-(4-methoxyphenyl)-3-phenyl-1-(2-chloro-6-fluorobenzyl)-5-(N-benzyl-N-methylaminomethyl)thieno[2,3-d]pyrimidine or its pharmaceutically acceptable salt.

3. A compound according to claim 1, which is 5-benzylaminomethyl-1-(2-chloro-6-fluorobenzyl)-2,4(1H,3H)-dioxo-6-(4-methoxyphenyl)-3-phenylthieno-[2,3-d]pyrimidine or its pharmaceutically acceptable salt.

4. A compound according to claim 1, which is 2,4(1H,3H)-dioxo-1-(2,6-difluorobenzyl)-6-(4-propionylaminophenyl)-5-(N-benzyl-N-methylaminomethyl)-3-(3-methoxyphenyl)thieno[2,3-d]pyrimidine or its pharmaceutically acceptable salt.

5. A compound according to claim 1, which is 2,4(1H,3H)-dioxo-1-(2,6)-difluoroabenzyl)-6-(4-isobutyrylaminophenyl)-5-(N-benzyl-N-methylaminomethyl)-3-(3-methoxyphenyl)thieno[2,3-d]pyrimidine or its pharmaceutically acceptable salt.

6. A compound according to claim 1, which is 5-(N-benzyl-N-methylaminomethyl)-1-(2,6-difluorobenzyl)-2,4(1H,3H)-dioxo-6-(4-propionylaminophenyl)-3-phenylthieno[2,3-d]pyrimidine or its pharmaceutically acceptable salt.

7. A pharmaceutical composition comprising a compound as defined in claim 1 and a carrier, excipient or diluent.

8. A method for treating a mammal suffering from a sex hormone dependent disease comprising administering an effective amount of a compound as defined in claim 1 to the mammal.

* * * * *